(12) United States Patent
Kawakami et al.

(10) Patent No.: US 8,110,122 B2
(45) Date of Patent: Feb. 7, 2012

(54) ANTHRACENE DERIVATIVE, MATERIAL FOR LIGHT-EMITTING ELEMENT, LIGHT-EMITTING ELEMENT, LIGHT-EMITTING DEVICE, AND ELECTRONIC APPLIANCE

(75) Inventors: Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 213 days.

(21) Appl. No.: 12/550,562

(22) Filed: Aug. 31, 2009

(65) Prior Publication Data

US 2010/0051926 A1 Mar. 4, 2010

(30) Foreign Application Priority Data

Sep. 2, 2008 (JP) ................................ 2008-224805

(51) Int. Cl.
 C09K 11/06 (2006.01)
 B32B 9/00 (2006.01)
 H01J 63/04 (2006.01)
 C07C 211/00 (2006.01)
 C07C 13/48 (2006.01)
(52) U.S. Cl. .................. 252/301.16; 428/690; 428/917; 313/504; 564/433; 564/434; 585/26
(58) Field of Classification Search ............ 252/301.16, 252/301.26
See application file for complete search history.

(56) References Cited

U.S. PATENT DOCUMENTS 6,815,094 B2 * 11/2004 Lee et al. ..................... 428/690

(Continued)

OTHER PUBLICATIONS

Min-Gi. Shin, Seul Ong Kim, Hyun Tae Park, Sung Jin Park, Han Sung Yu, Yun-Hi Kim, Soon-Ki Kwon, Synthesis and Characterization of Ortho-twisted Asymmetric Anthracene Derivatives for Blue Organic Light Emitting Diodes (OLEDs), Dyes and Pigments, in Press, Accepted Manuscript, Available online Mar. 10, 2011, ISSN 0143-7208, DOI: 10.1016/j.dyepig.201.*

(Continued)

*Primary Examiner* — Benjamin Sandvik
*Assistant Examiner* — Joseph Schoenholtz
(74) *Attorney, Agent, or Firm* — Husch Blackwell LLP

(57) ABSTRACT

An anthracene derivative represented by general formula (1) is provided. In the formula, $Ar^1$, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms, and $R^1$ to $R^8$ independently represent hydrogen or an alkyl group having 1 to 4 carbon atoms. $Ar^1$ to $Ar^6$ may independently have a substituent. When $Ar^1$ to $Ar^6$ independently have two or more substituents, the substituents may be bonded to each other to form a ring. When a carbon atom of $Ar^1$ to $Ar^6$ has two substituents, the substituents may be bonded to each other to form a spiro ring.

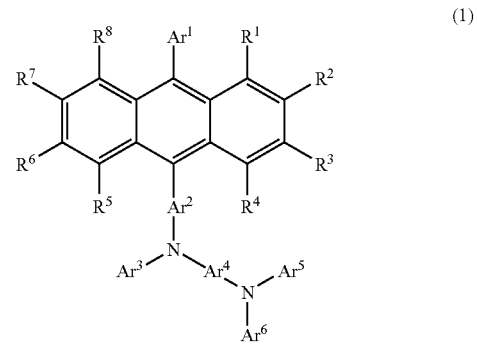

(1)

16 Claims, 47 Drawing Sheets

U.S. PATENT DOCUMENTS

| | | | |
|---|---|---|---|
| 7,541,099 B2* | 6/2009 | Yamagata et al. | 428/690 |
| 7,646,010 B2* | 1/2010 | Kawakami et al. | 257/40 |
| 7,914,911 B2 | 3/2011 | Yamagata et al. | |
| 2002/0037429 A1* | 3/2002 | Sato et al. | 428/690 |
| 2003/0143430 A1* | 7/2003 | Kawamura et al. | 428/690 |
| 2007/0049778 A1* | 3/2007 | Nomura et al. | 585/26 |
| 2007/0087222 A1* | 4/2007 | Kim et al. | 428/690 |
| 2008/0206447 A1* | 8/2008 | Inoue et al. | 427/64 |
| 2008/0241591 A1* | 10/2008 | Kawamura et al. | 428/690 |
| 2008/0286445 A1 | 11/2008 | Suzuki et al. | |
| 2009/0134781 A1* | 5/2009 | Jang et al. | 313/504 |
| 2009/0267498 A1 | 10/2009 | Kawakami et al. | |

OTHER PUBLICATIONS

Wen, S.-W., M.-T. Lee, and C.H. Chen. "Recent Development of Blue Fluorescent OLED Materials and Devices." Journal of Display Technology 1.1 (2005): 90-99.*

Tao, S., S. Xu, and X. Zhang. "Efficient Blue Organic Light-emitting Devices Based on Novel Anthracene Derivatives with Pronounced Thermal Stability and Excellent Film-forming Property." Chemical Physics Letters 429.4-6 (2006): 622-27. Print.*

Huang, Tai-Hsiang, Jiann T. Lin, Yu-Tai Tao, and Chang-Hao Chuen. "Benzo[]aceanthrylene Derivatives for Red-Emitting Electroluminescent Materials." Chemistry of Materials 15.25 (2003): 4854-862. Print.*

Yang, Wen Jun, Dae Young Kim, Mi-Yun Jeong, Hwan Myung Kim, Yun Kyoung Lee, Xingzhong Fang, Seung-Joon Jeon, and Bong Rae Cho. "Two-Photon Absorption Properties of 2,6-Bis-(styryl)anthracene Derivatives: Effects of Donor-Acceptor Substituents and the π Center." Chemistry—A European Journal 11.14 (2005): 4191-198. Print.*

Kim, Y.-H., H.-C. Jeong, S.-H. Kim, K. Yang, and S.-K. Kwon. "High-Purity-Blue and High-Efficiency Electroluminescent Devices Based on Anthracene." Advanced Functional Materials 15.11 (2005): 1799-805. Print.*

Shi, J. et al, "Anthracene Derivatives for Stable Blue-Emitting Organic Electroluminescence Devices," Applied Physics Letters, vol. 80, No. 17, Apr. 29, 2002, pp. 3201-3203.

* cited by examiner

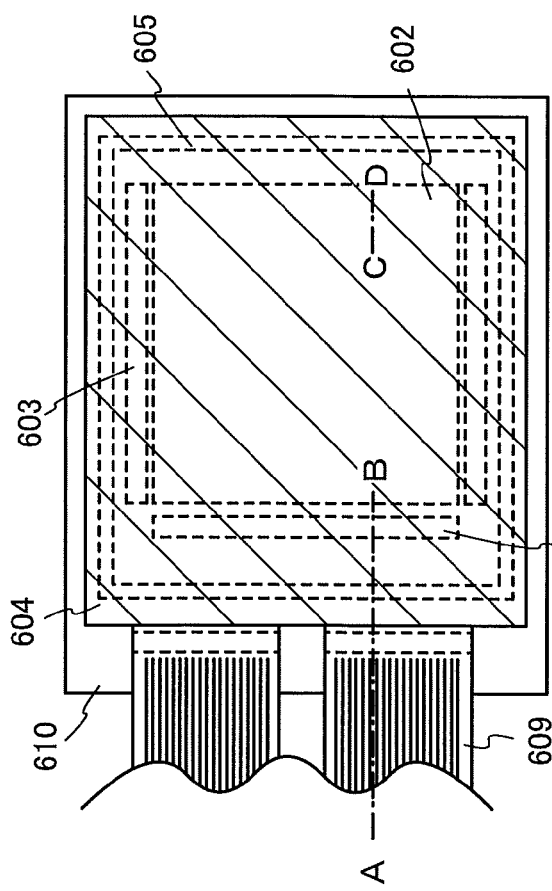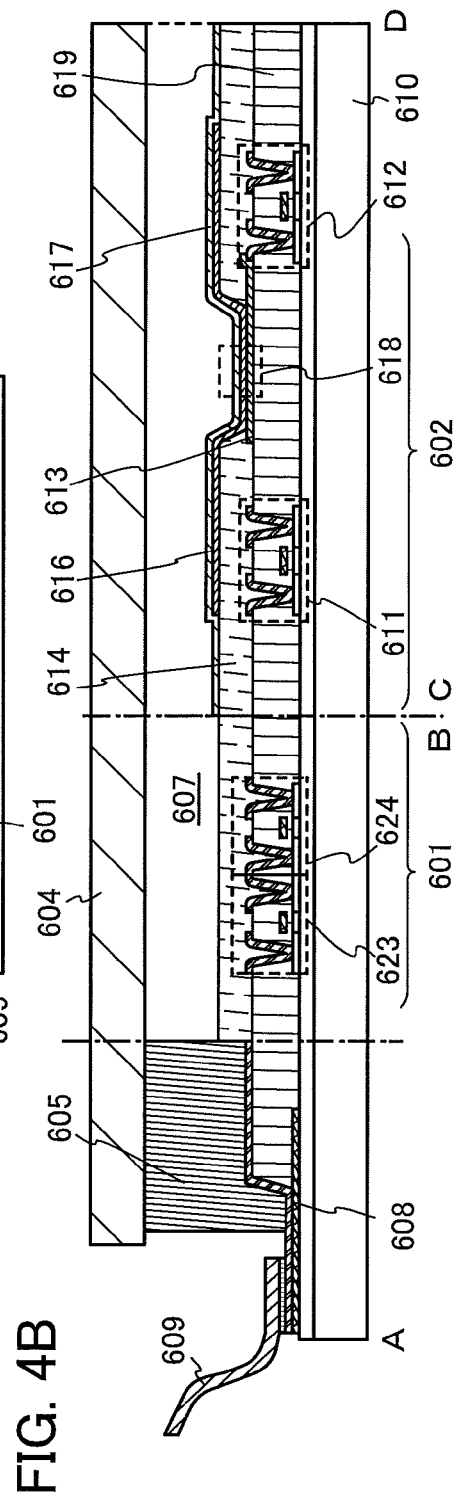
FIG. 4A
FIG. 4B 2001
2002

2011
2012

ANTHRACENE DERIVATIVE, MATERIAL FOR LIGHT-EMITTING ELEMENT, LIGHT-EMITTING ELEMENT, LIGHT-EMITTING DEVICE, AND ELECTRONIC APPLIANCE

BACKGROUND OF THE INVENTION

1. Field of the Invention

The present invention relates to an anthracene derivative. Further, the present invention relates to a light-emitting element material, a light-emitting element, and an electronic appliance using the anthracene derivative.

2. Description of the Related Art

A light-emitting element using a luminescent material has features of thinness and lightweight, high response speed, low direct-current voltage drive and the like, and is expected to be applied to a next-generation flat panel display. Further, a light-emitting device in which light-emitting elements are arranged in a matrix is said to have superiority in wide viewing angle and high visibility as compared with conventional liquid crystal display devices.

A light-emitting element is said to have the following light-emission mechanism: voltage is applied between a pair of electrodes with a light-emitting layer interposed therebetween, electrons injected from a cathode and holes injected from an anode are recombined in a light-emission center of the light-emitting layer to form a molecular exciton, and then light is emitted when the molecular exciton returns to a ground state by releasing energy. An excited singlet state and an excited triplet state are known as an excited state, and it is considered that light can be emitted through either state.

An emission wavelength of a light-emitting element is determined by energy difference between a ground state and an excited state, that is, a band gap, of a light-emitting molecule included in the light-emitting element. Therefore, various emission colors can be obtained by devising structures of the light-emitting molecules. A full-color light-emitting device can be manufactured by manufacturing a light-emitting device using light-emitting elements capable of emitting light of the three primary colors of light, red, blue, and green.

In order to manufacture a full-color light-emitting device having excellent color reproducibility, red, green, and blue light-emitting elements each having high reliability and excellent color purity are required. As a result of development of materials in recent years, as for red and green light-emitting elements, high reliability and excellent color purity have been already achieved. As for a blue light-emitting element however, enough efficiency and color purity have not been achieved. For example, in Non-Patent Document 1, a blue light-emitting element with relatively high reliability is reported. For the light-emitting element, however, enough luminous efficiency and color are not realized.

[Non-Patent Document 1] J. Shi et al., Applied Physics Letters, Vol. 80, No. 17, pp. 3201-3203, 2002.

SUMMARY OF THE INVENTION

The present invention has been made in view of the above-described problem. It is an object of the present invention to provide an anthracene derivative exhibiting blue to green light emission. Further, it is another object to provide a light-emitting element having high efficiency and long lifetime by use of the anthracene derivative. Furthermore, it is another object to provide a light-emitting device and electronic appliance with high quality and high reliability having the light-emitting element.

An aspect of the present invention is an anthracene derivative represented by a general formula (1).

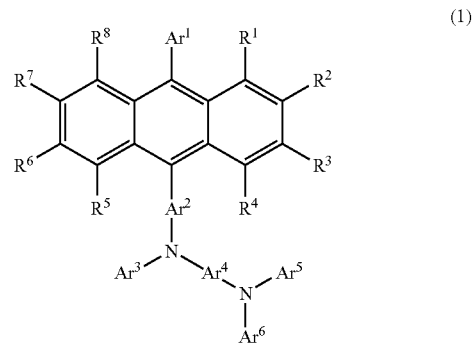

In the formula, $Ar^1$, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms, and $R^1$ to $R^8$ independently represent hydrogen or an alkyl group having 1 to 4 carbon atoms. Further, $Ar^1$ to $Ar^6$ may independently have a substituent. When $Ar^1$ to $Ar^6$ independently have two or more substituents, the substituents may be bonded to each other to form a ring. Further, with reference to $Ar^1$ to $Ar^6$, when a carbon atom has two substituents, the substituents may be bonded to each other to form a spiro ring.

Another aspect of the present invention is an anthracene derivative represented by a general formula (2).

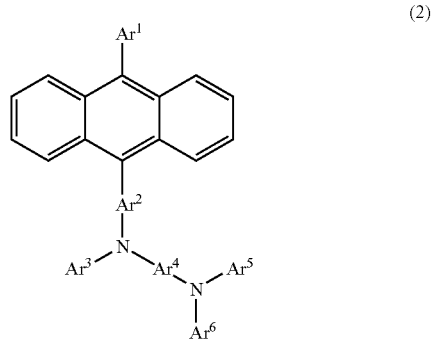

In the formula, $Ar^1$, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms. Further, $Ar^1$ to $Ar^6$ may independently have a substituent. When $Ar^1$ to $Ar^6$ independently have two or more substituents, the substituents may be bonded to each other to form a ring. Furthermore, with reference to $Ar^1$ to $Ar^6$, when a carbon atom has two substituents, the substituents may be bonded to each other to form a spiro ring.

Another aspect of the present invention is an anthracene derivative represented by a general formula (3).

(3)

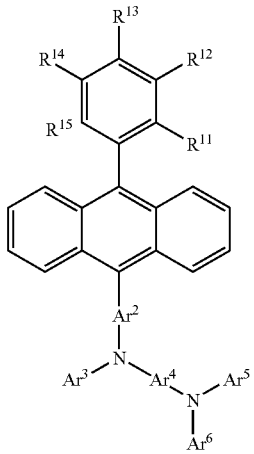

In the formula, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms, $R^{11}$ to $R^{15}$ independently represent hydrogen, an aryl group having 6 to 13 carbon atoms, an alkyl group having 1 to 4 carbon atoms, or a haloalkyl group having a carbon atom. Further, $Ar^2$ to $Ar^6$ may independently have a substituent. When $Ar^2$ to $Ar^6$ have two or more substituents, the substituents may be bonded to each other to form a ring. Furthermore, with reference to $Ar^2$ to $Ar^6$, when a carbon atom has two substituents, the substituents may be bonded to each other to form a spiro ring.

Another aspect of the present invention is an anthracene derivative represented by a general formula (4).

(3)

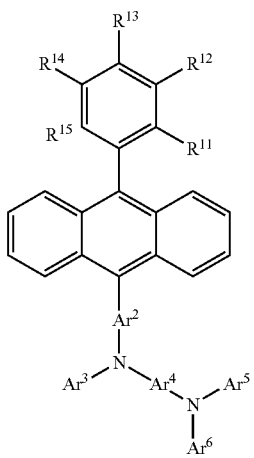

In the formula, $Ar^3$ represents an aryl group having 6 to 13 carbon atoms, $Ar^2$ and $Ar^4$ independently represent an arylene group having 6 to 13 carbon atoms, and $R^{11}$ to $R^{15}$ and $R^{21}$ to $R^{30}$ independently represent hydrogen, an aryl group having 6 to 13 carbon atoms, an alkyl group having 1 to 4 carbon atoms, or a haloalkyl group having a carbon atom. Further, $Ar^2$, $Ar^3$, and $Ar^4$ may independently have a substituent. When $Ar^2$, $Ar^3$, and $Ar^4$ independently have two or more substituents, the substituents may be bonded to each other to form a ring. Further, with reference to $Ar^2$, $Ar^3$, and $Ar^4$, when a carbon atom has two substituents, the substituents may be bonded to each other to form a spiro ring.

Another aspect of the present invention is an anthracene derivative represented by a general formula (5).

(5)

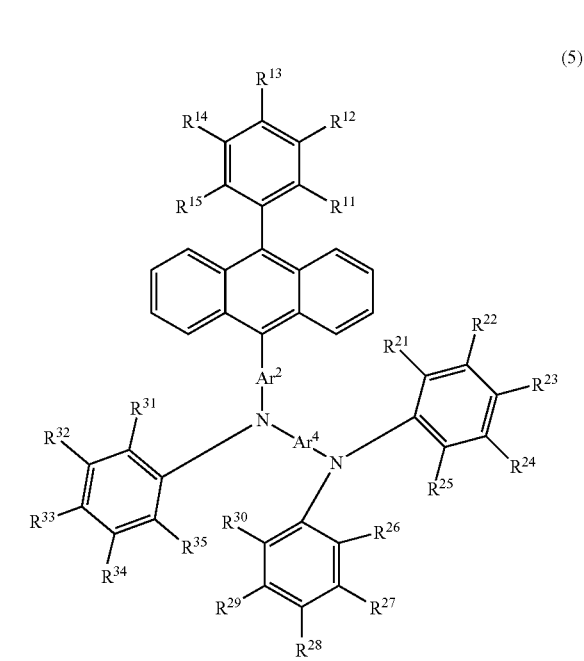

In the formula, $Ar^2$ and $Ar^4$ independently represent an arylene group having 6 to 13 carbon atoms, $R^{11}$ to $R^{15}$ and $R^{21}$ to $R^{35}$ independently represent hydrogen, an aryl group having 6 to 13 carbon atoms, an alkyl group having 1 to 4 carbon atoms, or a haloalkyl group having a carbon atom. Further, $Ar^2$ and $Ar^4$ may independently have a substituent. When $Ar^2$ and $Ar^4$ independently have two or more substituents, the substituents may be bonded to each other to form a ring. Furthermore, with reference to $Ar^2$ and $Ar^4$, when a carbon atom has two substituents, the substituents may be bonded to each other to form a spiro ring.

Another aspect of the present invention is an anthracene derivative represented by a general formula (6).

(6)

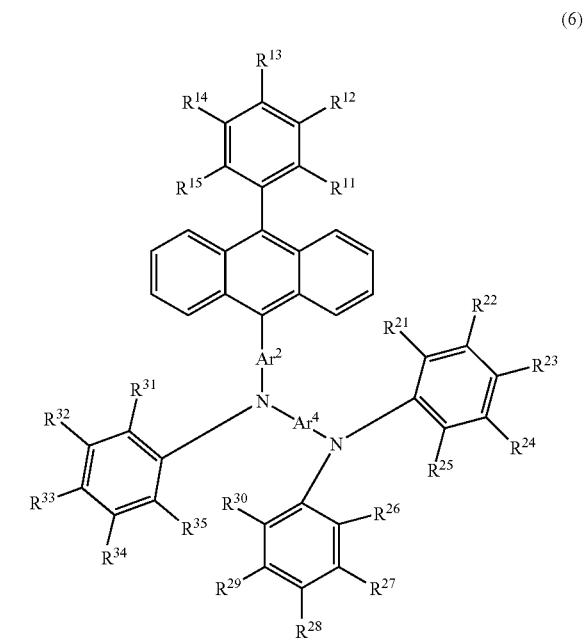

In the formula, $Ar^2$ and $Ar^4$ independently represent a phenylene group or a biphenyl-diyl group, $R^{11}$ to $R^{15}$ and $R^{21}$ to $R^{35}$ independently represent hydrogen, an aryl group having 6 to 13 carbon atoms, an alkyl group having 1 to 4 carbon atoms, or a haloalkyl group having a carbon atom.

Another aspect of the present invention is an anthracene derivative represented by a structural formula (101).

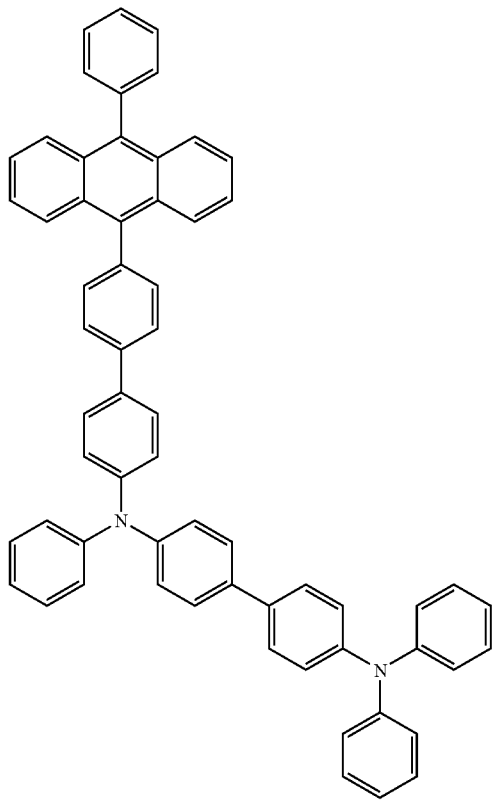

(101)

Another aspect of the present invention is an anthracene derivative represented by a structural formula (201).

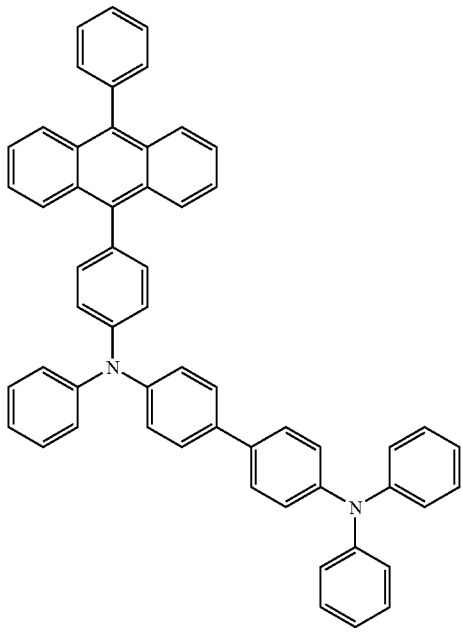

(201)

Another aspect of the present invention is an anthracene derivative represented by a structural formula (301).

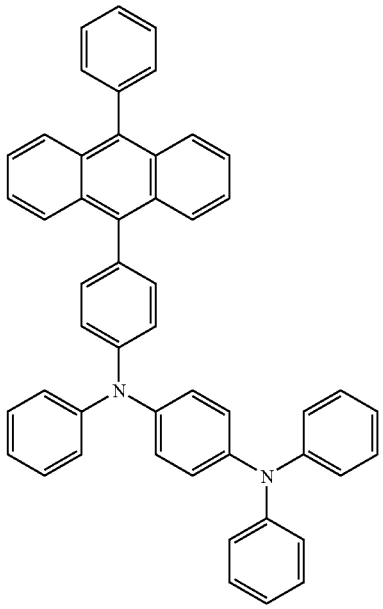

(301)

Another aspect of the present invention is an anthracene derivative represented by a structural formula (401).

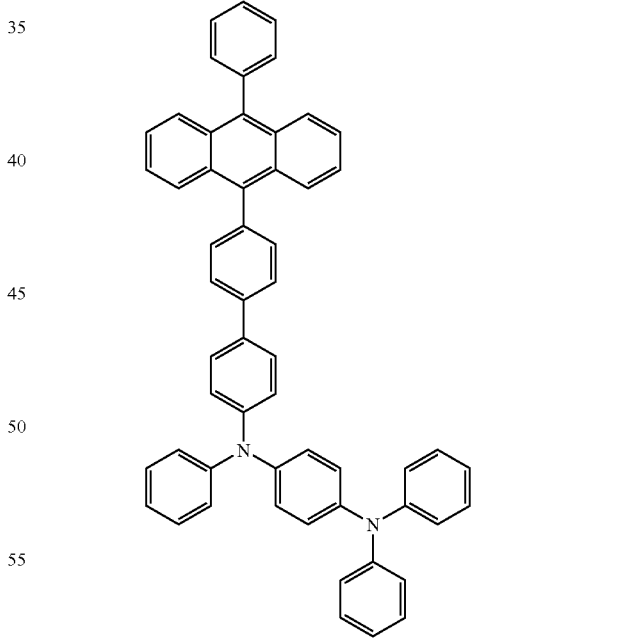

(401)

Another aspect of the present invention is a light-emitting element using the foregoing anthracene derivative. Specifically, the light-emitting element includes the anthracene derivative between a pair of electrodes.

Another aspect of the present invention is a light-emitting element having a light-emitting layer between a pair of electrodes, in which the light-emitting layer includes the above-mentioned anthracene derivative.

Another aspect of the present invention is a light-emitting element having the foregoing anthracene derivative as an emission center material in the light-emitting layer.

A light-emitting device of the present invention has a light-emitting element which includes a layer including a light-emitting substance between a pair of electrodes and in which the layer including a light-emitting substance includes any of the foregoing anthracene derivatives. The light-emitting device of the present invention also has means for controlling light emission (a power source, a switch or the like) of the light-emitting element. Note that the light-emitting device in this specification includes an image display device, a light-emitting device, and a light source (including a lighting apparatus). Further, the light-emitting device also includes all types of modules, e.g., a module in which a connector such as an FPC (flexible printed circuit), a TAB (tape automated bonding) tape, or a TCP (tape carrier package) is attached to a panel, a module in which a printed wiring board is provided at an end of a TAB tape or a TCP, and a module in which an IC (integrated circuit) is mounted over a substrate over which the light-emitting element is formed by a COG (chip on glass) method.

Further, an electronic appliance using the light-emitting element of the present invention in a display portion is also included in the scope of the invention. Accordingly, an electronic appliance of the present invention includes a display portion, in which the display portion is provided with the above-described light-emitting element and control means to control light emission of the light-emitting element.

An anthracene derivative of the present invention is a bipolar material that allows a hole and an electron to flow. In addition, an anthracene of the present invention has high electrochemical stability and high thermal stability.

An anthracene derivative of the present invention has an extremely large band gap and emits light having short wavelength; thus, blue to green light emission with high color purity can be obtained.

The anthracene derivative of the present invention is dispersed as a dopant material in a material having a larger band gap than the anthracene derivative of the present invention (host material); therefore, blue to green light emission with good color purity can be obtained from the anthracene derivative of the present invention.

An anthracene derivative of the present invention has an extremely large band gap. Therefore, in a light-emitting element using an anthracene derivative of the present invention as a host material, even with the use of a dopant material emitting light of a relatively short wavelength, particularly blue to green, light emission not from the anthracene derivative of the present invention but from the dopant material can be efficiently obtained.

Therefore, by use of an anthracene derivative of the present invention for a light-emitting element, a light-emitting element with high efficiency, high reliability, and a long lifetime can be obtained.

Further, by use of an anthracene derivative of the present invention, a light-emitting device and electronic appliance with high quality and high reliability can be obtained.

BRIEF DESCRIPTION OF THE DRAWINGS

FIGS. 4A and 4B illustrate a light-emitting device of the present invention;

DETAILED DESCRIPTION OF THE INVENTION

Figure 1A:
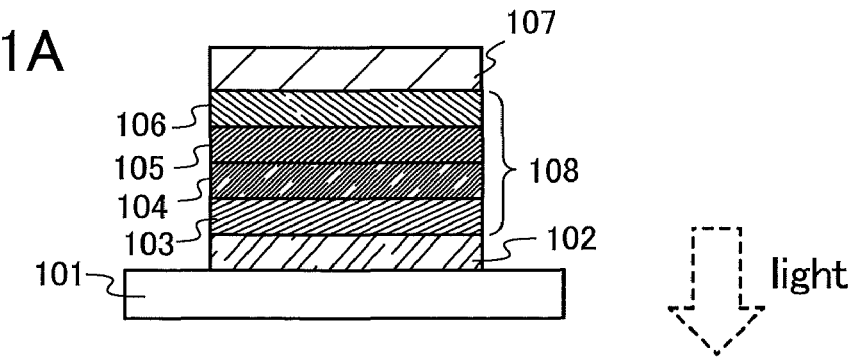
FIGS. 1A to 1C each illustrate a light-emitting element of the present invention.

Hereinafter, embodiments of the present invention will be described in detail with reference to the accompanying drawings. However, the present invention is not limited to the following description, and various changes and modifications for the modes and details thereof will be apparent to those skilled in the art unless such changes and modifications depart from the spirit and scope of the invention. Therefore, the present invention should not be interpreted as being limited to what is described in the embodiments described below.

Embodiment 1

An Anthracene derivative of the present invention will be described in this embodiment.

An anthracene derivative of this embodiment is represented by the following general formula (1).

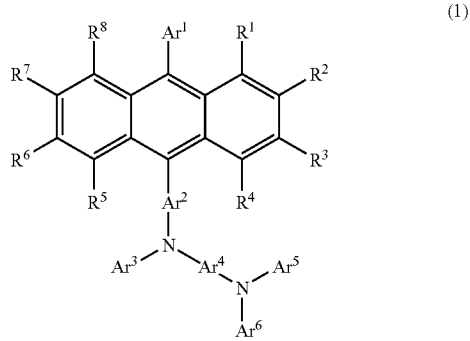

(1)

In the formula, $Ar^1$, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms, and $R^1$ to $R^8$ independently represent hydrogen or an alkyl group having 1 to 4 carbon atoms. Further, $Ar^1$ to $Ar^6$ may independently have a substituent. When $Ar^1$ to $Ar^6$ independently have two or more substituents, the substituents may be bonded to each other to form a ring. Furthermore, with reference to $Ar^1$ to $Ar^6$, when a carbon atom has two substituents, the substituents may be bonded to each other to form a spiro ring.

An anthracene derivative of this embodiment is represented by the following general formula (2).

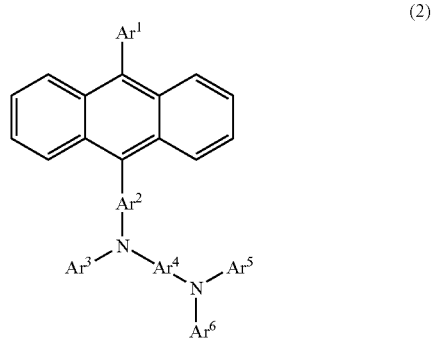

(2)

In the formula, $Ar^1$, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms. Further, $Ar^1$ to $Ar^6$ may independently have a substituent. When $Ar^1$ to $Ar^6$ independently have two or more substituents, the substituents may be bonded to each other to form a ring. Furthermore, with reference to $Ar^1$ to $Ar^6$, when a carbon atom has two substituents, the substituents may be bonded to each other to form a spiro ring.

An anthracene derivative of this embodiment is represented by the following general formula (3).

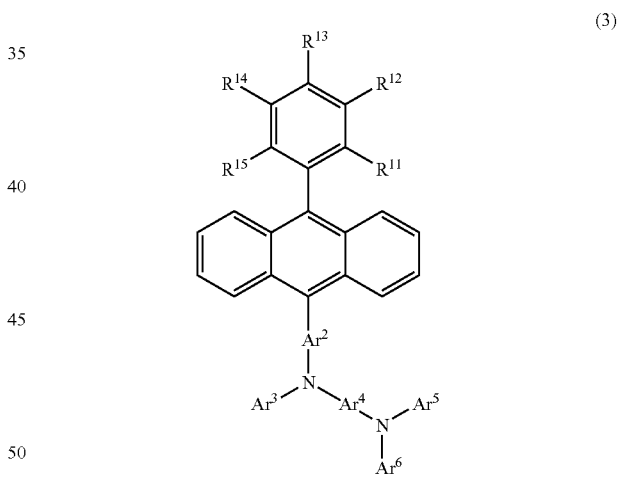

(3)

In the formula, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms, $R^{11}$ to $R^{15}$ independently represent hydrogen, an aryl group having 6 to 13 carbon atoms, an alkyl group having 1 to 4 carbon atoms, or a haloalkyl group having a carbon atom. Further, $Ar^2$ to $Ar^6$ may independently have a substituent. When $Ar^2$ to $Ar^6$ have two or more substituents, the substituents may be bonded to each other to form a ring. Furthermore, with reference to $Ar^2$ to $Ar^6$, when a carbon atom has two substituents, the substituents may be bonded to each other to form a spiro ring.

An anthracene derivative of this embodiment is represented by the following general formula (4).

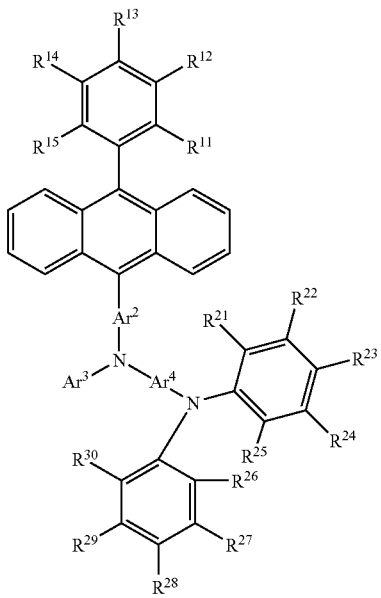

(4)

In the formula, $Ar^3$ represents an aryl group having 6 to 13 carbon atoms, $Ar^2$ and $Ar^4$ independently represent an arylene group having 6 to 13 carbon atoms, and $R^{11}$ to $R^{15}$ and $R^{21}$ to $R^{30}$ independently represent hydrogen, an aryl group having 6 to 13 carbon atoms, an alkyl group having 1 to 4 carbon atoms, or a haloalkyl group having a carbon atom. Further, $Ar^2$, $Ar^3$, and $Ar^4$ may independently have a substituent. When $Ar^2$, $Ar^3$, and $Ar^4$ independently have two or more substituents, the substituents may be bonded to each other to form a ring. Further, with reference to $Ar^2$, $Ar^3$, and $Ar^4$, when a carbon atom has two substituents, the substituents may be bonded to each other to form a spiro ring.

An anthracene derivative of this embodiment is represented by the following general formula (5).

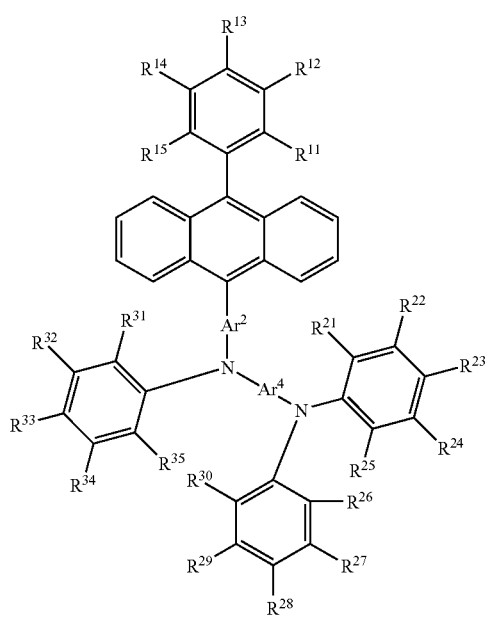

(5)

In the formula, $Ar^2$ and $Ar^4$ independently represent an arylene group having 6 to 13 carbon atoms, $R^{11}$ to $R^{15}$ and $R^{21}$ to $R^{35}$ independently represent hydrogen, an aryl group having 6 to 13 carbon atoms, an alkyl group having 1 to 4 carbon atoms, or a haloalkyl group having a carbon atom. Further, $Ar^2$ and $Ar^4$ may independently have a substituent. When $Ar^2$ and $Ar^4$ independently have two or more substituents, the substituents may be bonded to each other to form a ring. Furthermore, with reference to $Ar^2$ and $Ar^4$, when a carbon atom has two substituents, the substituents may be bonded to each other to form a spiro ring.

An anthracene derivative of this embodiment is represented by the following general formula (6).

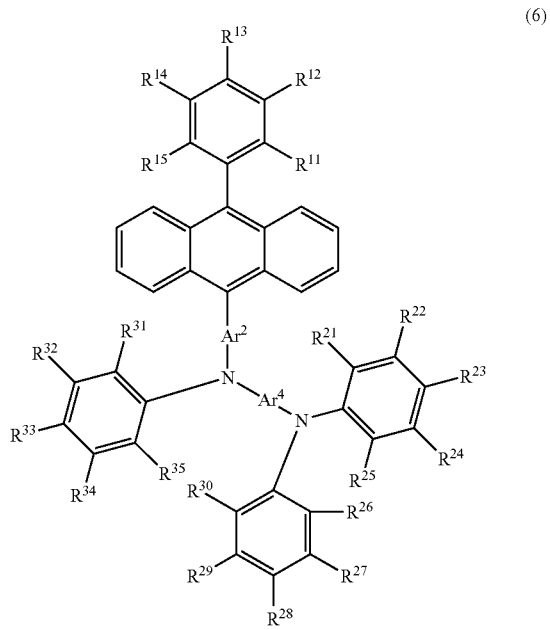

(6)

In the formula, $Ar^2$ and $Ar^4$ independently represent a phenylene group or a biphenyl-diyl group, $R^{11}$ to $R^{15}$ and $R^{21}$ to $R^{35}$ independently represent hydrogen, an aryl group having 6 to 13 carbon atoms, an alkyl group having 1 to 4 carbon atoms, or a haloalkyl group having a carbon atom.

Note that the carbon atoms of an aryl group or an arylene group described in this specification represent carbon atoms that form a ring of the main skeleton, and carbon atoms of a substituent bonded to the main skeleton are not included therein. As a substituent bonded to an aryl group or an arylene group, an alkyl group having 1 to 4 carbon atoms, an aryl group having 6 to 13 carbon atoms, or a haloalkyl group having a carbon atom are given. Specifically, a methyl group, an ethyl group, a propyl group, a butyl group, a phenyl group, a naphthyl group, a fluorenyl group, a trifluoromethyl group, and the like are given. Further, the aryl group or the arylene group may have one or more substituents. In the case where the aryl group or the arylene group has two substituents, the substituents may be bonded to each other to form a ring. For example, when the aryl group is a fluorenyl group, the carbon atom at the 9-position of a fluorine skeleton may have two phenyl groups, and the two phenyl groups may be further bound to each other to form a spiro ring structure.

In the general formulae (1) to (6), the aryl group or the arylene group having 6 to 13 carbon atoms may have a substituent. When the aryl group or the arylene group having 6 to 13 carbon atoms have a plurality of substituents, the substituents may be bonded to each other to form a ring. Further, when a carbon atom has two substituents, the substituents may be bonded to each other to form a spiro ring. For example, as specific examples of groups represented by $Ar^1$, $Ar^3$, $Ar^5$, or $Ar^6$, there are substituents represented by structural formulae (11-1) to (11-22).
(11-1)
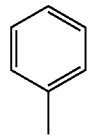
(11-2)
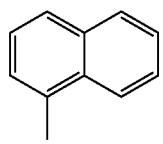
(11-3)
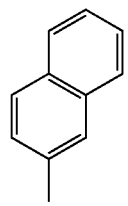
(11-4)
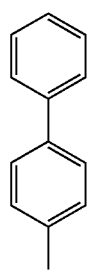
(11-5)
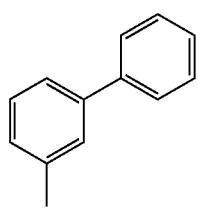
(11-6)
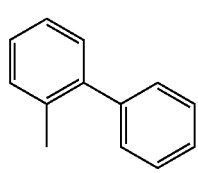
-continued
(11-7)
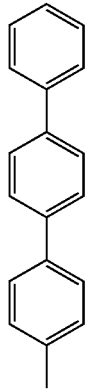
(11-8)
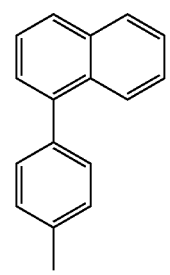
(11-9)
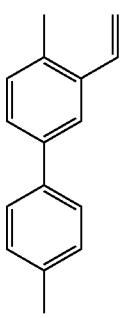
(11-10)
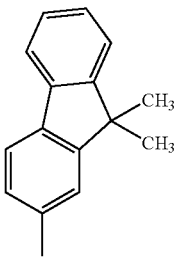
(11-11)
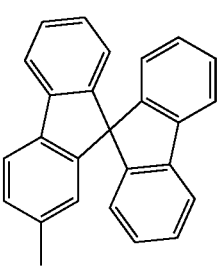

(11-12)
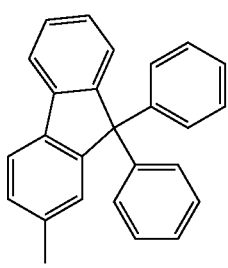
(11-13)
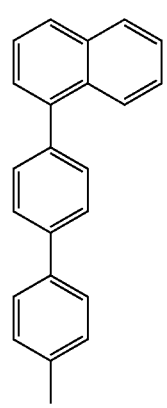
(11-14)
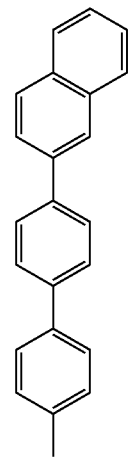
(11-15)
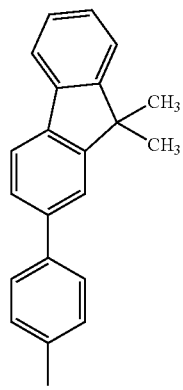
(11-16)
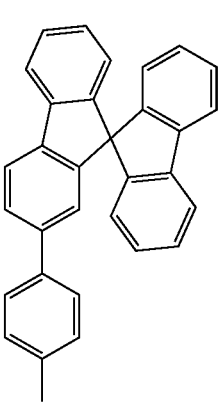
(11-17)
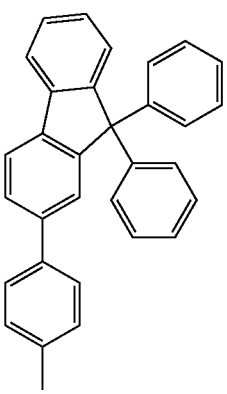
(11-18)
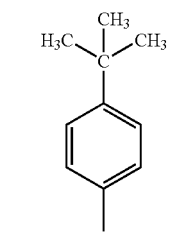
(11-19)
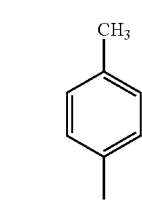
(11-20)
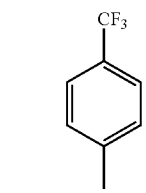
(11-21)
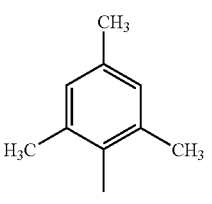

(11-22)
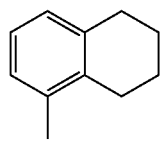
For example, as specific examples of groups shown with Ar² and Ar⁴, there are substituents represented by structural formulae (12-1) to (12-9).
(12-1)
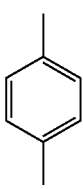
(12-2)
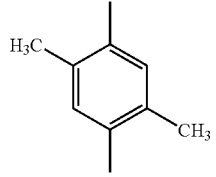
(12-3)
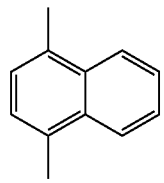
(12-4)
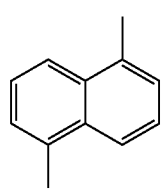
(12-5)
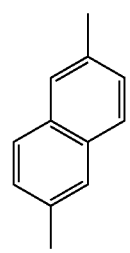
(12-6)
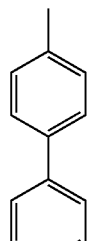
(12-7)
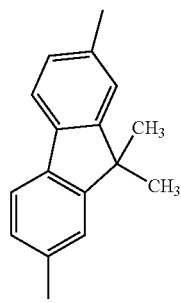
(12-8)
(12-9)
For example, as specific examples of groups represented by $R^{11}$ to $R^{13}$ and $R^{21}$ to $R^{35}$, there are substituents represented by structural formulae (13-1) to (13-19).
(13-1)
H |
(13-2)
CH₃ |
(13-3)
H₃C─CH₂ |
(13-4)
CH₃
H₂C─CH₂ |
(13-5)
H₃C─CH─CH₃ |

(13-6) 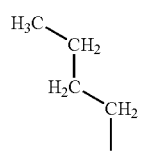

(13-7) 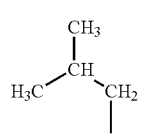

(13-8) 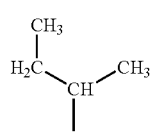

(13-9) 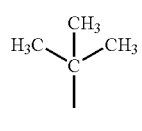

(13-10) 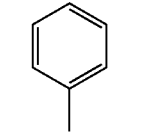

(13-11) 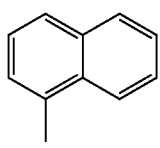

(13-12) 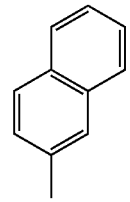

(13-13) 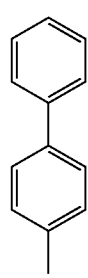

(13-14) 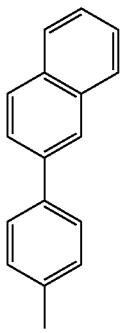

(13-15) 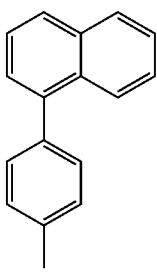

(13-16) 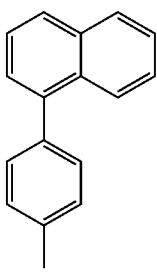

(13-17) 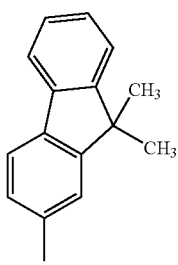

(13-18) 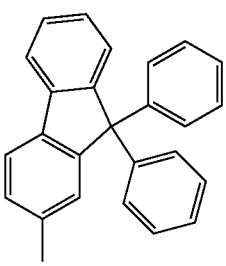

(13-19) 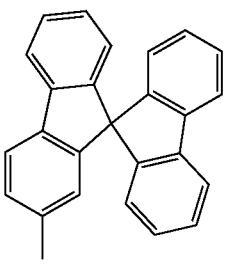

Further, in the anthracene derivatives represented by the general formulae (1) to (6), it is preferable that $Ar^1$, $Ar^3$, $Ar^5$, and $Ar^6$ are independently a phenyl group and that $Ar^2$ and $Ar^4$ are independently a phenylene group for easy synthesis and purification.

As the specific examples of the anthracene derivatives represented by general formulae (1) to (6), the anthracene derivatives represented by structural formulae (101), (201) to (242), (301) to (396), and (401) to (404) are given. However, the present invention is not limited to these examples.

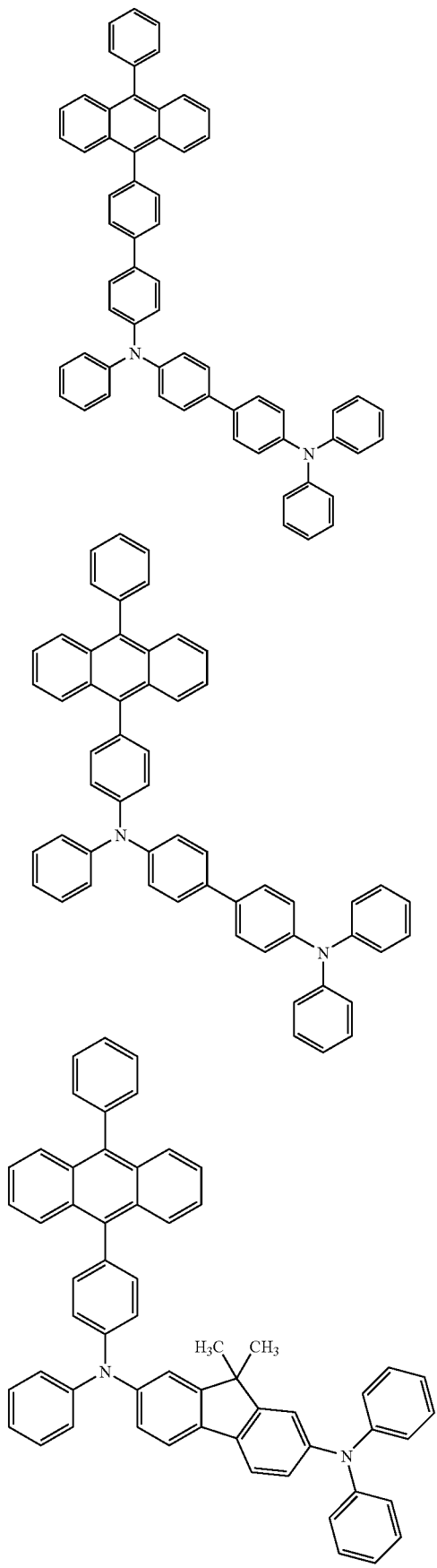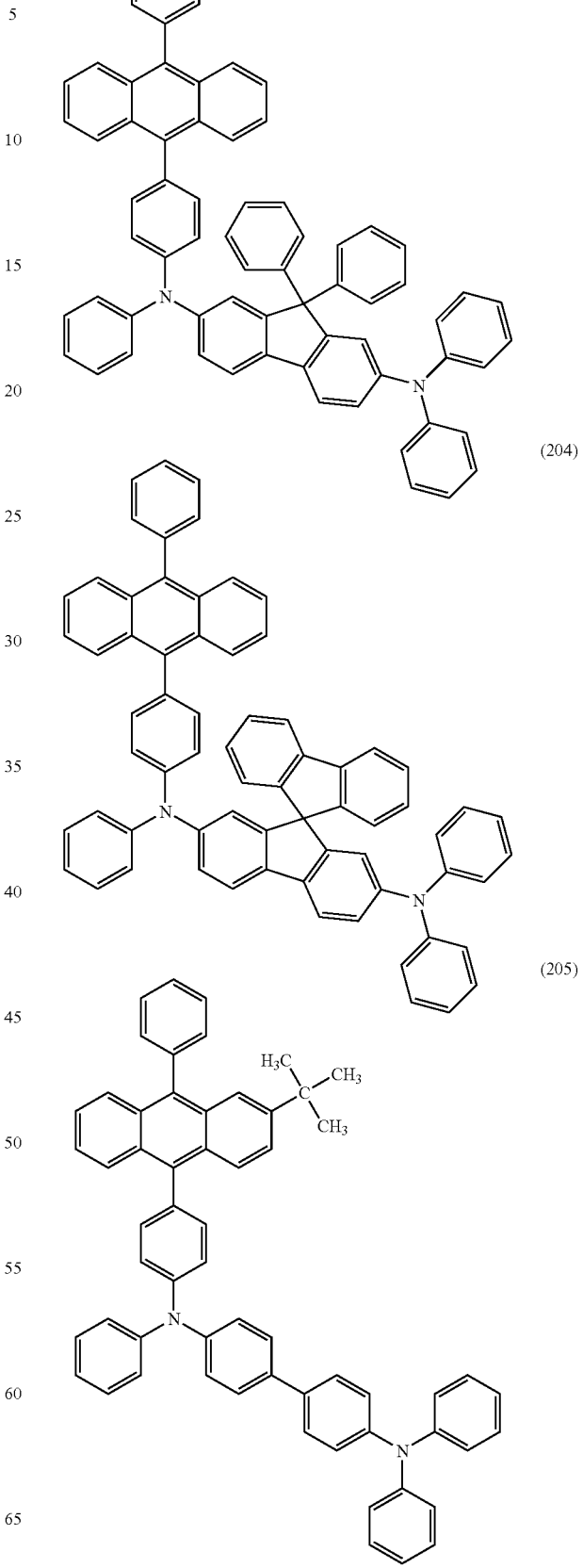

(206)
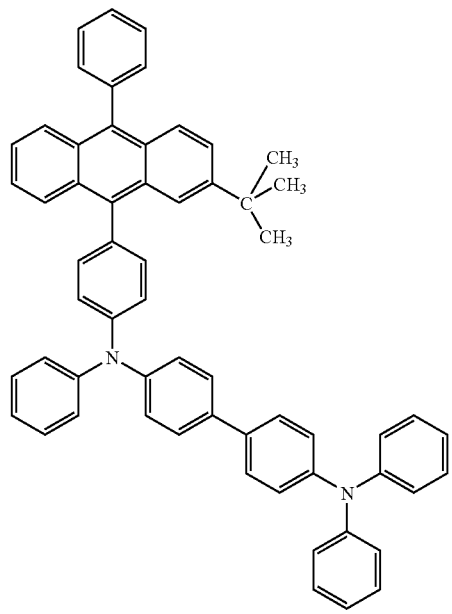
(208)
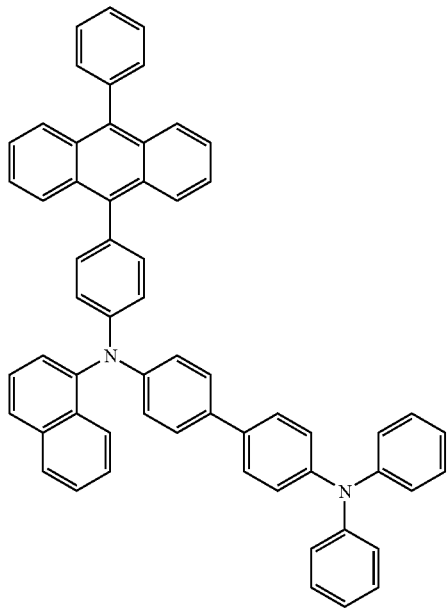
(207)
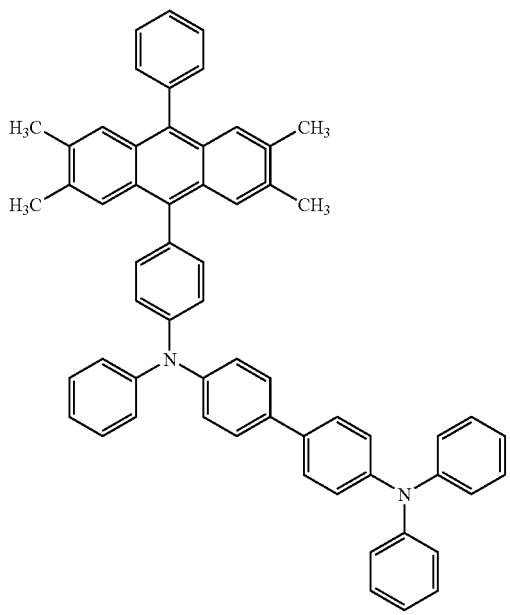
(209)
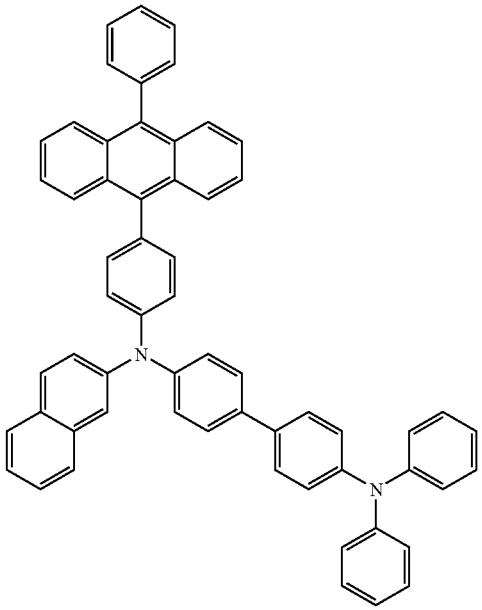

(210)
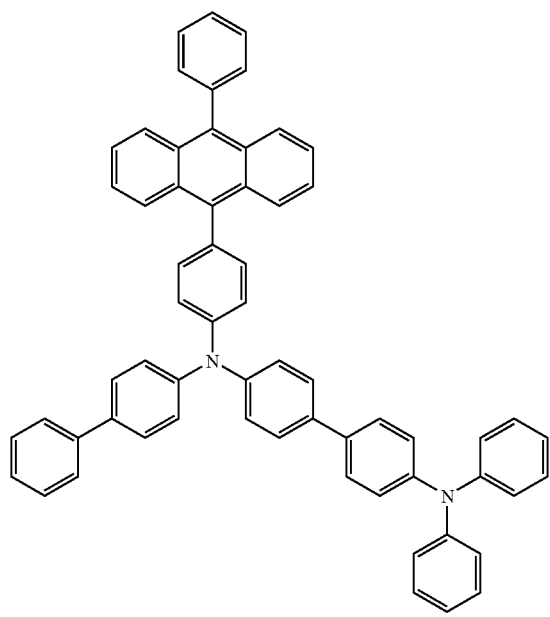
(212)
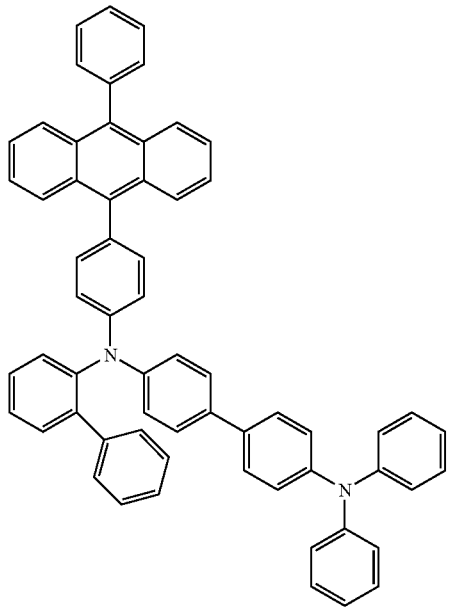
(211)
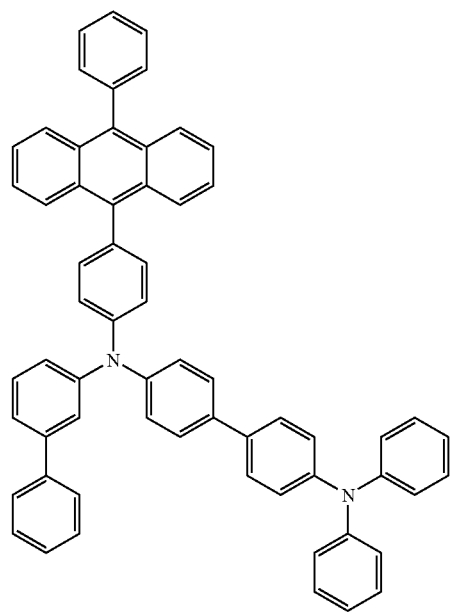
(213)
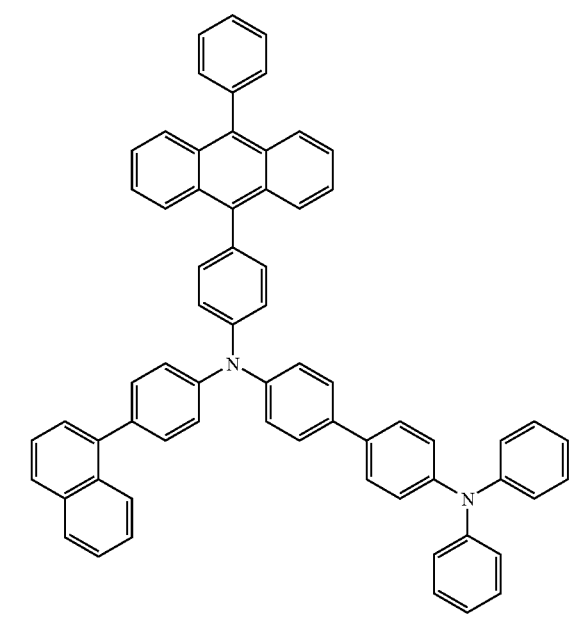

(214)
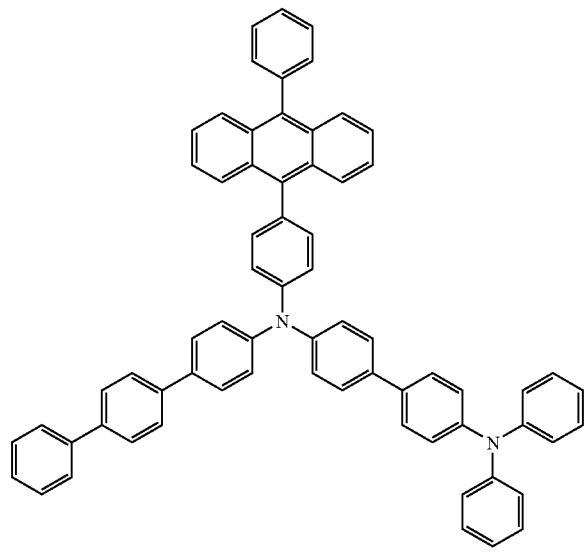
(216)
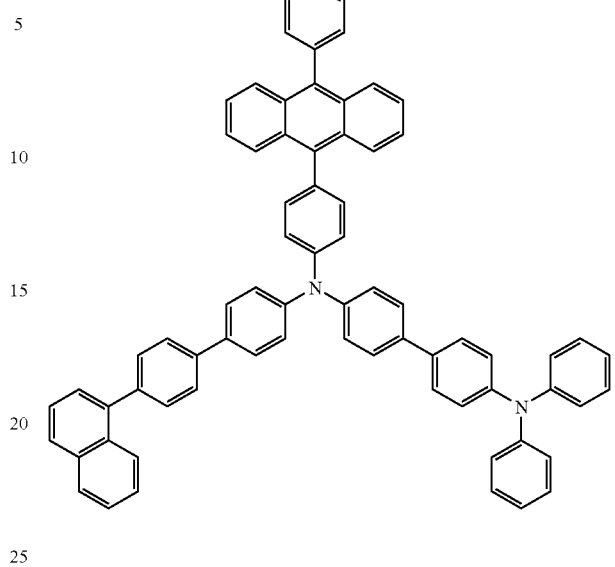
(215)
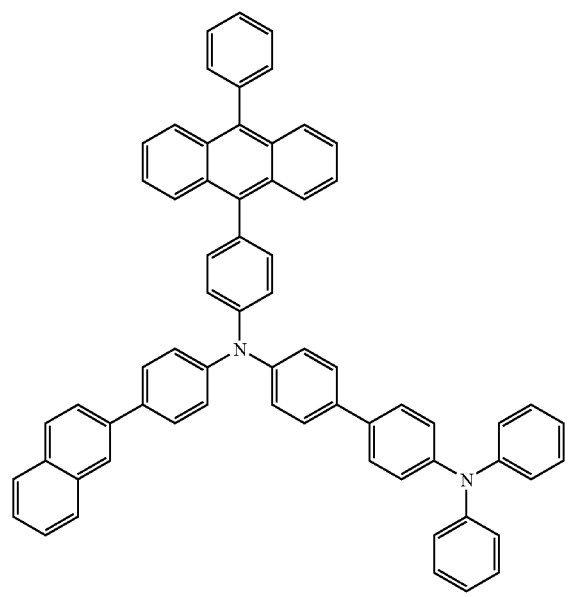
(217)
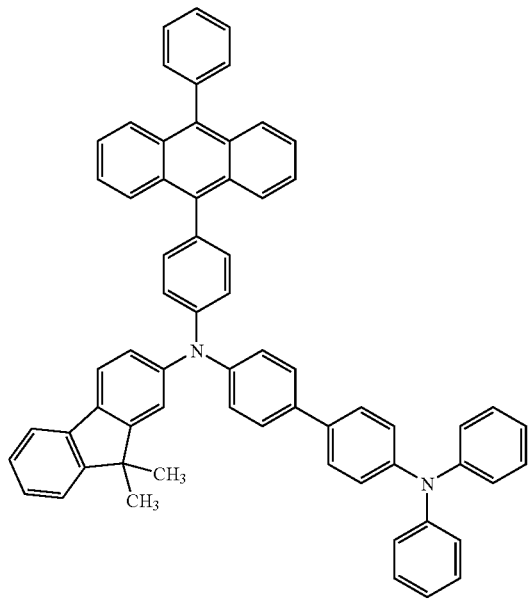

(218)
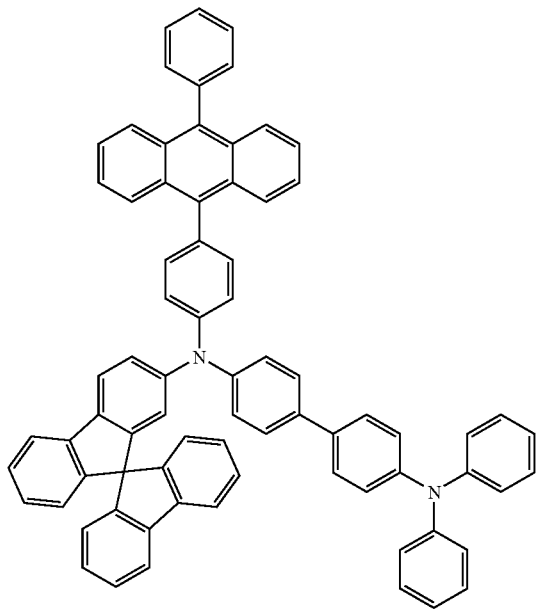
(220)
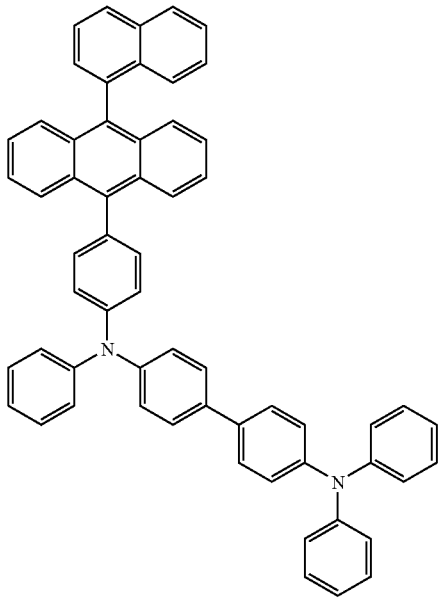
(219)
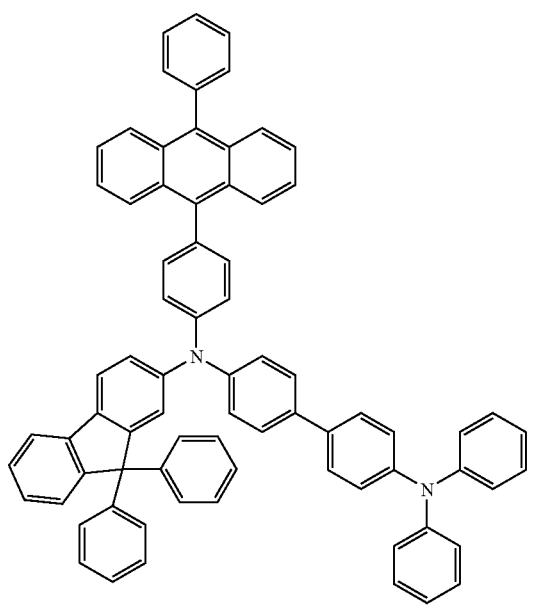
(221)
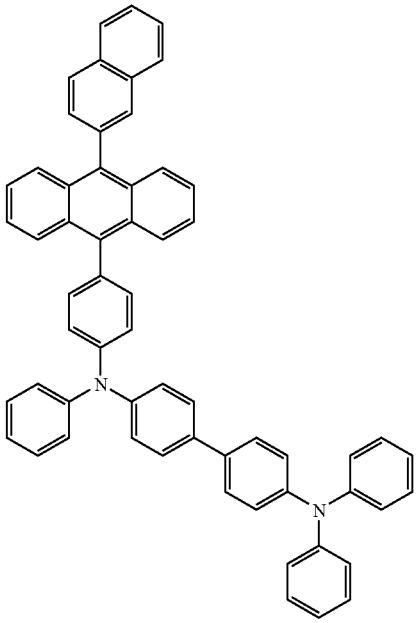

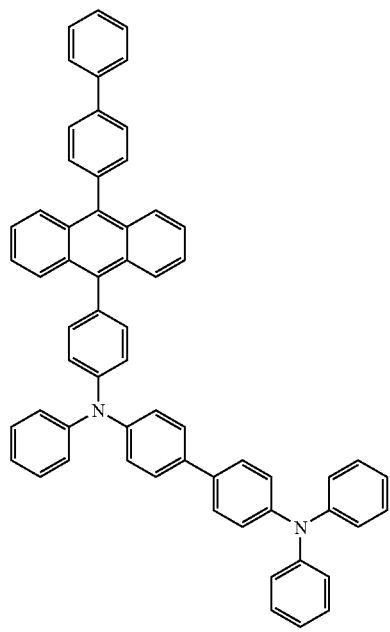
(222)
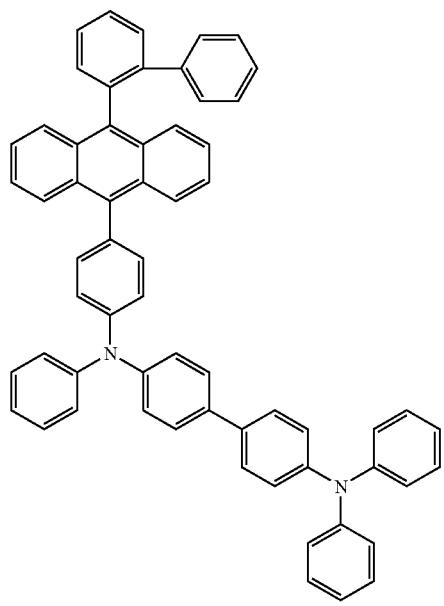
(224)
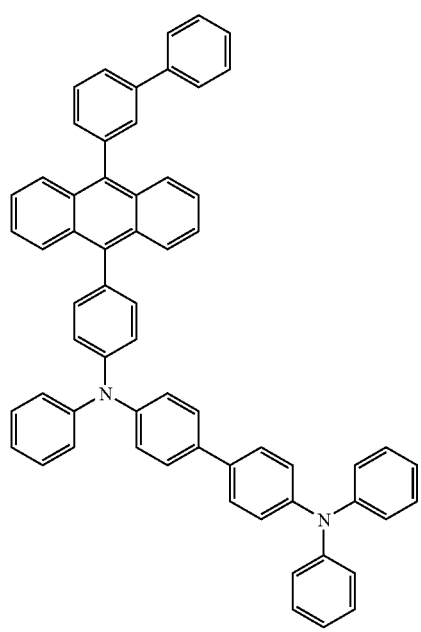
(223)
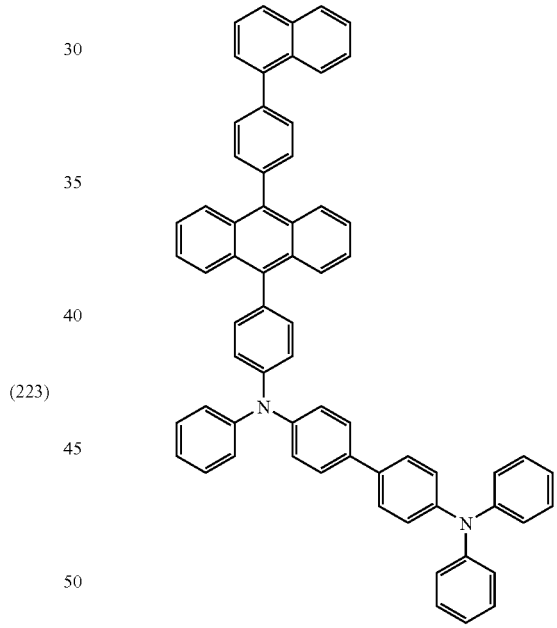
(225)
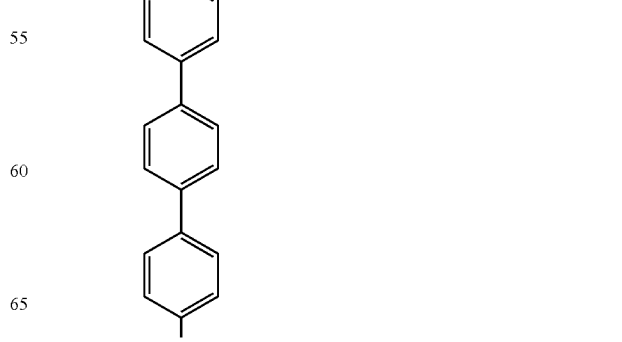
(226)

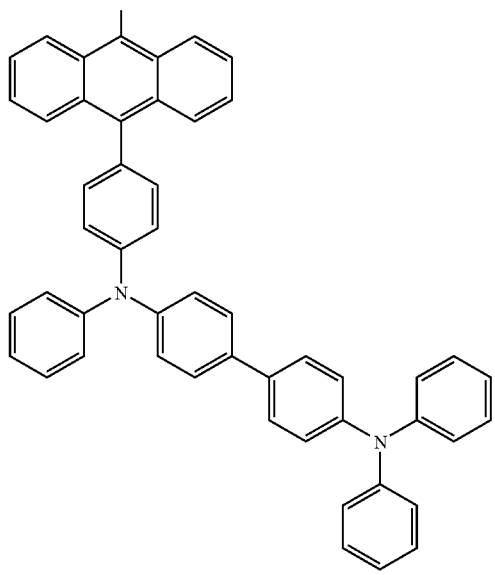
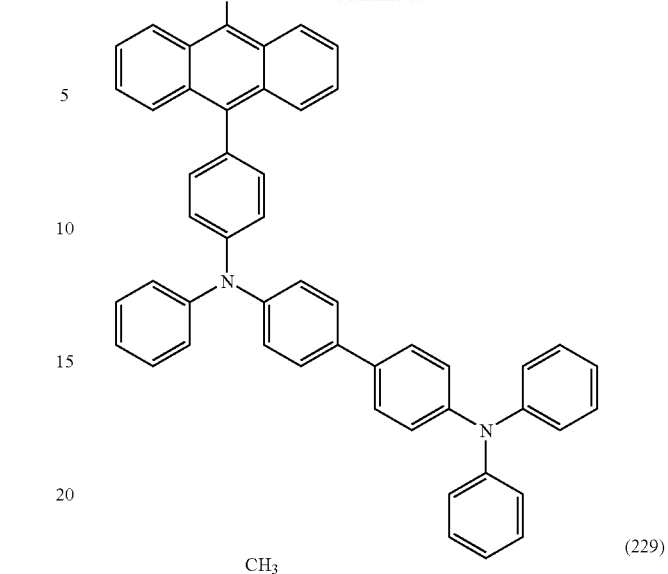
(227)
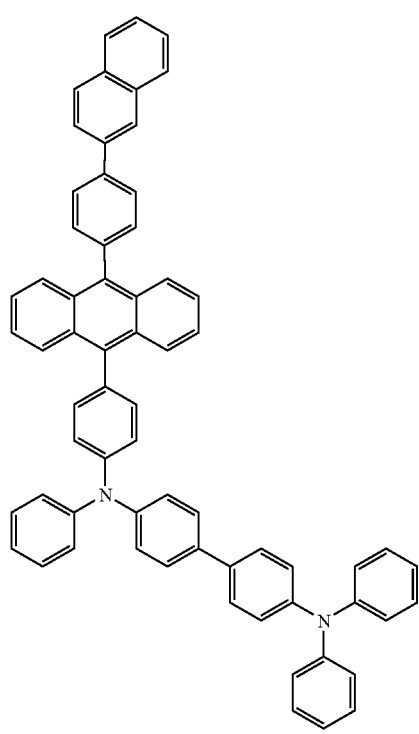
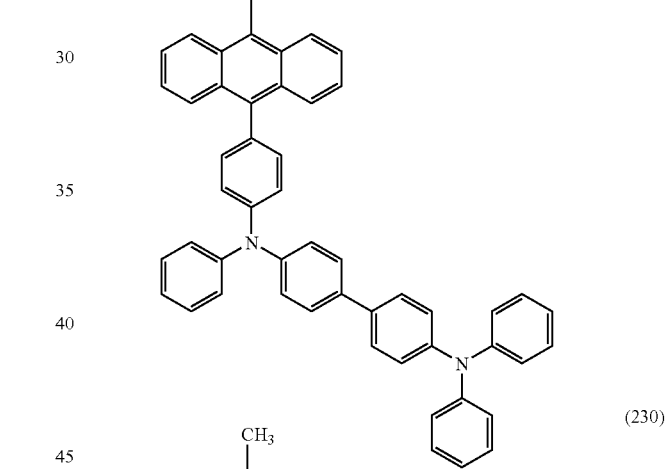
(229)
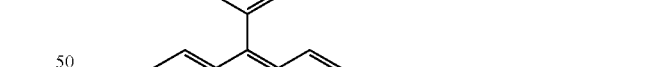
(230)
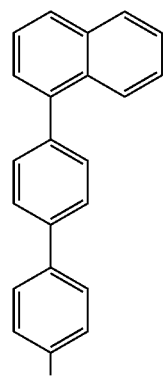
(228)

(231)
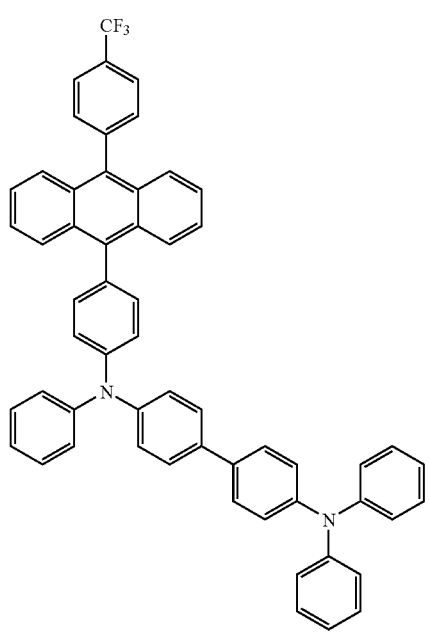
(233)
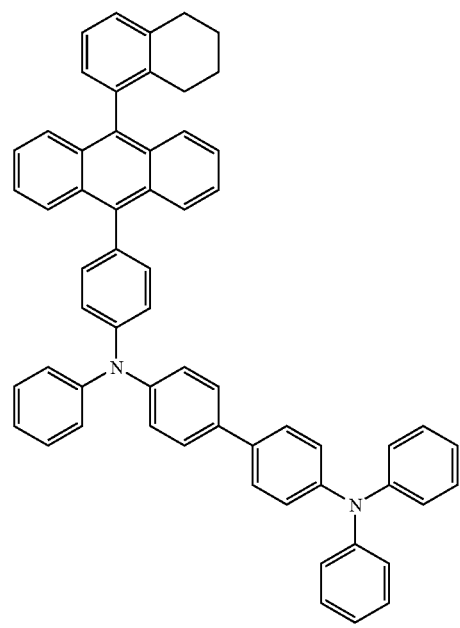
(232)
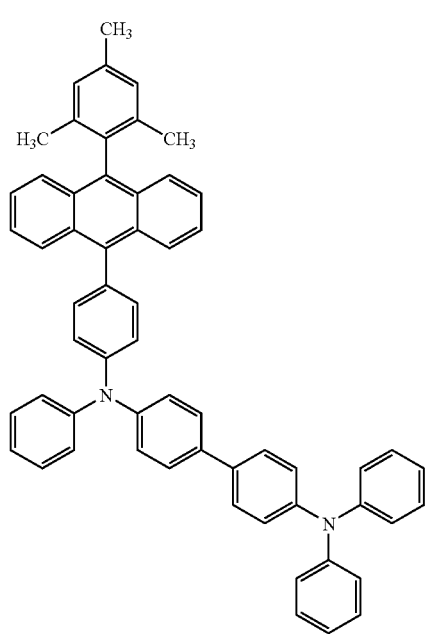
(234)
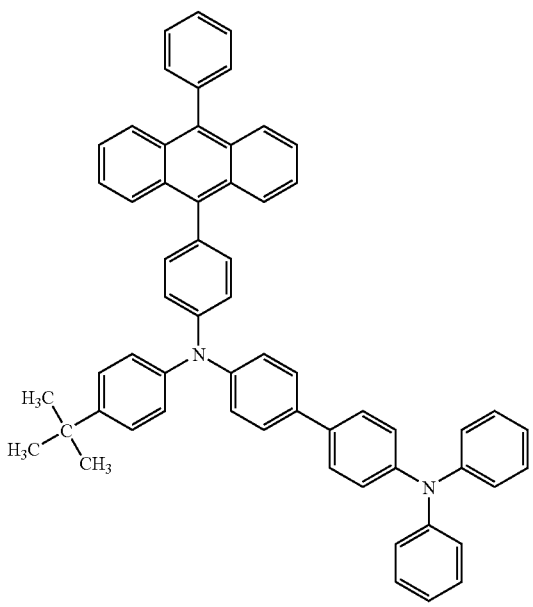

(235)
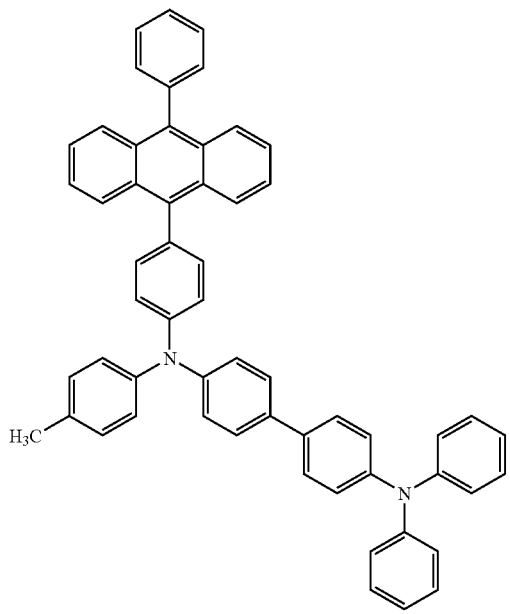
(236)
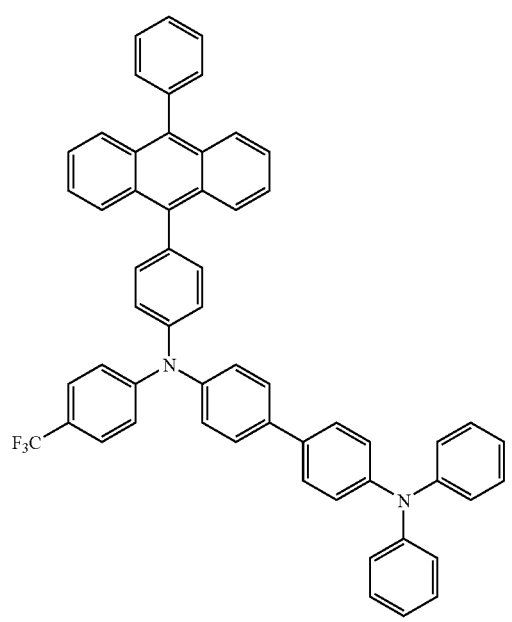
(237)
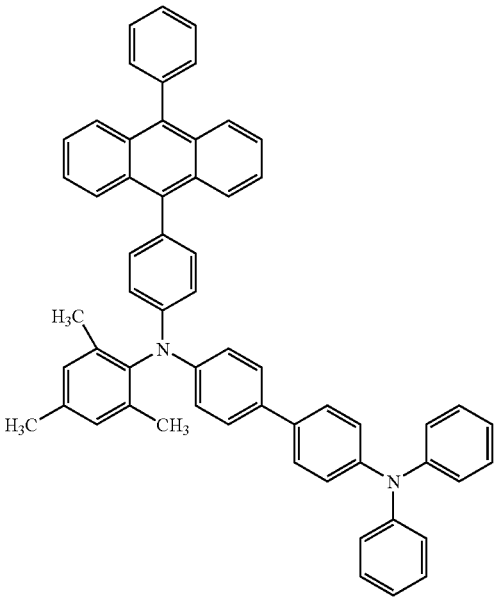
(238)
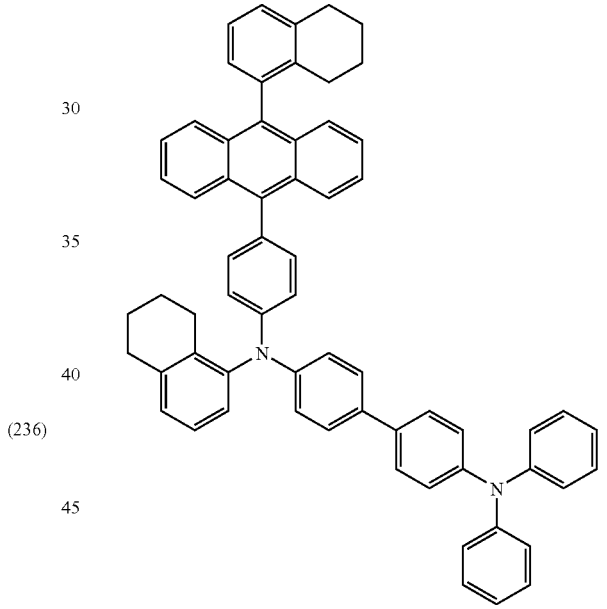
(239)
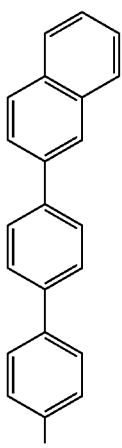

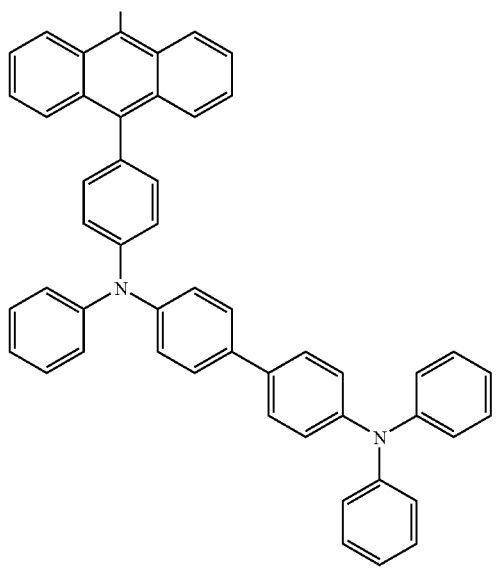
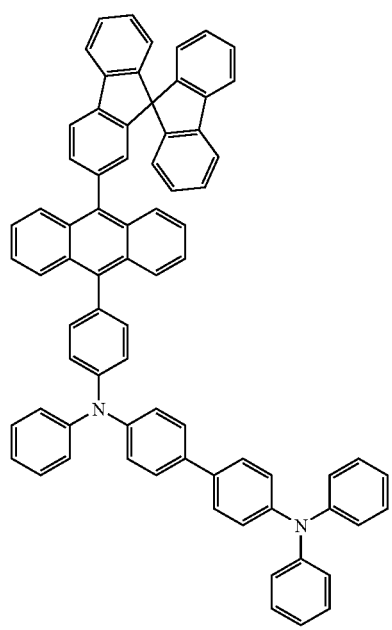
(241)
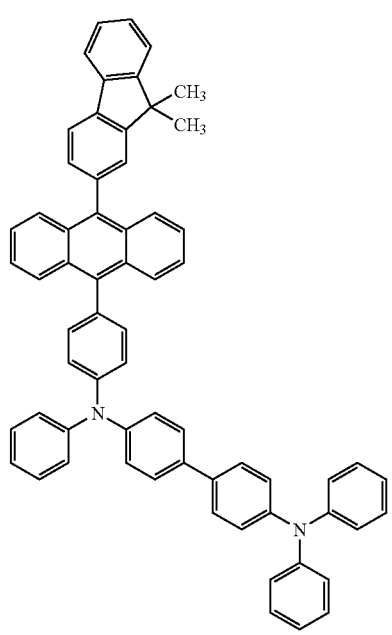
(240)
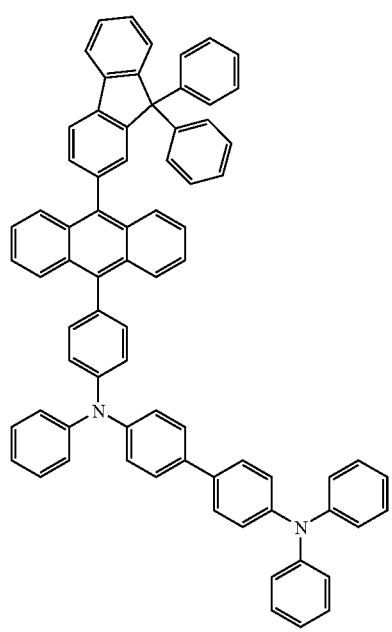
(242)

(301)
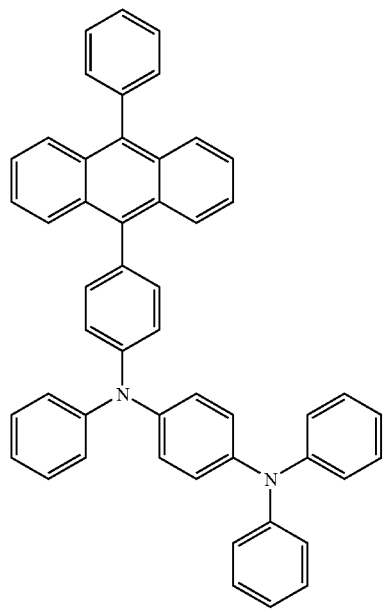
(302)
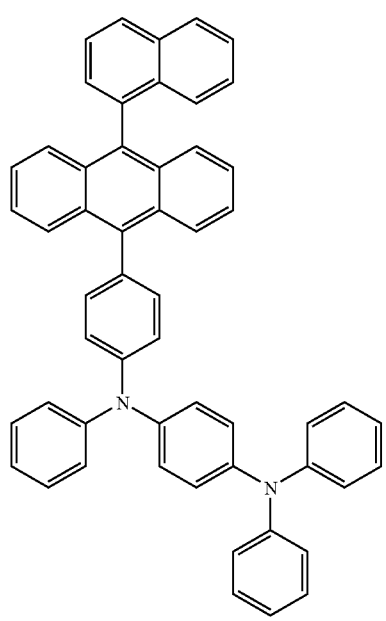
(303)
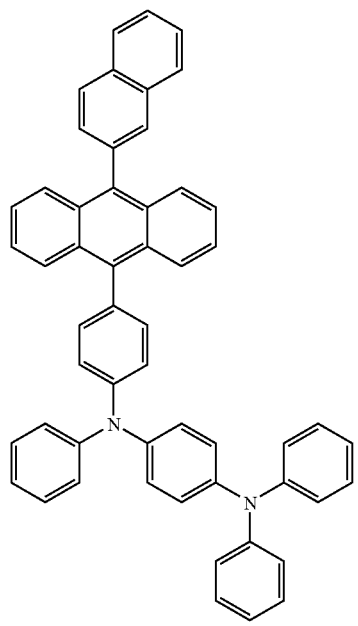
(304)
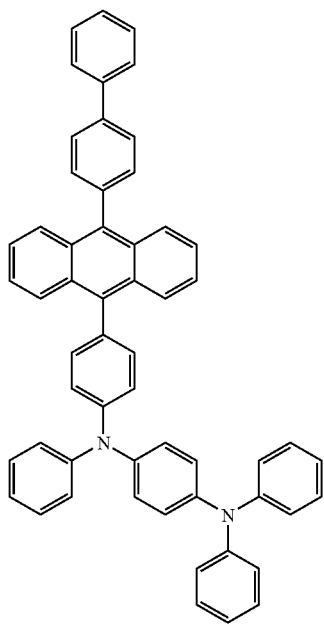

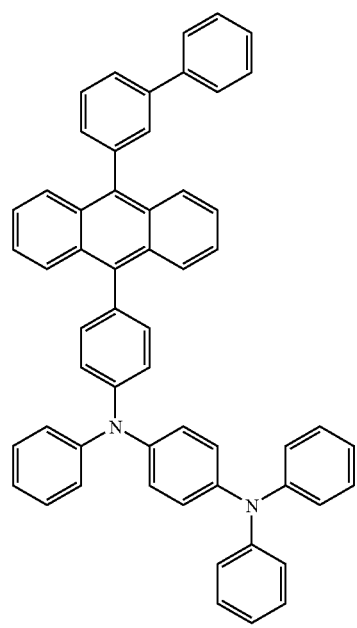
(305)
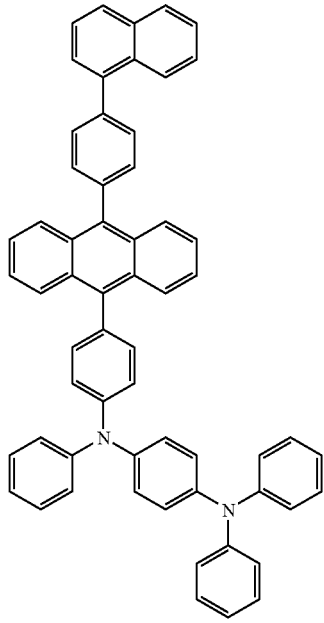
(307)
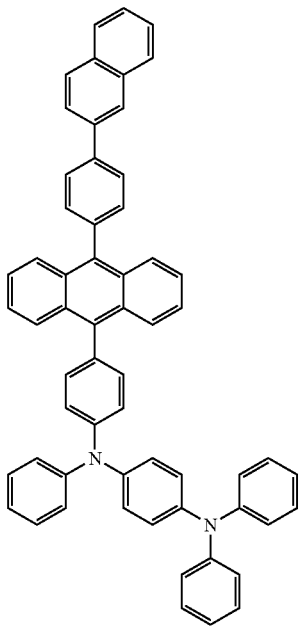
(308)
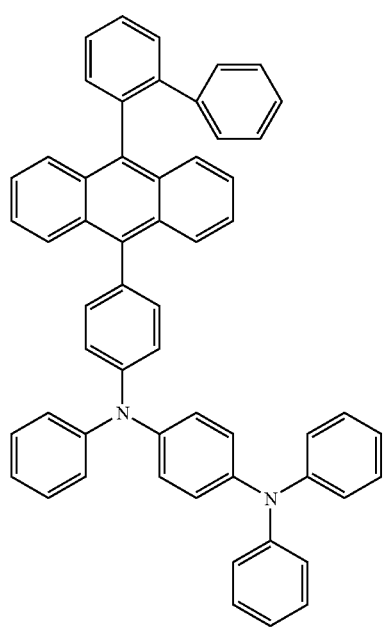
(306)

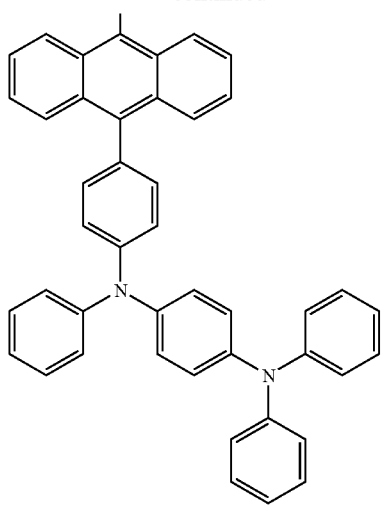
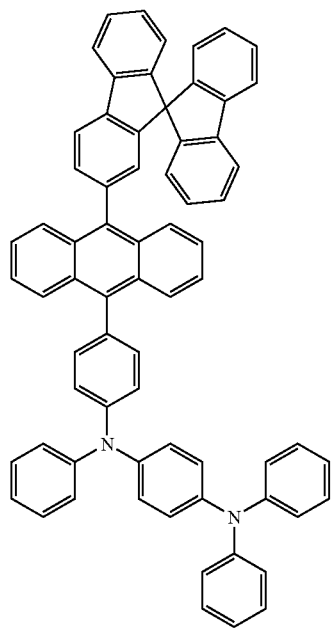
(311)
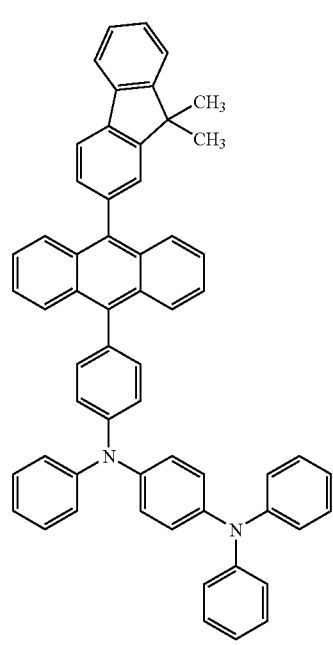
(310)
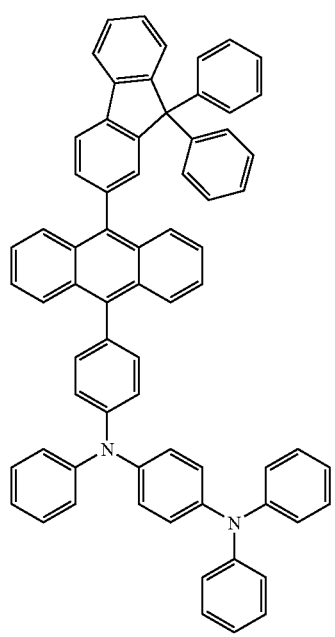
(312)

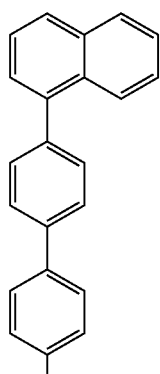
(313)
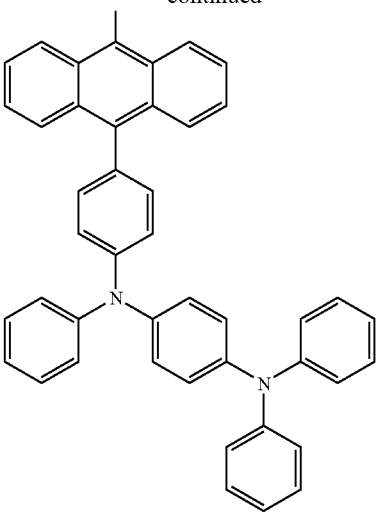
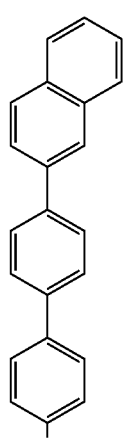
(314)
(315)
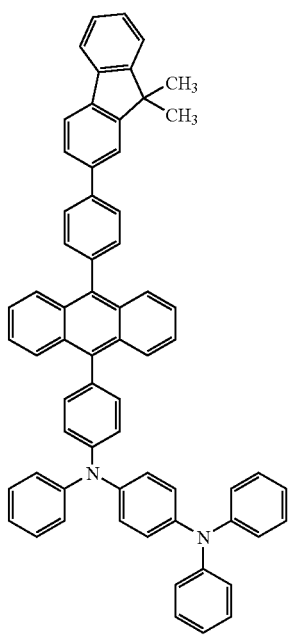

(316)
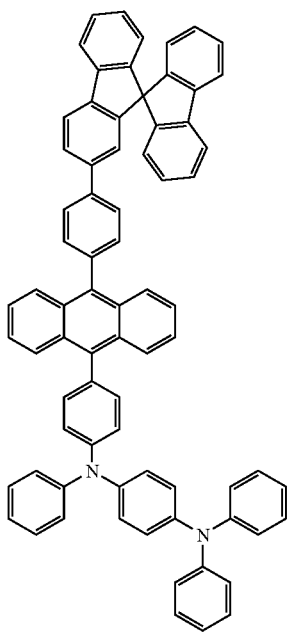
(318)
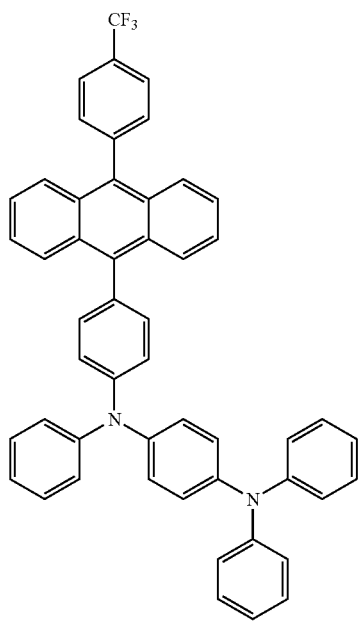
(317)
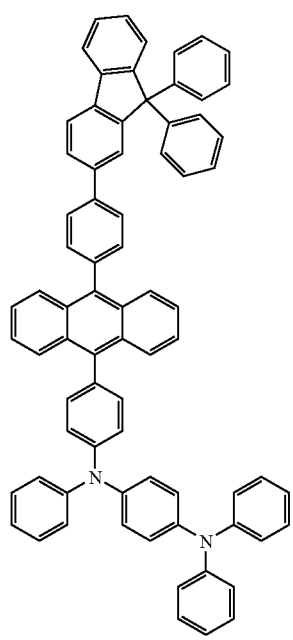
(319)
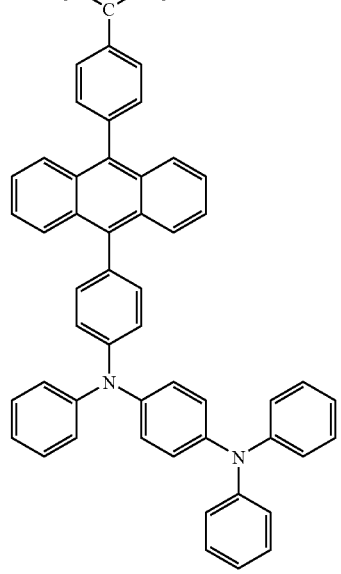

(320)
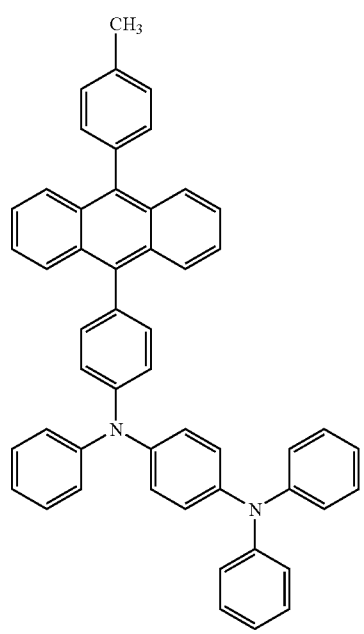
(322)
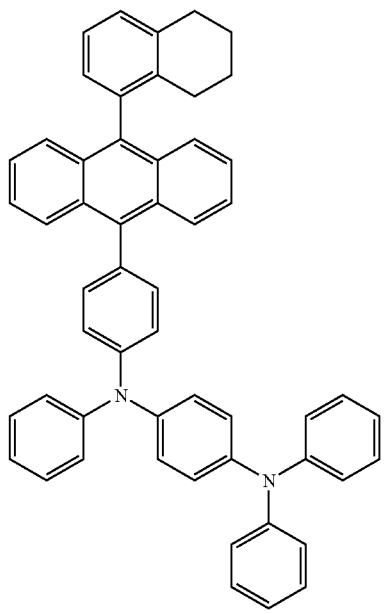
(321)
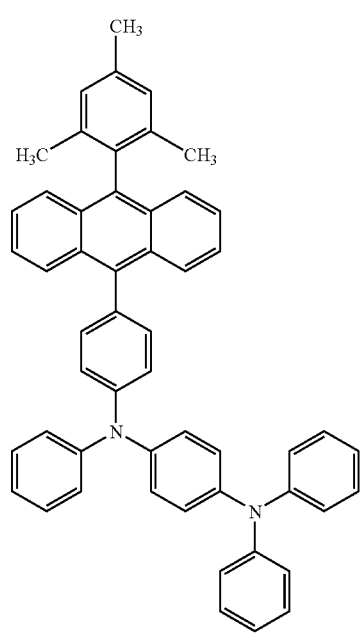
(323)
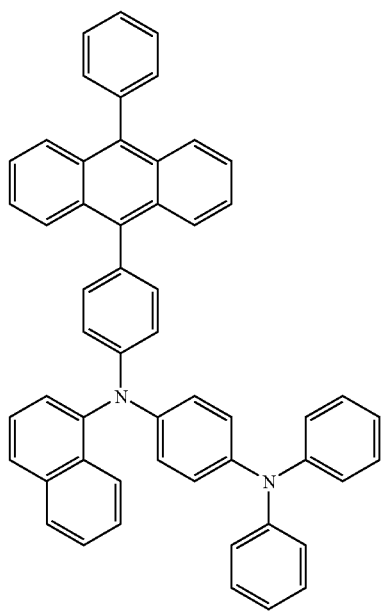

(324)
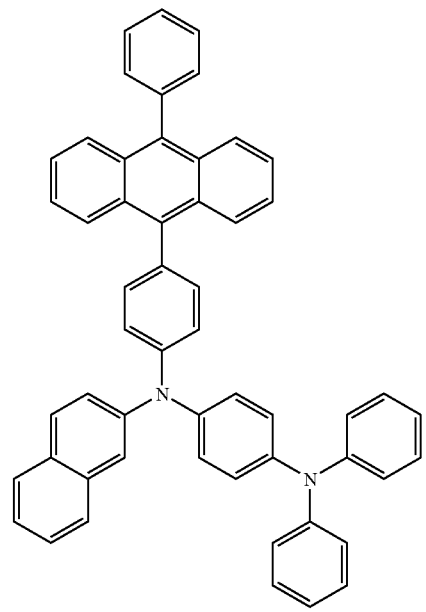
(326)
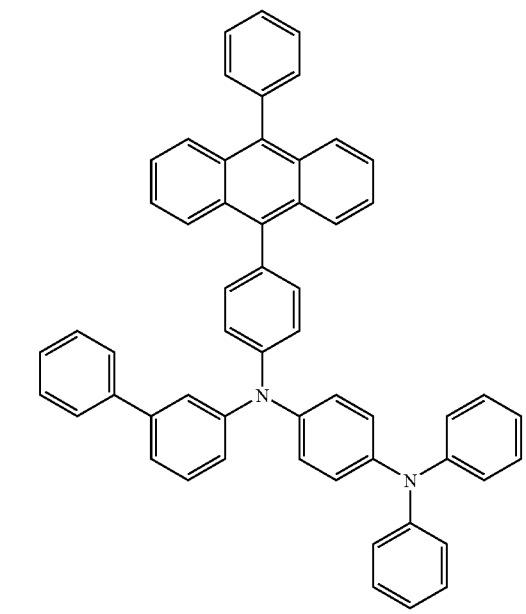
(325)
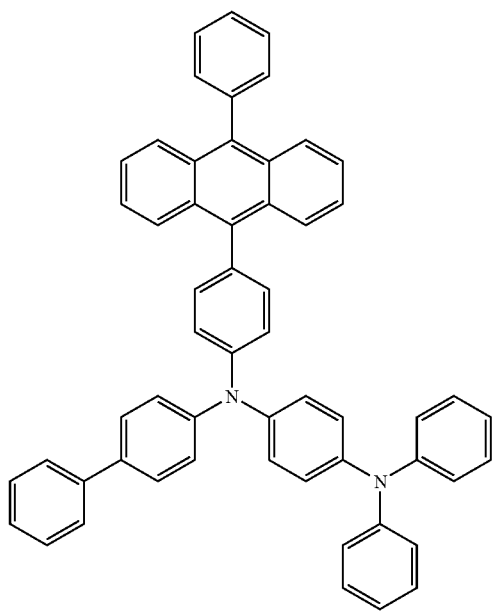
(327)
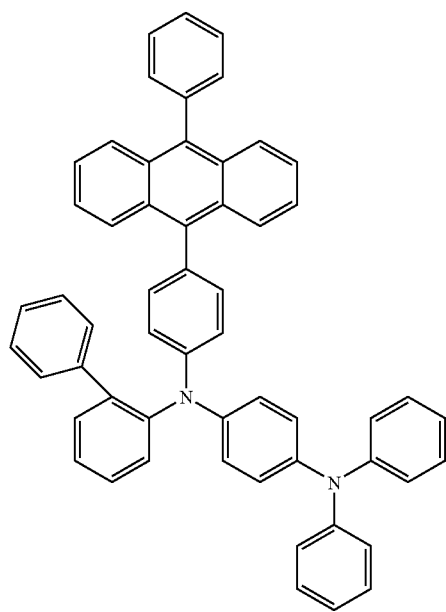

(328)
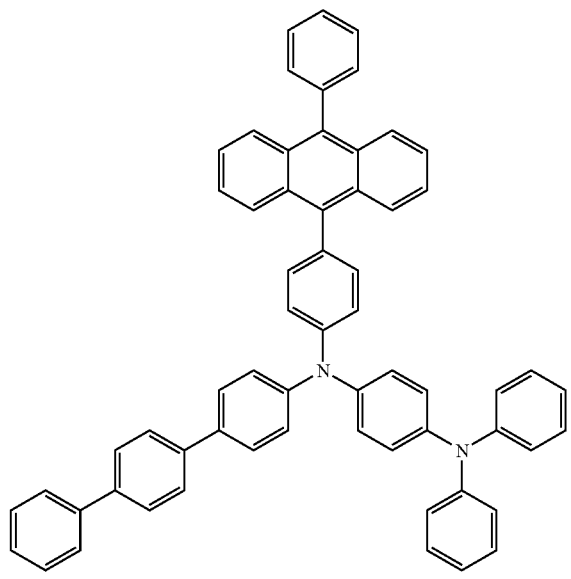
(329)
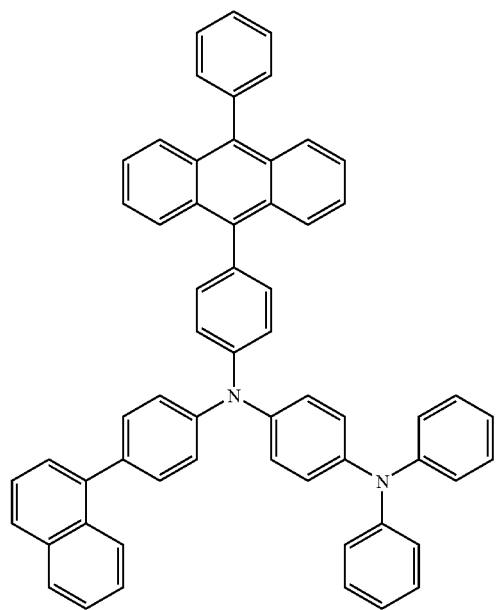
(330)
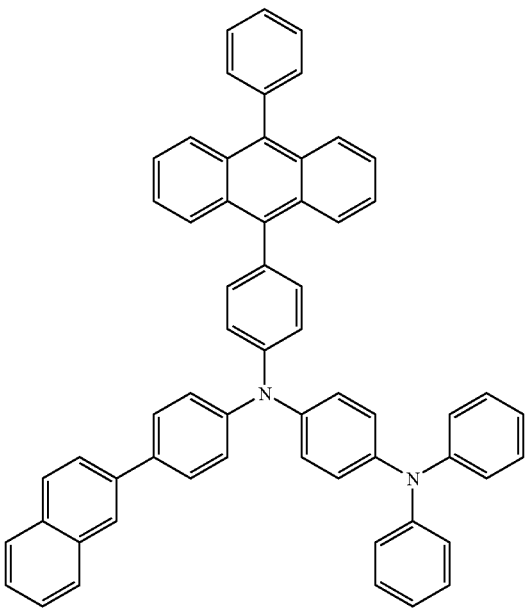
(331)
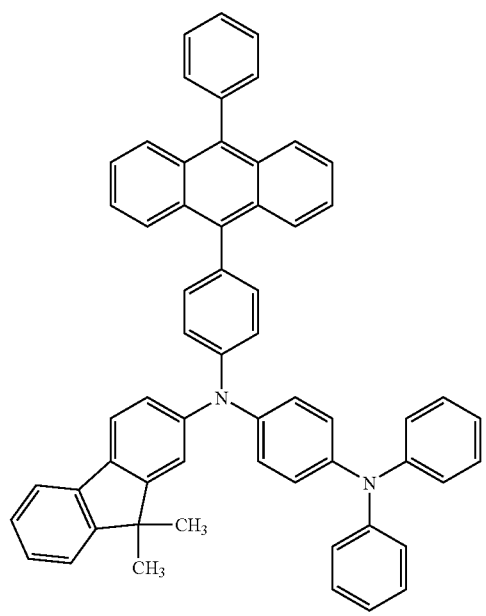

(332)
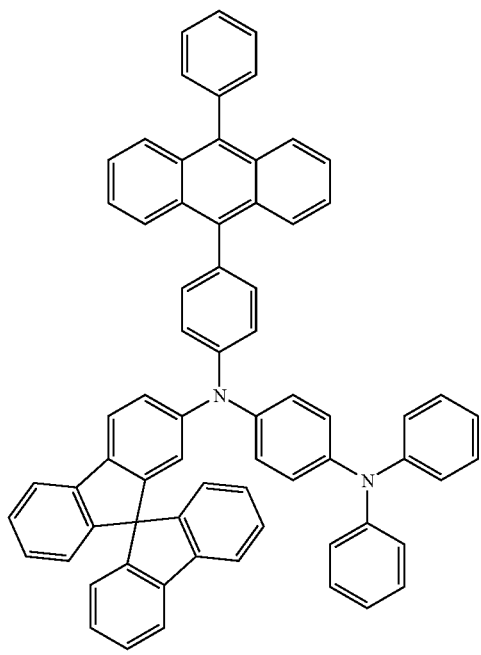
(333)
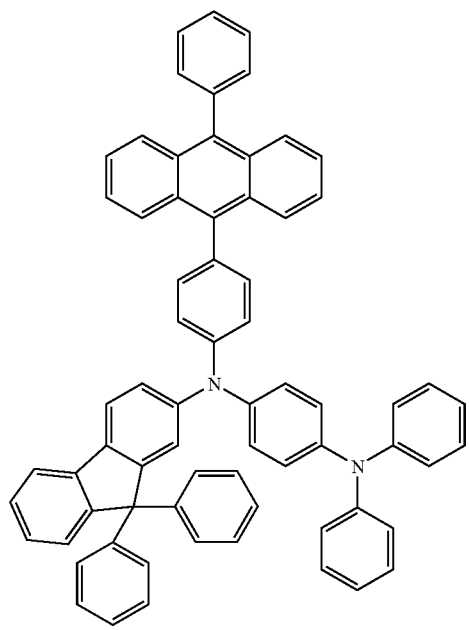
(334)
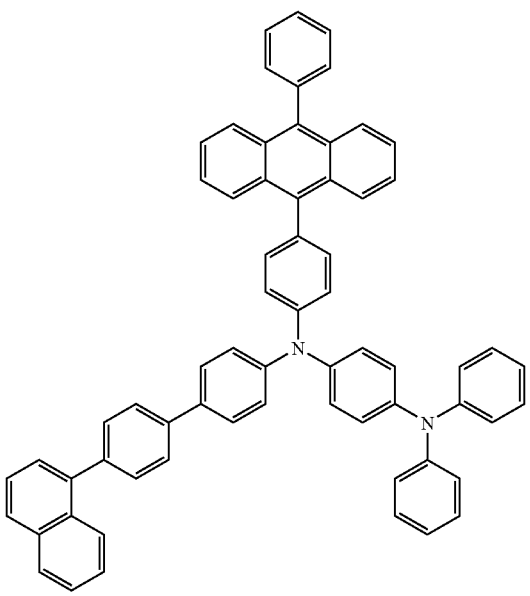
(335)
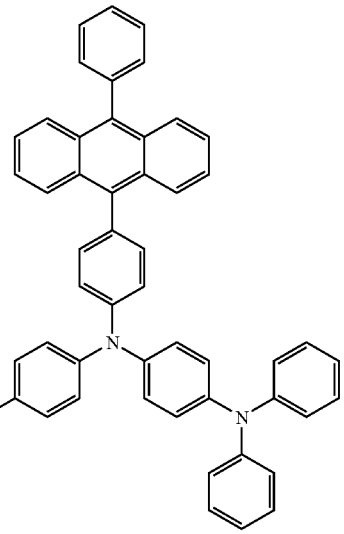

(336)
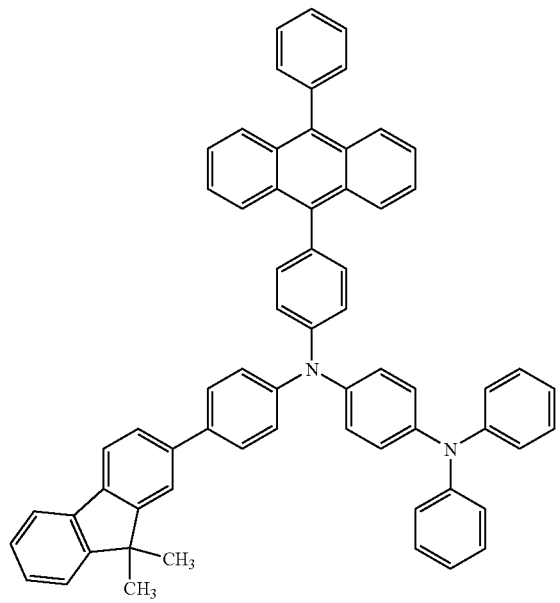
(338)
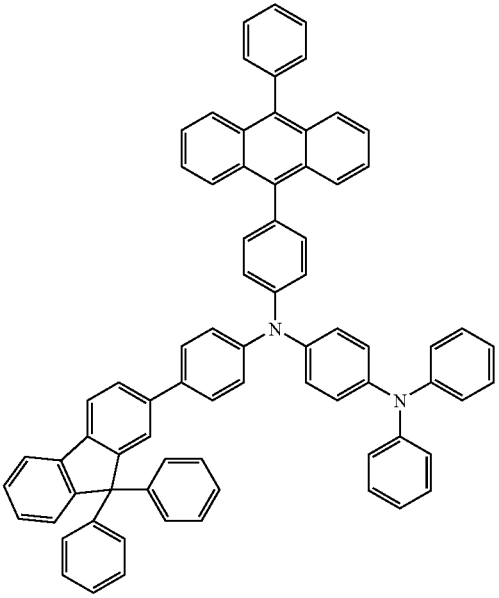
(337)
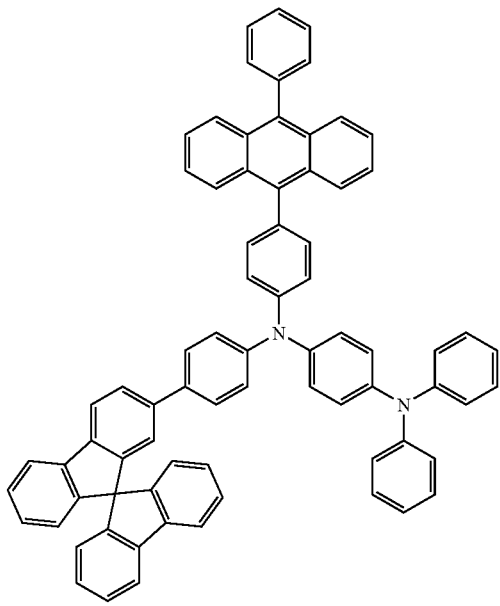
(339)
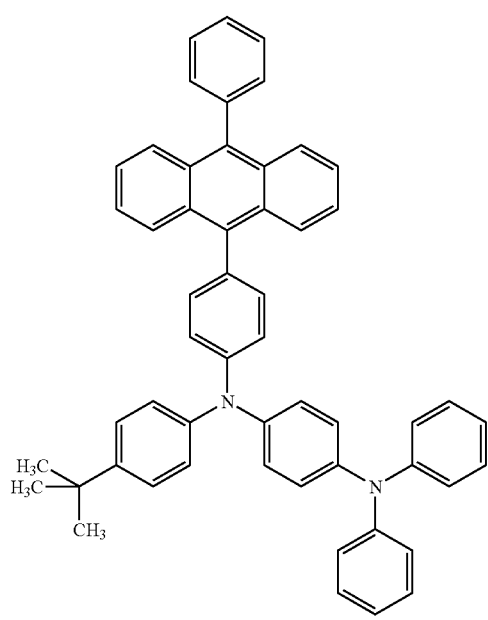

(340)
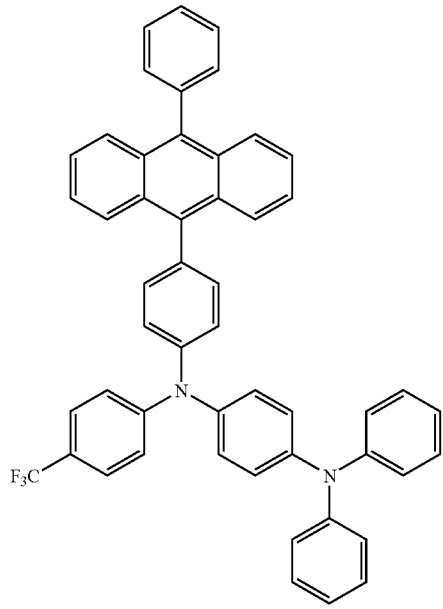
(342)
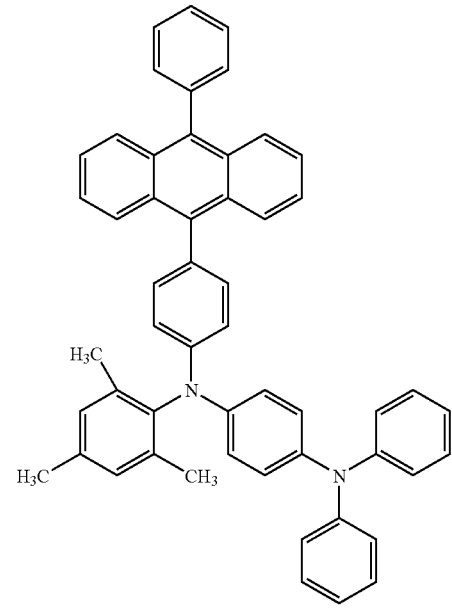
(341)
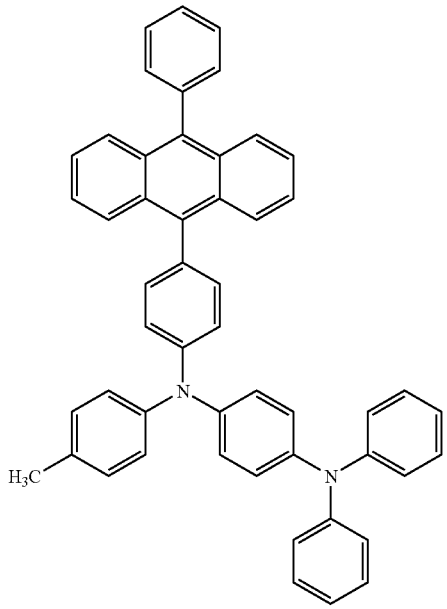
(343)
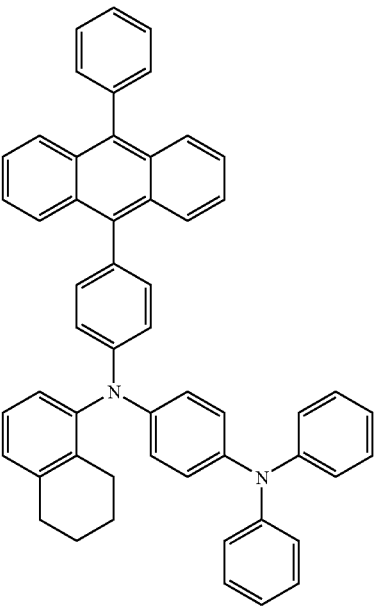

(344)
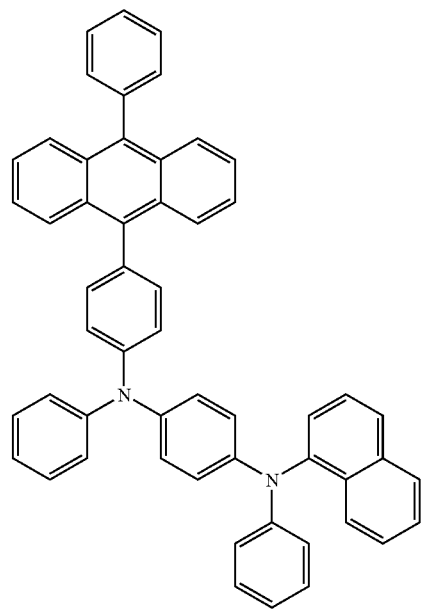
(346)
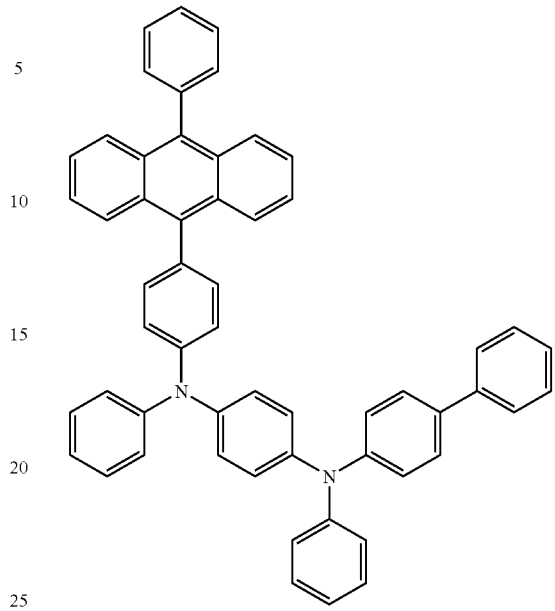
(345)
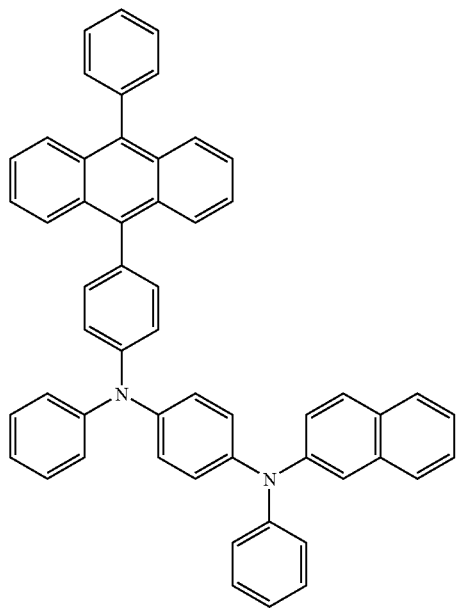
(347)
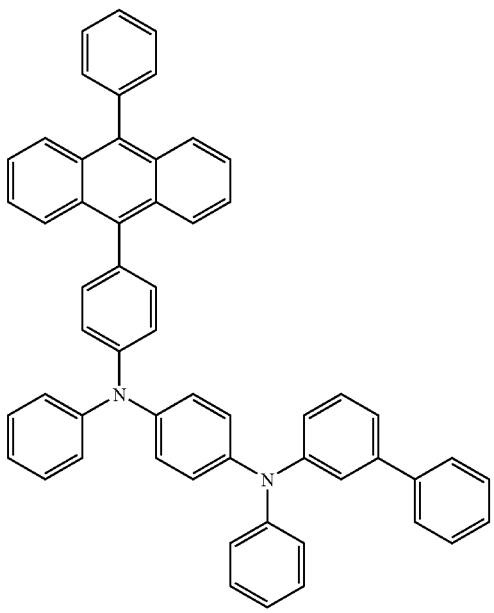

(348)
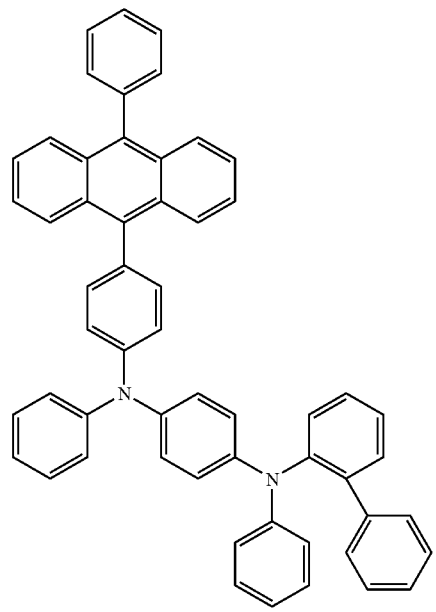
(349)
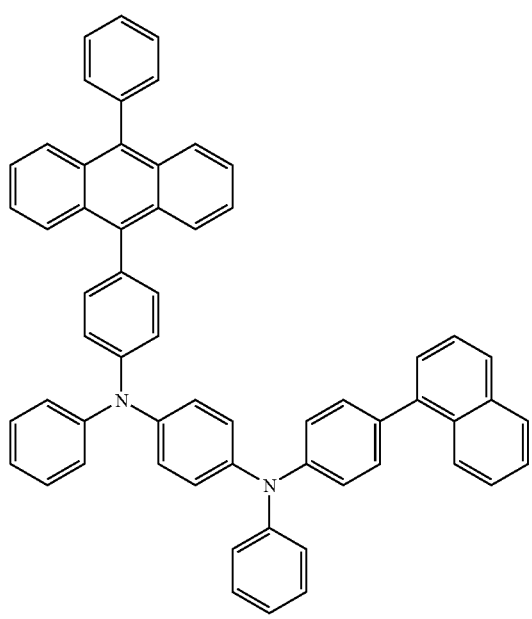
(350)
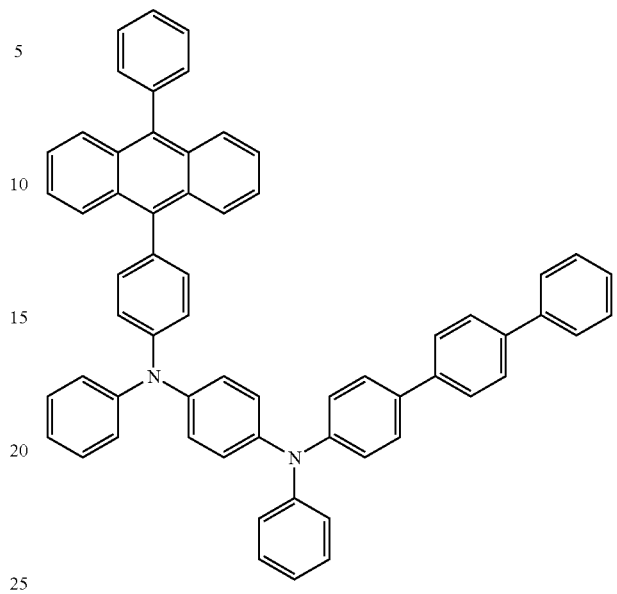
(351)
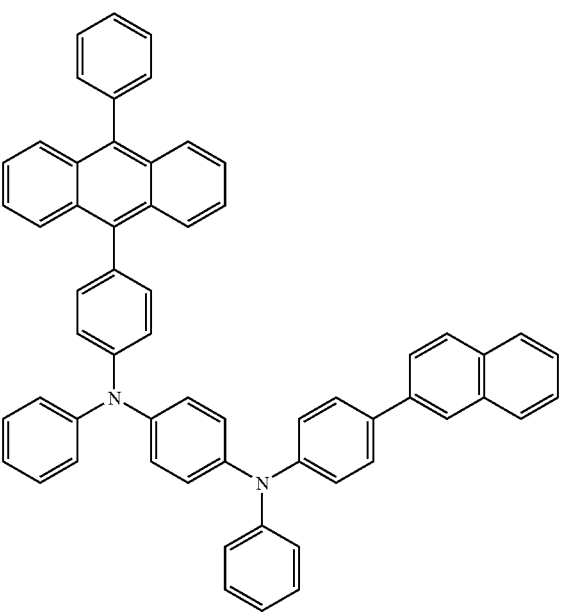

(352)
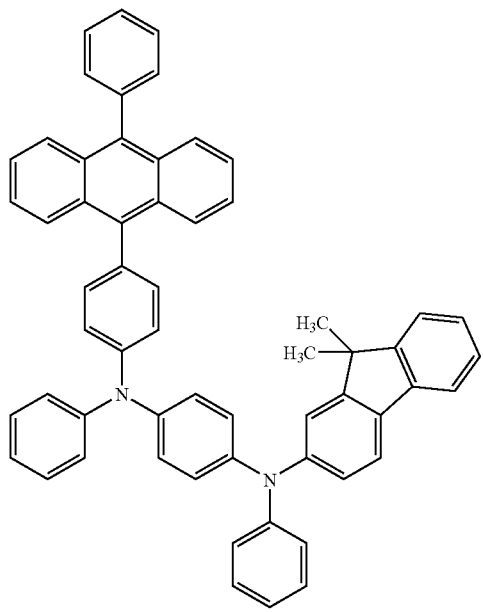
(353)
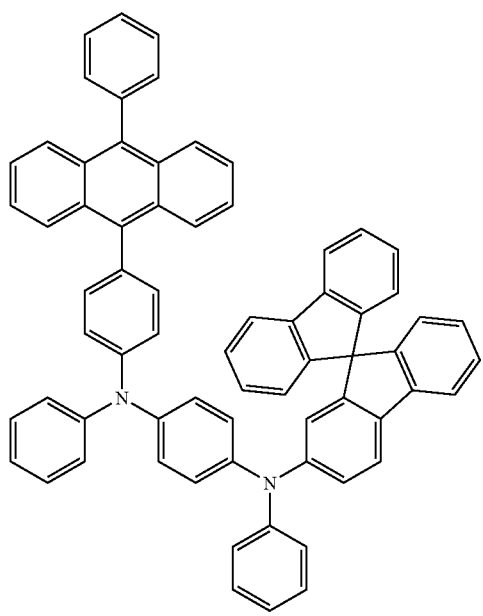
(354)
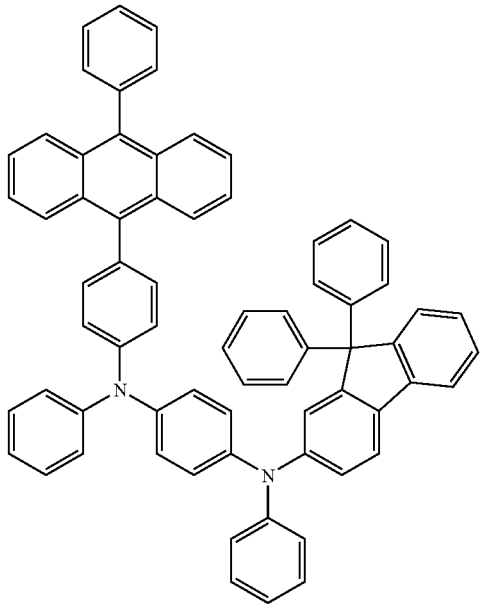
(355)
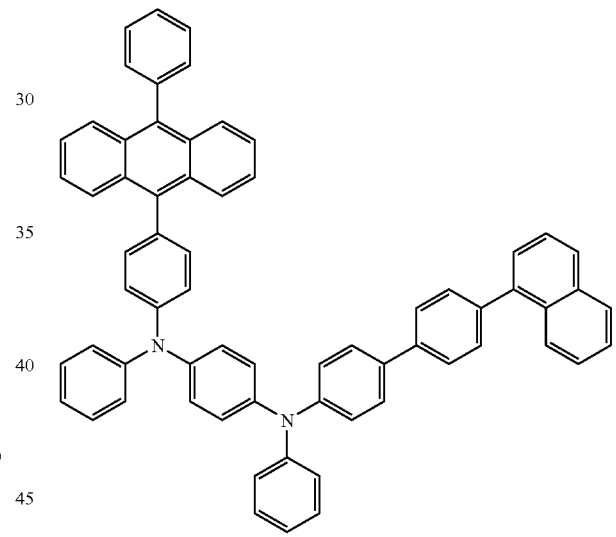
(356)
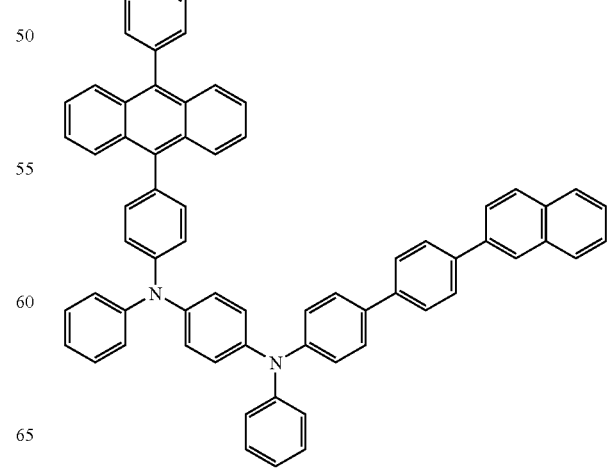

(357)
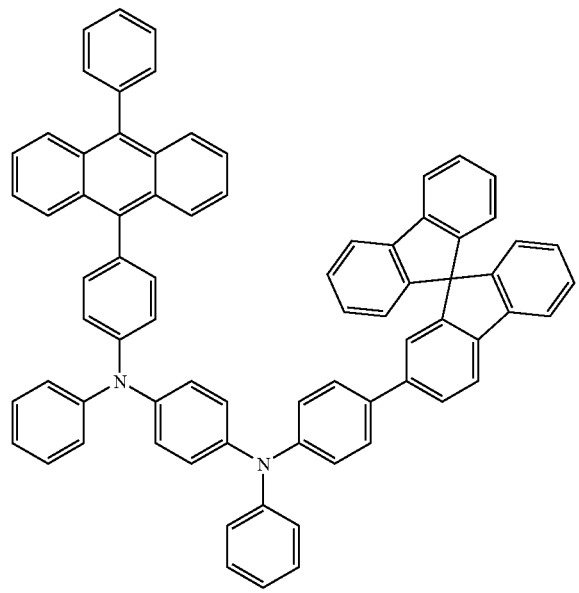
(359)
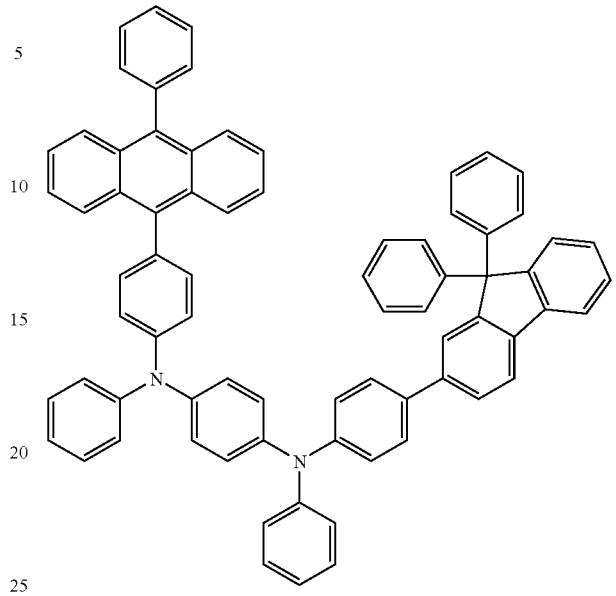
(358)
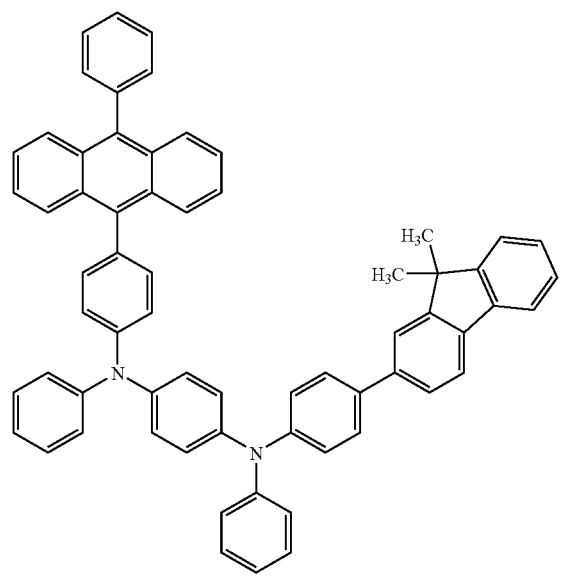
(360)
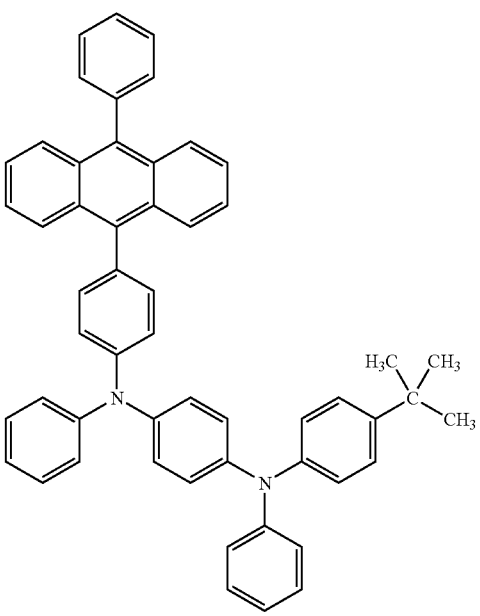

(361)
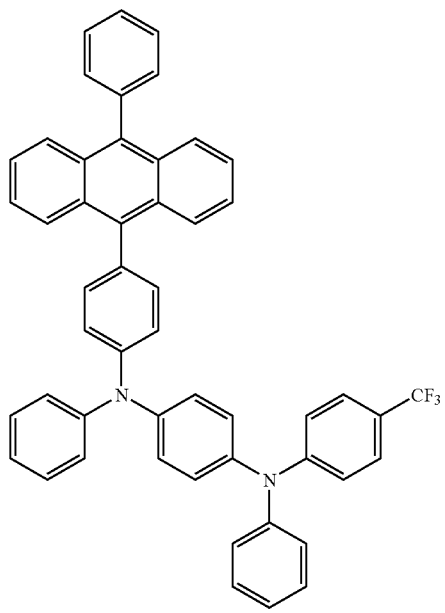
(362)
(363)
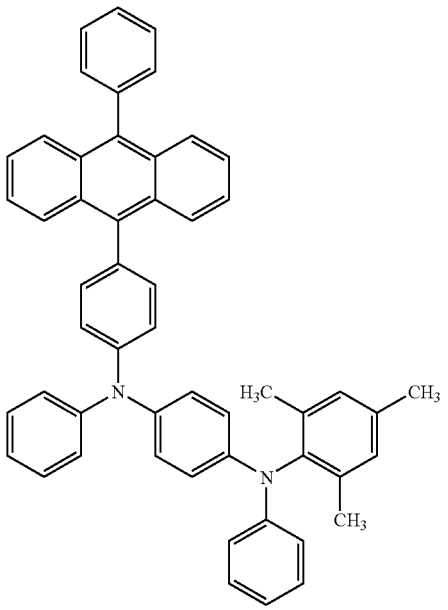
(364)
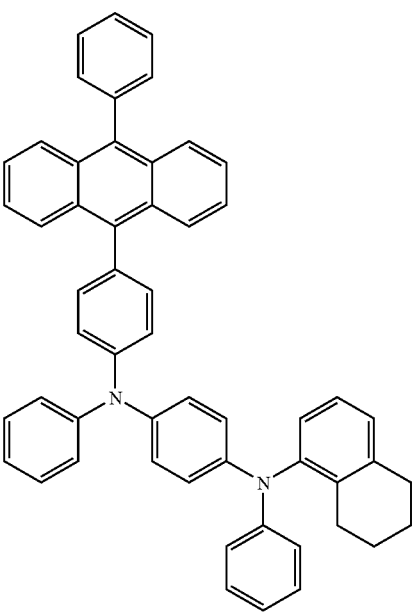

(365)
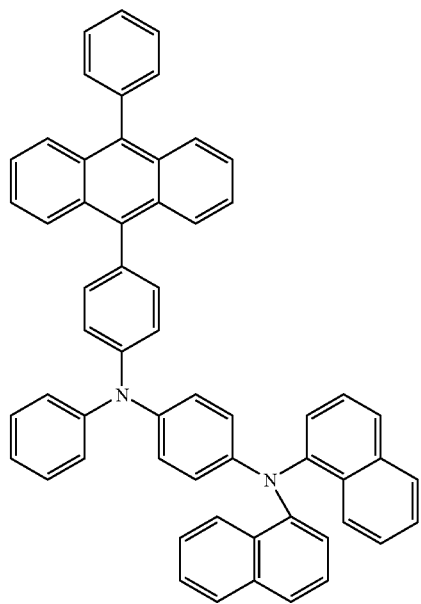
(366)
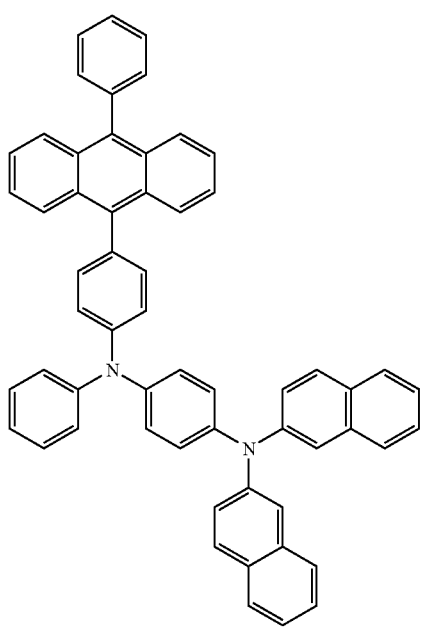
(367)
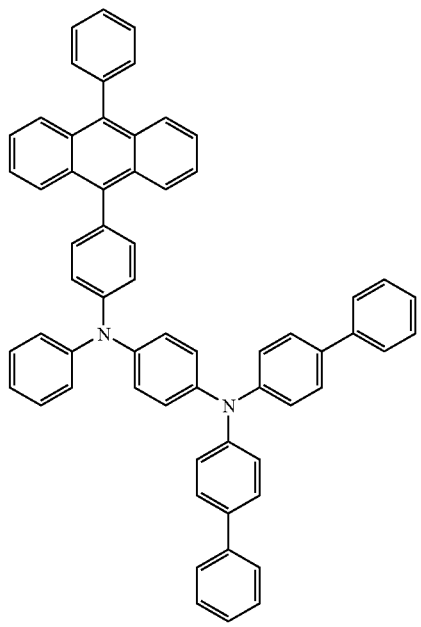
(368)
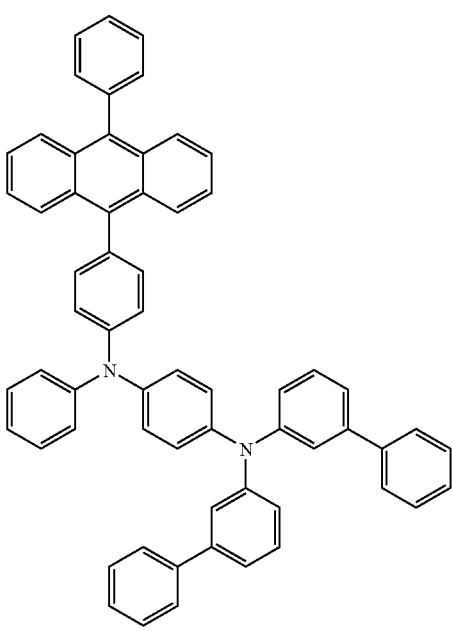

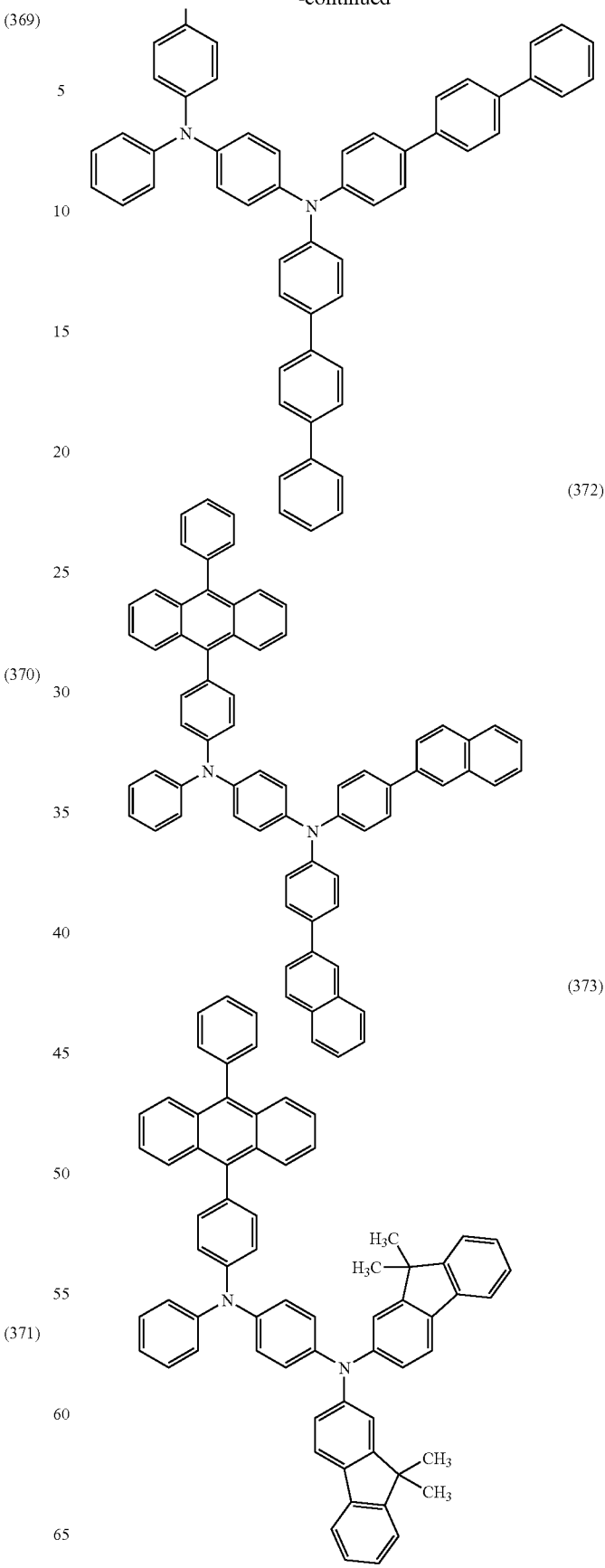

77
-continued
(374)
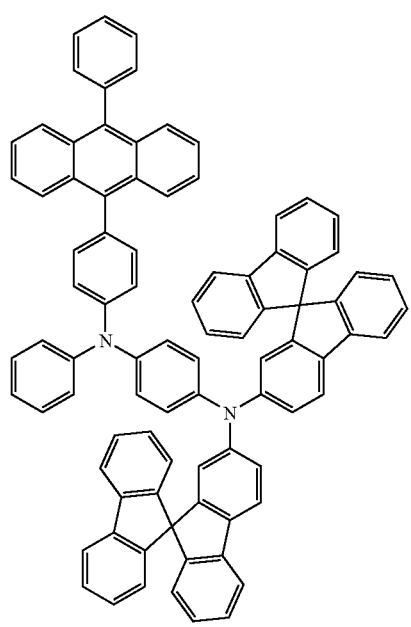
78
-continued
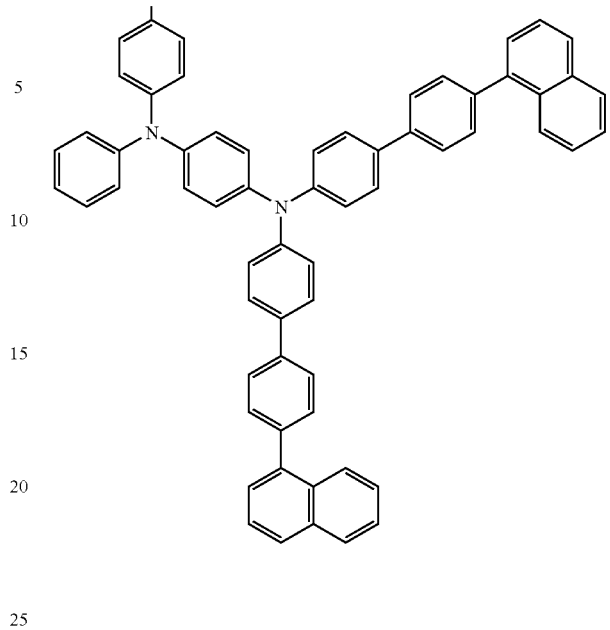
(375)
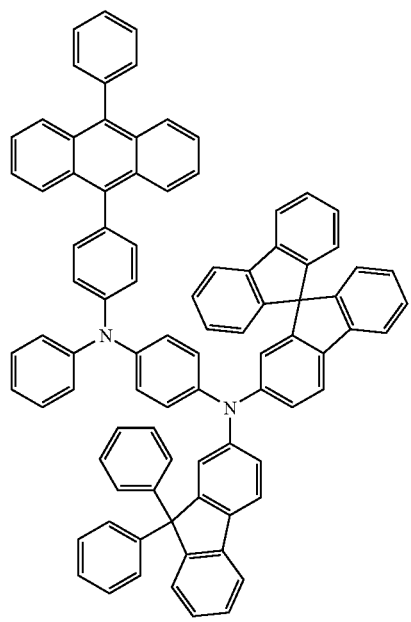
(377)
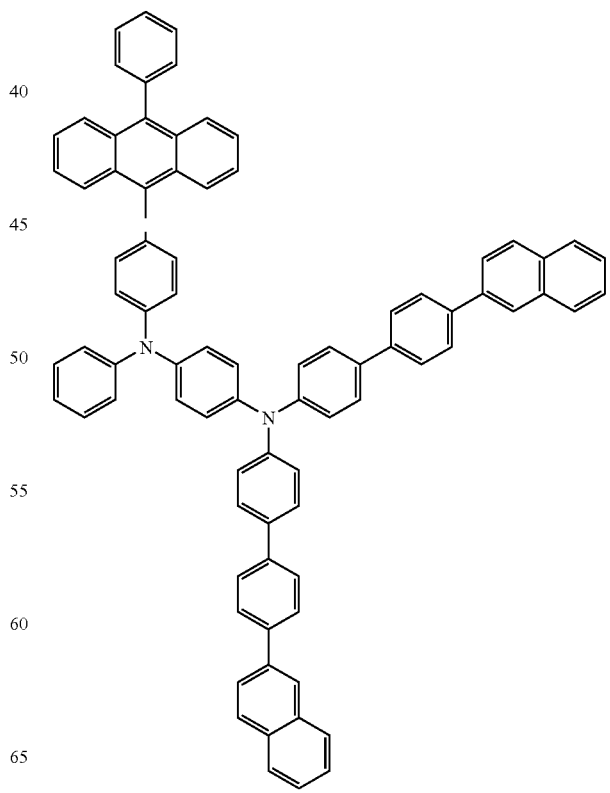
(376)
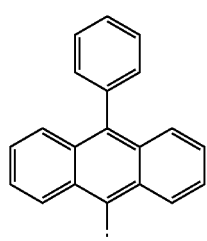

(378)
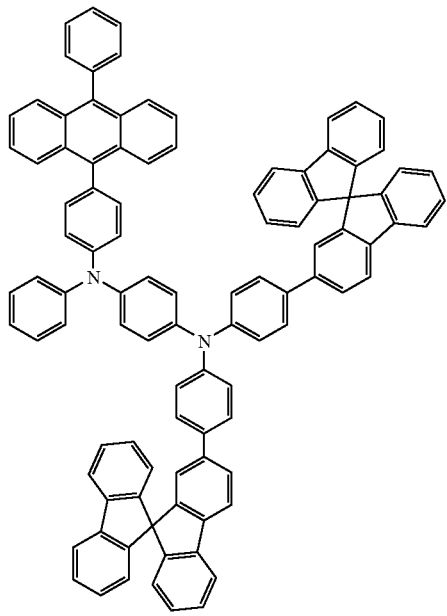
(380)
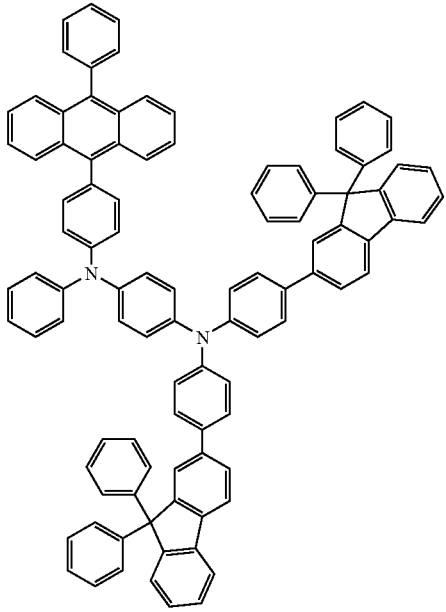
(379)
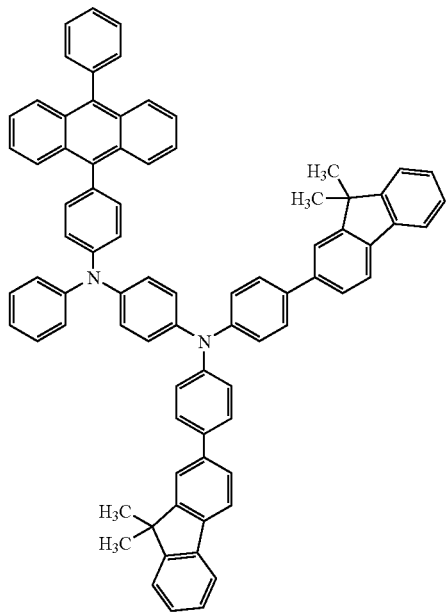
(381)
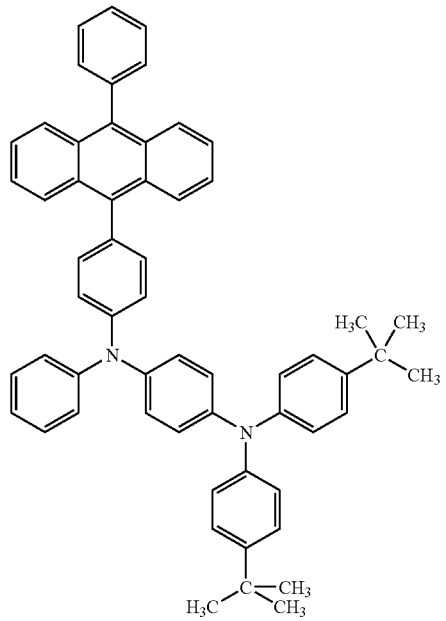

(382)
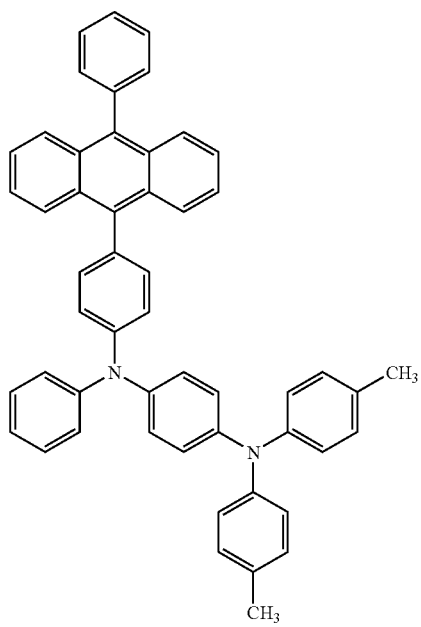
(383)
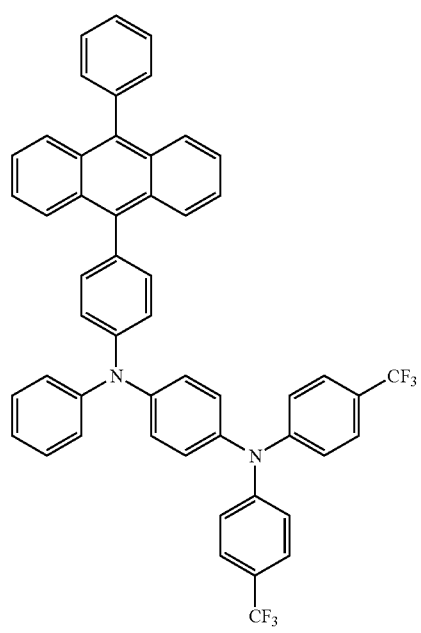
(384)
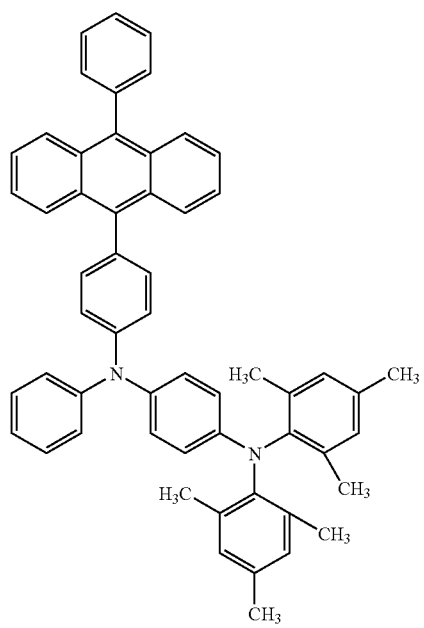
(385)
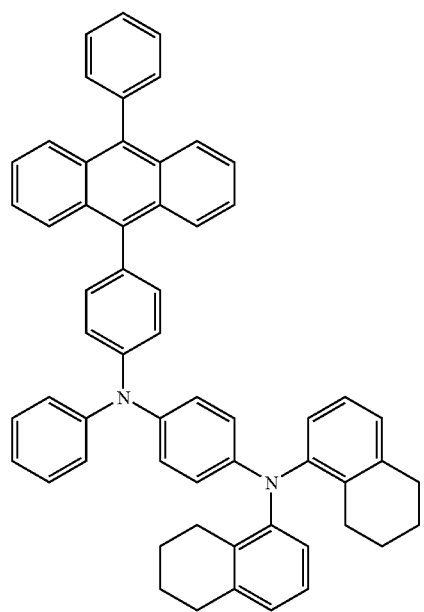

(386)
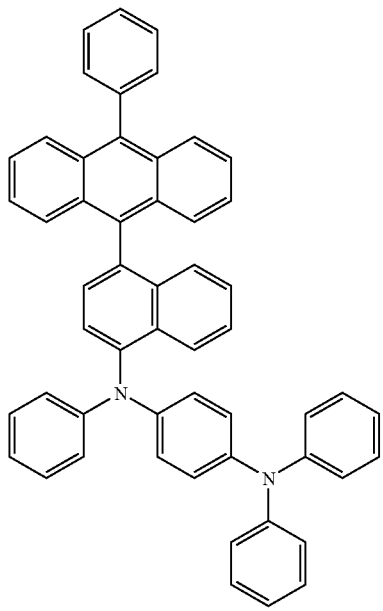
(387)
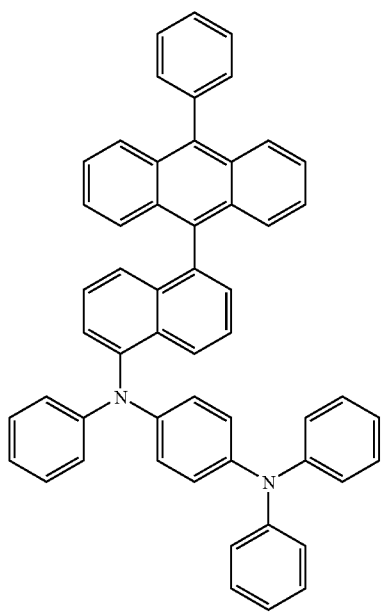
(388)
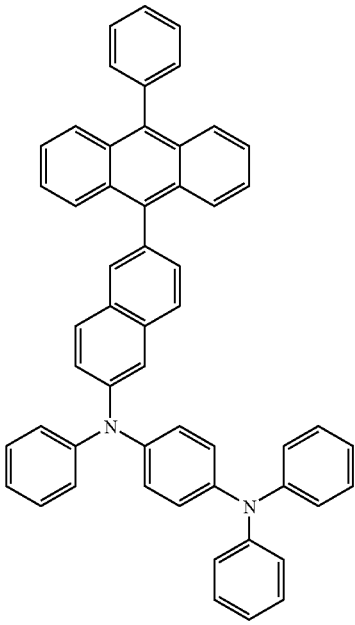
(389)
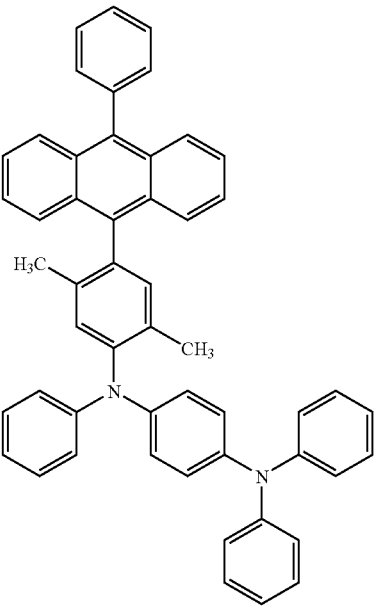

(390)
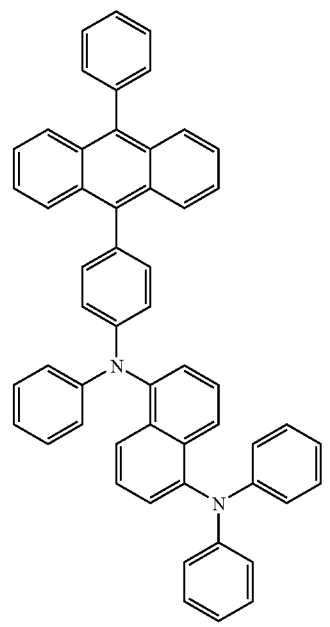
(392)
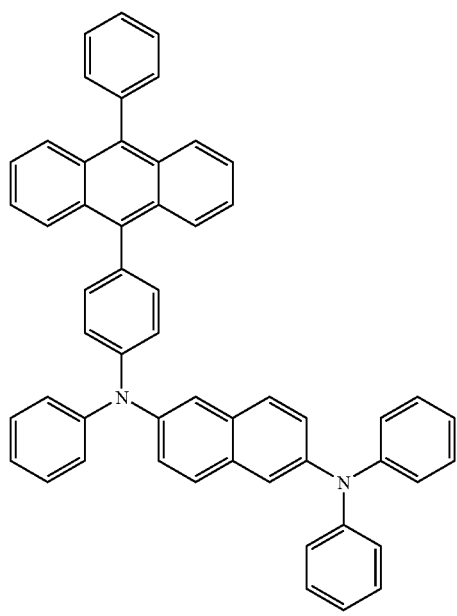
(391)
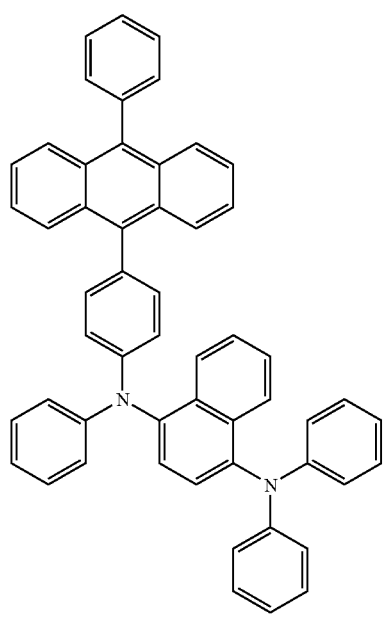
(393)
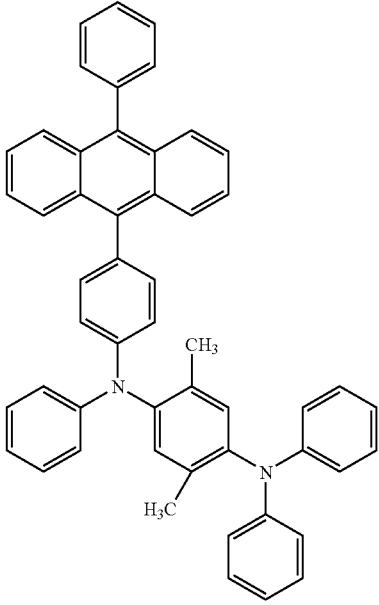

(394)
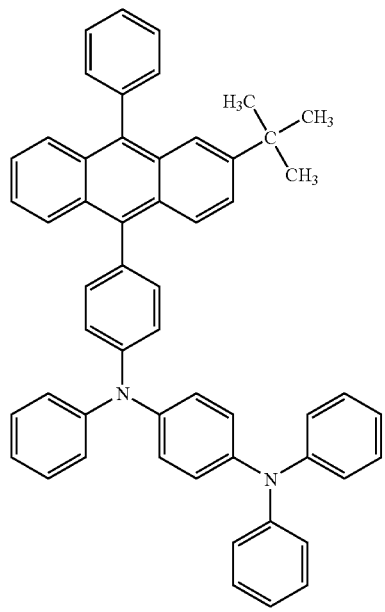
(396)
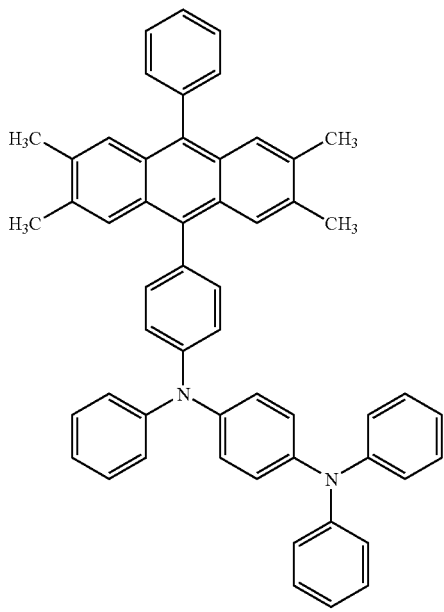
(395)
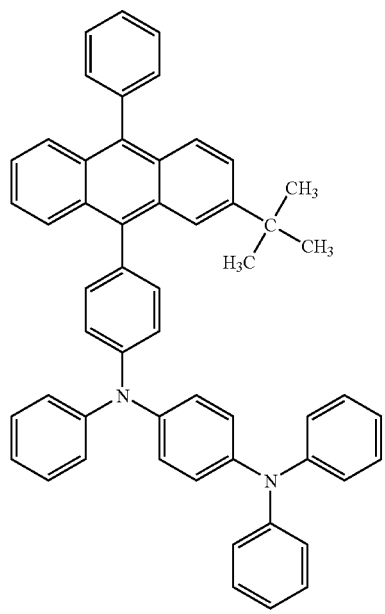
(401)
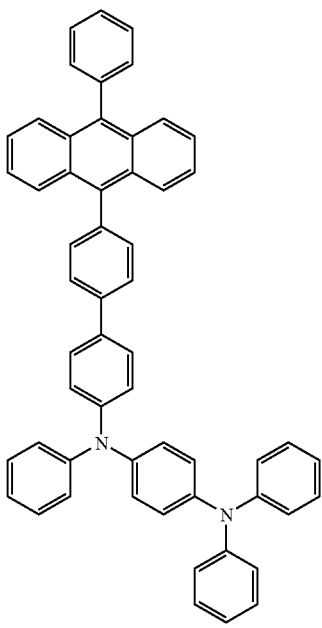

(402)

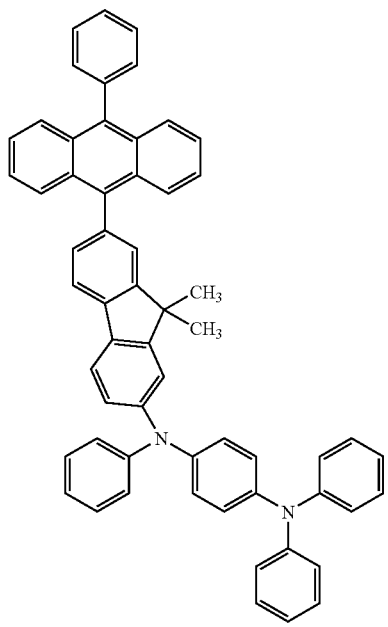

(404)

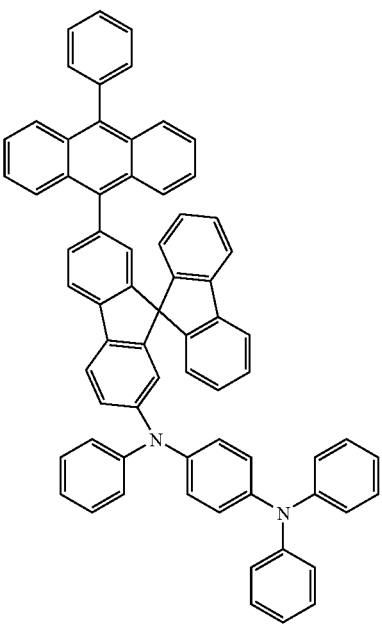

(403)

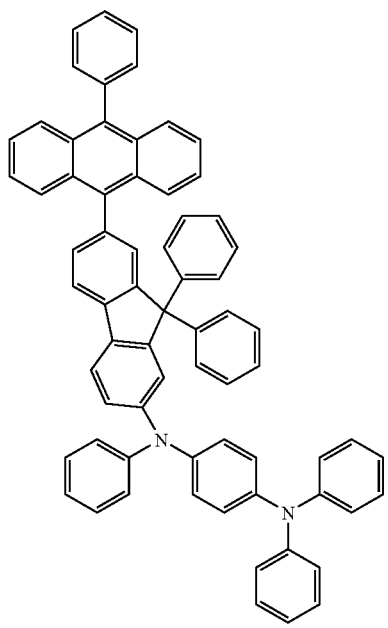

A variety of 00reactions can be applied as a synthesis method of an anthracene derivative of the present invention. For example, an anthracene derivative of the present invention can be synthesized by conducting the synthesis reactions shown in the following reaction formulae 1 and 2.

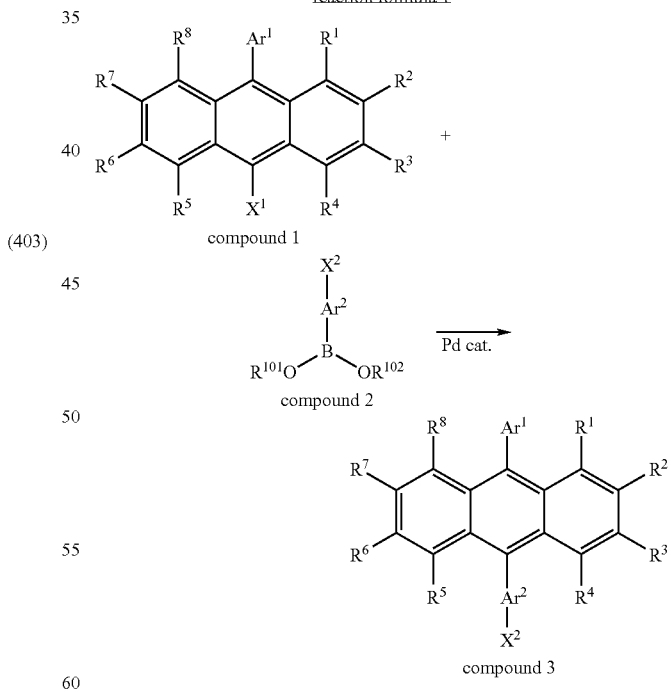

As shown in the reaction formula 1, the anthracene derivative (compound 1) and the halogenated aryl boronic acid or halogenated aryl organic boron compound (compound 2) are coupled by Suzuki-Miyaura Coupling using a palladium catalyst, whereby the halogenated aryl anthracene derivative (compound 3) can be obtained.

In the reaction formula 1, $Ar^1$ represents an aryl group having 6 to 13 carbon atoms. Further, the $Ar^1$ may have one or more substituents. When $Ar^1$ has two or more substituents, the substituents may be bonded to each other to form a ring. Furthermore, when a carbon atom of the $Ar^1$ has two substituents, the substituents may be bonded to each other to form a spiro ring. In the reaction formula 1, $Ar^2$ represents an arylene group having 6 to 13 carbon atoms. $Ar^2$ may have a substituent. When $Ar^2$ has two or more substituents, the substituents may be bonded to each other to form a ring. Furthermore, when a carbon atom of $Ar^2$ has two substituents, the substituents may be bonded to each other to form a spiro ring. In the reaction formula 1, $R^1$ to $R^8$ independently represent hydrogen or an alkyl group having 1 to 4 carbon atoms.

In the reaction formula 1, $X^1$ represents halogen or a triflate group, and $X^2$ represents halogen. When $X^1$ is halogen, $X^1$ and $X^2$ may be the same or different from each other. Use of iodine or bromine is preferable as the halogen, and the combination in which $X^1$ is iodine and $X^2$ is bromine is more preferable in order to suppress homocoupling of the compound 2. In the reaction formula 1, $R^{101}$ and $R^{102}$ independently represent hydrogen or an alkyl group having 1 to 6 carbon atoms, may be the same or different from each other, and may be combined with each other to form a ring. Examples of palladium catalysts that can be used in the reaction formula 1 include palladium(II)acetate, tetrakis(triphenylphosphine)palladium(0), and the like. Examples of ligands of palladium catalysts which can be used in the reaction formula 1 include tri(ortho-tolyl)phosphine, triphenylphosphine, tricyclohexylphosphine, and the like. Examples of bases that can be used in the reaction formula 1 include organic bases such as sodium tert-butoxide, inorganic bases such as potassium carbonate, and the like. Examples of solvents that can be used in the reaction formula 1 include a mixed solvent of toluene and water, a mixed solvent of toluene, alcohol such as ethanol, and water, a mixed solvent of xylene and water, a mixed solvent of xylene, alcohol such as ethanol, and water, a mixed solvent of benzene and water, a mixed solvent of benzene, alcohol such as ethanol, and water, a mixed solvent of ether such as ethylene glycol dimethyl ether, and water, and the like. Further, a mixed solvent of toluene and water or a mixed solvent of toluene, ethanol, and water is more preferable.

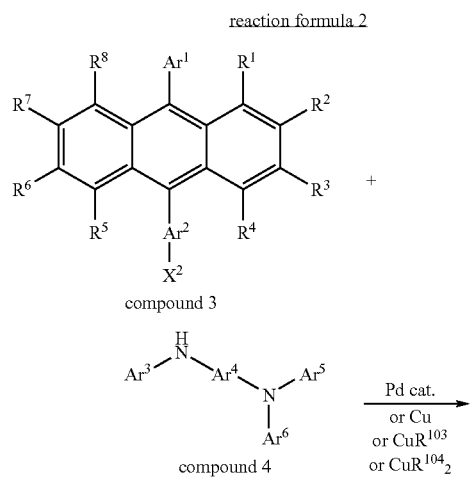

reaction formula 2 compound 3 compound 4

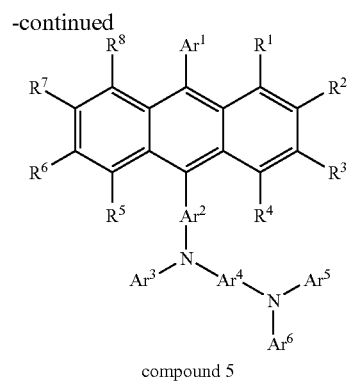

compound 5

Next, as shown in the reaction formula 2, the halogenated aryl anthracene derivative (compound 3), which is obtained in the reaction formula 1, and the compound having the amine skeleton (compound 4) are coupled by a Harwing-Buchwald reaction with a palladium catalyst or an Ullman reaction with copper or a copper compound, whereby the compound 5 represented by general formula (1) can be obtained.

In the reaction formula 2, $Ar^1$, $Ar^3$, $Ar^5$, and $Ar^6$ independently represent an aryl group having 6 to 13 carbon atoms. $Ar^1$, $Ar^3$, $Ar^5$, and $Ar^6$ may have a substituent. When $Ar^1$, $Ar^3$, $Ar^5$, and $Ar^6$ have more two or more substituents, the substituents may be bonded to each other to form a ring. Furthermore, when a carbon atom of the $Ar^1$, $Ar^3$, $Ar^5$, and $Ar^6$ has two substituents, the substituents may be bonded to each other to form a Spiro ring. In the reaction formula 2, $Ar^2$ and $Ar^4$ independently represent an arylene group having 6 to 13 carbon atoms. The $Ar^2$ and $Ar^4$ independently may have a substituent. When $Ar^2$ and $Ar^4$ have two or more substituents, the substituents may be bonded to each other to form a ring. Furthermore, when a carbon atom of the $Ar^2$ and $Ar^4$ has two substituents, the substituents may be bonded to each other to form a spiro ring. In the reaction formula 2, $R^1$ to $R^8$ independently represent either hydrogen or an alkyl group having 1 to 4 carbon atoms.

In the case where the Hartwig-Buchwald reaction is performed in the reaction formula 2, as a palladium catalyst that can be used, bis(dibenzylideneacetone)palladium(0), palladium(II)acetate, and the like are given. As a ligand of the palladium catalyst which can be used in the reaction formula 2, tri(tert-butyl)phosphine, tri(n-hexyl)phosphine, tricyclohexylphosphine, and the like are given. As a base that can be used in the reaction formula 2, organic bases such as sodium tert-butoxide, inorganic bases such as potassium carbonate, and the like are given. As a solvent that can be used in the reaction formula 2, toluene, xylene, benzene, tetrahydrofuran, and the like are given.

The case of performing the Ullmann reaction in the reaction formula 2 will be described. In the reaction formula 2, $R^{103}$ and $R^{104}$ independently represent halogen, an acetyl group, or the like, and as the halogen, chlorine, bromine, or iodine are given. Further, it is preferable to use copper(I) iodide where $R^{103}$ is iodine, copper(II) acetate where $R^{104}$ is an acetyl group, or the like. Furthermore, copper can be used instead of a copper compound. As a base that can be used in the reaction formula 2, inorganic bases such as potassium carbonate are given. As a solvent that can be used in the reaction formula 2,1,3-dimethyl-3,4,5,6-tetrahydro-2(1H) pyrimidinone (abbreviation: DMPU), toluene, xylene, benzene, and the like are given. In the Ullmann reaction, the target product can be obtained in a shorter time and in a higher yield when the reaction temperature is greater than or equal to 100° C.; therefore, it is preferable to use DMPU or xylene that has a high boiling point. Since it is further preferable that the reaction temperature is greater than or equal to 150° C., it is more preferable to use DMPU.

In the aforementioned manner, an anthracene derivative of this embodiment can be synthesized.

An anthracene derivative of this embodiment has an extremely large band gap; therefore, blue to green light emission with high color purity can be obtained. Further, an anthracene derivative of the present invention is a bipolar material having a hole-transporting property and an electron-transporting property. Furthermore, an anthracene derivative of this embodiment has high electrochemical stability and thermal stability.

An anthracene derivative of this embodiment can be used alone as an emission center material in a layer containing a light-emitting substance (a light-emitting layer). Alternatively, a layer in which an anthracene derivative of this embodiment is dispersed as a dopant material in a material (host material) having a larger band gap than the anthracene derivative of this embodiment can be applied to a layer containing a light-emitting substance; therefore, light emission can be obtained from the anthracene derivative of this embodiment. Hereupon, the anthracene derivative of this embodiment has an extremely large band gap, and emits light of a short wavelength; thus, a light-emitting element that can provide blue to green light emission with high color purity can be manufactured.

Further, an anthracene derivative of the present invention can be used as a host material, and light emission can be obtained from a dopant material that serves as a light-emitting substance with a structure where the dopant material that serves as a light-emitting substance is dispersed in the anthracene derivative of the present invention. When the anthracene derivative is used as a host material, blue to green light emission with high color purity can be obtained.

An anthracene derivative of the present invention can be used as a carrier-transporting material for a functional layer of the light-emitting element. For example, the anthracene derivative can be used as a hole-transporting layer, a hole-injecting layer, an electron-transporting layer, or an electron-injecting layer. In this specification, a layer including a substance with a high carrier-injecting property or a substance with a high carrier-transporting property is also referred to as a functional layer that functions, for example, to inject or transport carriers.

By the use of an anthracene derivative of the present invention for a light-emitting element, a light-emitting element with high efficiency, high reliability, and a long lifetime can be obtained.

Embodiment 2

One mode of a light-emitting element using an anthracene derivative of the present invention will be described below with reference to FIG. 1A.

In the light-emitting element of the present invention, an EL layer including at least a layer that contains a light-emitting substance (also referred to as a light-emitting layer) is interposed between a pair of electrodes. The EL layer may also have a plurality of layers in addition to the layer that contains a light-emitting substance. The plurality of layers are stacked by combining a layer including a substance with a high carrier-injecting property and a layer including a substance with a high carrier-transporting property so that a light-emitting region is formed apart from the electrodes, that is, so that carriers recombine in a portion apart from the electrodes. In this specification, a layer including a substance with a high carrier-injecting property or a substance with a high carrier-transporting property is also referred to as a functional layer that functions, for example, to inject or transport carriers. A layer containing a substance with a high hole-injecting property (also referred to as a hole-injecting layer), a layer containing a substance with a high hole-transporting property (also referred to as a hole-transporting layer), a layer containing a substance with a high electron-injecting property (also referred to as an electron-injecting layer), a layer containing a substance with a high electron-transporting property (also referred to as an electron-transporting layer), or the like can be used as the functional layer.

Figure 1B:
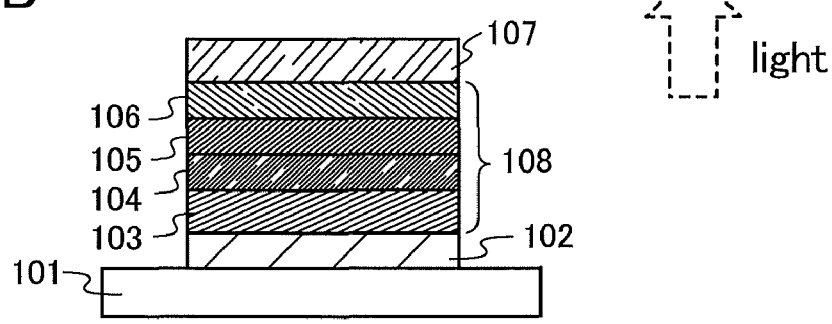
Figure 1C:
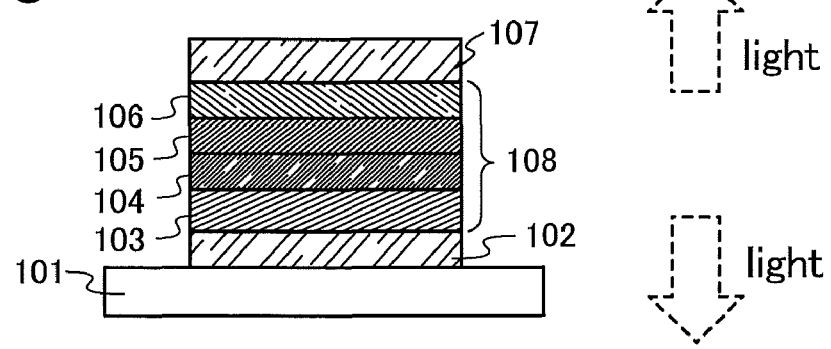

In a light-emitting element of this embodiment illustrated in each of FIGS. 1A to 1C, an EL layer 108 is provided between a first electrode 102 and a second electrode 107 over a substrate 101. The EL layer 108 has a first layer 103, a second layer 104, a third layer 105, and a fourth layer 106. In the light-emitting element of each of FIGS. 1A to 1C, the first electrode 102 is provided over a substrate 101; the first layer 103, the second layer 104, the third layer 105, and the fourth layer 106 are stacked over the first electrode 102 in this order; and a second electrode 107 is provided thereover. Note that in the description below, it is assumed that the first electrode 102 functions as an anode and the second electrode 107 functions as a cathode in this embodiment.

The substrate 101 is used as a support of the light-emitting element. As the substrate 101, for example, glass, quartz, plastic, or the like can be used. Alternatively, a flexible substrate may be used. The term flexible substrate means a substrate that can be bent. As the flexible substrate, for example, a plastic substrate made of polycarbonate, polyarylate, polyether sulfone, or the like can be given. Alternatively, a film (made of polypropylene, polyester, vinyl, polyvinyl fluoride, vinyl chloride, or the like), a film formed by evaporation of an inorganic material can be used. Note that any other material may be used as long as the material functions as a support of the light-emitting element in the manufacturing process.

As the first electrode 102, it is preferable to use metal, an alloy, a conductive compound, a mixture thereof, or the like having a high work function (specifically, of greater than or equal to 4.0 eV). Specifically, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. These conductive metal oxide films are generally formed by sputtering; however, the films may be manufactured by applying a sol-gel method or the like. For example, indium oxide-zinc oxide (IZO) can be formed by a sputtering method using a target in which zinc oxide is added to indium oxide at 1 to 20 wt %. Indium oxide containing tungsten oxide and zinc oxide (IWZO) can be formed by sputtering method using a target in which tungsten oxide and zinc oxide are added to indium oxide at 0.5 to 5 wt % and at 0.1 to 1 wt % respectively. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like are given.

The first layer 103 includes a substance with a high hole-injecting property. For the first layer 103, molybdenum oxide, vanadium oxide, ruthenium oxide, tungsten oxide, manganese oxide, or the like can be used. Alternatively, the first layer 103 can be formed by using phthalocyanine (abbreviation: $H_2Pc$), a phthalocyanine-based compound such as copper phthalocyanine (CuPc), an aromatic amine compound such as 4,4'-bis[N-(4-diphenylaminophenyl)-N-phenylamino]biphenyl (abbreviation: DPAB) or 4,4'-bis(N-{4-[N-(3-methylphenyl)-N-phenylamino]phenyl}-N-phenylamino)biphenyl (abbreviation: DNTPD), a high molecular material such as poly (3,4-ethylene dioxythiophene)/poly(styrenesulfonic acid) (PEDOT/PSS), or the like.

Moreover, the first layer 103 can be formed using a composite material including an organic compound and an inorganic compound. In particular, a composite material including an organic compound and an inorganic compound that shows an electron-accepting property with respect to the organic compound is excellent in hole-injecting property and hole-transporting property since electrons are transferred between the organic compound and the inorganic compound and the carrier density of the organic compound is increased.

When the first layer 103 is formed using a composite material including an organic compound and an inorganic compound, the first layer 103 can have an ohmic contact with the first electrode 102; therefore, a material for the first electrode can be selected regardless of its work function.

The inorganic compound used for the composite material is preferably an oxide of a transition metal. In addition, oxides of metal that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferably used because of their high electron-accepting property. Molybdenum oxide is particularly preferably used among them because of its stability in the atmosphere, low hygroscopicity, and easiness of handling.

As the organic compound used for the composite material, various compounds such as an aromatic amine compound, a carbazole derivative, aromatic hydrocarbon, and a high molecular compound (oligomer, dendrimer, polymer, or the like) can be used. Note that the organic compound used for the composite material is preferably an organic compound with a high hole-transporting property. Specifically, a substance having a hole mobility of greater than or equal to $10^{-6}$ cm$^2$/Vs is preferably used. However, any substance other than the above substances may also be used as long as the hole-transporting property thereof is higher than the electron-transporting property. Hereinafter, organic compounds that can be used for the composite material are given specifically.

As aromatic amine compounds that can be used for the composite material, N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), or the like can be given.

As specific examples of the carbazole derivative that can be used as the composite material, the following can be given: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1), and the like.

Moreover, 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene, or the like can be used.

As the aromatic hydrocarbon which can be used for the composite material, for example, the following can be given: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene, or the like. In addition, pentacene, coronene, or the like can also be used. As these aromatic hydrocarbons listed here, it is more preferable to use an aromatic hydrocarbon having hole mobility of more than or equal to $1 \times 10^{-6}$ cm$^2$/Vs and having 14 to 42 carbon atoms.

Note that an aromatic hydrocarbon that can be used for the composite material may have a vinyl skeleton. As an aromatic hydrocarbon having a vinyl group, for example, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like can be given.

Further, a high molecular compound such as poly(N-vinylcarbazole) (abbreviation: PVK) or poly(4-vinyltriphenylamine) (abbreviation: PVTPA) can also be used.

As a substance forming the second layer 104, a substance with a high hole-transporting property, specifically, an aromatic amine compound (that is, a compound having a benzene ring-nitrogen bond) is preferable. As examples of a material which are widely used, the following are given: 4,4'-bis[N-(3-methylphenyl)-N-phenylamino]biphenyl, a derivative thereof such as 4,4'-bis[N-(1-naphthyl)-N-phenylamino]biphenyl (hereinafter referred to as NPB), and a starburst aromatic amine compound such as 4,4',4''-tris(N,N-diphenyl-amino)triphenylamine, and 4,4',4''-tris[N-(3-methylphenyl)-N-phenylamino]triphenylamine. The substances described here are mainly substances having hole mobility of greater than or equal to $10^{-6}$ cm$^2$/Vs. Further, any substance other than above substances may also be used as long as a hole-transporting property thereof is higher than an electron-transporting property. Note that the second layer 104 is not limited to a single layer, but may be a mixed layer or a stacked layer having two or more layers formed of the aforementioned substances.

Further, the second layer 104 may be a layer where a hole-transporting material is added to a high molecular compound that is electrically inert such as PMMA.

A high molecular compound such as poly(N-vinylcarbazole) (abbreviation: PVK); poly(4-vinyltriphenylamine) (abbreviation: PVTPA); poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) may be used. Further, aforementioned materials with a hole-transporting property may be added to these high molecular compounds properly.

The third layer 105 is a layer containing a light-emitting substance (also referred to as a light-emitting layer). In this embodiment, the third layer 105 is formed using an anthracene derivative of the present invention which is described in Embodiment 1. An anthracene derivative of the present invention exhibits light emission of blue to green; therefore, an anthracene derivative of the present invention can favorably be applied to a light-emitting element as a light-emitting substance.

Further, an anthracene derivative of the present invention can be used as a dopant material dispersed in a material (host) having a larger band gap than the anthracene derivative of the present invention; therefore, light emission can be obtained from the anthracene derivative of the present invention. That is, an anthracene derivative of the present invention functions as a dopant material. Hereupon, an anthracene derivative of the present invention has an extremely large band gap and emits light of a short wavelength; thus, a light-emitting element that can provide blue to green light emission with high color purity can be manufactured.

Since an anthracene derivative of the present invention has high emission efficiency, a light-emitting element with high emission efficiency can be obtained by use of the anthracene derivative of the present invention for a light-emitting element.

Further, by use of an anthracene derivative of the present invention, a light-emitting element with a long lifetime can be obtained.

Hereupon, any of various materials can be used as a substance in which one of the anthracene derivatives of the present invention is dispersed. In addition to the substances having high hole-transporting property or high electron-transporting property, 4,4'-bis(N-carbazolyl)-biphenyl (abbreviation: CBP), 2,2',2''-(1,3,5-benzenetriyl)tris[1-phenyl-1H-benzimidazole] (abbreviation: TPBI), 9,10-di(2-naphthyl)anthracene (abbreviation: DNA), 2-tert-butyl-9,10-di(2-naphthyl)anthracene (abbreviation: t-BuDNA); 9-[4-(N-carbazolyl)]phenyl-10-phenylanthracene (abbreviation: CzPA), or the like can be used. Further, as a substance to disperse an anthracene derivative of the present invention, a high molecular material can be used. For example, poly(N-vinylcarbazole) (abbreviation: PVK); poly(4-vinyltriphenylamine) (abbreviation: PVTPA); poly[N-(4-{N'-[4-(4-diphenylamino)phenyl]phenyl-N'-phenylamino}phenyl)methacrylamide] (abbreviation: PTPDMA); poly[N,N'-bis(4-butylphenyl)-N,N'-bis(phenyl)benzidine] (abbreviation: Poly-TPD), poly[(9,9-dihexylfluorene-2,7-diyl)-co-(pyridine-3,5-diyl)] (abbreviation: PF-Py); poly[(9,9-dioctylfluorene-2,7-diyl)-co-(2,2'-bipyridine-6,6'-diyl)] (abbreviation: PF-BPy), or the like can be used.

The light-emitting element in which an anthracene derivative of the present invention is used can emit blue to green light with high color purity, high efficiency, and a long lifetime; therefore, the light-emitting element is suitable for use for a full-color display.

Further, an anthracene derivative of the present invention can also be used as a host material of the third layer 105. Light emission from a dopant material that serves as a light-emitting substance can be obtained with a structure in which the dopant material is dispersed in the anthracene derivative of the present invention.

When an anthracene derivative of the present invention is used as a material in which another light-emitting substance is dispersed, an emission color depending on the light-emitting substance can be obtained.

Hereupon, any of a variety of materials can be used as the light-emitting substance dispersed in the anthracene derivative of the present invention. Specifically, fluorescent substances that emit fluorescence, such as 9,10-diphenyl-2-[N-phenyl-N-(9-phenyl-9H-carbazol-3-yl)amino]anthracene (abbreviation: 2PCAPA); 4-(dicyanomethylene)-2-methyl-6-(p-dimethylaminostyryl)-4H-pyran (abbreviation: DCM1); 4-(dicyanomethylene)-2-methyl-6-(julolidin-4-yl-vinyl)-4H-pyran (abbreviation: DC2); N,N-dimethylquinacridone (abbreviation: DMQd); rubrene; N,N'-bis[4-(9H-carbazol-9-yl)phenyl]-N,N'-diphenylstilbene-4,4'-diamine (abbreviation: YGA2S), or 4-(9H-carbazol-9-yl)-4'-(10-phenyl-9-anthryl)triphenylamine (abbreviation: YGAPA) can be used. Alternatively, phosphorescent substances that emit phosphorescence, such as (acetylacetonato)bis[2,3-bis(4-fluorophenyl)quinoxalinato]iridium(III) (abbreviation: Ir(Fdpq)$_2$(acac)), or 2,3,7,8,12,13,17,18-octaethyl-21H,23H-porphyrinplatinum(II) (abbreviation: PTOEP) can also be used.

The fourth layer 106 can be formed of a substance with a high electron-transporting property. For example, the fourth layer 106 is a layer including a metal complex having a quinoline skeleton or a benzoquinoline skeleton, such as tris(8-quinolinolato)aluminum (abbreviation: Alq); tris(4-methyl-8-quinolinolato)aluminum (abbreviation: Almq$_3$); bis(10-hydroxybenzo[h]quinolinato)beryllium (abbreviation: BeBq$_2$), or bis(2-methyl-8-quinolinolato)(4-phenylphenolato)aluminum (abbreviation: BAlq). Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can be used. Besides the metal complexes, 2-(4-biphenylyl)-5-(4-tert-butylphenyl)-1,3,4-oxadiazole (abbreviation: PBD; 1,3-bis[5-(p-tert-butylphenyl)-1,3,4-oxadiazole-2-yl]benzene (abbreviation: OXD-7); 3-(4-biphenylyl)-4-phenyl-5-(4-tert-butylphenyl)-1,2,4-triazole (abbreviation: TAZ); bathophenanthroline (abbreviation: BPhen); bathocuproine (abbreviation: BCP), or the like can also be used. The substances described here are mainly substances having electron mobility of greater than or equal to $10^{-6}$ cm$^2$/Vs. Note that a substance other than the above substances may be used for an electron-transporting layer as long as it has a higher electron-transporting property than a hole-transporting property. Further, the electron-transporting layer is not limited to a single layer, and a stacked layer having two or more layers formed of the aforementioned substances may be used.

Furthermore, a layer having a function of promoting electron injection (an electron-injecting layer) may be provided between the fourth layer 106 and the second electrode 107. As the layer having a function of promoting electron injection, an alkali metal, an alkaline earth metal, or a compound thereof such as lithium fluoride (LiF), cesium fluoride (CsF), or calcium fluoride (CaF$_2$) can be used. For example, a layer of a substance having an electron-transporting property which contains an alkali metal, an alkaline earth metal, or a compound thereof such as a layer of Alq which contains magnesium (Mg), may be used. Note that as the electron-injecting layer, a layer of a substance having an electron-transporting property which contains an alkali metal or an alkaline earth metal is preferably used, in which case electron injection from the second electrode 107 is efficiently performed.

As a substance for forming the second electrode 107, metal, an alloy, a conductive compound, a mixture thereof, or the like with a low work function (specifically, of less than or equal to 3.8 eV) can be used. As a specific example of such a cathode material, there are elements which belong to Group 1 or Group 2 of the periodic table, that is, alkali metals such as lithium (Li) and cesium (Cs), alkaline earth metals such as magnesium (Mg), calcium (Ca) and strontium (Sr), alloys containing such metals (e.g., MgAg, AlLi), rare earth metals such as europium (Eu) and ytterbium (Yb), alloys containing these elements, and the like. However, various conductive materials such as Al, Ag, ITO, or ITO containing silicon or silicon oxide can be used for the second electrode 107 regardless of the work function by providing a layer having a function of promoting electron injection between the second electrode 107 and the fourth layer 106 so that a layer having a function of promoting electron injection is stacked with the second electrode.

Further, the anthracene derivative of the present invention can also be used for a functional layer of the light-emitting element.

For the formation method of the first layer 103, the second layer 104, the third layer 105, and the fourth layer 106, various methods such as an evaporation method, a sputtering method, a droplet discharging method (an inkjet method), a spin coating method, or a printing method can be employed. Further, different formation methods may be employed for respective electrodes or layers.

When a thin film is formed by a wet process using a composition in a solution state in which an anthracene derivative of the present invention dissolves in a solvent, the composition including the anthracene derivative of the present invention and the solvent is attached to a region where the thin film is to be formed, the solvent is removed, and the resulting material is solidified, whereby the thin film is formed.

For the wet process, any of the following methods can be employed: a spin coating method, a roll coating method, a spray method, a casting method, a dipping method, a droplet discharging (ejection) method (an inkjet method), a dispenser method, and a variety of printing method (a method by which a thin film can be formed to have a desired pattern, such as screen (stencil) printing, offset (planographic) printing, letterpress printing, or gravure (intaglio) printing). Note that the composition of the present invention can be used without limitation to the above methods, as long as a liquid composition is used in the method.

Further, in the above-described composition, a variety of solvents can be used as the solvent. For example, the anthracene derivative of the present invention can be dissolved in the solvent that has aromatic rings (e.g., a benzene ring), such as toluene, xylene, methoxybenzene (anisole), dodecylbenzene, or a mixed solvent of dodecylbenzene and tetralin. The above-described anthracene derivatives can also be dissolved in an organic solvent that does not have aromatic rings, such as dimethylsulfoxide (DMSO), dimethylformamide (DMF), or chloroform.

Further, examples of other solvents include ketone solvents such as acetone, methyl ethyl ketone, diethyl ketone, n-propyl methyl ketone, and cyclohexanone, ester solvents such as ethyl acetate, n-propyl acetate, n-butyl acetate, ethyl propionate, γ-butyrolactone, and diethyl carbonate, ether solvents such as diethyl ether, tetrahydrofuran, and dioxane, alcohol solvents such as ethanol, isopropanol, 2-methoxyethanol, and 2-ethoxyethanol, and the like.

Further, the composition described in this embodiment may also contain any other organic material. For the organic material, any of aromatic compounds or heteroaromatic compounds which are solid at room temperature can be used. For the organic material, any of low molecular compounds or high molecular compounds can be used. When a low molecular compound is used, a low molecular compound (also referred to as a medium molecular compound) having a substituent that is capable of increasing the solubility in a solvent is preferably used.

The composition described in this embodiment may further include a binder in order to improve quality of the formed film. As the binder, it is preferable to use a high molecular compound that is electrically inactive. Specifically, polymethylmethacrylate (abbreviation: PMMA), polyimide, or the like can be used.

The light-emitting element of the present invention which has the above-mentioned structure emits light in such a manner that current flows due to a potential difference generated between the first electrode 102 and the second electrode 107 and holes and electrons recombine in the third layer 105 which is a layer containing a substance with a high light-emitting property. In other words, a light-emitting region is formed in the third layer 105.

Light emission is extracted outside through either or both the first electrode 102 and the second electrode 107. Accordingly, either or both the first electrode 102 and the second electrode 107 are formed using a light-transmitting substance. In the case where only the first electrode 102 is formed using a light-transmitting substance, light emission is extracted from the substrate side through the first electrode 102 as shown in FIG. 1A. In the case where only the second electrode 107 is formed using a light-transmitting substance, light emission is extracted from a side opposite the substrate through the second electrode 107 as shown in FIG. 1B. In the case where both the first electrode 102 and the second electrode 107 are formed using light-transmitting substances, the light emission is extracted from both the substrate side and the side opposite the substrate through the first electrode 102 and the second electrode 107 as shown in FIG. 1C.

Note that a structure of the layers provided between the first electrode 102 and the second electrode 107 is not limited to the structure described above. A structure other than the above-mentioned structure may be used as long as the light-emitting region in which holes and electrons are recombined is located away from the first electrode 102 and the second electrode 107, so as to prevent the quenching due to proximity of the light-emitting region and metal.

In other words, there is no particular limitation on the stacked-layer structure: the light-emitting layer including an anthracene derivative of the present invention may freely be combined with layers each including any of a substance having a high electron-transporting property, a substance having a high hole-transporting property, a substance having a high electron-injecting property, a substance having a high hole-injecting property, a bipolar substance (a substance having a high electron-transporting property and a high hole-transporting property), a hole-blocking material, or the like.

Figure 2:
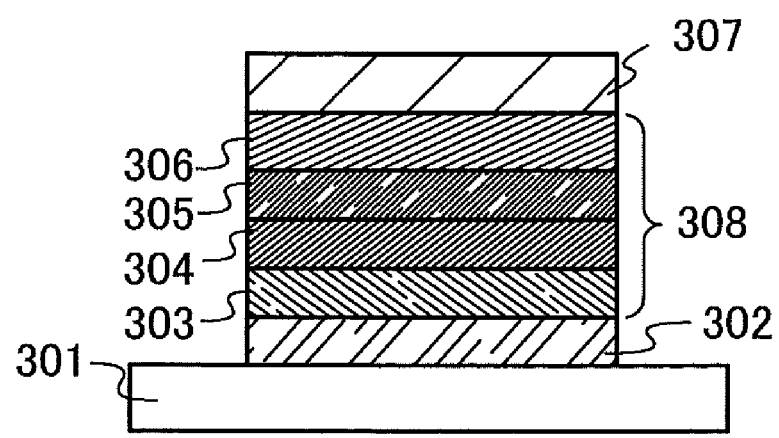
FIG. 2 illustrates a light-emitting element of the present invention.

In a light-emitting element shown in FIG. 2, an EL layer 308 is provided between a pair of electrodes that are a first electrode 302 and a second electrode 307 over a substrate 301. The EL layer 308 has a first layer 303 which includes a substance with a high electron-transporting property, a second layer 304 which includes a light-emitting substance, a third layer 305 which includes a substance with a high hole-transporting property, and a fourth layer 306 which includes a substance with a high hole-injecting property. The first electrode 302 which functions as a cathode, the first layer 303 which includes a substance with a high electron-transporting property, the second layer 304 which includes a light-emitting substance, the third layer 305 which includes a substance with a high hole-transporting property, the fourth layer 306 which includes a substance with a high hole-injecting property, and the second electrode 307 which functions as an anode are stacked in this order.

Hereinafter, specific methods of forming the light-emitting elements will be described.

In the light-emitting element of the present invention, the EL layer is interposed between the pair of electrodes. The EL layer includes at least a layer that contains a light-emitting substance (also referred to as a light-emitting layer) formed using an anthracene derivative of the present invention. Further, the EL layer may include a functional layer (e.g., a hole-injecting layer, a hole-transporting layer, an electron-transporting layer, or an electron-injecting layer) in addition to the layer which contains a light-emitting substance. Each of the electrodes (the first electrode and the second electrode), the layer which contains a light-emitting substance, and each functional layer may be formed by any of wet processes such as a droplet discharging method (an inkjet method), a spin coating method, or a printing method, or by any of dry processes such as a vacuum evaporation method, a CVD method, or a sputtering method. The use of a wet process enables the formation at atmospheric pressure using a simple device and a process; thus has the effects of simplifying the process and improving the productivity. In contrast, in a dry process, dissolution of a material is not needed and a material that has low solubility in a solution can be used so that the range of material choices is expanded.

All the formation of the thin films included in the light-emitting element may be conducted by a wet process. In this case, the light-emitting element can be fabricated with only facilities needed for a wet process. Alternatively, the stacked layers before the formation of the layer containing a light-emitting substance may be formed by a wet process, whereas the functional layer, the second electrode, and the like which are stacked over the layer containing a light-emitting substance may be formed by a dry process. Alternatively, the first electrode and the functional layer may be formed by a dry process before the formation of the layer containing a light-emitting substance, whereas the layer containing a light-emitting substance, the functional layer stacked thereover, and the second electrode may be formed by a wet process. Needless to say, the present invention is not limited to such methods, and the light-emitting element can be fabricated by appropriate selection from a wet process and a dry process depending on a material that is to be used, necessary film thickness, and the state of an interface.

In this embodiment, the light-emitting element is manufactured over a substrate including glass, plastic, or the like. A passive matrix light-emitting device can be manufactured by forming a plurality of such light-emitting elements over a substrate. Further, for example, a thin film transistor (TFT) may be formed over a substrate including glass, plastic, or the like, and a light-emitting element may be manufactured over an electrode electrically connected to the TFT. Thus, an active matrix light-emitting device in which a TFT controls the driving of a light-emitting element can be manufactured. Note that there is no particular limitation on a structure of the TFT. Either a staggered TFT or an inverted staggered TFT may be employed. In addition, there is also no particular limitation on crystallinity of a semiconductor used for the TFT, and an amorphous semiconductor may be used, or a crystalline semiconductor may be used. A driver circuit formed over a TFT substrate may be formed using either or both of n-channel transistors and p-channel transistors.

An anthracene derivative of the present invention is a bipolar material that allows both a hole and an electron to flow. In addition, an anthracene of the present invention has high electrochemical stability and thermal stability.

An anthracene derivative of the present invention has an extremely large band gap and emits light of a short wavelength; thus, blue to green light emission with high color purity can be obtained.

An anthracene derivative of the present invention has an extremely large band gap. Therefore, in a light-emitting element using an anthracene derivative of the present invention as a host material, even with the use of a dopant material emitting light of a relatively short wavelength, particularly blue, light emission not from the anthracene derivative of the present invention but from the dopant material can be efficiently obtained.

By using an anthracene derivative of the present invention as a light-emitting element, the light-emitting element with high efficiency, high reliability, and a long lifetime can be obtained.

Further, by using an anthracene derivative of the present invention, a light-emitting device and an electronic appliance each with high quality and high reliability can be obtained.

Embodiment 3

In this embodiment, a light-emitting element having a different structure from those described in Embodiment 2 will be described with reference to FIGS. 47A and 47B.

Figure 47A:
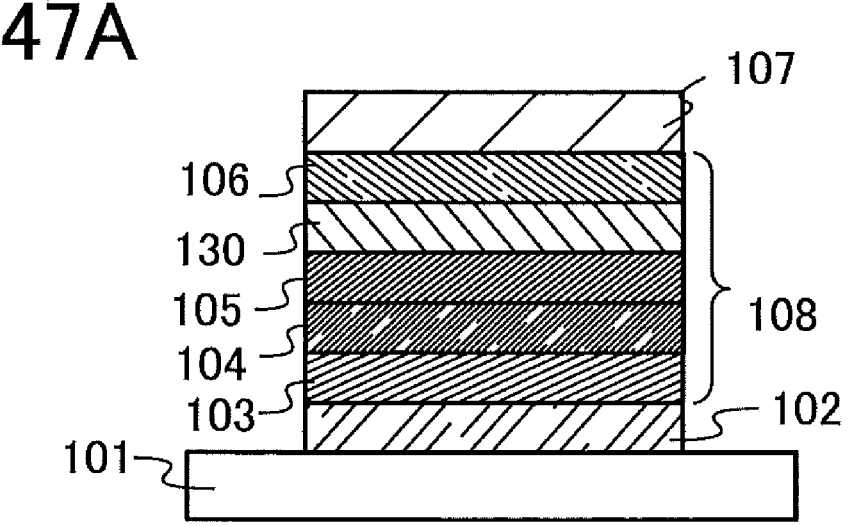
FIGS. 47A and 47B each illustrate a light-emitting element of the present invention.

In FIG. 47A, a layer for controlling transport of electron carriers may be provided between the electron-transporting layer and the light-emitting layer. A structure in which a layer 130 for controlling transport of electron carriers is provided between a fourth layer 106 that is an electron-transporting layer and a third layer 105 that is a light-emitting layer (also referred to as a light-emitting layer 105). This layer for controlling transport of electron carriers is formed by adding a small amount of substance with a high electron-trapping property to a material with a high electron-transport property as aforementioned, or alternatively, by adding a material with a low lowest unoccupied molecular orbital (LUMO) energy level and a hole-transport property to a material with a high electron-transport property. By suppressing transport of electron carriers, carrier balance can be adjusted. Such a structure is very effective in suppressing problems (e.g., shortening of element lifetime) caused when electrons pass through the third layer 105.

Figure 47B:
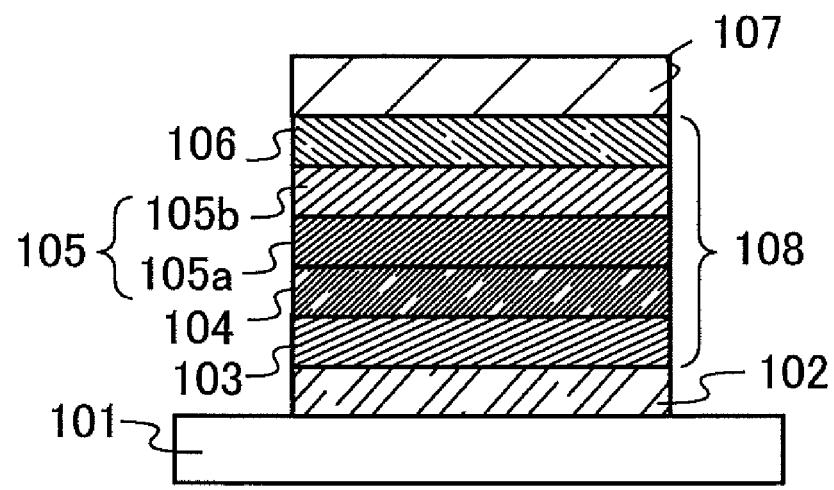

Further, in FIG. 47B, the light-emitting layer 105 may include a plurality of layers, greater than or equal to two layers, as another structure. An example in which the light-emitting layer 105 is formed of two layers of a first light-emitting layer 105a and a second light-emitting layer 105b.

For example, in the case where the light-emitting layer 105 is formed by stacking the first light-emitting layer 105a and the second light-emitting layer 105b in that order from the second layer 104 side which is the hole-transporting layer, a structure in which the first light-emitting layer 105a is formed using a substance with a hole-transporting property as a host material and the second light-emitting layer 105b is formed using a substance with an electron-transporting property may be employed.

An anthracene derivative of the present invention can be used alone for a light-emitting layer, and further can be used as a dopant material or as a host material.

In the case where an anthracene derivative of the present invention is used as a dopant material, light emitted from the anthracene derivative of the present invention can be obtained by adding an anthracene derivative of the present invention to a layer including a material having a larger band gap than the anthracene derivative of the present invention (hereinafter referred to as a host).

On the other hand, in the case where an anthracene derivative of the present invention is used as a host material, light emission can be obtained from a dopant material which serves as a light-emitting substance with the use of a structure where the dopant material which serves as a light-emitting substance is dispersed in the anthracene derivative of the present invention.

Further, an anthracene derivative of the present invention can be used for the first light-emitting layer 105a and the second light-emitting layer 105b since the anthracene derivative of the present invention has a bipolar property including a hole-transporting property and an electron-transporting property. An anthracene derivative of the present invention may be used alone for a light-emitting layer, and also may be used as a host material, or a dopant material of the first light-emitting layer 105a and the second light-emitting layer 105b.

Note that this embodiment can be appropriately combined with any other embodiment.

Embodiment 4

A mode of a light-emitting element having a structure in which a plurality of light-emitting units according to the present invention is stacked (hereinafter referred to as a stacked element) will be described with reference to FIG. 3 in this embodiment. This light-emitting element is a light-emitting element having a plurality of light-emitting units between a first electrode and a second electrode.

Figure 3:
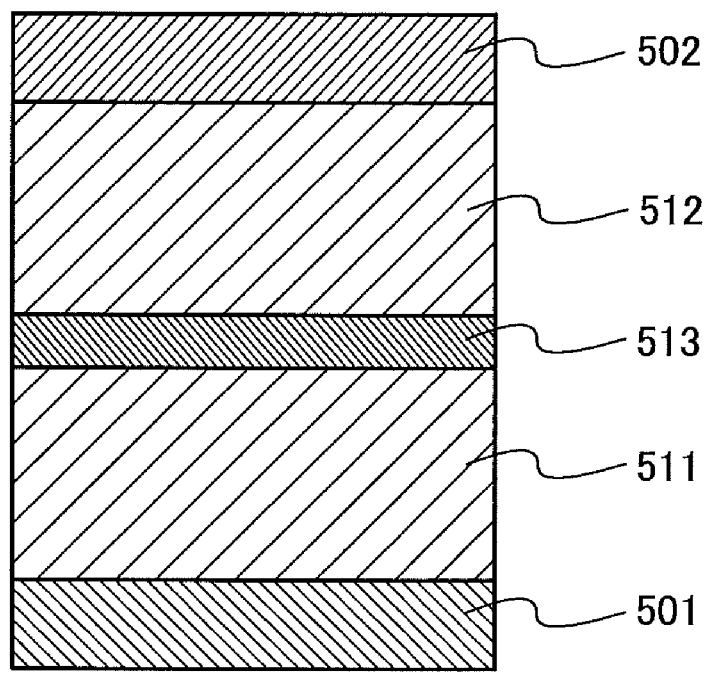
FIG. 3 illustrates a light-emitting element of the present invention.

In FIG. 3, a first light-emitting unit 511 and a second light-emitting unit 512 are stacked between a first electrode 501 and a second electrode 502. Electrodes similar to those in Embodiment 2 can be applied to the first electrode 501 and the second electrode 502. The first light-emitting unit 511 and the second light-emitting unit 512 may have either the same or a different structure, which can be similar to that in Embodiment 2.

A charge-generating layer 513 includes a composite material of an organic compound and metal oxide. This composite material of an organic compound and metal oxide is described in Embodiments 2 or 5, and includes an organic compound and metal oxide such as vanadium oxide, molybdenum oxide, or tungsten oxide. As the organic compound, various compounds such as an aromatic amine compound, a carbazole derivative, aromatic hydrocarbon, and a high molecular compound (oligomer, dendrimer, polymer, or the like) can be used. Note that an organic compound having a hole mobility of greater than or equal to $10^{-6}$ cm$^2$/Vs is preferably used as a hole-transporting organic compound. However, any substance other than the above-mentioned substances may also be used as long as a hole-transporting property thereof is higher than an electron-transporting property. The composite material of an organic compound and metal oxide is superior in carrier-injecting property and carrier-transporting property, and accordingly, low-voltage driving and low-current driving can be realized.

Note that a composite material of an organic compound and metal oxide may be combined with any other material to form the charge-generating layer 513. For example, a combination of a layer including the composite material of an organic compound and metal oxide may be combined with a layer including one compound selected from electron donating substances and a compound having a high electron-transporting property to form the charge generation layer 513. Alternatively, a layer including the composite material of an organic compound and metal oxide may be combined with a transparent conductive film to form the charge-generating layer 513.

In any case, the charge-generating layer 513 interposed between the first light-emitting unit 511 and the second light-emitting unit 512 may have any structure as long as electrons are injected to a light-emitting unit on one side and holes are injected to a light-emitting unit on the other side when a voltage is applied to the first electrode 501 and the second electrode 502.

Although the light-emitting element having two light-emitting units is described in this embodiment, a light-emitting element in which three or more light-emitting units are stacked can be similarly employed. When a charge-generating layer is provided between a pair of electrodes so as to partition the plural light-emitting units like the light-emitting element of this embodiment, light emission in a high luminous region can be obtained while low current density is kept, and accordingly a long lifetime element can be realized. In the case where the light-emitting element is applied to lighting as an application example, voltage drop due to resistance of an electrode material can be reduced; thus, light can be uniformly emitted in a large area. Moreover, a light-emitting device of low power consumption, which can be driven at low voltage, can be realized.

Note that this embodiment can be appropriately combined with any other embodiment.

Embodiment 5

A light-emitting device manufactured using an anthracene derivative of the present invention will be described in this embodiment.

In this embodiment, a light-emitting device manufactured using an anthracene derivative of the present invention will be described with reference to FIGS. 4A and 4B. Note that FIG. 4A represents a top view illustrating a light-emitting device, and FIG. 4B represents a cross-sectional view taken along lines A-B and C-D of FIG. 4A. A reference numeral 601 shown with dotted line represents a driver circuit portion (source side driver circuit), a reference numeral 602 represents a pixel portion, and a reference numeral 603 represents a driver circuit portion (gate side driver circuit). In addition, a reference numeral 604 represents a sealing substrate, a reference numeral 605 represents a sealant and a portion surrounded by the sealant 605 represents a space 607.

A lead wiring 608 is a wiring for transmitting signals input to the source side driver circuit 601 and a gate side driver circuit 603. The lead wiring 608 receives a video signal, a clock signal, a start signal, a reset signal, and the like from an FPC (flexible printed circuit) 609 which is an external input terminal. Note that only the FPC is shown here, but this FPC may be attached to a PWB (printed wiring board). The light-emitting device of this specification includes not only a light-emitting device itself but also a state in which an FPC or a PWB is attached thereto.

Next, a cross-sectional structure of the light-emitting device will be described with reference to FIG. 4B. Although the driver circuit portions and the pixel portion are formed over an element substrate 610, here, the source side driver circuit 601 that is the driver circuit portion and a pixel in the pixel portion 602 are shown.

Note that a CMOS circuit that is a combination of n-channel TFT 623 and p-channel TFT 624 is formed in the source side driver circuit 601. Alternatively, a TFT forming each driver circuit may be formed using any of various types of circuits such as a CMOS circuit, a PMOS circuit, and an NMOS circuit. A driver integration type in which a driver circuit is formed over a substrate is described in this embodiment, but a driver circuit is not necessarily formed over a substrate and can be formed outside a substrate.

The pixel portion 602 has a plurality of pixels, each of which includes a switching TFT 611, a current control TFT 612, and a first electrode 613 which is electrically connected to a drain of the current control TFT 612. Note that an insulator 614 is formed to cover an edge portion of the first electrode 613. Here, a positive photosensitive acrylic resin film is used.

In order to improve the coverage, the insulator 614 is formed to have a curved surface with curvature at an upper edge portion or a lower edge portion thereof. For example, in the case of using positive photosensitive acrylic as a material for the insulator 614, the insulator 614 is preferably formed to have a curved surface with a curvature radius (0.2 µm to 0.3 µm) only at the upper edge portion. Further, the insulator 614 can be formed using either negative photosensitive acrylic that becomes insoluble in an etchant due to light irradiation, or positive photosensitive acrylic that becomes dissoluble in an etchant due to light irradiation.

A layer 616 containing a light-emitting substance and the second electrode 617 are formed over the first electrode 613. Here, as a material used for the first electrode 613 that functions as an anode, it is preferable to use a material that has a high work function. For example, a single layer film such as an ITO (indium tin oxide) film, an indium tin oxide film containing silicon, an indium oxide film containing zinc oxide of 2 to 20 wt %, a titanium nitride film, a chromium film, a tungsten film, a Zn film, or a Pt film, a stacked layer formed of a titanium nitride and a film mainly containing aluminum, a three-layer stacked structure of a titanium nitride film, a film mainly containing aluminum and a titanium nitride film, or the like can be used. Note that if the first electrode 613 is formed to have a stacked structure, resistance as a wiring can be suppressed low, favorable ohmic contact can be obtained, and further it can function as an anode.

In addition, the layer 616 containing a light-emitting substance is formed by any of various methods such as an evaporation method using an evaporation mask, a droplet discharging method like an ink-jet method, a printing method, and a spin coating method. The layer 616 containing a light-emitting substance includes an anthracene derivative of the present invention described in Embodiment 1. Further, the layer 616 containing a light-emitting substance may include another material such as a low molecular material, oligomer, dendrimer, or a high molecular material.

As a material used for the second electrode 617 which is formed over the layer 616 containing a light-emitting substance and functions as a cathode, a material having a low work function (Al, Mg, Li, Ca, an alloy or a compound thereof such as MgAg, MgIn, AlLi, LiF, $CaF_2$, or the like) is preferably used. Note that, in the case where light generated in the layer 616 containing a light-emitting substance is transmitted through the second electrode 617, stacked layers of a metal thin film having a reduced thickness and a transparent conductive film (ITO, indium oxide containing zinc oxide at 2 to 20 wt %, indium oxide-tin oxide containing silicon or silicon oxide, zinc oxide (ZnO), or the like) are preferably used as the second electrode 617.

Further, the sealing substrate 604 is attached to the element substrate 610 with the sealant 605, whereby a light-emitting element 618 is provided in the space 607 surrounded by the element substrate 610, the sealing substrate 604, and the sealant 605. Note that the space 607 is filled with filler. There is the case where the space 607 is filled with the sealant 605 in addition to the case where the space 607 is filled with an inert gas (nitrogen, argon, or the like).

Note that it is preferable to use an epoxy-based resin as the sealant 605. In addition, it is preferable that such a material allow penetration of as little moisture or oxygen as possible. As a material used for the sealing substrate 604, a plastic substrate formed of FRP (fiberglass-reinforced plastics), PVF (polyvinyl fluoride), polyester, acrylic, or the like can be used instead of a glass substrate or a quartz substrate.

As described above, a light-emitting device manufactured using an anthracene derivative of the present invention can be obtained.

An anthracene derivative of the present invention is a bipolar substance having a large band gap and allows both a hole and an electron to flow. Therefore, a light-emitting element with a good carrier balance and high reliability can be obtained.

Further, a light-emitting device and an electronic appliance each with high reliability can be obtained by use of an anthracene derivative of the present invention.

Figure 5A:
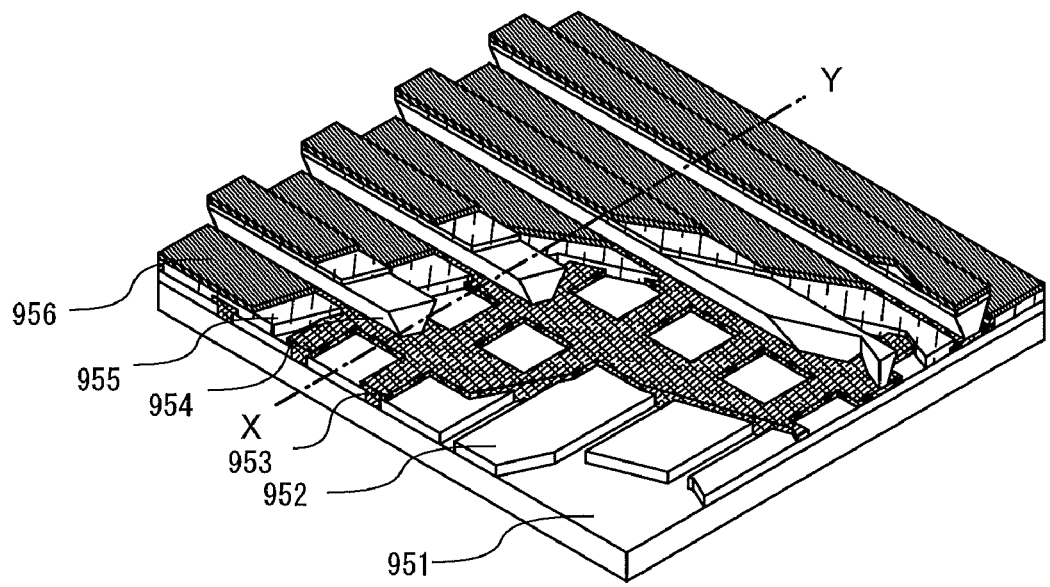
FIGS. 5A and 5B illustrate a light-emitting device of the present invention.
Figure 5B:
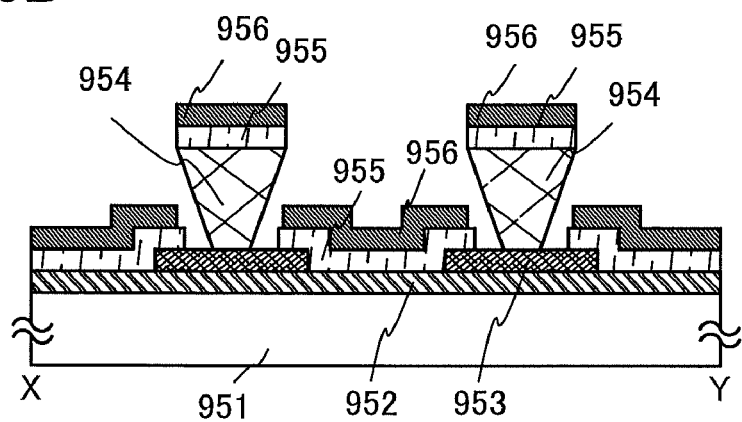

Although as described above, an active matrix light-emitting device in which operation of a light-emitting element is controlled by a transistor is described in this embodiment, the light-emitting element may also be a passive matrix light-emitting device. FIG. 5A shows a perspective view of a passive matrix light-emitting device that is manufactured by application of the present invention. In FIGS. 5A and 5B, a layer 955 containing a light-emitting substance is provided between an electrode 952 and an electrode 956 over a substrate 951. The edge portion of the electrode 952 is covered with an insulating layer 953. Then, a partition layer 954 is provided over the insulating layer 953. The sidewalls of the partition layer 954 are aslope so that a distance between both sidewalls is gradually narrowed toward the surface of the substrate. That is, a cross section in the direction of a narrow side of the partition layer 954 has a trapezoidal shape, and a lower side (which faces a surface of the insulating layer 953 and is in contact with the insulating layer 953) is shorter than an upper side (which faces the surface of the insulating layer 953 and is not in contact with the insulating layer 953). By providing the partition layer 954 in this manner, defects of the light-emitting element due to static charge or the like can be prevented. A light-emitting device with high reliability can be obtained also in the case of the passive-matrix light-emitting device by including a light-emitting element of the present invention.

Embodiment 6

In this embodiment an electronic appliance of the present invention which includes the light-emitting device described in Embodiment 5 as a part will be described. The electronic appliance of the present invention includes an anthracene derivative described in Embodiment 1, and has a display portion with high reliability.

There are examples of an electronic appliance including a light-emitting element manufactured using an anthracene derivative of the present invention, a camera such as a video camera or a digital camera, a goggle type display, a navigation system, an audio replay device (a car audio system, an audio system, and the like), a computer, a game machine, a portable information terminal (a mobile computer, a cellular phone, a portable game machine, an electronic book, and the like), and an image replay device provided with a recording medium (specifically, a device capable of replaying a recording medium such as a digital versatile disc (DVD) and provided with a display device that can display the image), and the like. Specific examples of these electronic appliances are shown in FIGS. 6A to 6E.

Figure 6A:
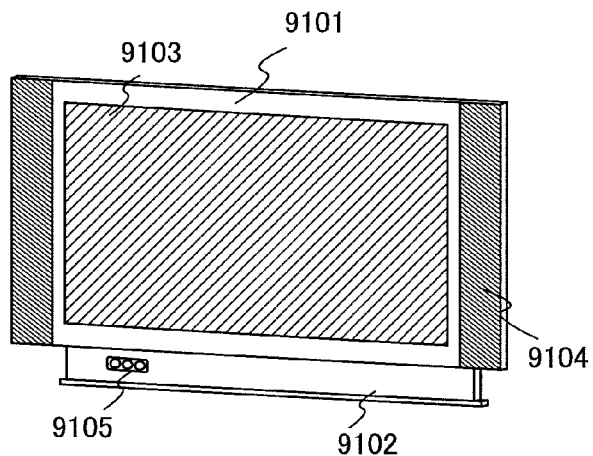
FIGS. 6A to 6E each illustrate electronic appliances of the present invention.

FIG. 6A illustrates a television set according to the present invention, which includes a housing 9101, a supporting base 9102, a display portion 9103, a speaker portion 9104, a video input terminal 9105, and the like. In this television set, the display portion 9103 includes light-emitting elements similar to those described in Embodiment 2 or Embodiment 3, which are arranged in matrix. The light-emitting element has a feature of high reliability. The display portion 9103 that includes the light-emitting elements has similar features; therefore, in the television set, image quality hardly deteriorates and high reliability is achieved. With such features, the number or size of deterioration compensation functions and power source circuits of the television set can be significantly reduced; therefore, the housing 9101 and the supporting base 9102 can be reduced in size and weight. An improvement in image quality and reductions in size and weight are achieved in the television set of the present invention; therefore, a product that is suitable for the living environment can be provided.

Figure 6B:
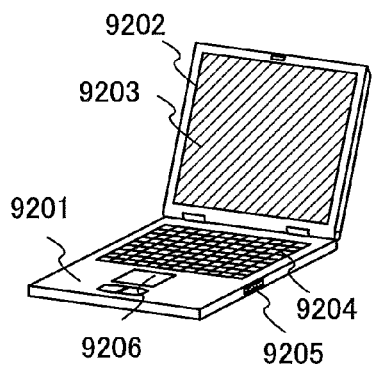

FIG. 6B illustrates a computer according to the present invention, which includes a main body 9201, a housing 9202, a display portion 9203, a keyboard 9204, an external connection port 9205, a pointing device 9206, and the like. In this computer, the display portion 9203 includes light-emitting elements similar to those described in Embodiment 2 or Embodiment 3, which are arranged in matrix. The light-emitting element has a feature of high reliability. The display portion 9203 that includes the light-emitting elements has similar features; therefore, in the computer, image quality hardly deteriorates and high reliability is achieved. With such features, the number or size of deterioration compensation functions and power source circuits of the computer can be significantly reduced; therefore, the main body 9201 and the housing 9202 can be reduced in size and weight. An improvement in image quality and reductions in size and weight are achieved in the computer of the present invention; therefore, a product that is suitable for the environment can be provided.

Figure 6C:
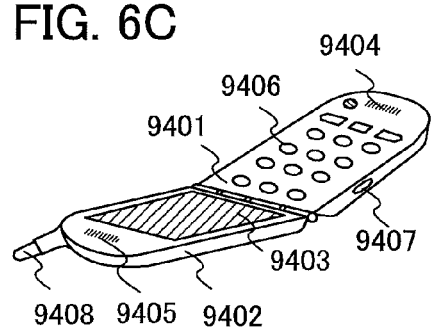

FIG. 6C illustrates a cellular phone according to the present invention, which includes a main body 9401, a housing 9402, a display portion 9403, an audio input portion 9404, an audio output portion 9405, operation keys 9406, an external connection port 9407, an antenna 9408, and the like. In this cellular phone, the display portion 9403 includes light-emitting elements similar to those described in Embodiment 2 or Embodiment 3, which are arranged in matrix. The light-emitting element has a feature of high reliability. The display portion 9403 that includes the light-emitting elements has similar features; therefore, in the cellular phone, image quality hardly deteriorates and high reliability is achieved. With such features, the number or size of deterioration compensation functions and power source circuits of the cellular phone can be significantly reduced; therefore, the main body 9401 and the housing 9402 can be reduced in size and weight. An improvement in image quality and reductions in size and weight are achieved in the cellular phone of the present invention; therefore, a product that is suitable for being carried can be provided.

Figure 6D:
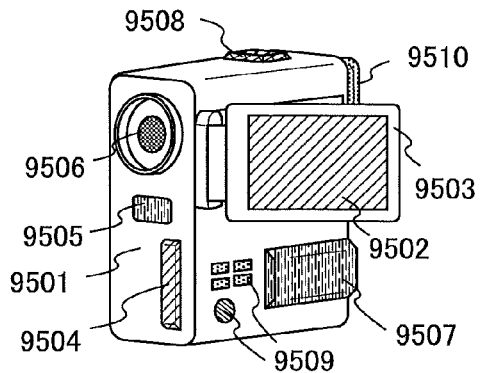

FIG. 6D illustrates a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In this camera, the display portion 9502 includes light-emitting elements similar to those described in Embodiment 2 or Embodiment 3, which are arranged in matrix. The light-emitting element has a feature of high reliability. The display portion 9502 that includes the light-emitting elements has similar features; therefore, in the camera, image quality hardly deteriorates and high reliability is achieved. With such features, the number or size of deterioration compensation functions and power source circuits of the camera can be significantly reduced; therefore, the main body 9501 can be reduced in size and weight. An improvement in image quality and reductions in size and weight are achieved in the camera of the present invention; therefore a product which is suitable for being carried can be provided.

Figure 6E:
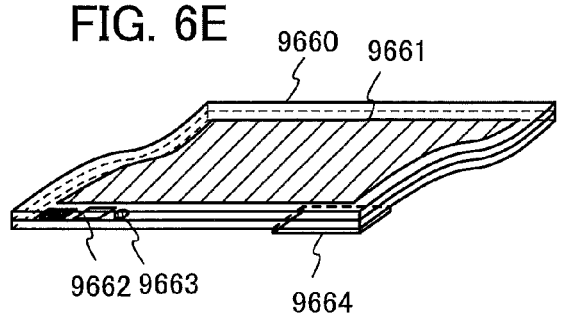

FIG. 6E shows a flexible electronic appliance having display function according to the present invention and includes a main body 9660, a display portion 9661 which displays images, a driver IC 9662, a receiver 9663, a film battery 9664, and the like. The driver IC, the receiver, or the like may be mounted using a semiconductor component. In the electronic appliance of the present invention, the main body 9660 is formed using a flexible material such as plastic or a film. In the electronic appliance, the display portion 9661 has light-emitting elements similar to those described in Embodiment 2 or Embodiment 3 arranged in matrix. The light-emitting element has a feature of high reliability. The display portion 9661 that includes the light-emitting elements has similar features; therefore, in the electronic appliance, image quality hardly deteriorates and high reliability is achieved. With such features, the number or size of deterioration compensation functions and power source circuits of the television set can be significantly reduced; therefore, the main body 9660 can be reduced in size and weight.

Furthermore, an improvement in image quality and reductions in size and weight are achieved in the flexible electronic appliance having the display function according to the present invention; therefore the electronic appliance is suitable for being carried can be provided and can be rolled into a cylinder shape as well; thus, the electronic appliance has a great advantage in terms of portability. The electronic appliance of the present invention allows a display medium having a large screen to be freely carried.

As described above, the applicable range of the light-emitting device of the present invention is wide so that the light-emitting device can be applied to electronic appliances in various fields. By use of an anthracene derivative of the present invention, electronic appliances having display portions with high reliability can be provided.

Further, the light-emitting device of the present invention can also be used as a lighting apparatus. One mode using the light-emitting element of the present invention as a lighting apparatus will be described with reference to FIG. 7.

Figure 7:
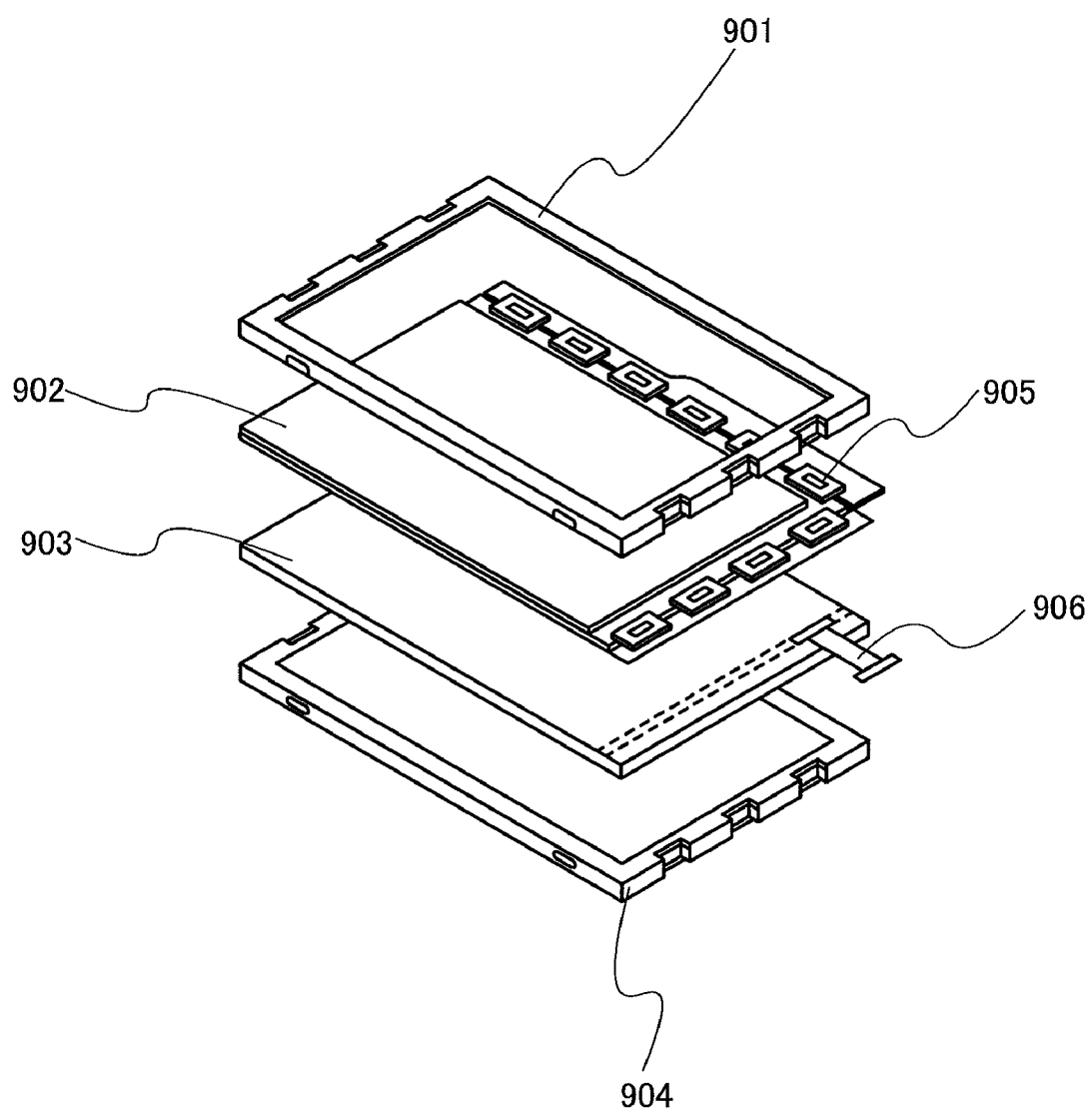
FIG. 7 illustrates an electronic appliance of the present invention.

FIG. 7 illustrates an example of a liquid crystal display device in which the light-emitting device of the present invention is used as a backlight. The liquid crystal display device shown in FIG. 7 includes a housing 901, a liquid crystal layer 902, a backlight 903, and a housing 904, and the liquid crystal layer 902 is connected to a driver IC 905. The light-emitting device of the present invention is used as the backlight 903, and current is supplied through a terminal 906.

By use of the light-emitting device of the present invention as the backlight of the liquid crystal display device, a backlight with high reliability can be obtained. Further, the light-emitting device of the present invention is a plane emission type lighting apparatus and can have a large area; therefore, the backlight can have a large area, and a liquid crystal display device can also have a large area. Furthermore, since the light-emitting device of the present invention is thin, a thinner shape display device can also be achieved.

Figure 8A:
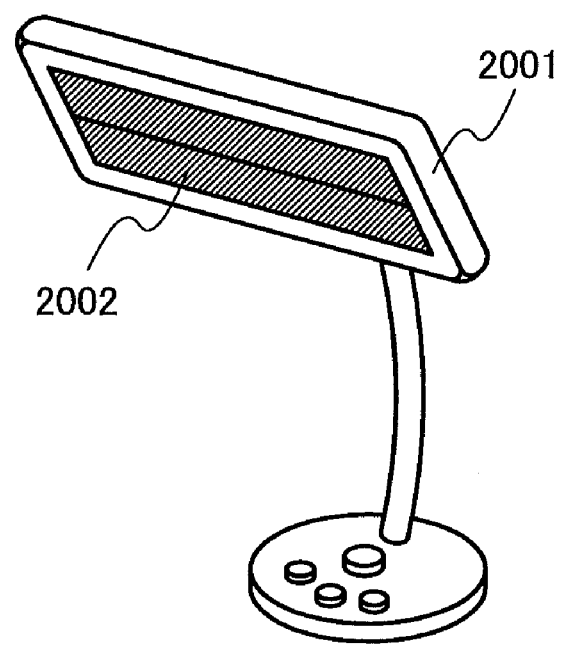
FIGS. 8A and 8B each illustrate lighting apparatuses of the present invention.
Figure 8B:
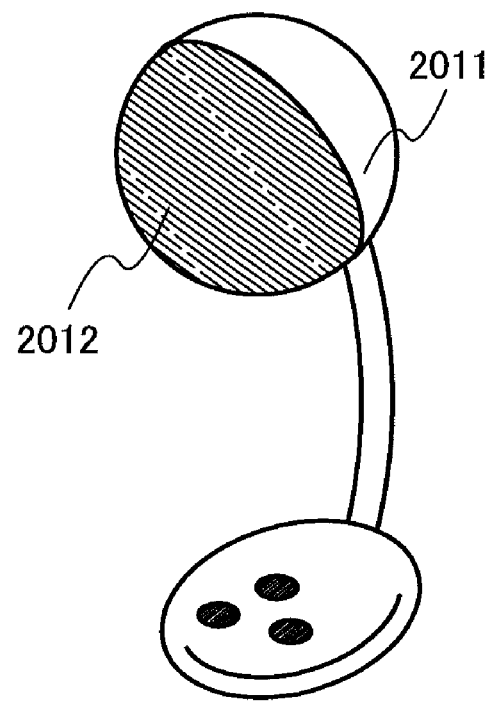

Each of FIGS. 8(A) and (B) illustrates an example of using the light-emitting device to which the present invention is applied as a desk lamp, which is a lighting apparatus. A desk lamp shown in FIG. 8(A) includes a housing 2001 and a light source 2002, and the light-emitting device of the present invention is used as the light source 2002. A desk lamp shown in FIG. 8(A) includes a housing 2011 and a light source 2012, and the light-emitting device of the present invention is used as the light source 2012. Since the light-emitting device of the present invention is highly reliable, the desk lamp also has high reliability.

Figure 9:
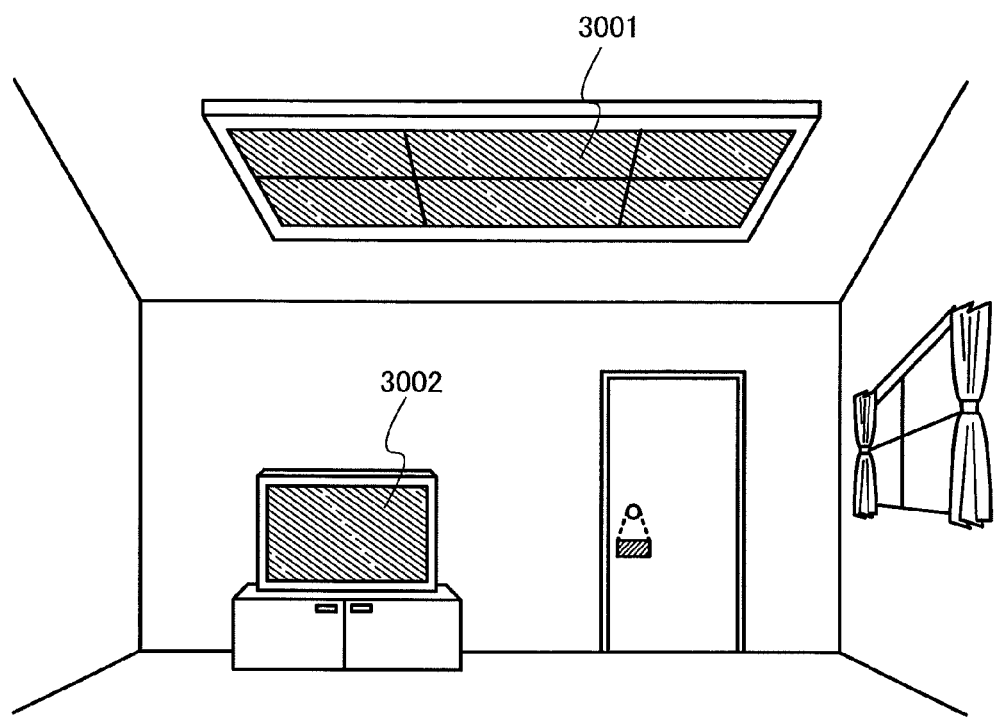
FIG. 9 illustrates a lighting apparatus of the present invention.

FIG. 9 illustrates an example of using the light-emitting device to which the present invention is applied as an indoor lighting apparatus 3001. Since the light-emitting device of the present invention can have a large area, it can be used as a lighting apparatus having a large area. Furthermore, since the light-emitting device of the present invention is thin, a thinner shape display device can also be achieved. A television set 3002 according to the present invention as illustrated in FIG. 6A is placed in a room where the light-emitting device to which the present invention is applied is used in this manner as the indoor lighting apparatus 3001, so that public broadcasting and movies can be watched.

Example 1

In this example, a synthesis method of N-[4'-(10-phenyl-9-anthryl)biphenyl-4-yl]-N,N',N'-triphenyl-benzidine (abbreviation: DPBAPBA), which is an anthracene derivative of the present invention represented by the structural formula (101), will be specifically described.

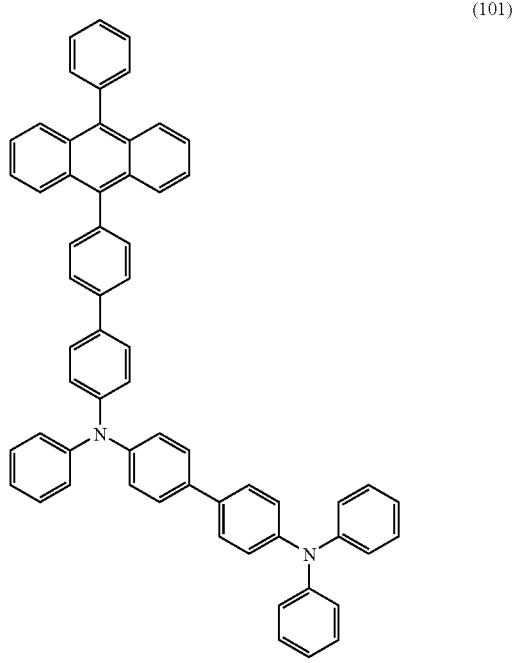

(101)

[Step 1] Synthesis of 9-phenylanthracene

A synthesis scheme of 9-phenylanthracene is shown in (a-1).

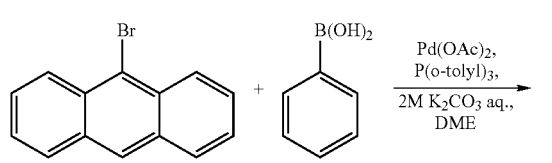

(a-1)

In a 200 mL three-neck flask, 6.4 g (25 mmol) of 9-bromoanthracene, 3.0 g (25 mmol) of phenylboronic acid, 0.76 g (2.5 mmol) of tri(ortho-tolyl)phosphine, 60 mL of 1,2-dimethoxyethane (DME), and 25 mL of a 2.0 M potassium carbonate aqueous solution were added. The mixture was degassed by being stirred under reduced pressure, and the atmosphere in the flask was replaced with nitrogen. To the mixture, 0.11 g (0.50 mmol) of palladium(II) acetate was added and stirred under a nitrogen stream at 80° C. for 3 hours. After a predetermined time, water was added to the mixture, and an aqueous layer was extracted with toluene. The obtained extracted solution and the organic layer were combined and washed with saturated saline, and the organic layer was dried with magnesium sulfate. The obtained mixture was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was concentrated to give a solid. The obtained solid was recrystallized with toluene/methanol to give 5.8 g of white powder, which was the object of the synthesis, in a yield of 92%.

[Step 2] Synthesis of 9-iodo-10-phenylanthracene

A synthesis scheme of 9-iodo-10-phenylanthracene is shown in (a-2).

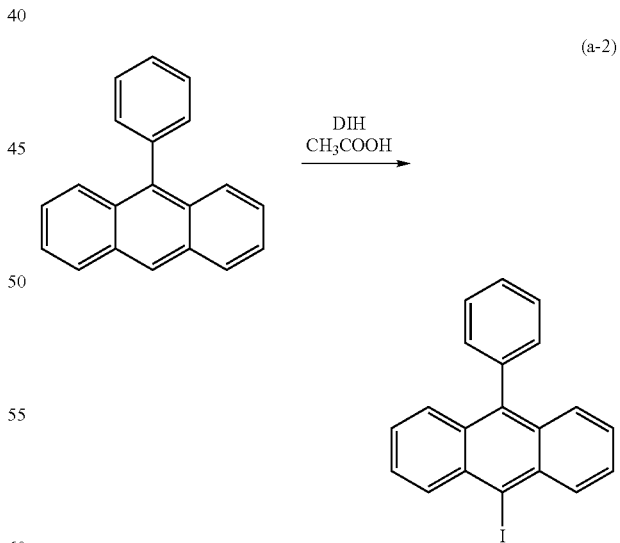

(a-2)

Into a 500 mL Erlenmeyer flask was put 4.5 g (18 mmol) of 9-phenylanthracene. Then 200 mL of acetic acid was added to the flask, followed by heating to 70° C., and 9-phenylanthracene was dissolved therein. Into this solution, 5.2 g (13 mmol) of 1,3-diiodo-5,5-dimethylimidazolidine-2,4-dione (abbreviation: DIH) was added. This solution was stirred in air at 70° C. for 3 hours. After the stirring, about 100 mL of water and about 200 mL of chloroform were added to this solution. This mixture was washed with water twice, and the aqueous layer was extracted with chloroform. The extracted solution was combined with the organic layer and washed with a saturated saline, and then the organic layer was dried with magnesium sulfate. This mixture was gravity filtered, and the obtained filtrate was concentrated to give a brown solid. This solid was washed with hexane to give 5.8 g of a yellow solid, which was the object of the synthesis, in a yield of 86%.

[Step 3] Synthesis of 9-(4'-bromobiphenyl-4-yl)-10-phenylanthracene

A synthesis scheme of 9-(4'-bromobiphenyl-4-yl)-10-phenylanthracene is shown in (a-3).

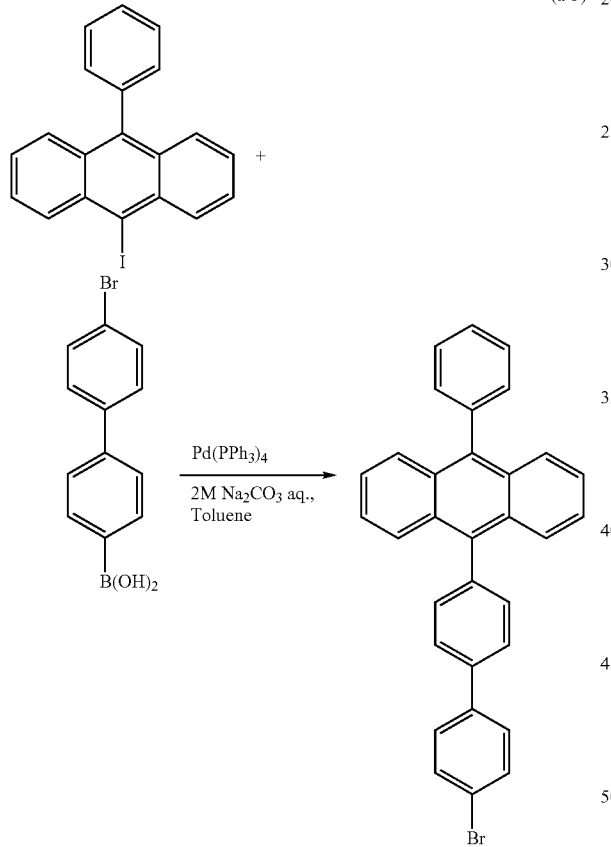

Into a 100 mL three-neck flask were put 2.8 g (7.2 mmol) of 9-iodo-10-phenylanthracene and 1.5 g (7.2 mmol) of 4'-bromobiphenyl-4-boronic acid, and the atmosphere in the flask was replaced with nitrogen. To the mixture, 40 mL of toluene and 10 mL (2.0 mol/L) of a sodium carbonate aqueous solution were added. The mixture was stirred under reduced pressure to be degassed. After the degassing, 120 mg (0.10 mmol) of tetrakis(triphenylphosphine)palladium(0) was added to the mixture. The mixture was stirred at 90° C. for 4 hours. After the stirring, about 50 mL of toluene was added to the mixture. The mixture was subjected to suction filtration through alumina, Celite (produced by Wako Pure Chemical Industries, Ltd., Catalog No. 531-16855), and Florisil (produced by Wako Pure Chemical Industries, Ltd., Catalog No. 540-00135). The solid obtained by condensation of the obtained filtrate was purified by high-performance liquid chromatography (the mobile phase: chloroform) to give a light yellow solid. The obtained solid was recrystallized with chloroform/hexane to give 1.4 g of a light yellow powdered solid, which was the object of the synthesis, in a yield of 40%.

[Step 4] Synthesis of triphenylamine-4-boronic acid

A synthesis scheme of triphenylamine-4-boronic acid is shown in (a-5).

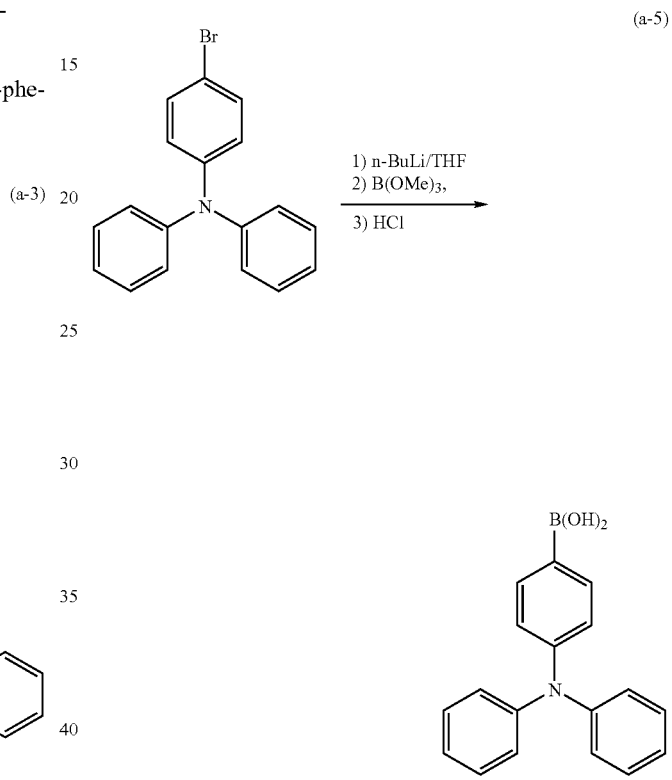

Into a 500 mL three-neck flask was put 10 g (31 mmol) of 4-bromotriphenylamine, and the atmosphere in the flask was replaced with nitrogen. Into the mixture, 150 mL of tetrahydrofuran (THF) was added and the solution was cooled to −80° C. Then 20 mL (32 mmol) of n-butyllithium (1.58 mol/L hexane solution) was dropped with a syringe into this solution. After the dropping, the solution was stirred at the same temperature for one hour. After 3.8 mL (34 mmol) of trimethyl borate was added into this solution, the solution was stirred for about 15 hours while the temperature of the solution was being increased to room temperature. After the stirring, about 150 mL (1.0 mol/L) of dilute hydrochloric acid was added into this solution and stirred for one hour. After the stirring, an aqueous layer of the mixture was extracted with ethyl acetate and the extracted solution was combined with the organic layer and washed with a saturated sodium hydrogen carbonate aqueous solution. The organic layer was dried with magnesium sulfate, the mixture was filtered, and the filtrate was concentrated to give an oily light-brown substance. About 20 mL of chloroform was added into this oily substance, and further about 50 mL of hexane was added thereto. Then the mixture was left for one hour, so that a white solid was precipitated. This solid was collected by suction filtration, so that 5.2 g of the white solid was obtained in a yield of 58%.

113

[Step 5] Synthesis of N,N',N'-triphenylbenzidine

A synthesis scheme of N,N',N'-triphenylbenzidine is shown in (a-6).

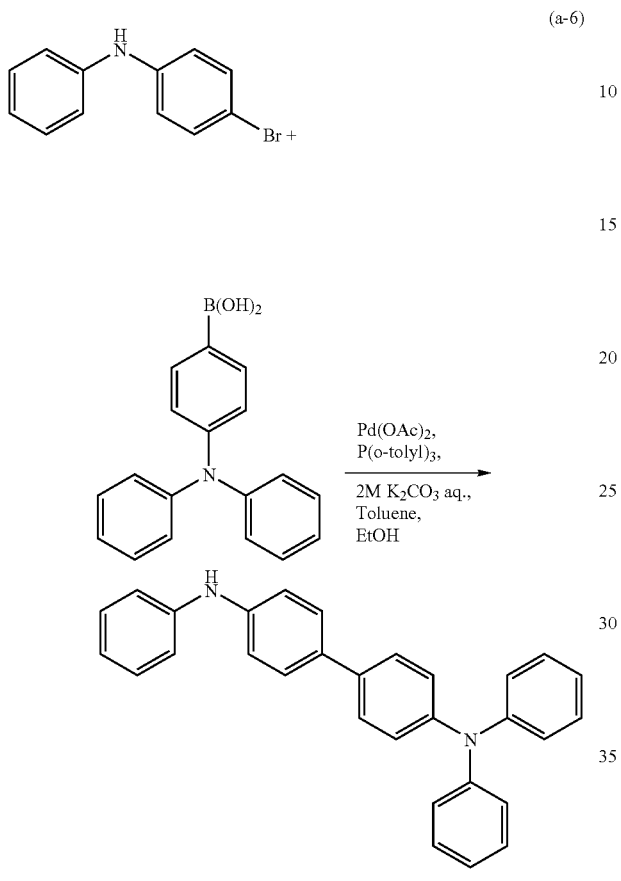

(a-6)

Into a 500 mL three-neck flask were put 4.3 g (17 mmol) of 4-bromodiphenylamine, 5 g (17 mmol) of triphenylamine-4-boronic acid, and 532 mg (1.8 mmol) of tri(o-tolyl)phosphine, and the atmosphere in the flask was replaced with nitrogen. Then, 60 mL of toluene, 40 mL of ethanol, and 14 mL of potassium carbonate aqueous solution (0.2 mol/L) were added to this mixture. After this mixture was degassed under reduced pressure, 75 mg (0.35 mmol) of palladium (II) acetate was added. This mixture was refluxed at 100° C. for 10.5 hours. After the reflux, the aqueous layer of the mixture was extracted with toluene. The extracted solution was combined with an organic layer and washed with a saturated saline, and magnesium sulfate was added thereto for drying. This mixture was filtered and the filtrate was concentrated to give an oily light-brown substance. The oily substance was dissolved in toluene of about 50 mL, and then subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135). A solid obtained by concentrating the filtrate was purified by a silica gel column chromatography (developing solvent was a mixed solvent of hexane:toluene 4:6) to give a white solid. The obtained white solid was recrystallized with chloroform/hexane, so that 3.5 g of a white solid was obtained in a yield of 49%.

114

[Step 6] Synthesis of N-[4'-(10-phenyl-9-anthryl)biphenyl-4-yl]-N,N',N'-triphenyl-benzidine (abbreviation: DPBAPBA A synthesis scheme of DPBAPBA is shown in (a-7).

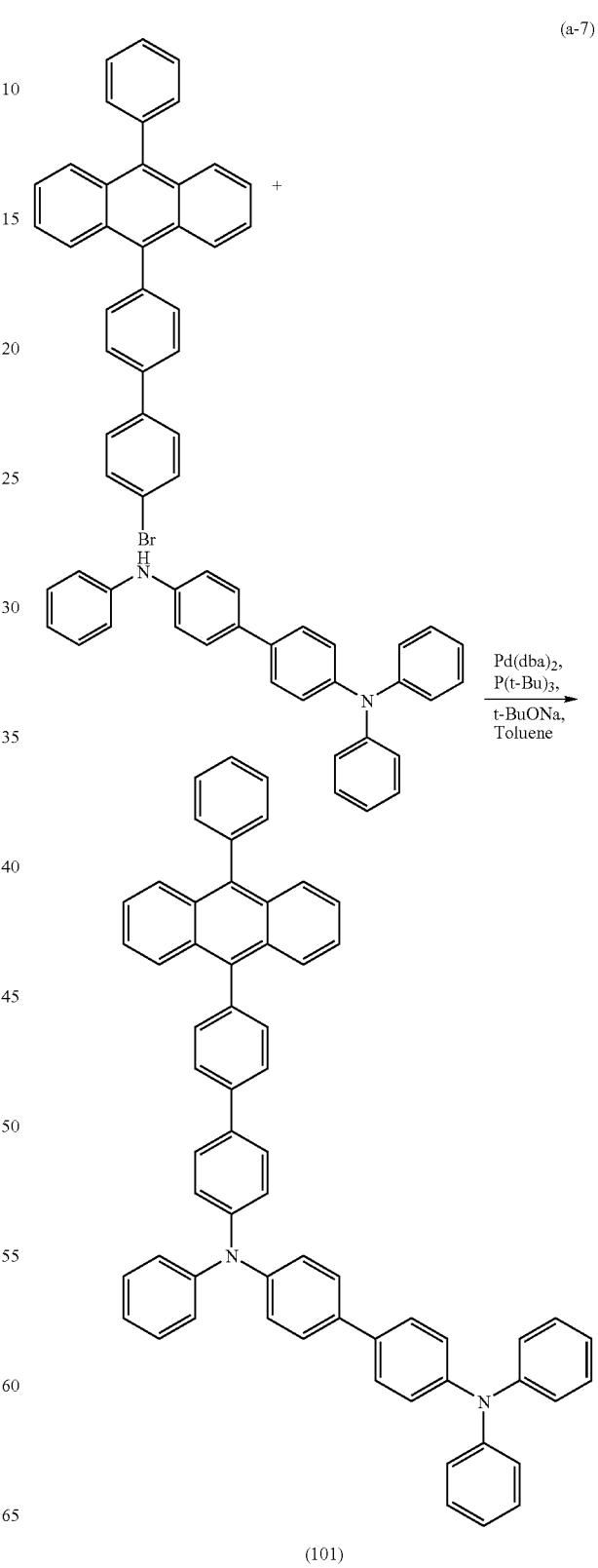

(a-7)

(101)

Into a 50 mL three-neck flask were put 1.1 g (2.2 mmol) of 9-(4'-bromobiphenyl-4-yl)-10-phenylanthracene, 0.93 g (2.2 mmol) of N,N',N'-triphenylbenzidine (abbreviation: DPBA), and 1.0 g (10 mmol) of sodium tert-butoxide, and the atmosphere in the flask was replaced with nitrogen. Then, 15 mL of toluene and 0.10 mL of tri(tert-butyl)phosphine (10 wt % hexane solution) were added into this mixture. After this mixture was degassed under reduced pressure while being stirred, 58 mg (0.10 mmol) of bis(dibenzylideneacetone)palladium(0) was added thereto. Then, the mixture was stirred at 90° C. for 3 hours. After the stirring, about 20 mL of toluene was added into the mixture. The mixture was subjected to suction filtration to remove the solid, the obtained filtrate was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135). A solid obtained by concentration of the filtrate was recrystallized with toluene/hexane to give 0.92 g of a light yellow solid, which was the object of the synthesis, in a yield of 50%.

Then, 0.92 g of the obtained light yellow solid was sublimated and purified by a train sublimation method. For sublimation purification conditions, the light yellow solid was heated at 340° C. under a reduced pressure with a flow rate of argon gas of 3.0 mL/min. After the sublimation purification, 0.50 g of a light yellow solid was obtained in a yield of 54%.

By a nuclear magnetic resonance (NMR) measurement, it was confirmed that this compound was N-[4'-(10-phenyl-9-anthryl)biphenyl-4-yl]-N,N',N'-triphenylbenzidine (abbreviation: DPBAPBA).

$^1$H NMR data of the obtained compound is shown below.
$^1$H NMR (CDCl3, 300 MHz): δ 7.15 (d, J=8.7 Hz, 5H), 7.32-7.38 (m, 8H), 7.48-7.65 (m, 15H), 7.67-7.72 (m, 8H), 7.77-7.80 (m, 4H), 7.82 (d, J=8.4 Hz, 4H).

Figure 10A:
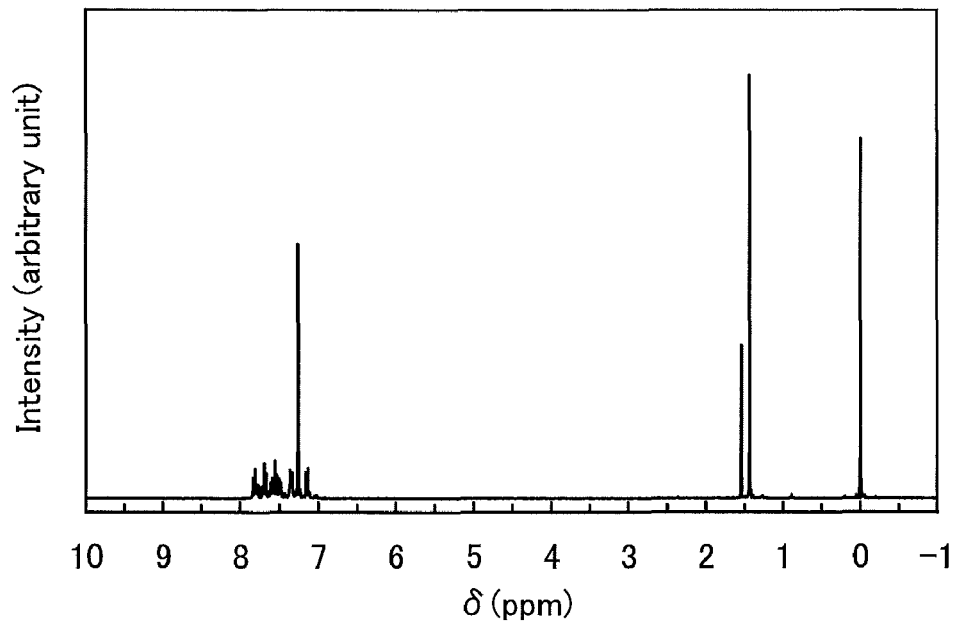
FIGS. 10A and 10B a $^1$H-NMR chart of DPBAPBA.
Figure 10B:
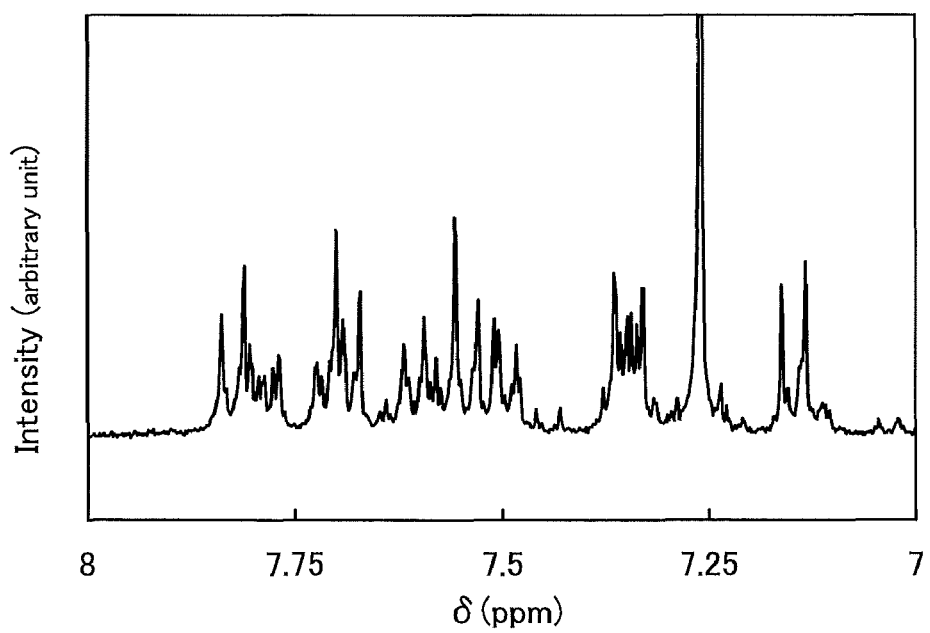

In addition, the $^1$H NMR chart is shown in FIGS. 10A and 10B. Note that FIG. 10B is a chart showing an enlargement of FIG. 10A in the range of 7.0 to 8.0 ppm.

Figure 11:
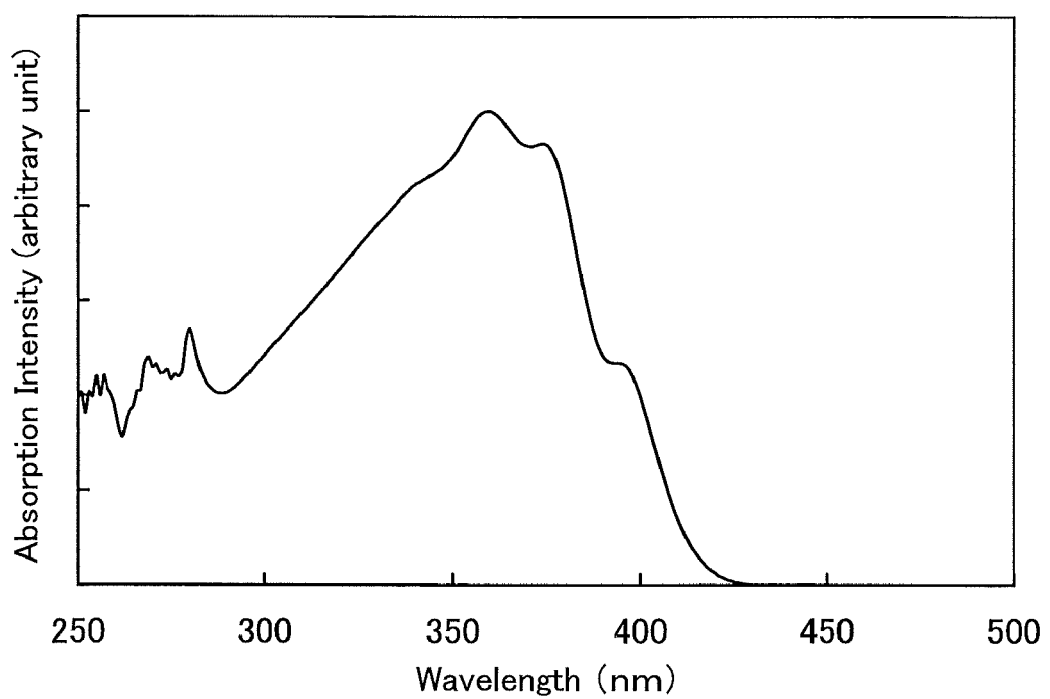
FIG. 11 is a graph showing an absorption spectrum of a toluene solution of DPBAPBA.
Figure 12:
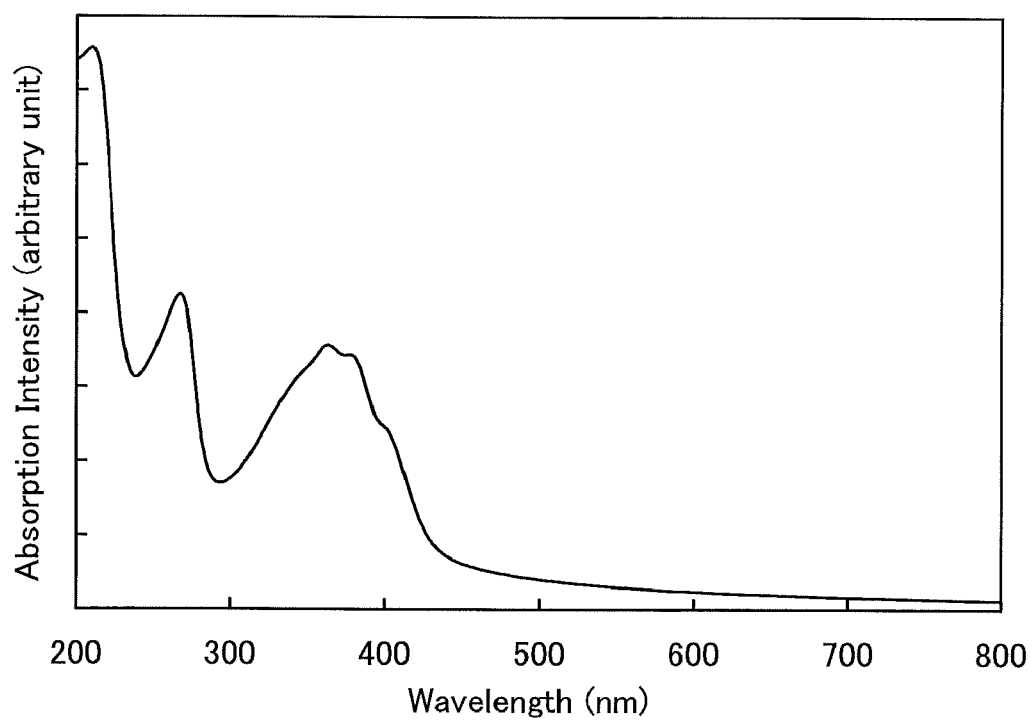
FIG. 12 is a graph showing an absorption spectrum of a thin film of DPBAPBA.
Figure 13:
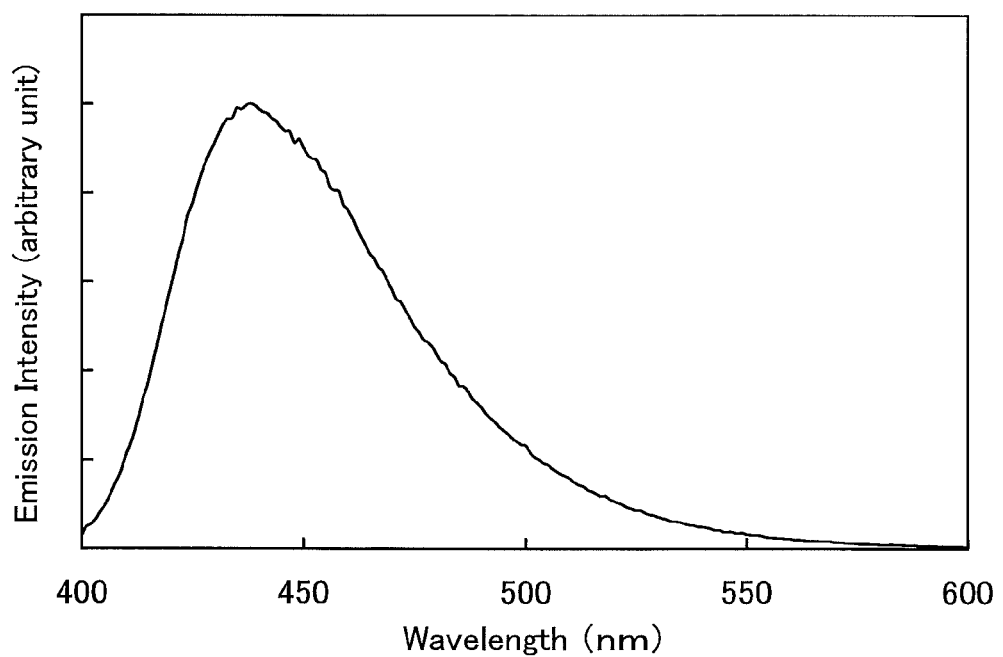
FIG. 13 is a graph showing an absorption spectrum of a toluene solution of DPBAPBA.
Figure 14:
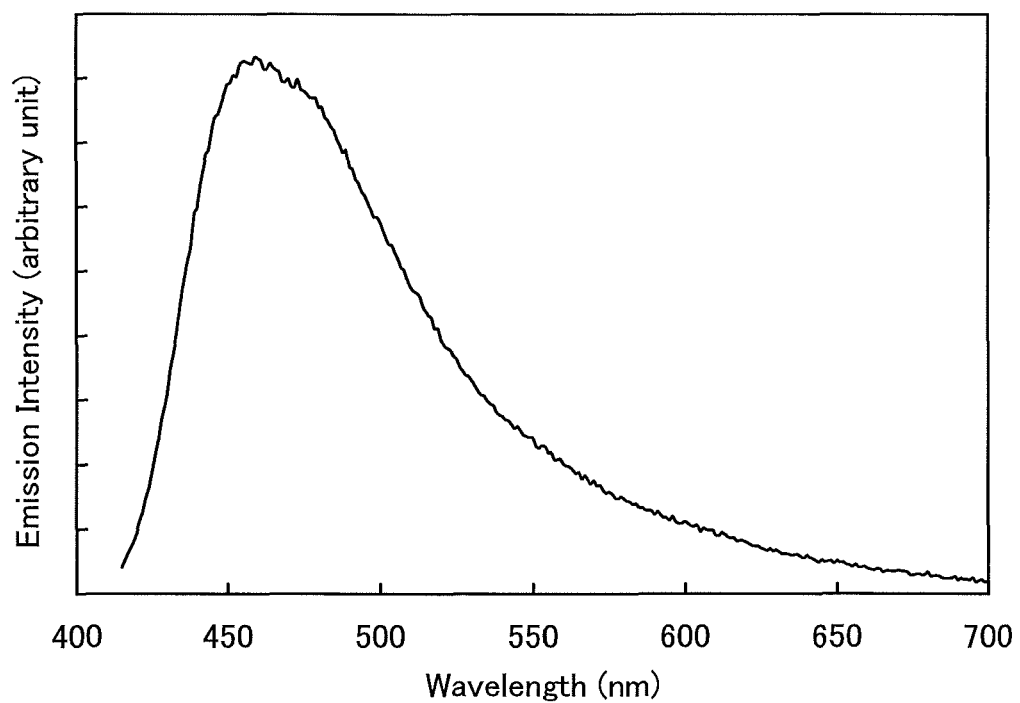
FIG. 14 is a graph showing an emission spectrum of a thin film of DPBAPBA.

FIG. 11 shows an absorption spectrum of a toluene solution of DPBAPBA. Further, FIG. 12 shows an absorption spectrum of a thin film of DPBAPBA. An ultraviolet-visible spectrophotometer (V-550, produced by JASCO Corporation) was used for the measurement. The solution was put into a quartz cell. The thin film was formed by evaporation over a quartz substrate to form a sample. As for the spectrum of the solution, the absorption spectrum in FIG. 11 was obtained by subtracting the absorption spectrum of the quartz cell including only toluene. As for the spectrum of the thin film, the absorption spectrum in FIG. 12 was obtained by subtracting the absorption spectrum of the quartz substrate. In each of FIG. 11 and FIG. 12, the horizontal axis indicates the wavelength (nm) and the vertical axis indicates the absorption intensity (arbitrary unit). In the case of the toluene solution, absorption was observed at around 356, 373, and 393 nm, and in the case of the thin film, it was observed at around 344, 363, 377, and 409 nm. The emission spectrum of the toluene solution of DPBAPBA (excitation wavelength: 370 nm) is shown in FIG. 13. The emission spectrum of the thin film of DPBAPBA (excitation wavelength: 400 nm) is shown in FIG. 14. In each of FIG. 13 and FIG. 14, the horizontal axis indicates the wavelength (nm), and the vertical axis indicates the emission intensity (arbitrary unit). In the case of the toluene solution, the maximum emission wavelength was 438 nm (excitation wavelength: 370 nm), and in the case of the thin film, it was 459 nm (excitation wavelength: 400 nm).

The results of measuring the thin film of DPBAPBA by photoelectron spectrometry (AC-2, produced by Riken Keiki Co., Ltd.) in the atmosphere indicated that the HOMO level of DPBAPBA was −5.44 eV. Moreover, the absorption edge was obtained from Tauc plot assuming direct transition with the absorption spectrum data of the thin film of DPBAPBA in FIG. 12. When the absorption edge was estimated as an optical energy gap, the energy gap was 2.91 eV. The LUMO level, which was estimated from the HOMO level and the energy gap, was −2.53 eV.

Example 2

In this example, a synthesis method of N-[4-(10-phenyl-9-anthryl)phenyl]-N,N',N'-triphenylbenzidine (abbreviation: DPBAPA), which is an anthracene derivative of the present invention represented by the structural formula (201) will be specifically described.

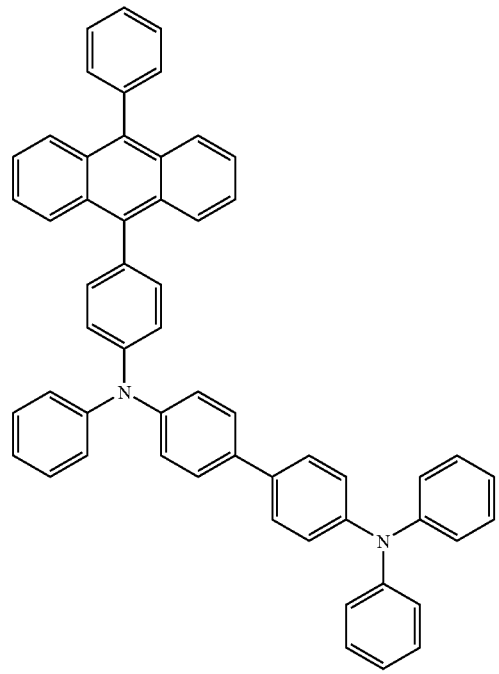

(201)

[Step 1] Synthesis of
9-(4-bromophenyl)-10-phenylanthracene

A synthesis scheme of 9-(4-bromophenyl)-10-phenylanthracene is shown in (a-4).

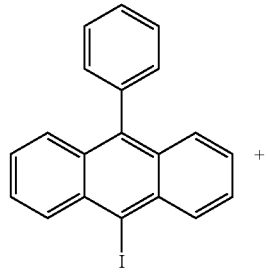

(a-4)

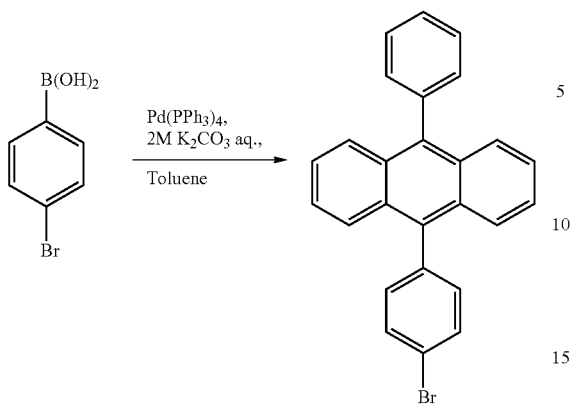

Into a 50 mL three-neck flask were put 1.0 g (2.63 mmol) of 9-iodo-10-phenylanthracene and 542 mg (2.70 mmol) of p-bromophenyl boronic acid. The atmosphere in the flask was replaced with nitrogen. After that, 10 mL of toluene and 3 mL of potassium carbonate aqueous solution (2.0 M) were added to the flask. This mixture was degassed under reduced pressure, then 46 mg (0.03 mmol) of tetrakis(triphenylphosphine)palladium(0) was added to the mixture. The mixture was stirred under a nitrogen stream at 80° C. for 9 hours. After the stirring, about 20 mL of toluene was added to this mixture. Then, the mixture was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was washed with water and a saturated saline, and then dried with magnesium sulfate. This mixture was gravity filtered, and the obtained filtrate was concentrated to give a solid. The obtained solid was recrystallized with chloroform/hexane to give 0.56 g of a light-brown solid, which was the object of the synthesis, in a yield of 45%.

[Step 2] Synthesis of N-[4-(10-phenyl-9-anthryl)phenyl]-N,N',N'-triphenylbenzidine (abbreviation: DPBAPA)

A synthesis scheme of DPBAPA is shown in (a-8).

(a-8)

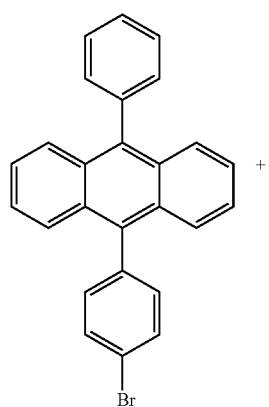

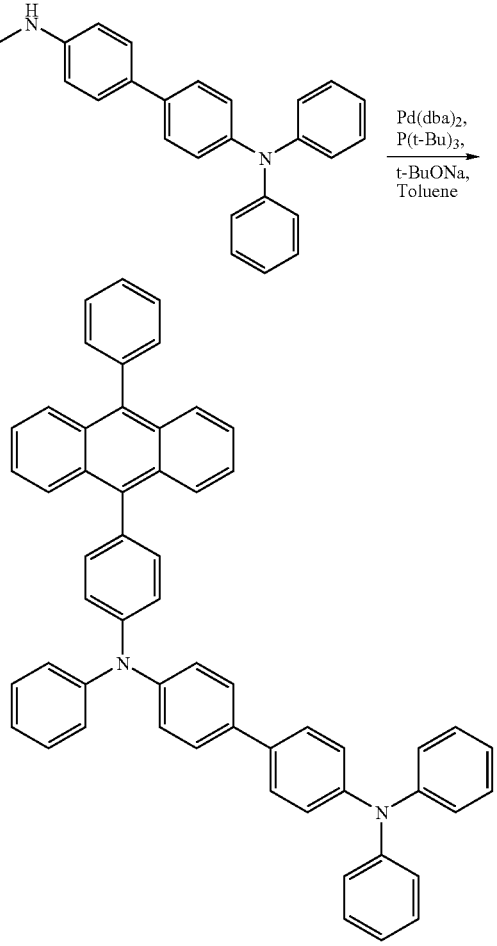

(201)

Into a 50 mL three-neck flask were put 1.0 g (2.4 mmol) of 9-(4-bromophenyl)-10-phenylanthracene, 1.0 g (2.4 mmol) of N,N',N'-triphenylbenzidine (abbreviation: DPBA), and 1.0 g (10 mmol) of sodium tert-butoxide. The atmosphere in the flask was replaced with nitrogen. To the mixture, 15 mL of toluene and 0.10 mL of tri(tert-butyl)phosphine (10 wt % hexane solution) were added. This mixture was degassed under reduced pressure while being stirred, then 58 mg (0.10 mmol) of bis(dibenzylideneacetone)palladium(0) was added thereto. This mixture was stirred at 90° C. for 7.5 hours. After the stirring, about 20 mL of toluene was added to the mixture. The mixture was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135). A solid obtained by concentrating the obtained filtrate was purified by silica gel column chromatography (developing solvent was a mixed solvent of toluene:hexane 4:6) to give a yellow solid. This yellow solid was recrystallized with toluene/hexane to give 1.6 g of a light yellow powdered solid, which was the object of the synthesis, in a yield of 86%.

Then, 1.0 g of the obtained light yellow solid was sublimated and purified by a train sublimation method. For sublimation purification conditions, the light yellow solid was heated at 300° C. under 4.7 Pa pressure with a flow rate of argon gas of 10 mL/min. After the sublimation purification, 0.98 g of a yellow prism crystal was obtained in a yield of 95%.

Figure 15A:
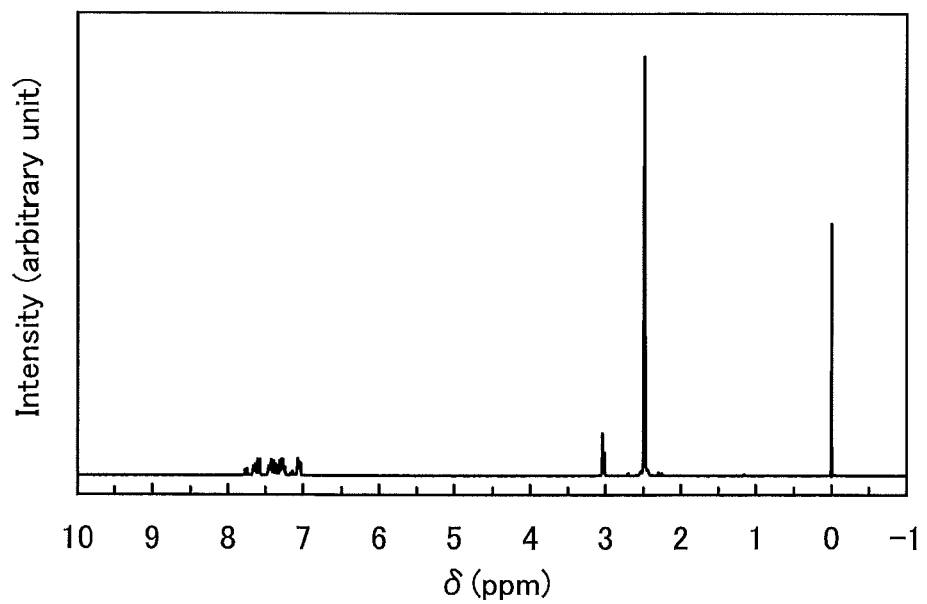
FIGS. 15A and 15B are a $^1$H NMR chart of DPBAPA.
Figure 15B:
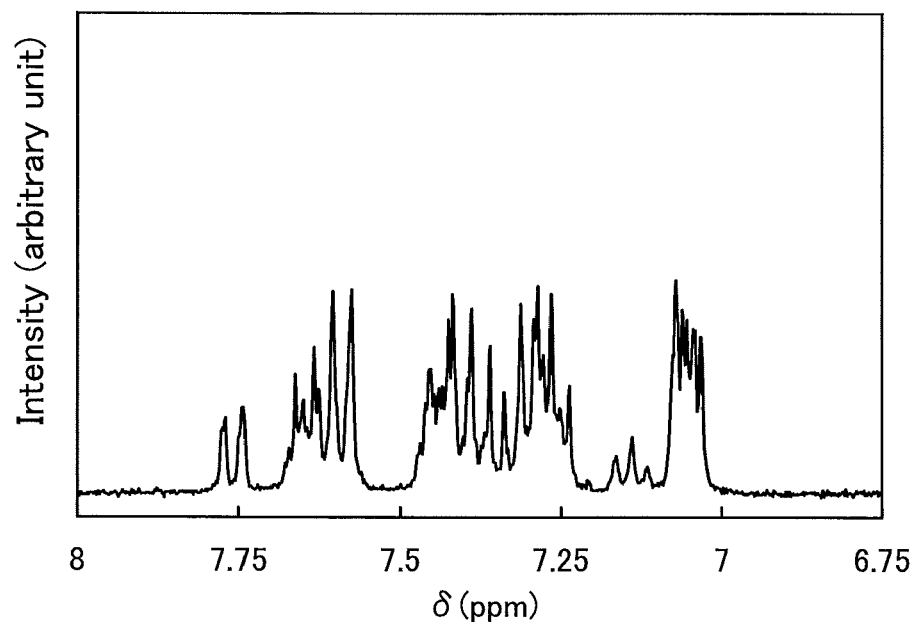

By a nuclear magnetic resonance (NMR) measurement, it was confirmed that this compound was N-[4-(10-phenyl-9-anthryl)phenyl]-N,N',N'-triphenylbenzidine (abbreviation: DPBAPA). $^1$H NMR data of the obtained compound is shown below. $^1$H NMR (DMSO-d$_6$, 300 MHz): δ=7.03-7.16 (m, 9H), 7.24-7.47 (m, 20H), 7.58-7.67 (m, 9H), 7.76 (d, J=7.8 Hz, 2H). The $^1$H NMR chart is shown in FIGS. 15A and 15B. Note that FIG. 15B is a chart showing an enlargement of FIG. 15A in the range of 6.75 to 8.0 ppm.

Figure 16:
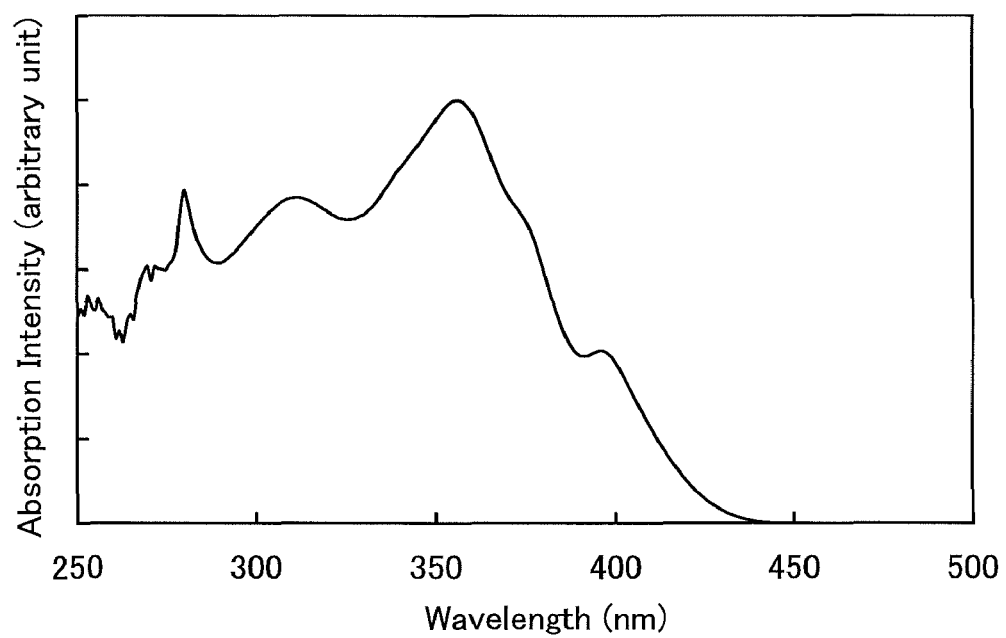
FIG. 16 is a graph showing an absorption spectrum of a toluene solution of DPBAPA.
Figure 17:
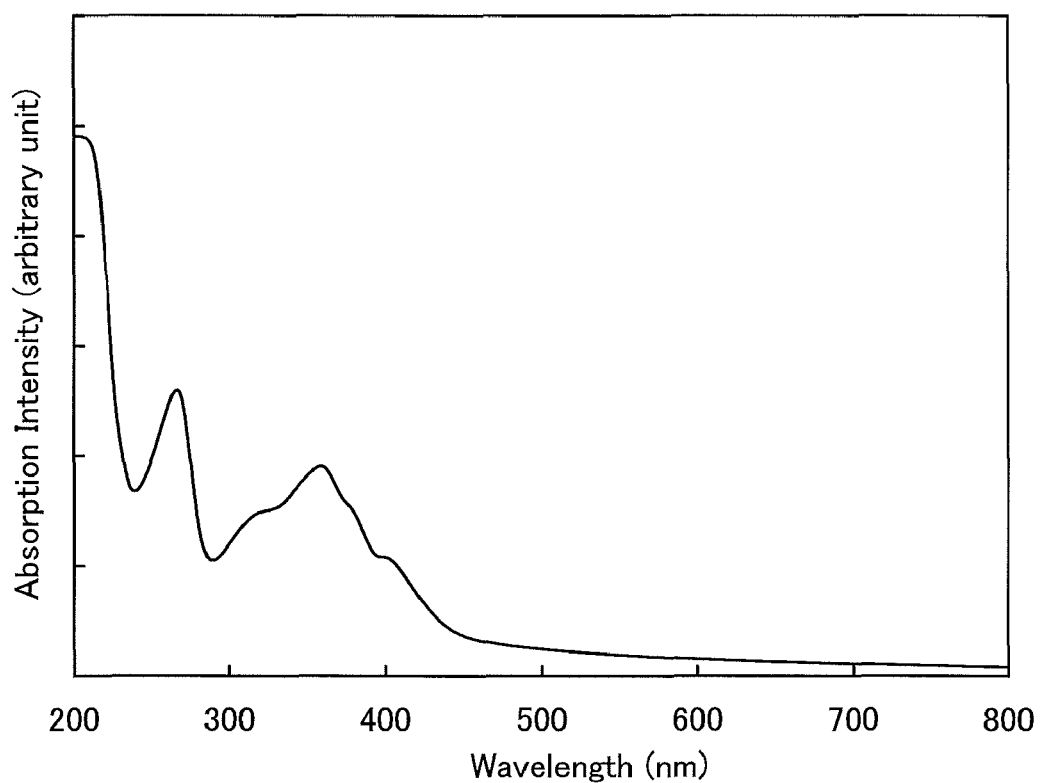
FIG. 17 is a graph showing an absorption spectrum of a thin film of DPBAPA.
Figure 18:
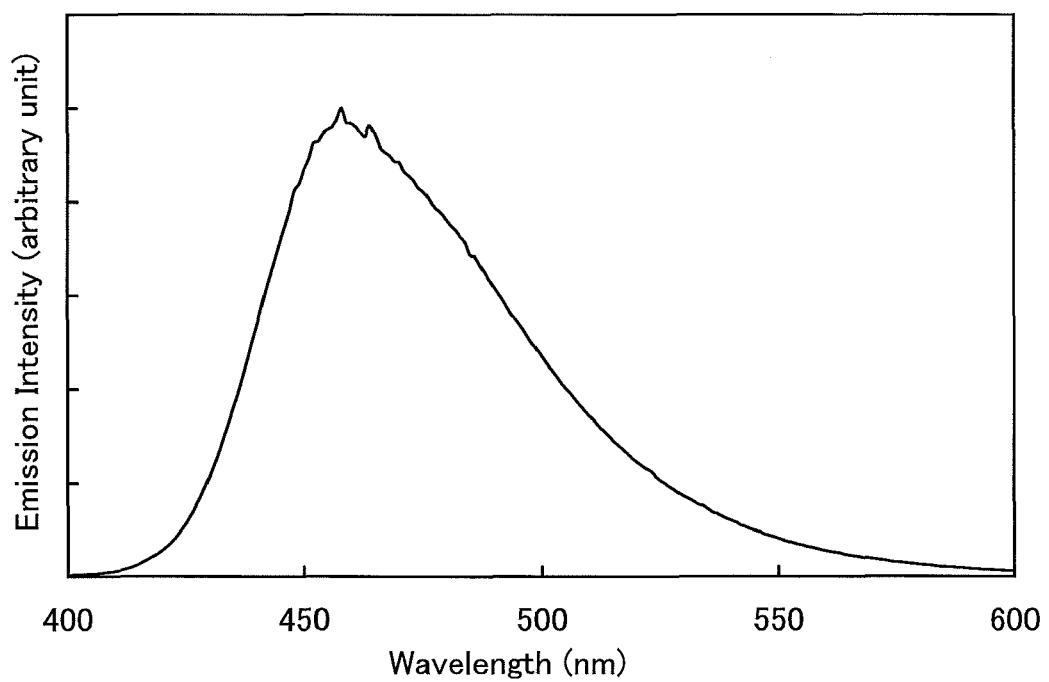
FIG. 18 is a graph showing an emission spectrum of a toluene solution of DPBAPA.
Figure 19:
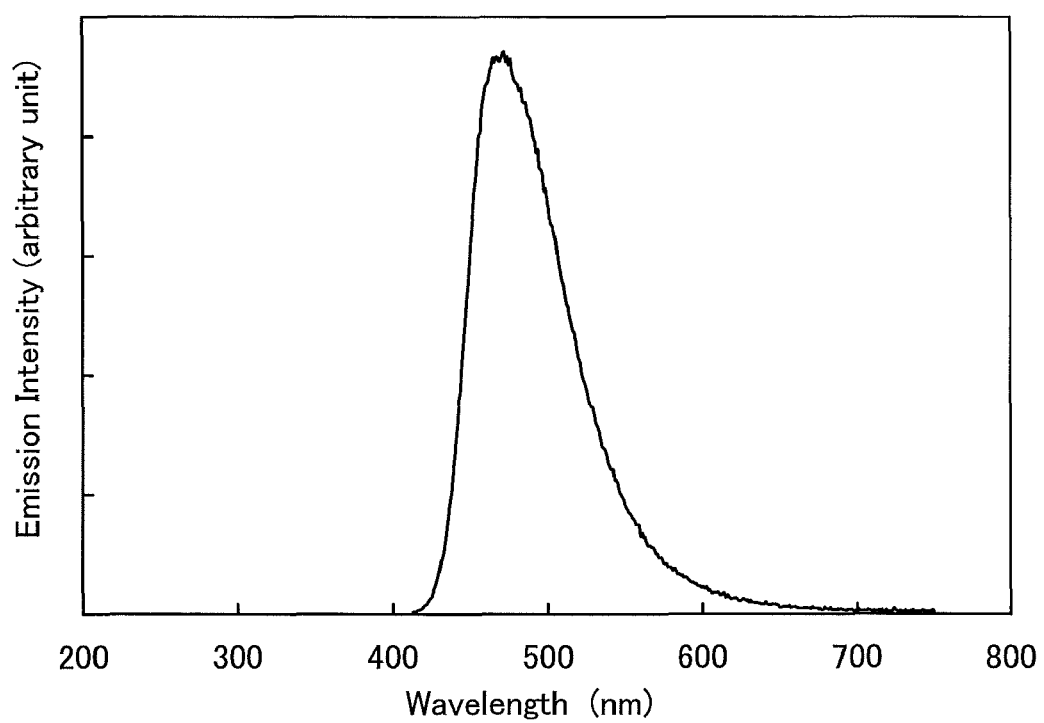
FIG. 19 is a graph showing an emission spectrum of a thin film of DPBAPA.

FIG. 16 shows an absorption spectrum of a toluene solution of DPBAPA. Further, FIG. 17 shows an absorption spectrum of a thin film of DPBAPA. An ultraviolet-visible spectrophotometer (V-550, produced by JASCO Corporation) was used for the measurement. The solution was put into a quartz cell. The thin film was formed by evaporation over a quartz substrate to form a sample. As for the spectrum of the solution, the absorption spectrum in FIG. 16 was obtained by subtracting the absorption spectrum of the quartz cell including only toluene. As for the spectrum of the thin film, the absorption spectrum in FIG. 17 was obtained by subtracting the absorption spectrum of the quartz substrate. In each of FIG. 16 and FIG. 17, the horizontal axis indicates the wavelength (nm) and the vertical axis indicates the absorption intensity (arbitrary unit). In the case of the toluene solution, absorption was observed at around 307, 353, and 392 nm, and in the case of the thin film, it was observed at around 318, 358, 378, and 402 nm. The emission spectrum of the toluene solution of DPBAPA (excitation wavelength: 370 nm) is shown in FIG. 18. The emission spectrum of the thin film of DPBAPA (excitation wavelength: 398 nm) is shown in FIG. 19. In each of FIG. 18 and FIG. 19, the horizontal axis indicates the wavelength (nm), and the vertical axis indicates the emission intensity (arbitrary unit). In the case of the toluene solution, the maximum emission wavelength was 458 nm (excitation wavelength: 370 nm), and in the case of the thin film, it was 468 nm (excitation wavelength: 398 nm).

The results of measuring the thin film of DPBAPA by photoelectron spectrometry (AC-2, produced by Riken Keiki Co., Ltd.) in the atmosphere indicated that the HOMO level of DPBAPA was −5.44 eV. Moreover, the absorption edge was obtained from Tauc plot assuming direct transition with the absorption spectrum data of the thin film of DPBAPA in FIG. 17. When the absorption edge was estimated as an optical energy gap, the energy gap was 2.85 eV. The LUMO level, which was estimated from the HOMO level and the energy gap, was −2.59 eV.

Further, oxidation-reduction reaction characteristics of DPBAPA were measured. The oxidation-reduction reaction characteristics were measured by a cyclic voltammetry (CV) measurement. Note that an electrochemical analyzer (ALS model 600A, produced by BAS Inc.) was used for the measurement.

As for a solution used for the CV measurement, dehydrated dimethylformamide (DMF) (99.8%, Catalog No. 22705-6, produced by Sigma-Aldrich Co.) was used as a solvent. Tetraperchlorate-n-butylammonium (n-Bu$_4$NClO$_4$) (Catalog No. T0836, produced by Tokyo Kasei Co., Ltd.), which was a supporting electrolyte, was dissolved in the solvent at a concentration of 100 mmol/L. Further, an object to be measured was dissolved at a concentration of 1 mmol/L. A platinum electrode (a PTE platinum electrode, produced by BAS Inc.) was used as a work electrode. A platinum electrode (a VC-3 Pt counter electrode (5 cm), produced by BAS Inc.) was used as an auxiliary electrode. An Ag/Ag$^+$ electrode (RE-5 reference electrode for nonaqueous solvent, produced by BAS Inc.) was used as a reference electrode. Note that the measurement was conducted at room temperature.

An oxidation reaction characteristic of DPBAPA was measured as follows: after the electric potential of the work electrode with respect to the reference electrode was changed from 0.27 V to 0.70 V, a scan for changing the electric potential from 0.70 V to 0.27 V was set as one cycle, and the measurement was performed for 100 cycles. Note that the scanning speed of the CV measurement was set to be 0.1 V/s.

A reduction reaction characteristic of DPBAPA was measured as follows: after the electric potential of the work electrode with respect to the reference electrode was changed from −1.23 V to −2.49 V, a scan for changing the electric potential from −2.49 V to −1.23 V was set as one cycle, and the measurement was performed for 100 cycles. Note that the scanning speed of the CV measurement was set to be 0.1 V/s.

Figure 20:
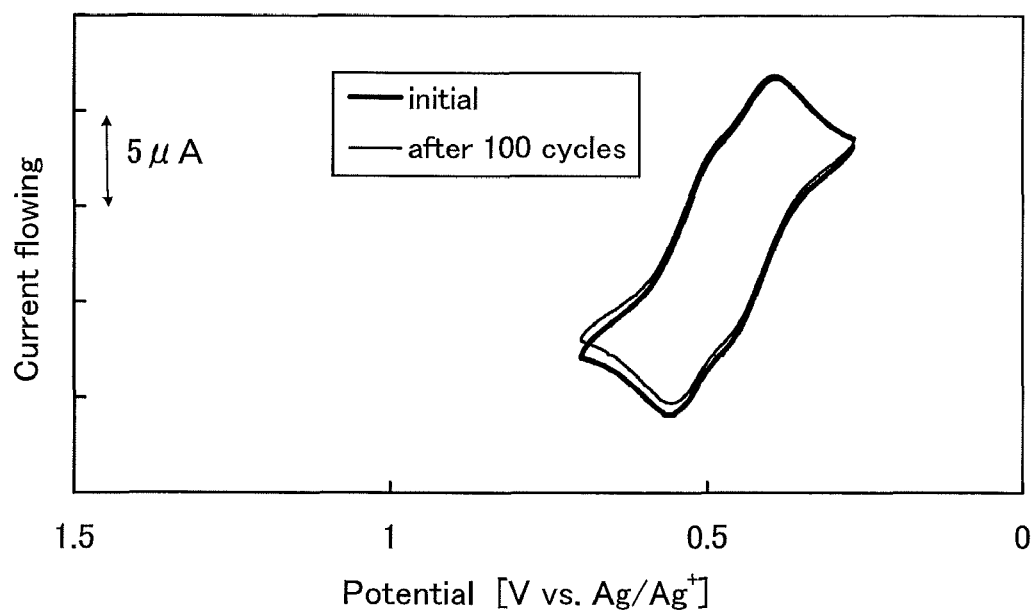
FIG. 20 is a graph showing a result of a CV measurement of DPBAPA.
Figure 21:
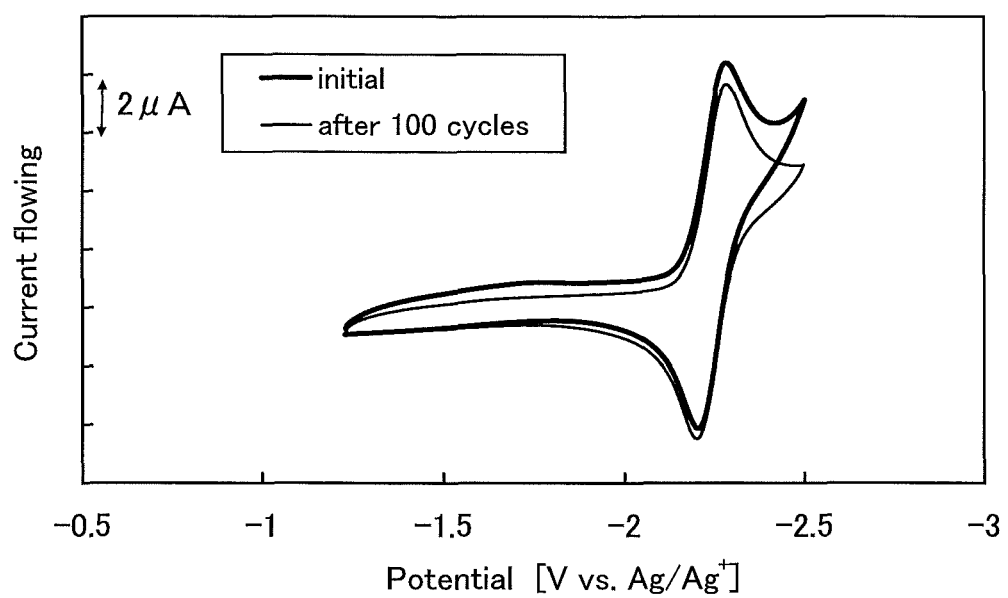
FIG. 21 is a graph showing a result of a CV measurement of DPBAPA.

FIG. 20 shows results of CV measurement on the oxidation reaction characteristic of DPBAPA and FIG. 21 shows results of CV measurement on the reduction reaction characteristic of DPAPBA. In FIG. 20 and FIG. 21, the horizontal axis shows potential (V) of the work electrode with respect to the reference electrode, and the vertical axis shows a value (μA) of current flowing between the work electrode and the auxiliary electrode. According to FIG. 20, a current indicating oxidation was observed at around +0.43 V (vs. Ag/Ag$^+$ electrode). According to FIG. 21, a current indicating reduction was observed at around −2.24 V (vs. Ag/Ag$^+$ electrode).

In spite of the fact that as many as 100 cycles of scanning were performed, a peak position and a peak intensity of the CV curve hardly changed in the oxidation-reduction reaction, which reveals that the anthracene derivative of the present invention is extremely stable against repetition of oxidation-reduction reaction.

Example 3

In this example, a synthesis method of N-[4-(10-phenyl-9-anthryl)phenyl-N,N',N'-triphenyl-1,4-phenylenediamine (abbreviation: DPAPA), which is an anthracene derivative of the present invention represented by the structural formula (301), will be specifically described.

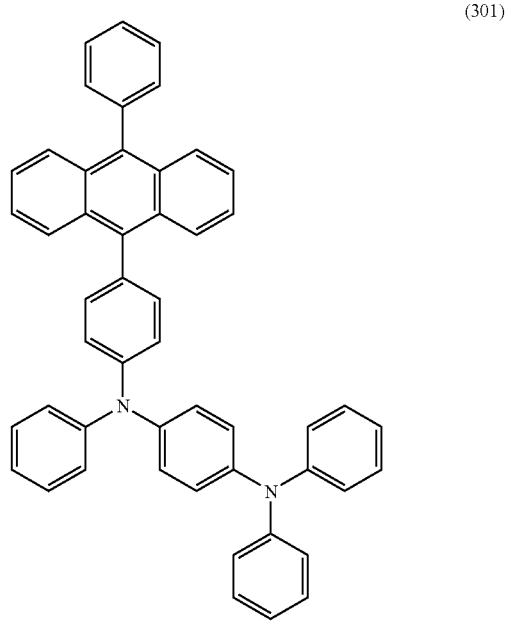

(301)

A synthesis scheme of DPAPA is shown in (a-9).

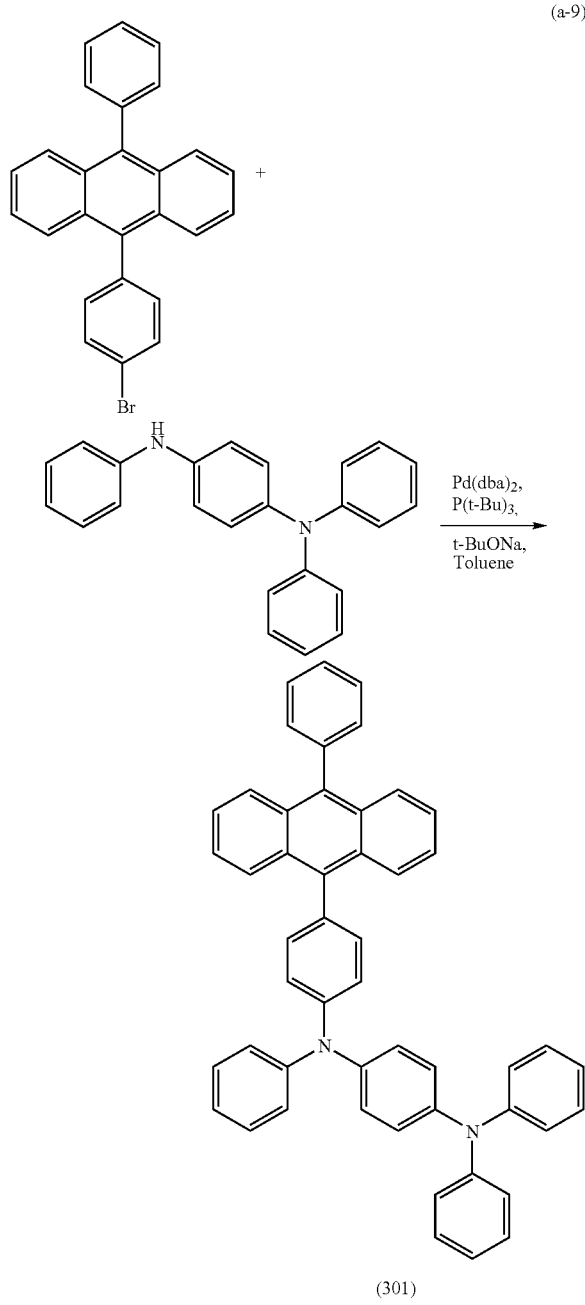

Into a 100 mL three-neck flask were put 1.0 g (2.4 mmol) of 9-(4-bromophenyl)-10-phenylanthracene, 824 mg (2.4 mmol) of N,N',N'-triphenyl-1,4-phenylenediamine (abbreviation: DPA), and 1.1 g (10 mmol) of sodium tert-butoxide, and the atmosphere in the flask was replaced with nitrogen. Then 25 mL of toluene and 0.1 mL of tri(tert-butyl)phosphine (10 wt % hexane solution) were added to this mixture. Under reduced pressure, this mixture was degassed while being stirred. After the degassing, 14 mg (0.024 mmol) of bis(dibenzylideneacetone)palladium(0) were added. This mixture was stirred at 80° C. for five hours. After the stirring, the obtained mixture was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was concentrated to give an oily substance. The obtained oily substance was recrystallized with chloroform/hexane to give 1.3 g of a yellow powdered solid, which was the object of the synthesis, in a yield of 80%.

By a nuclear magnetic resonance (NMR) measurement, it was confirmed that this compound was N-[4-(10-phenyl-9-anthryl)phenyl-N,N',N'-triphenyl-1,4-phenylenediamine (abbreviation: DPAPA).

Figure 29A:
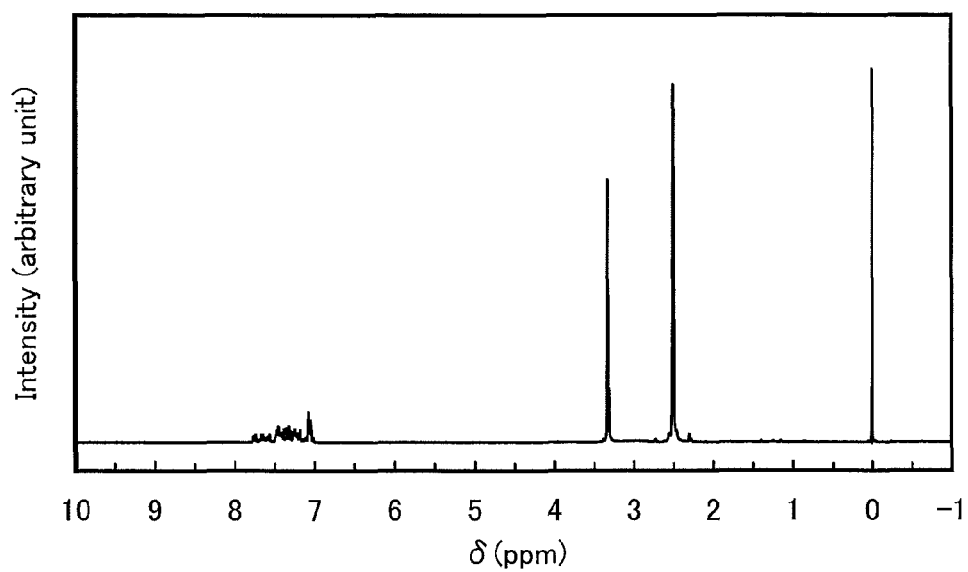
FIGS. 29A and 29B are a H NMR chart of DPAPA.
Figure 29B:
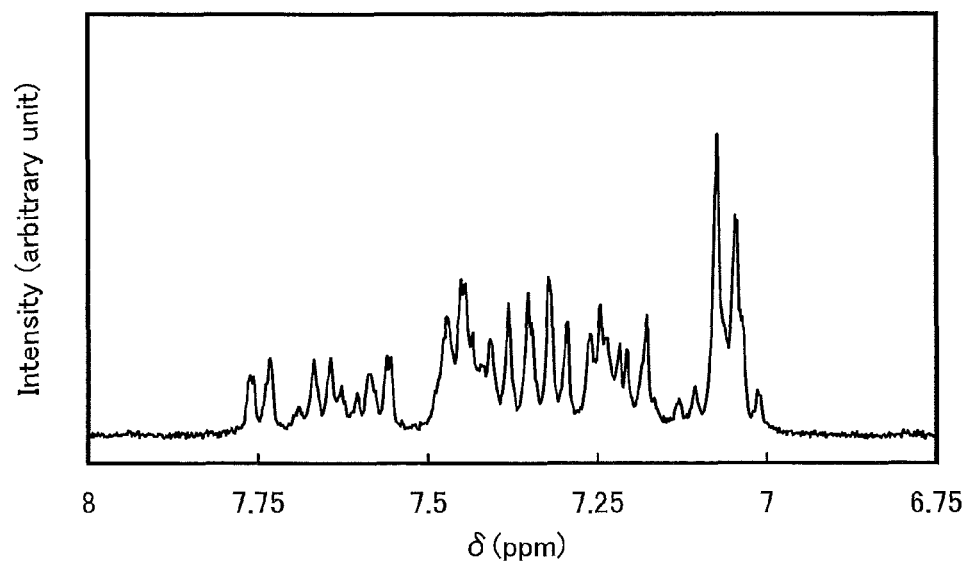

$^1$H NMR data of the obtained compound is shown below. $^1$H NMR (DMSO-$d_6$, 300 MHz): δ=7.05-7.13 (m, 8H), 7.18-7.26 (m, 7H), 7.29-7.47 (m, 14H), 7.56-7.69 (m, 5H), 7.73-7.76 (m, 2H). The $^1$H NMR chart is shown in FIGS. 29A and 29B. Note that FIG. 29B is a chart showing an enlargement of FIG. 29A in the range of 6.75 to 8.0 ppm.

Figure 30:
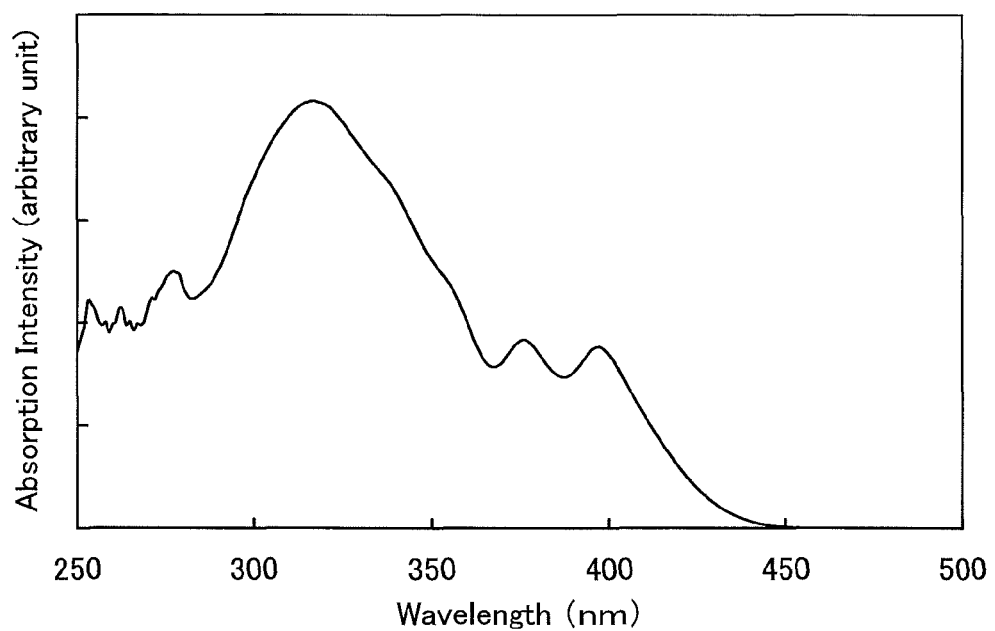
FIG. 30 is a graph showing an absorption spectrum of a toluene solution of DPAPA.
Figure 31:
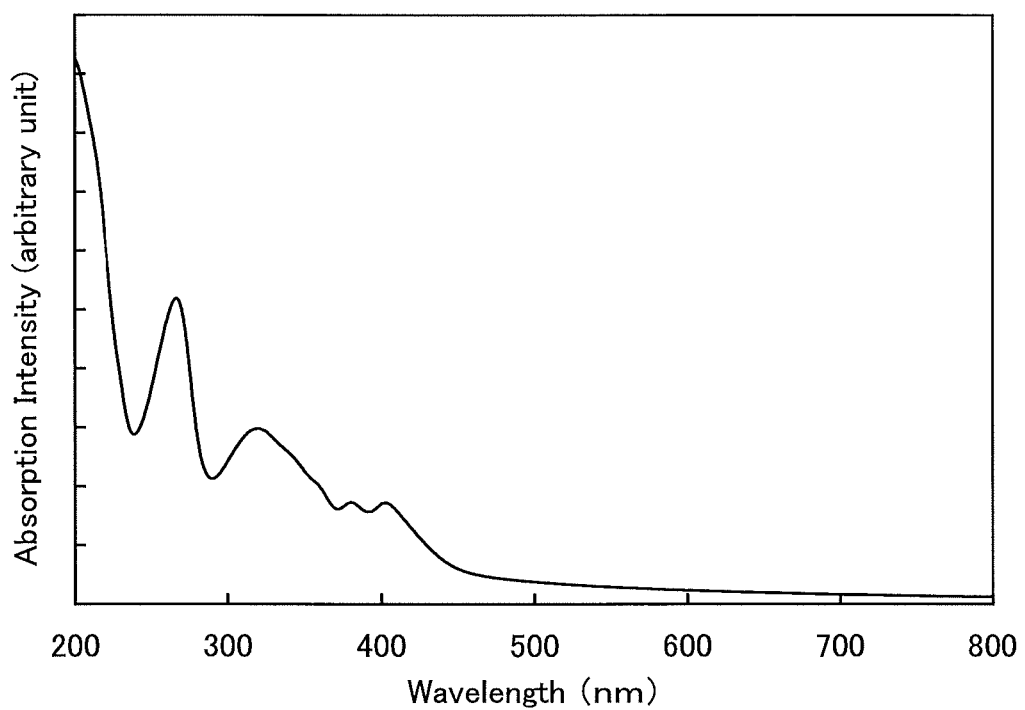
FIG. 31 is a graph showing an absorption spectrum of a thin film of DPAPA.
Figure 32:
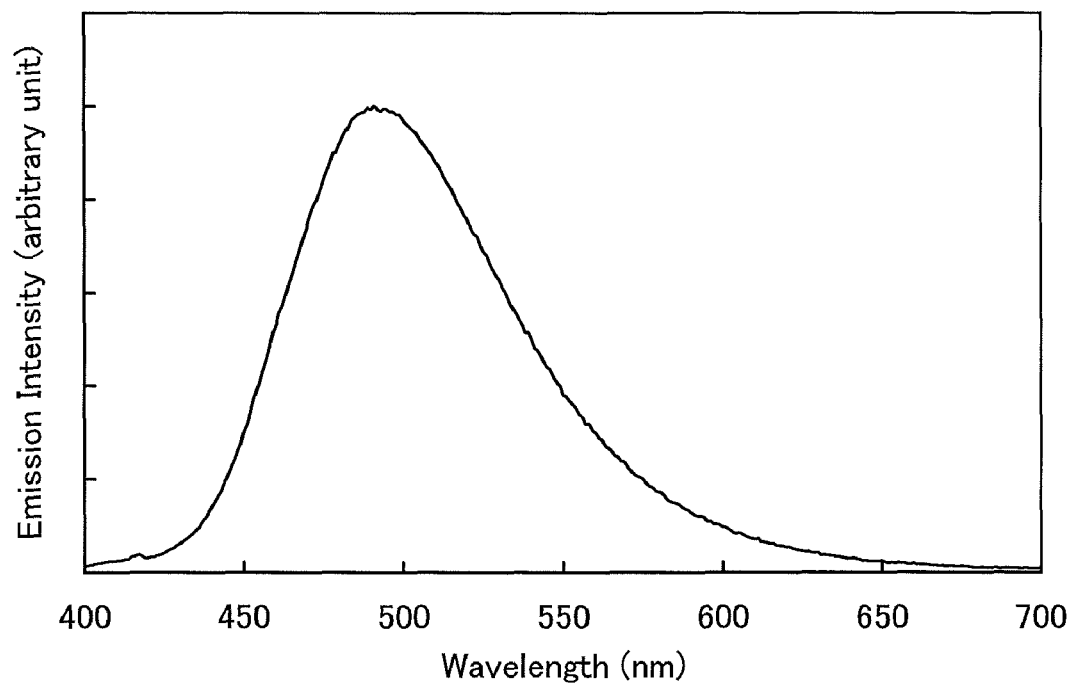
FIG. 32 is a graph showing an emission spectrum of a toluene solution of DPAPA.
Figure 33:
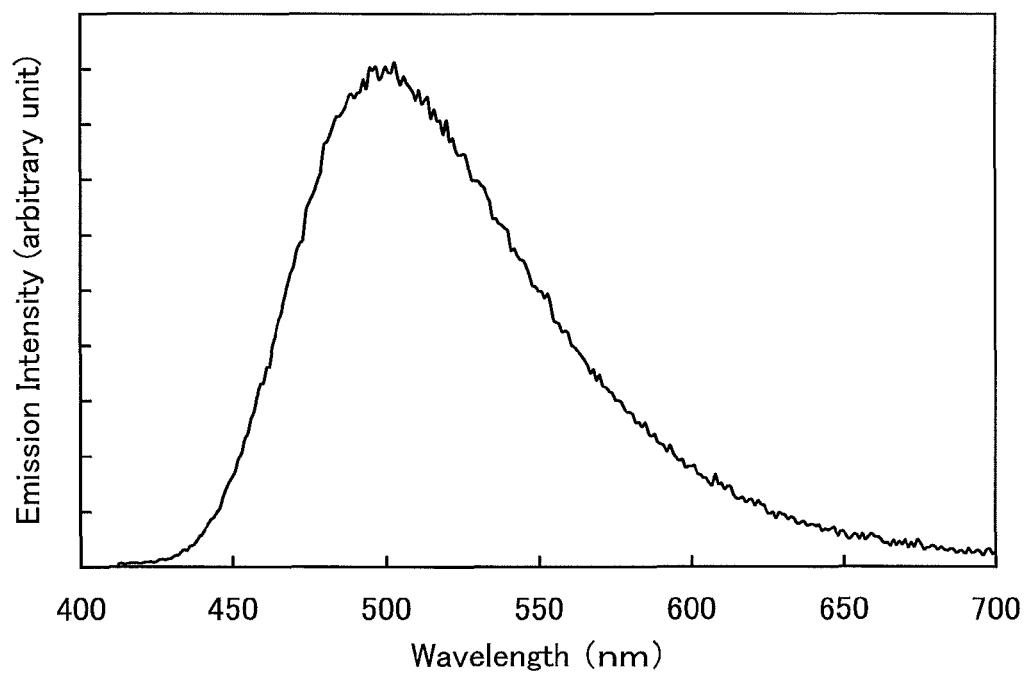
FIG. 33 is a graph showing an emission spectrum of a thin film of DPAPA.

FIG. 30 shows an absorption spectrum of a toluene solution of DPAPA. Further, FIG. 31 shows an absorption spectrum of a thin film of DPAPA. An ultraviolet-visible spectrophotometer (V-5550, produced by JASCO Corporation) was used for the measurement. The solution was put into a quartz cell. The thin film was formed by evaporation over a quartz substrate to form a sample. As for the spectrum of the solution, the absorption spectrum in FIG. 30 was obtained by subtracting the absorption spectrum of the quartz cell including only toluene. As for the spectrum of the thin film, the absorption spectrum in FIG. 31 was obtained by subtracting the absorption spectrum of the quartz substrate. In each of FIG. 30 and FIG. 31, the horizontal axis indicates the wavelength (nm) and the vertical axis indicates the absorption intensity (arbitrary unit). In the case of the toluene solution, absorption was observed at around 314, 373, and 395 nm, and in the case of the thin film, it was observed at around 314, 376, and 402 nm. The emission spectrum of the toluene solution of DPAPA (excitation wavelength: 370 nm) is shown in FIG. 32. The emission spectrum of the thin film of DPAPA (excitation wavelength: 402 nm) is shown in FIG. 33. In each of FIG. 32 and FIG. 33, the horizontal axis indicates the wavelength (nm), and the vertical axis indicates the emission intensity (arbitrary unit). In the case of the toluene solution, the maximum emission wavelength was 496 nm (excitation wavelength; 370 nm), and in the case of the thin film, it was 502 nm (excitation wavelength: 402 nm).

The result of measuring the thin film of DPAPA using a photoelectron spectrometer (AC-2, produced by Riken Keiki Co., Ltd.) in the atmosphere indicated that the HOMO level thereof was 5.31 eV. Further, an absorption edge was obtained from a Tauc plot assuming direct transition with the absorption spectrum data of the thin film of DPAPA in FIG. 31, and when the absorption edge was estimated as an optical energy gap, the energy gap was 2.83 eV. The LUMO level, which was estimated from the HOMO level and the energy gap, was 2.48 eV.

Further, oxidation-reduction reaction characteristics of DPAPA were measured. The oxidation-reduction reaction characteristics were measured by cyclic voltammetry (CV) measurement. Note that an electrochemical analyzer (ALS model 600A, produced by BAS Inc.) was used for the measurement.

As for a solution used for the CV measurement, dehydrated dimethylformamide (DMF) (99.8%, Catalog No. 22705-6, produced by Sigma-Aldrich Co.) was used as a solvent. Tetra-n-butylammonium perchlorate (n-Bu4NClO4) (Catalog No. T0836, produced by Tokyo Kasei Co., Ltd.), which was a supporting electrolyte, was dissolved in the solvent at a concentration of 100 mmol/L. Further, an object to be measured was dissolved at a concentration of 1 mmol/L. Further, a platinum electrode (a PTE platinum electrode, produced by BAS Inc.) was used as a work electrode. A platinum electrode (a VC-3 Pt counter electrode (5 cm), produced by BAS Inc.) was used as an auxiliary electrode. An Ag/Ag$^+$ electrode (RE-5 reference electrode for nonaqueous solvent, produced by BAS Inc.) was used as a reference electrode. Note that the measurement was conducted at room temperature.

An oxidation reaction characteristic of DPAPA was measured as follows: after the electric potential of the work electrode with respect to the reference electrode was changed from −0.46 V to 0.50 V, a scan for changing the electric potential from 0.50 V to −0.46 V was set as one cycle, and the measurement was performed for 100 cycles. Note that the scanning speed of the CV measurement was set to be 0.1 V/s.

A reduction reaction characteristic of DPAPA was measured as follows: after the electric potential of the work electrode with respect to the reference electrode was changed from −0.43 V to −2.50 V, a scan for changing the electric potential from −2.50 V to −0.43 V was set as one cycle, and the measurement was performed for 100 cycles. Note that the scanning speed of the CV measurement was set to be 0.1 V/s.

Figure 34:
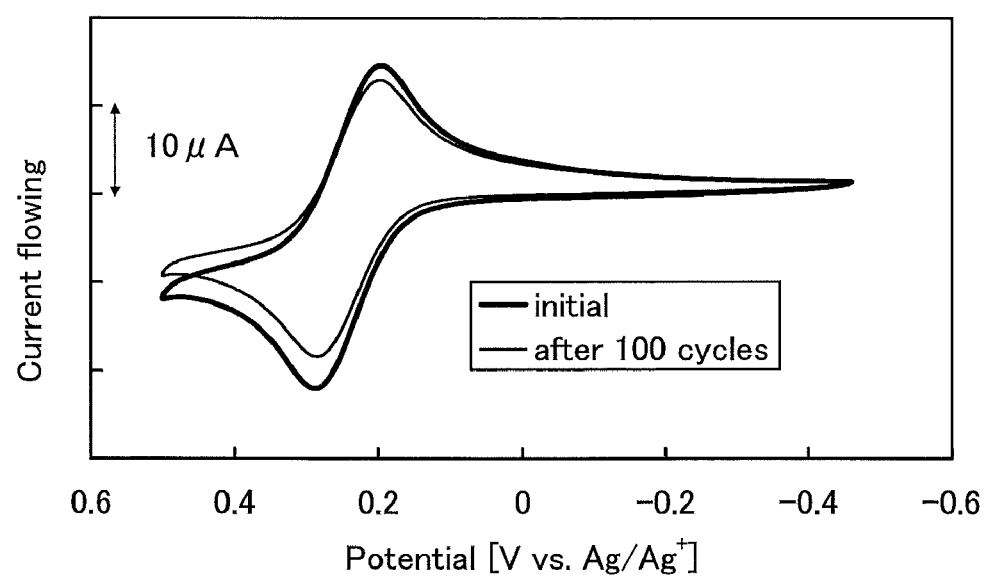
FIG. 34 is a graph showing a result of a CV measurement of DPAPA.
Figure 35:
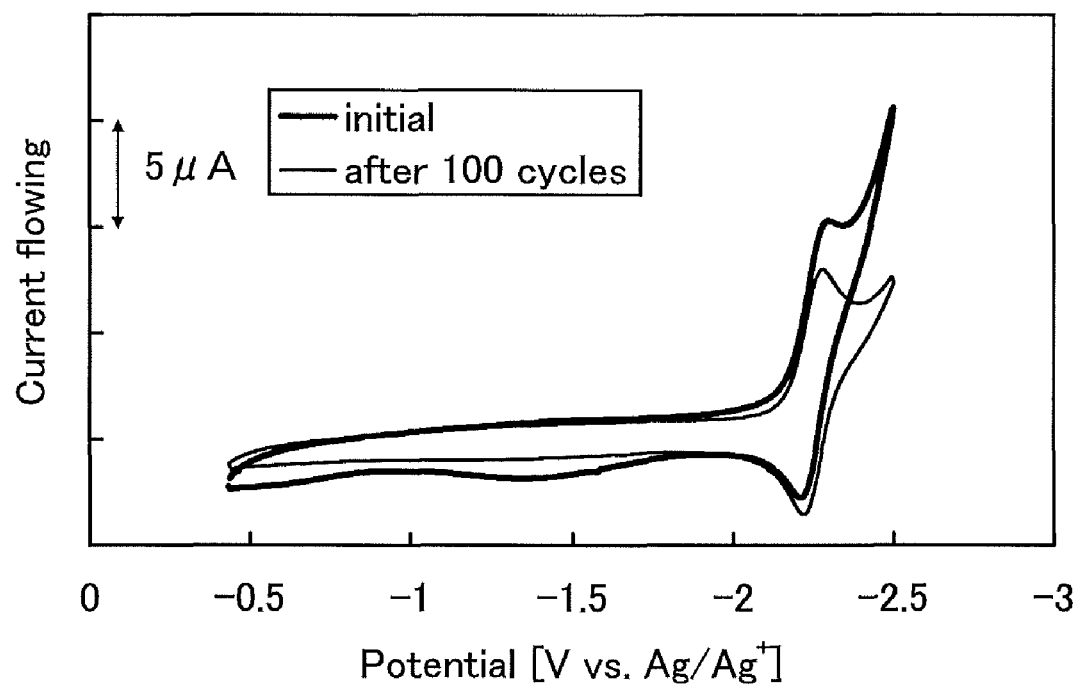
FIG. 35 is a graph showing a result of a CV measurement of DPAPA.

FIG. 34 shows results of CV measurement on the oxidation reaction characteristic of DPAPA and FIG. 35 shows results of CV measurement on the reduction reaction characteristic of DPAPA. In FIG. 34 and FIG. 35, the horizontal axis shows electric potential (V) of the work electrode with respect to the reference electrode, and the vertical axis shows a value (μA) of current flowing between the work electrode and the auxiliary electrode. According to FIG. 34, a current indicating oxidation was observed at around +0.25 V (vs. Ag/Ag$^+$ electrode). According to FIG. 35, a current indicating reduction was observed at around −2.30 V (vs. Ag/Ag$^+$ electrode).

In spite of the fact that as many as 100 cycles of scanning were performed, a peak position and a peak intensity of the CV curve hardly changed in the oxidation-reduction reaction, which reveals that the anthracene derivative of the present invention is extremely stable against repetition of oxidation-reduction reaction.

Example 4

In this example, a synthesis method of N-[4'-(10-phenyl-9-anthryl)biphenyl-4-yl]-N,N',N'-triphenyl-1,4-phenylenediamine (abbreviation: DPAPBA) will be specifically described.

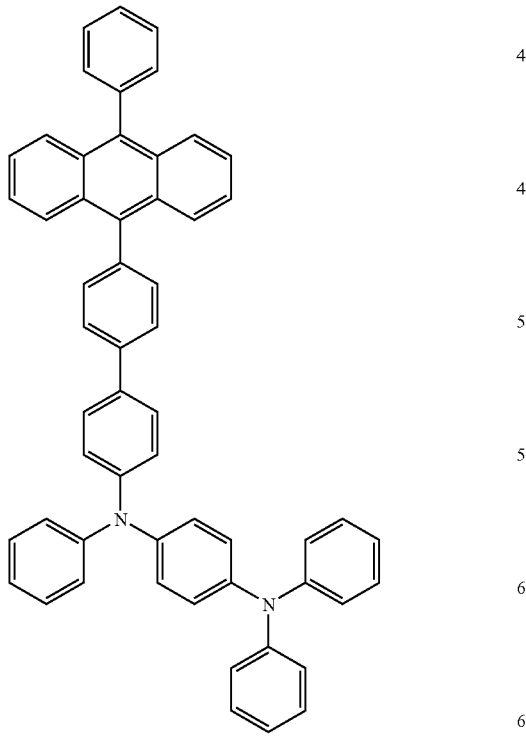

(401)

A synthesis scheme of DPAPBA is shown in (a 10).

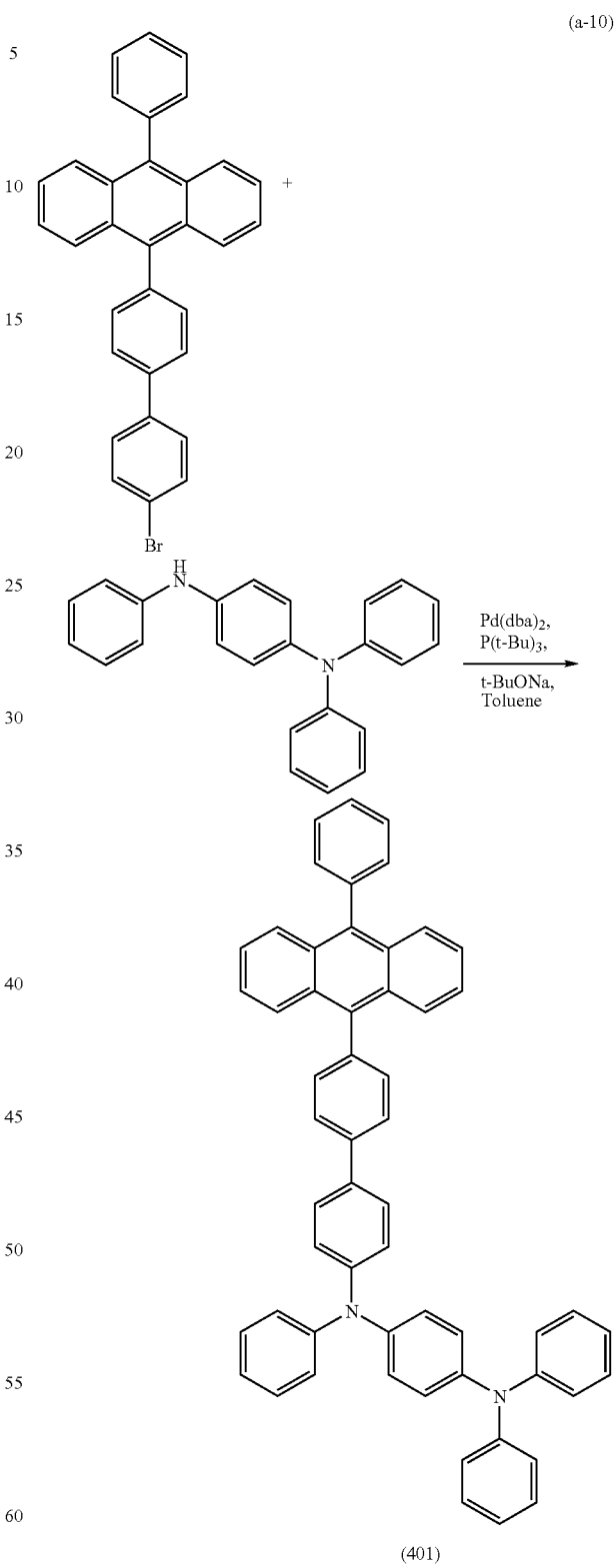

(a-10)

Into a 50 mL three-neck flask were put 0.49 g (1.0 mmol) of 9-(4'-bromobiphenyl-4-yl)-10-phenylanthracene and 0.32 g (3.1 mmol) of sodium tert-butoxide, and the atmosphere in the flask was replaced with nitrogen. Then, 15 mL of toluene and 0.10 mL of tri(tert-butyl)phosphine (10 wt % hexane solution) were added into this mixture. Under reduced pressure, this mixture was degassed while being stirred. After the degassing, this mixture was stirred at 80° C., then 0.34 g (1.0 mmol) of N,N',N'-triphenyl-1,4-phenylenediamine (DPA), 58 mg (0.10 mmol) of bis(dibenzylideneacetone)palladium (0) were added into this mixture. This mixture was stirred at 80° C. for 2.5 hours. After the stirring, this mixture was added into a 500 mL beaker containing about 100 mL of toluene, then this suspension was heated and stirred to dissolve the precipitate. After that, the obtained solution was subjected to suction filtration through Florisil (produced by Wako Pure Chemical Industries, Ltd., Catalog No. 540-00135) and Celite (produced by Wako Pure Chemical Industries, Ltd., Catalog No. 531-16855). When the obtained filtrate was concentrated, a yellow solid was obtained. This solid was recrystallized with toluene to give 0.52 g of a yellow solid, which was the object of the synthesis, in a yield of 70%.

Then 0.51 g of the obtained yellow solid was sublimated and purified by a train sublimation method. For sublimation purification conditions, the yellow solid was heated at 330° C. under reduced pressure with argon gas at a flow rate of 3 mL/min. After the sublimation purification, 0.48 g of a yellow powdered solid was obtained in a yield of 94%.

By a nuclear magnetic resonance (NMR) measurement it was confirmed that this compound was N-[4'-(10-phenyl-9-anthryl)biphenyl-4-yl]-N,N',N'-triphenyl-1,4-phenylenediamine (abbreviation: DPAPBA).

Figure 22A:
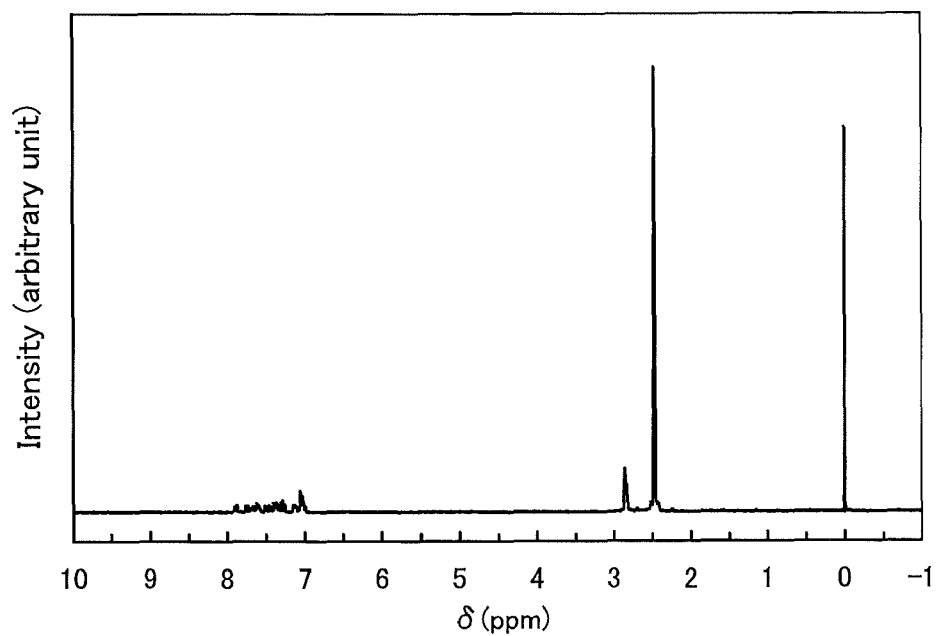
FIGS. 22A and 22B are a $^1$H-NMR chart of DPAPBA.
Figure 22B:
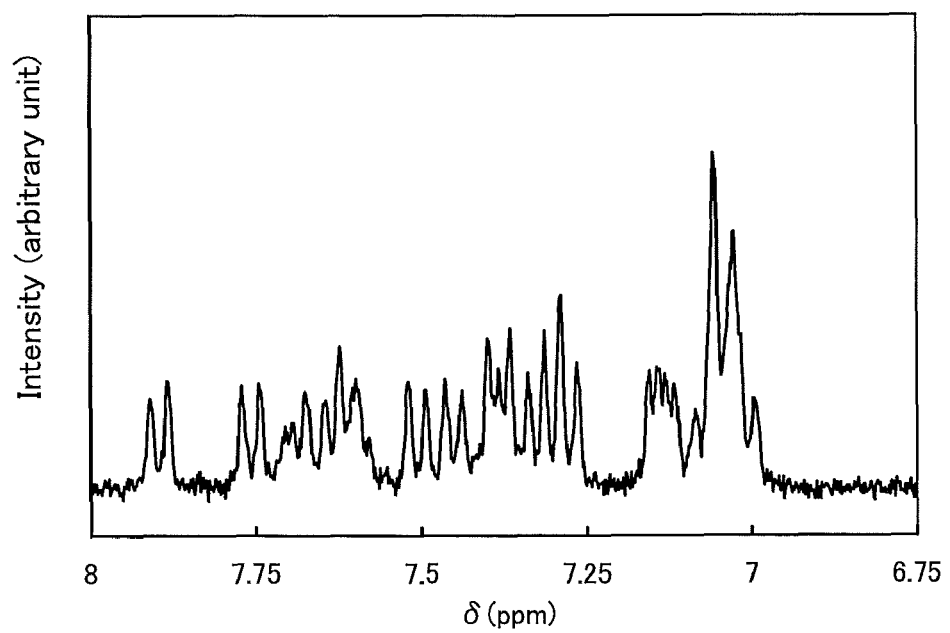

$^1$H NMR data of the obtained compound is shown below. $^1$H NMR (DMSO-d$_6$, 300 MHz): δ=7.00-7.09 (m, 11H), 7.14-7.16 (m, 4H), 7.27-7.40 (m, 10H), 7.45 (d, J=7.8 Hz, 2H), 7.51 (d, J=7.8 Hz, 2H), 7.60-7.69 (m, 7H), 7.76 (d, J=7.8 Hz, 2H), 7.90 (d, J=7.2 Hz, 2H). Further, the $^1$H NMR chart is shown in FIGS. 22A and 22B. Note that FIG. 22B is a chart showing an enlargement of FIG. 22A in the range of 6.75 to 8.0 ppm.

Figure 23:
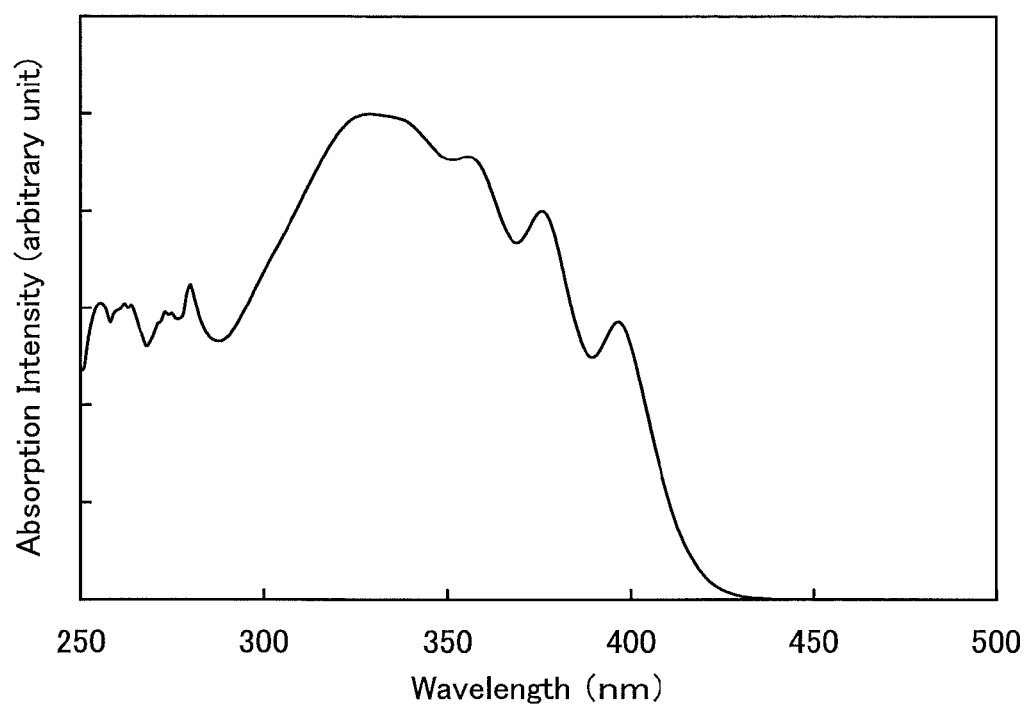
FIG. 23 is a graph showing an absorption spectrum of a toluene solution of DPAPBA.
Figure 24:
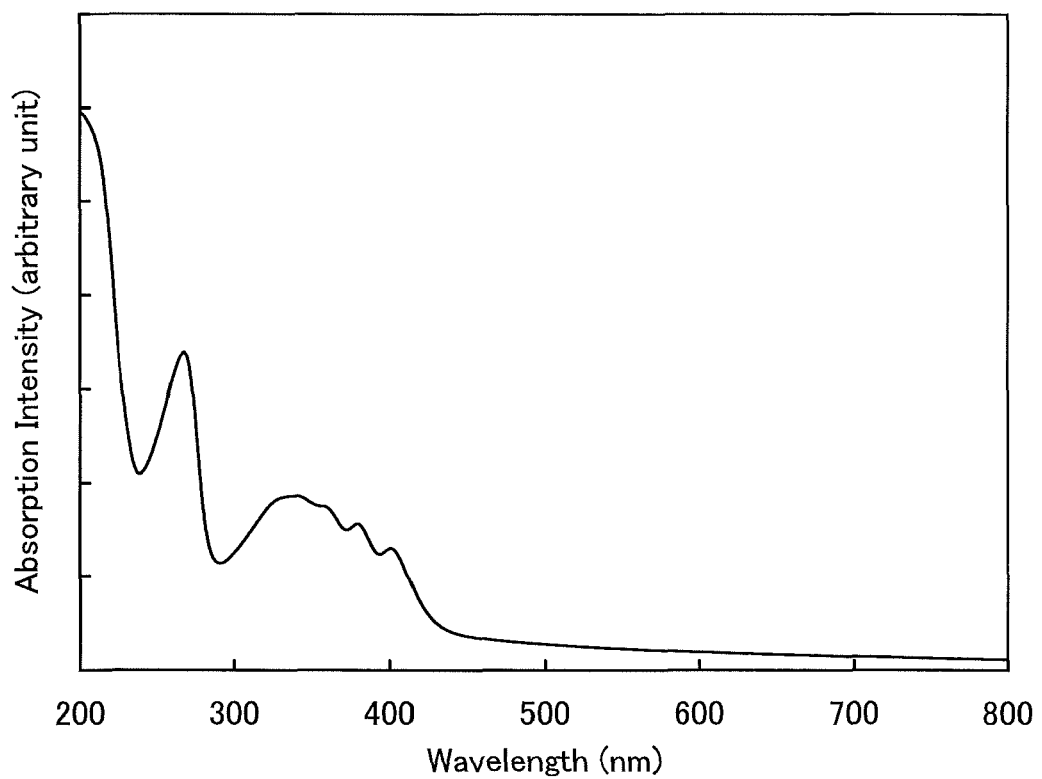
FIG. 24 is a graph showing an absorption spectrum of a thin film of DPAPBA.
Figure 25:
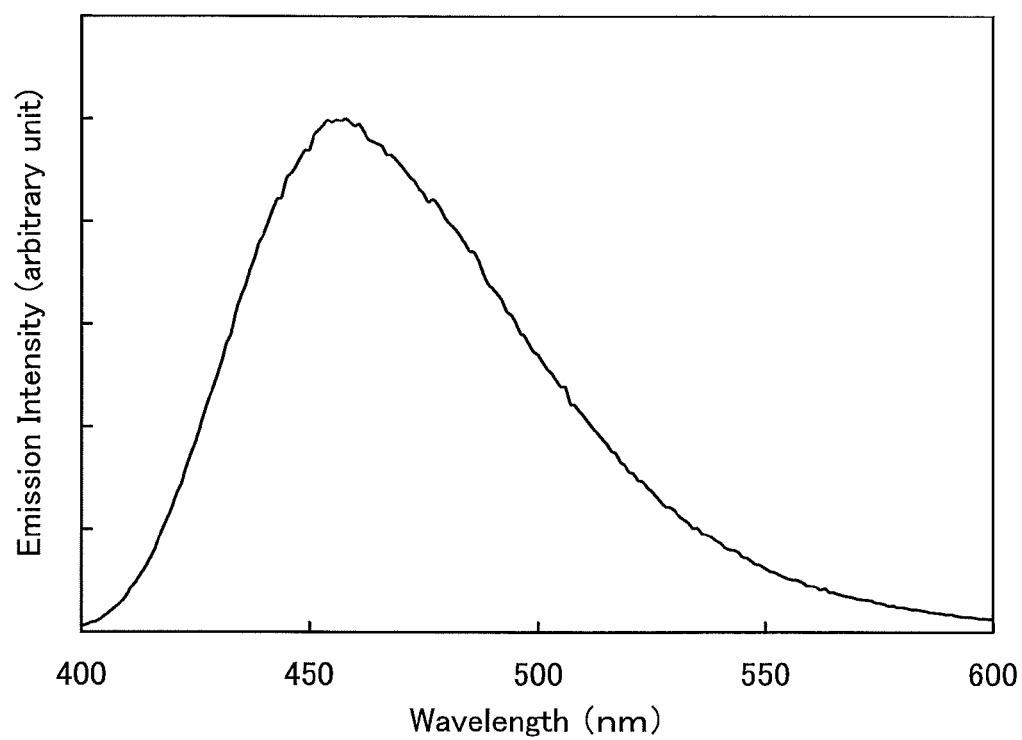
FIG. 25 is a graph showing an emission spectrum of a toluene solution of DPAPBA.
Figure 26:
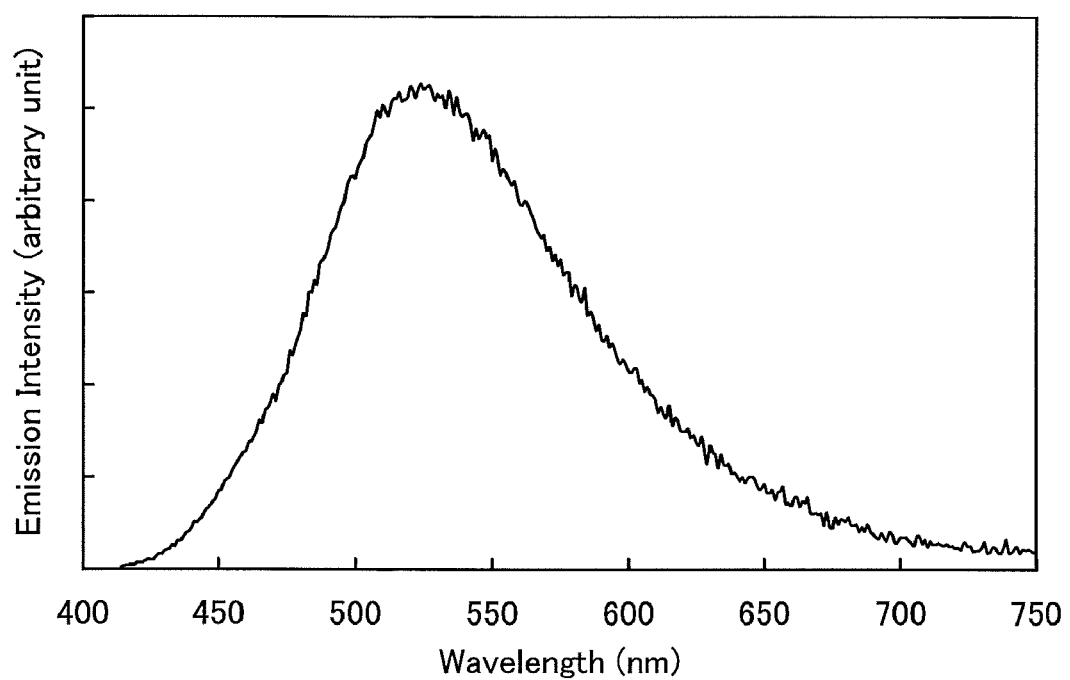
FIG. 26 is a graph showing an emission spectrum of a thin film of DPAPBA.

FIG. 23 shows an absorption spectrum of a toluene solution of DPAPBA. Further, FIG. 24 shows an absorption spectrum of a thin film of DPAPBA. An ultraviolet-visible spectrophotometer (V-550, produced by JASCO Corporation) was used for the measurement. The solution was put into a quartz cell. The thin film was formed by evaporation over a quartz substrate to form a sample. As for the spectrum of the solution, the absorption spectrum in FIG. 23 was obtained by subtracting the absorption spectrum of the quartz cell including only toluene. As for the spectrum of the thin film, the absorption spectrum in FIG. 24 was obtained by subtracting the absorption spectrum of the quartz substrate. In each of FIG. 23 and FIG. 24, the horizontal axis indicates the wavelength (nm) and the vertical axis indicates the absorption intensity (arbitrary unit). In the case of the toluene solution, absorption was observed at around 327, 353, 373, and 396 nm, and in the case of the thin film, it was observed at around 339, 359, 380, and 401 nm. The emission spectrum of the toluene solution of DPAPBA (excitation wavelength: 370 nm) is shown in FIG. 25. The emission spectrum of the thin film of DPAPBA (excitation wavelength: 399 nm) is shown in FIG. 26. In each of FIG. 25 and FIG. 26, the horizontal axis indicates the wavelength (nm), and the vertical axis indicates the emission intensity (arbitrary unit). In the case of the toluene solution, the maximum emission wavelength was 458 nm (excitation wavelength: 370 nm), and in the case of the thin film, it was 526 nm (excitation wavelength: 399 nm).

The results of measuring the thin film of DPAPBA using a photoelectron spectrometer (AC-2, produced by Riken Keiki Co., Ltd.) in the atmosphere indicated that the HOMO level thereof was −5.31 eV. Further, an absorption edge was obtained from a Tauc plot assuming direct transition with the absorption spectrum data of the thin film of DPAPBA in FIG. 24, and when the absorption edge was estimated as an optical energy gap, the energy gap was 2.90 eV. The LUMO level, which was estimated from the HOMO level and the energy gap, was −2.41 eV.

Further, oxidation-reduction characteristics of DPAPBA were measured. The oxidation-reduction reaction characteristics were measured by cyclic voltammetry (CV) measurement. Note that an electrochemical analyzer (ALS model 600A, produced by BAS Inc.) was used for the measurement.

As for a solution used for the CV measurement, dehydrated dimethylformamide (DM) (99.8%, Catalog No. 22705-6, produced by Sigma-Aldrich Co.) was used as a solvent. Tetra-n-butylammonium perchlorate (n-Bu$_4$NClO$_4$) (Catalog No. T0836, produced by Tokyo Kasei Co., Ltd.), which was a supporting electrolyte, was dissolved in the solvent at a concentration of 100 mmol/L. Further, an object to be measured was dissolved at a concentration of 1 mmol/L. Further, a platinum electrode (a PTE platinum electrode, produced by BAS Inc.) was used as a work electrode. A platinum electrode (a VC-3 Pt counter electrode (5 cm), produced by BAS Inc.) was used as an auxiliary electrode. An Ag/Ag$^+$ electrode (RE-5 reference electrode for nonaqueous solvent, produced by BAS Inc.) was used as a reference electrode. Note that the measurement was conducted at room temperature.

An oxidation reaction characteristic of DPAPBA was measured as follows: after the electric potential of the work electrode with respect to the reference electrode was changed from 0.10 V to 0.80 V, a scan for changing the electric potential from 0.80 V to 0.10 V was set as one cycle, and the measurement was performed for 100 cycles. Note that the scanning speed of the CV measurement was set to be 0.1 V/s.

A reduction reaction characteristic of DPAPBA was measured as follows: after the electric potential of the work electrode with respect to the reference electrode was changed from −1.04 V to −2.50 V, a scan for changing the electric potential from −2.50 V to −1.04 V was set as one cycle, and the measurement was performed for 100 cycles. Note that the scanning speed of the CV measurement was set to be 0.1 V/s.

Figure 27:
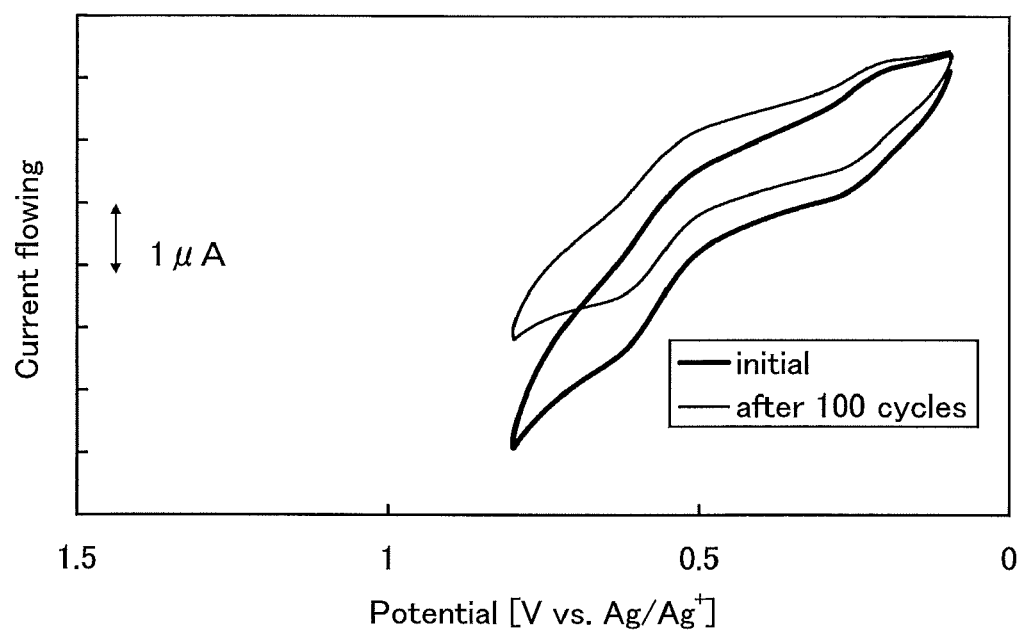
FIG. 27 is a graph showing a result of a CV measurement of DPAPBA.
Figure 28:
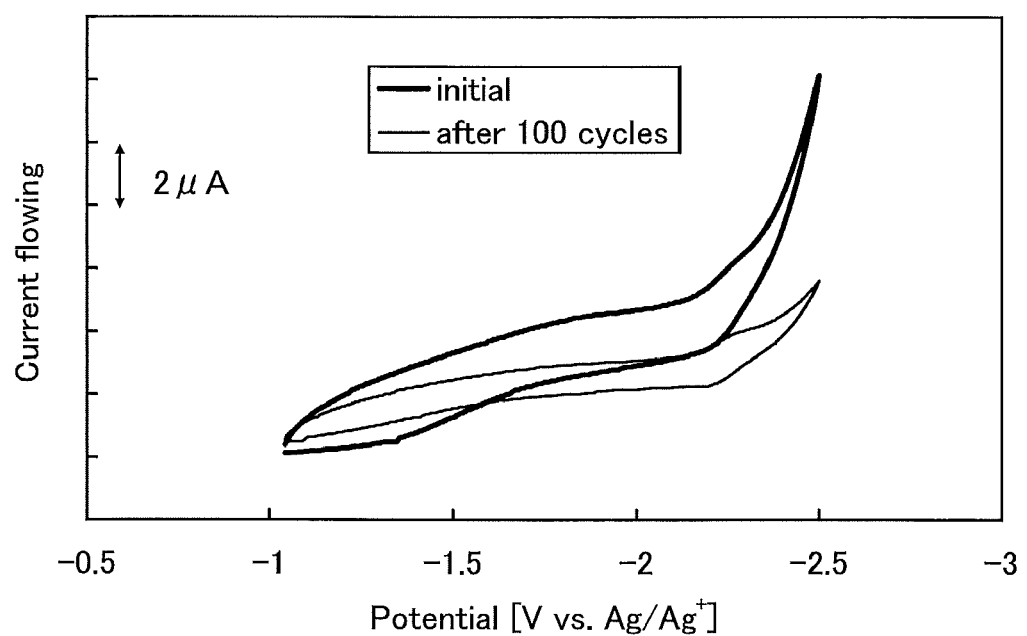
FIG. 28 is a graph showing a result of a CV measurement of DPAPBA.

FIG. 27 shows results of CV measurement on the oxidation reaction characteristic of DPAPBA and FIG. 28 shows results of CV measurement on the reduction reaction characteristic of DPAPBA. In FIG. 27 and FIG. 28, the horizontal axis shows potential (V) of the work electrode with respect to the reference electrode, and the vertical axis shows a value (μA) of current flowing between the work electrode and the auxiliary electrode. According to FIG. 27, a current indicating oxidation was observed at around +0.24 V (vs. Ag/Ag$^+$ electrode). According to FIG. 28, a current indicating reduction was observed at around −2.25 V (vs. Ag/Ag$^+$ electrode).

In spite of the fact that as many as 100 cycles of scanning were performed, a peak position and a peak intensity of the CV curve hardly changed in the oxidation-reduction reaction, which reveals that the anthracene derivative of the present invention is extremely stable against repetition of oxidation-reduction reaction.

Example 5

In this example, as a light-emitting element of the present invention, a light-emitting element having a light-emitting layer that has a single layer structure will be described.

Figure 46A:
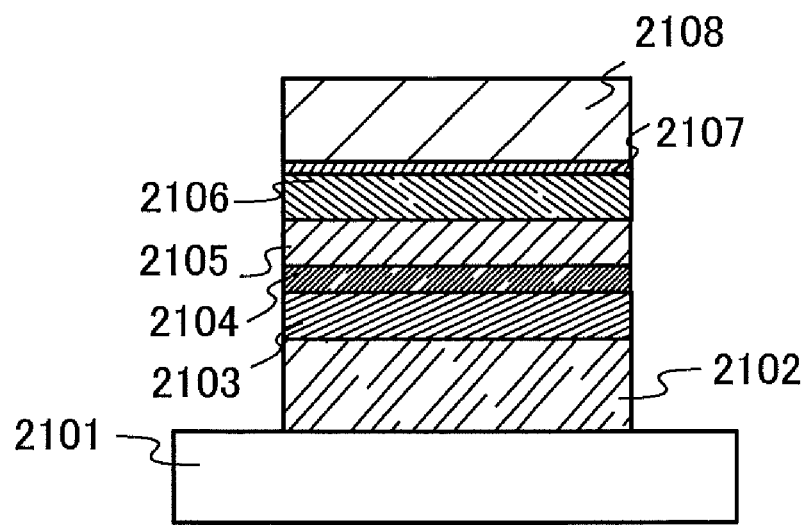
FIGS. 46A and 46B illustrate light-emitting elements in Examples 5 and 6.

The structure of a light-emitting element of this example is shown in FIG. 46A. The light-emitting element of this example has a structure in which a first electrode 2102, a first layer 2103, a second layer 2104, a third layer 2105, a fourth layer 2106, a fifth layer 2107, and a second electrode 2108 are sequentially stacked over a substrate 2101. In this example, the third layer 2105, which is a single light-emitting layer, is formed using an anthracene derivative of the present invention.

The element structures of light-emitting elements A to C manufactured in this example are shown in Table 1. In Table 1, the mixture ratios are all expressed in weight ratios.

TABLE 1

| | first electrode 2102 | first layer 2103 | second layer 2104 | third layer 2105 | fourth layer 2106 | | fifth layer 2107 | second electrode 2108 |
|---|---|---|---|---|---|---|---|---|
| light-emitting element A | ITSO 110 nm | NPB:MoOx (=4:1) 50 nm | NPB 10 nm | CzPA:DPBAPBA (=1:0.1) 30 nm | Alq 10 nm | Bphen 20 nm | LiF 1 nm | Al 200 nm |
| light-emitting element B | ITSO 110 nm | NPB:MoOx (=4:1) 50 nm | NPB 10 nm | CzPA:DPBAPA (=1:0.1) 30 nm | Alq 10 nm | Bphen 20 nm | LiF 1 nm | Al 200 nm |
| light-emitting element C | ITSO 110 nm | NPB:MoOx (=4:1) 50 nm | NPB 10 nm | CzPA:DPAPA (=1:0.05) 30 nm | Alq 30 nm | | LiF 1 nm | Al 200 nm |

Hereinafter; a manufacturing method of the light-emitting elements A to C of this embodiment will be described.

As to each of the light-emitting elements A to C, a film of indium tin oxide containing silicon oxide (ITSO) was formed over a substrate 2101 formed using a glass substrate by a sputtering method, whereby a first electrode 2102 was formed. Note that the thickness of the first electrode 2102 was set to be 110 nm, the area of the first electrode 2102 was set to be 2 mm×2 mm.

Next, the substrate 2101 was fixed to a substrate holder provided in a vacuum evaporation apparatus so that a surface of the substrate 2101 over which the first electrode 2102 was formed faced down. Then, after reducing the pressure of the vacuum evaporation appliance to about $10^{-4}$ Pa, a first layer 2103 was formed using a layer containing a composite material of an organic compound and an inorganic compound over the first electrode 2102 by co-evaporating 4,4'-bis[N-(1-naphthyl)-N-phenylamino]biphenyl (abbreviation: NPB) and molybdenum(VI) oxide. The film thickness was set to be 50 nm and the weight ratio of NPB to molybdenum(VI) oxide was adjusted to be 4:1 (=NPB:molybdenum oxide). Note that the co-evaporation method is an evaporation method by which evaporation is performed simultaneously from a plurality of evaporation sources in one chamber.

Next, NPB was evaporated to be 10 nm thick, whereby a second layer 2104 was formed as a hole-transporting layer.

As to the light-emitting element A, a third layer 2105 was formed as a light-emitting layer by co-evaporating CzPA and DPBAPBA synthesized in Example 1 with a weight ratio of CzPA:DPBAPBA=1:0.1 over the second layer 2104. The thickness of the light-emitting layer was set to be 30 nm.

As to the light-emitting element B, a third layer 2105 was formed as a light-emitting layer by co-evaporating CzPA and DPBAPA synthesized in Example 2 with the weight ratio of CzPA:DPBAPA=1:0.1 over the second layer 2104. The thickness of the light-emitting layer was set to be 30 nm.

As to the light-emitting element C, a third layer 2105 was formed as a light-emitting layer by co-evaporating CzPA and DPAPA synthesized in Example 3 with the weight ratio of CzPA:DPAPA=1:0.05 over the second layer 2104. The thickness of the light-emitting layer was set to be 30 nm.

As to the light-emitting elements A and B, a fourth layer 2106 was formed as an electron-transporting layer by evaporating 10 nm of Alq film and 20 nm of Bphen film which were sequentially stacked over the third layer 2105.

As to the light-emitting element C, an Alq film was deposited over the third layer 2105 to a thickness of 30 nm, whereby the fourth layer 2106 was formed as an electron-transporting layer.

As to the light-emitting elements A to C, lithium fluoride (LiF) was deposited over the fourth layer 2106 to a thickness of 1 nm, whereby the fifth layer 2107 was formed as an electron-injecting layer. Lastly, aluminum was deposited to a thickness of 200 nm as the second electrode 2108 which serves as a cathode. Accordingly, the light-emitting elements A to C of this example were obtained. Note that in all of the above evaporation steps, a resistance heating method was adopted. In addition, structure formulae of NPB, CzPA, Alq, and Bphen are shown below.

NPB

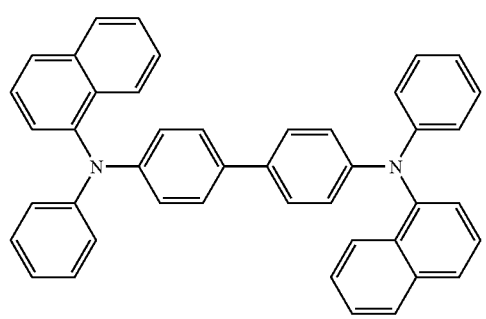

Alq

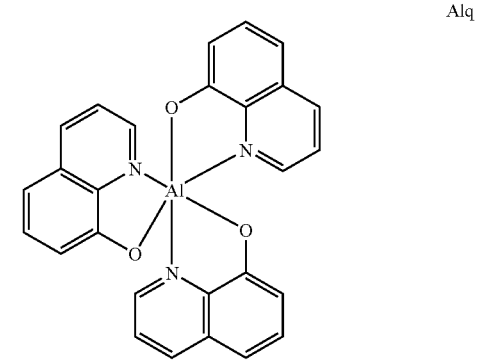

-continued

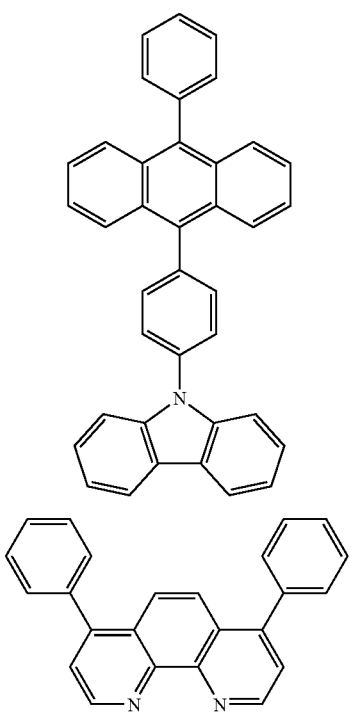

CzPA

BPhen

The light-emitting elements A to C thus obtained were sealed in a glove box under a nitrogen atmosphere without being exposed to atmosphere. Then, the operation characteristics of the light-emitting elements A to C were measured. Note that the measurement was performed at a room temperature (in the atmosphere kept at 25° C.).

Figure 36:
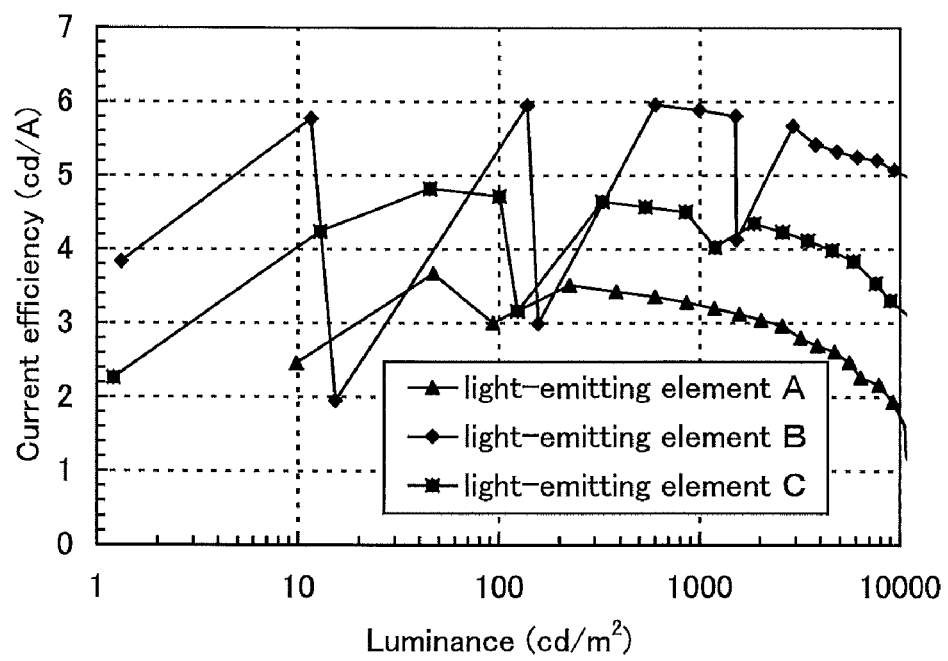
FIG. 36 is a graph showing luminance-current efficiency characteristics of light-emitting elements A to C.
Figure 37:
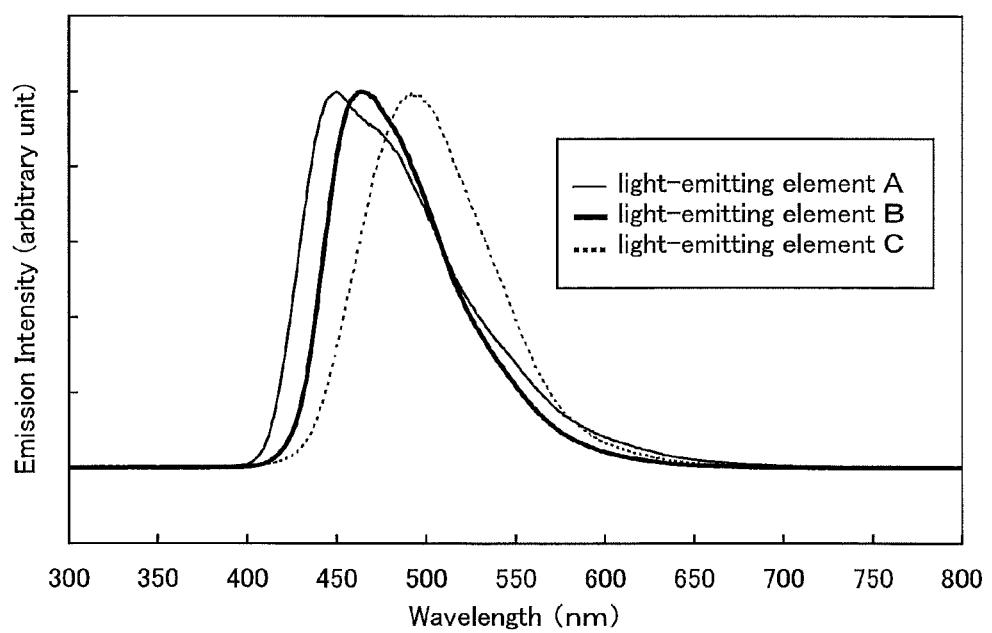
FIG. 37 is a graph showing an emission spectrum of the light-emitting elements A to C.
Figure 38:
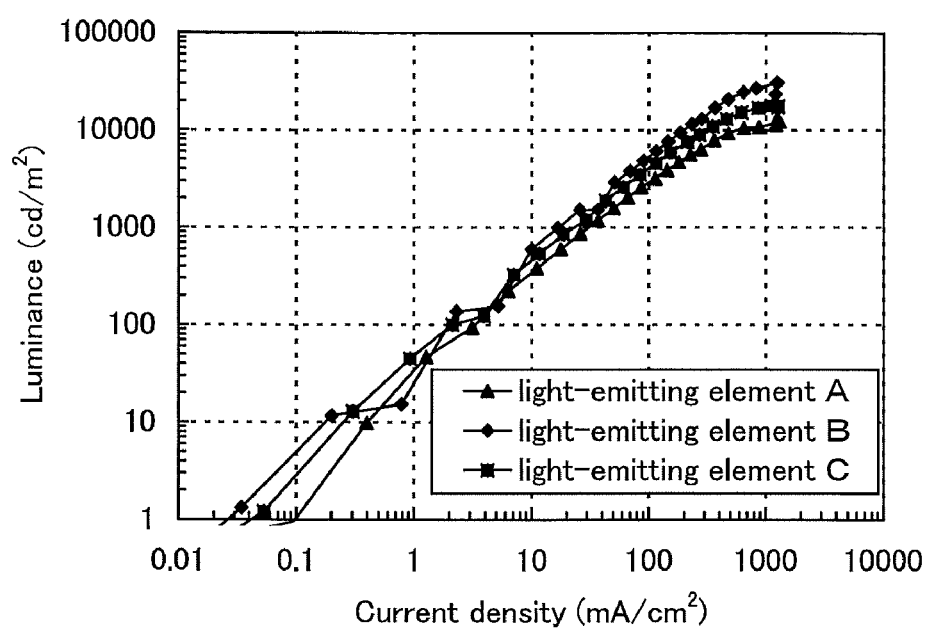
FIG. 38 is a graph showing current density-luminance characteristics of the light-emitting elements A to C.
Figure 39:
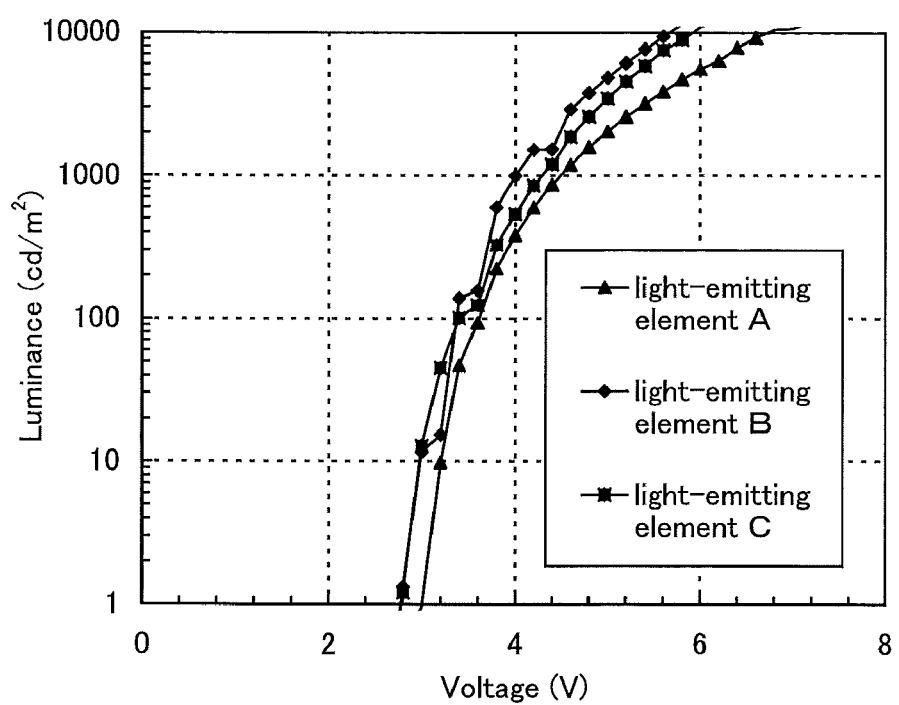
FIG. 39 is a graph showing voltage-luminance characteristics of the light-emitting elements A to C.

As to the light-emitting elements A to C, FIG. 36 shows the luminance-current efficiency characteristics thereof, FIG. 38 shows the current density-luminance characteristics thereof, and FIG. 39 shows the voltage-luminance characteristics thereof. In addition, FIG. 37 shows the emission spectrum which was obtained at a current supply of 1 mA.

According to FIG. 37, it was found that excellent blue light emission of IDPBAPBA having a peak at 450 nm was obtained from the light-emitting element A. The light-emitting element A bad CIE chromaticity coordinates (x=0.17, y=0.19) at a luminance of 860 cd/m² and exhibited favorable blue light emission. Further, the current efficiency, external quantum efficiency, voltage, current density, and power efficiency at the luminance of 860 cd/m² were 3.3 cd/A, 2.2%, 4.4 V, 26.3 mA/cm², and 2.3 lm/W, respectively.

According to FIG. 37, it was found that excellent blue light emission of DPBAPA having a peak at 464 nm was obtained from the light-emitting element B. The light-emitting element B had CIE chromaticity coordinates (x=0.16, y=0.21) at a luminance of 990 cd/m² and exhibited blue light emission. Further, the current efficiency, external quantum efficiency, voltage, current density, and power efficiency at the luminance of 990 cd/m² were 5.9 cd/A, 3.8%, 4.0 V, 16.8 mA/cm², and 4.6 lm/W, respectively.

According to FIG. 37, it was found that excellent blue light emission of DPAPA having a peak at 472 nm was obtained from the light-emitting element C. The light-emitting element C had CIE chromaticity coordinates (x=0.19, y=0.38) at a luminance of 860 cd/m² and exhibited blue green light emission. Further, the current efficiency, external quantum efficiency, voltage, current density, and power efficiency at the luminance of 850 cd/m² were 4.5 cd/A, 2.0%, 4.2 V, 18.8 mA/cm², and 3.4 lm/W, respectively.

Figure 40:
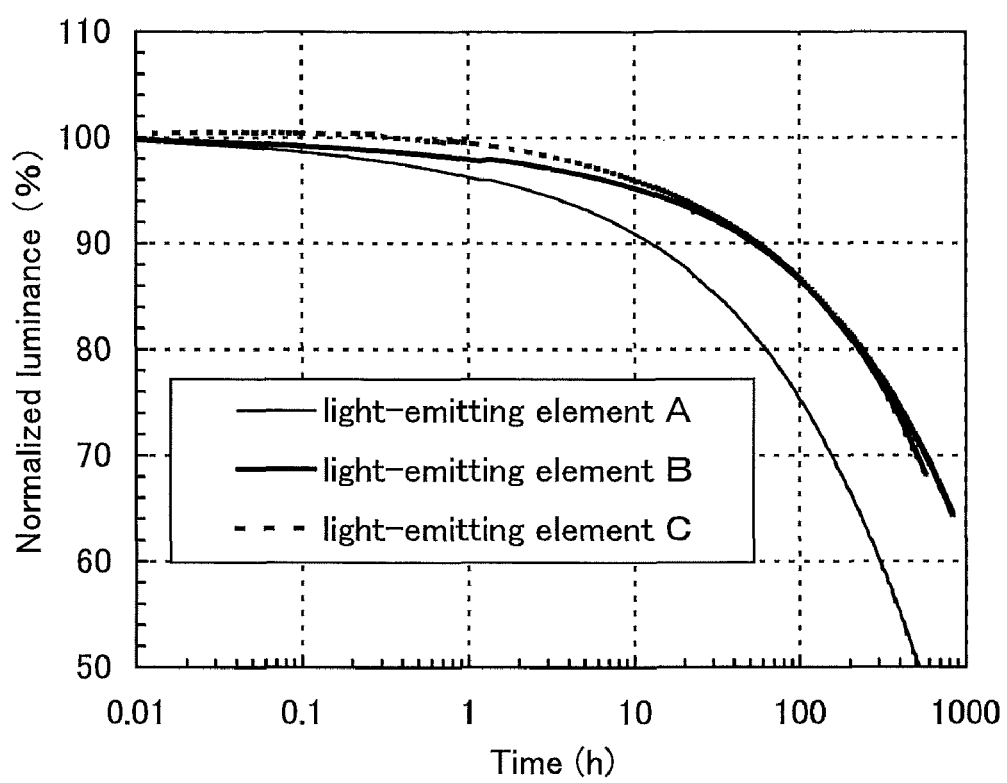
FIG. 40 is a graph showing a result of a reliability test of the light-emitting elements A to C.

Furthermore, a reliability test of the manufactured light-emitting elements A to C was performed as follows. A current having the same value as that flows the light-emitting elements A to C that emit light with a luminance of 1000 cd/m² in an initial state was continued to be made flow. Then, every time a certain period passed, a luminance was measured. Results obtained by the reliability test of the light-emitting elements A to C are shown in FIG. 40. FIG. 40 shows the change with time of luminance. Note that in FIG. 40, the horizontal axis represents current flow time (hour) and the vertical axis represents the proportion of luminance with respect to the initial luminance at each time, that is, normalized luminance (%).

As described above, according to this example, the light-emitting elements A to C with high efficiency and high reliability can be obtained.

According to this example, it was confirmed that the light-emitting element of the present invention has sufficient characteristics to function as a light-emitting element. Further, from the results of the reliability test, it was found that a highly reliable light-emitting element was obtained in which a short circuit due to defects of the film or the like is not caused even if the element is made to emit light continuously.

Example 6

In this example, as to a light-emitting element of the present invention, a light-emitting element having a light-emitting layer that has a stacked structure will be described.

Figure 46B:
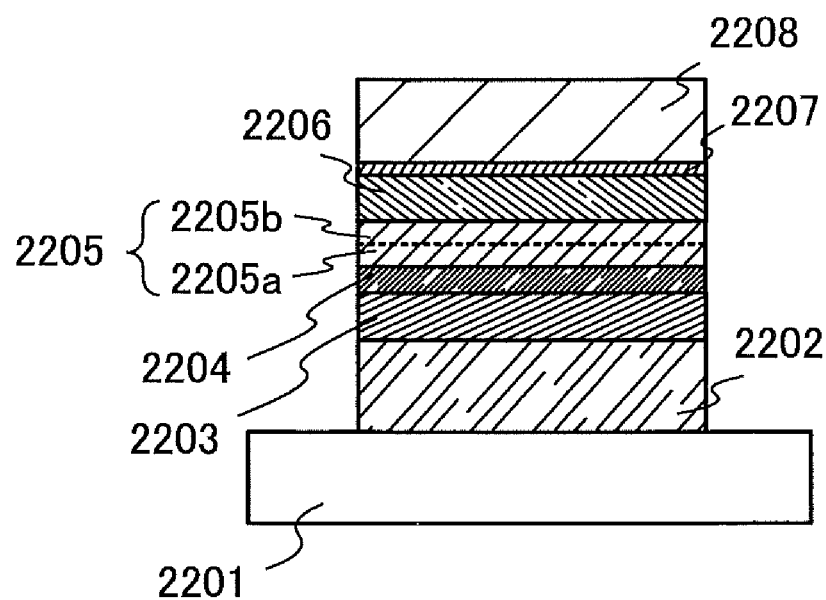

A structure of a light-emitting element of this example is shown in FIG. 46B. The light-emitting element of this example has a structure in which a first electrode 2202, a first layer 2203, a second layer 2204, a third layer 2205 (2205a, 2205b), a fourth layer 2206, a fifth layer 2207, and a second electrode 2208 are stacked over a substrate 2201. In this example, the third layer 2205 (2205a, 2205b) which is a stacked light-emitting layer is formed using an anthracene derivative of the present invention.

The element structures of light-emitting elements D and E manufactured in this example are shown in Table 2. In Table 2, the mixture ratios are all represented in weight ratios.

TABLE 2

| | first electrode 2202 | first layer 2203 | second layer 2204 | third layer 2205 | | fourth layer 2206 | fifth layer 2207 | second electrode 2208 |
|---|---|---|---|---|---|---|---|---|
| light-emitting element D | ITSO 110 nm | NPB:MoOx (=4:1) 50 nm | NPB 10 nm | DPBAPBA 30 nm | CzPA:DPBAPBA (=1:0.1) 30 nm | Alq 10 nm | Bphen 20 nm | LiF 1 nm | Al 200 nm |
| light-emitting element E | ITSO 110 nm | NPB:MoOx (=4:1) 50 nm | NPB 10 nm | DPBAPBA 30 nm | CzPA:DPBAPBA (=1:0.1) 30 nm | Alq 10 nm | Bphen 20 nm | LiF 1 nm | Al 200 nm |

*The mixture ratios are all weight ratios.

A manufacturing method of the light-emitting elements D and E of this example will be described below.

First, as to the light-emitting elements D and B, a film of indium tin oxide including silicon oxide (ITSO) was formed by sputtering over a substrate 2201 formed using a glass substrate to form a first electrode 2202. Note that the thickness of the first electrode 2202 was set to be 110 nm and the area thereof was set to be 2 mm×2 mm.

Next, the substrate 2201 was fixed to a substrate holder provided in a vacuum evaporation apparatus so that a surface of the substrate 2201 over which the first electrode 2202 was formed faced down. Then, after reducing the pressure of the vacuum evaporation apparatus to about $10^{-4}$ Pa, a first layer 2203 was formed using a layer containing a composite material of an organic compound and an inorganic compound over the first electrode 2202 by co-evaporating 4,4'-bis[N-(1-naphthyl)-N-phenylamino]biphenyl (abbreviation: NPB) and molybdenum(VI) oxide. The film thickness was set to be 50 nm and the weight ratio of NPB to molybdenum(VI) oxide was adjusted to be 4:1 (=NPB:molybdenum oxide). Note that the co-evaporation method is an evaporation method by which evaporation is performed simultaneously from a plurality of evaporation sources in one chamber.

Next, NPB was evaporated to be 10 nm thick, whereby a second layer 2204 was formed as a hole-transporting layer.

As to the light-emitting element D, DPBAPBA synthesized in Example 1 was evaporated over the second layer 2204 to form a film of DPBAPBA with a thickness of 30 nm. Next, CzPA and DPBAPBA were co-evaporated with the weight ratio of CzPA:DPBAPBA 1:0.1 over the film of DPBAPBA with a thickness of 30 nm. The co-evaporated film of CzPA and DPBAPBA was stacked over the film of DPBAPBA to form the third layer 2205 as a light-emitting layer.

As to the light-emitting element E, DPBAPA synthesized in Example 1 was evaporated over the second layer 2204 to form a film of DPBAPA with a thickness of 30 nm. Next, CzPA and DPBAPA were co-evaporated with the weight ratio of CzPA:DPBAPA=1:0.1 over the film of DPBAPA with a thickness of 30 nm. The co-evaporated film of CzPA and DPBAPA was stacked over the film of DPBAPA to form the third layer 2205 as a light-emitting layer.

As to the light-emitting elements D and E, a fourth layer 2206 was formed as an electron-transporting layer by evaporating 10 nm of Alq film and 20 nm of Bphen film which were sequentially stacked over the third layer 2205.

Lithium fluoride (LiF) was deposited over the fourth layer 2206 to a thickness of 1 nm, whereby a fifth layer 2207 was formed as an electron-injecting layer. Lastly, aluminum was deposited to a thickness of 200 nm as a second electrode 2208 which serves as a cathode. Accordingly, the light-emitting elements D and E of this example were obtained. Note that in all of the above evaporation steps, a resistance heating method was adopted.

The light-emitting elements D and E thus obtained were sealed in a glove box under a nitrogen atmosphere without being exposed to atmosphere. Then, the operation characteristics of the light-emitting elements D and E were measured. Note that the measurement was performed at a room temperature (in the atmosphere kept at 25° C.).

Figure 41:
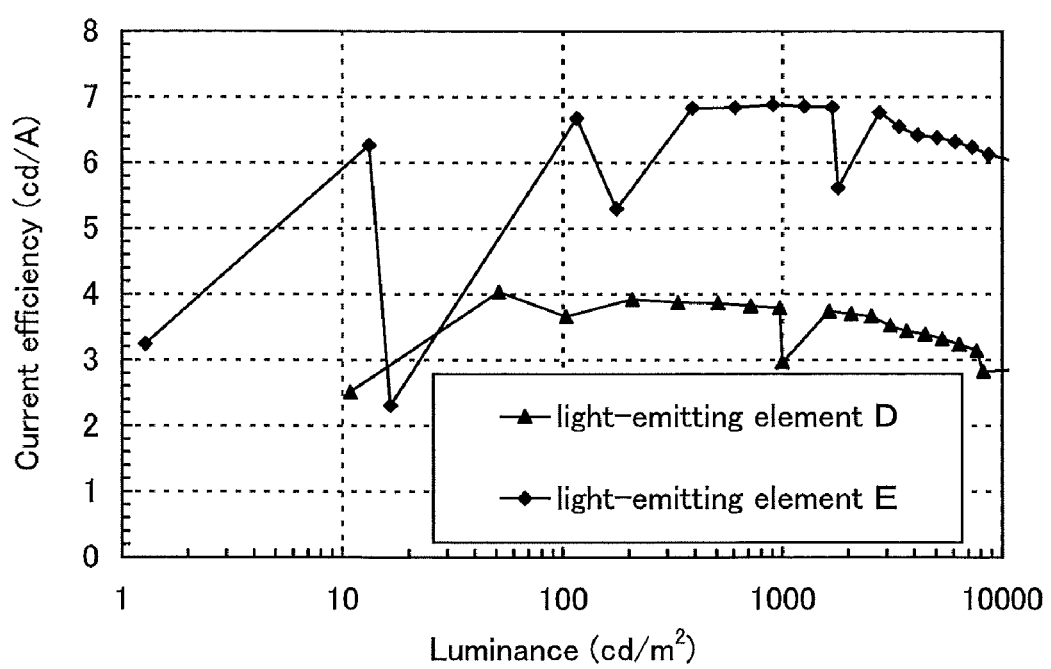
FIG. 41 is a graph showing the luminance-current efficiency characteristics of light-emitting elements D and E.
Figure 42:
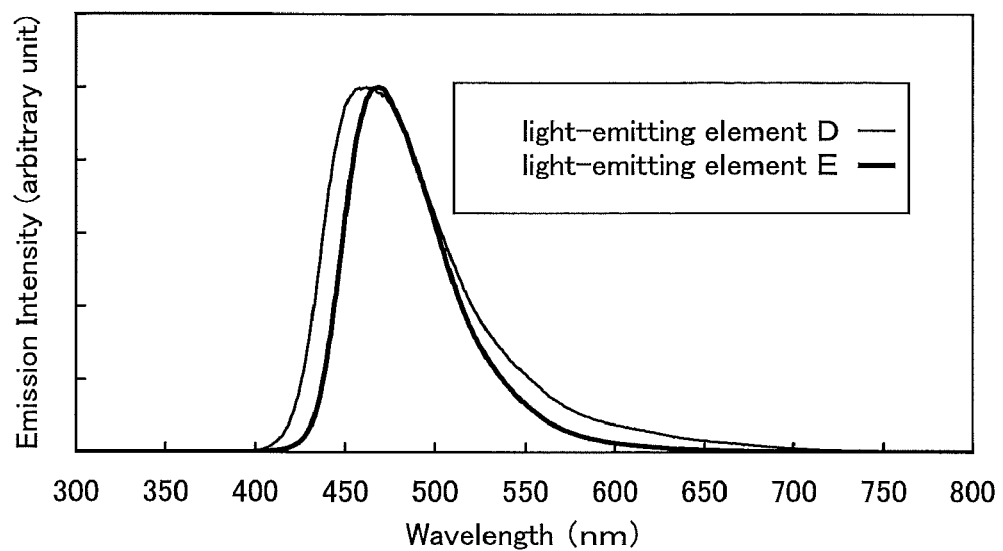
FIG. 42 is a graph showing an emission spectrum of the light-emitting elements D and E.
Figure 43:
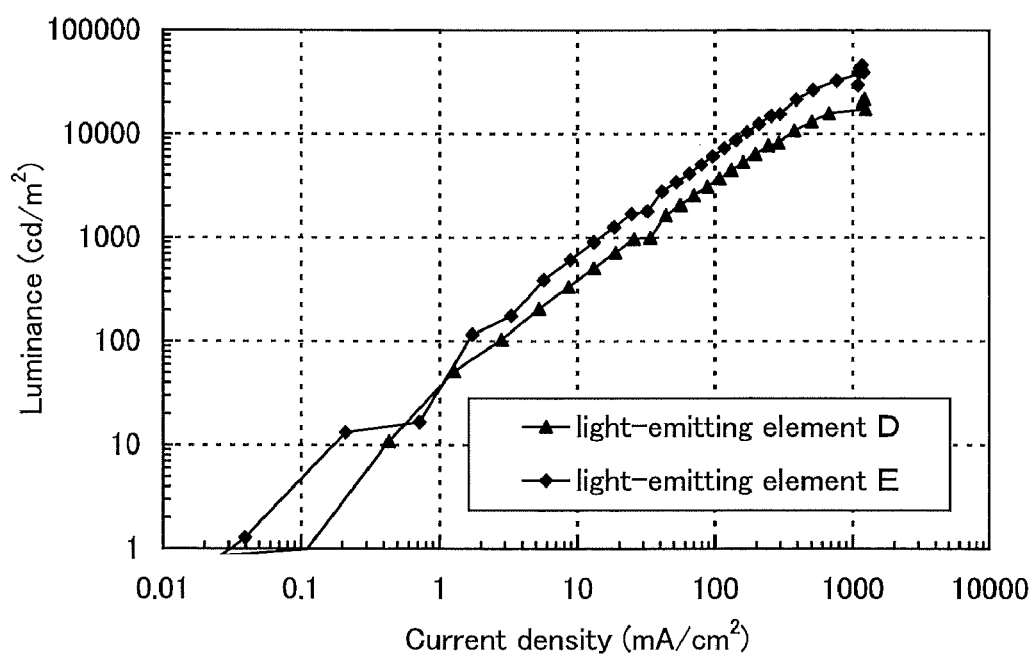
FIG. 43 is a graph showing the current density-luminance characteristics of the light-emitting elements D and E.
Figure 44:
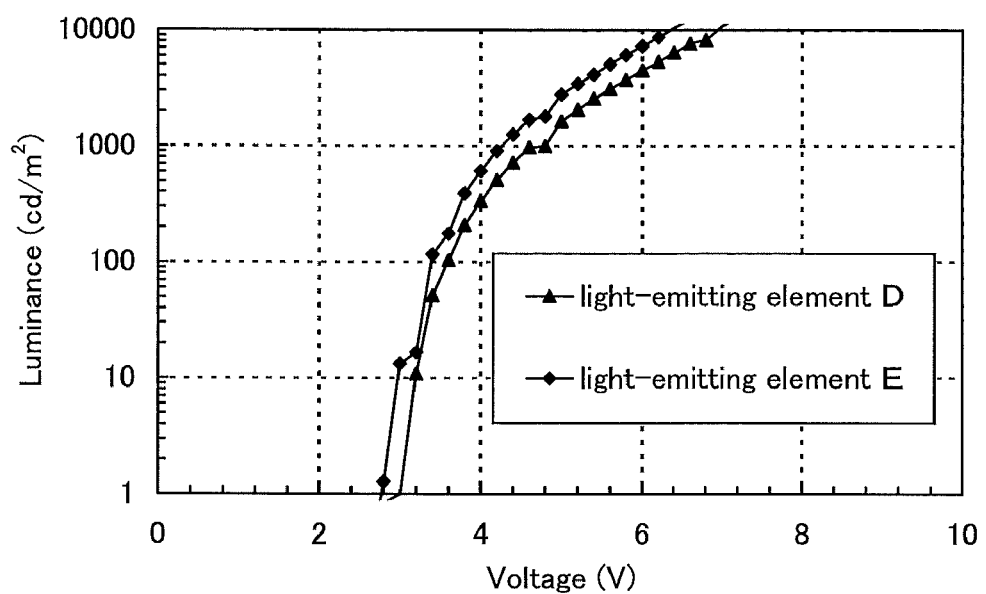
FIG. 44 is a graph showing the voltage-luminance characteristics of the light-emitting elements D and E.

As to the light-emitting elements D and E, FIG. 41 shows the luminance-current efficiency characteristics thereof, FIG. 43 shows the current density-luminance characteristics thereof and FIG. 44 shows the voltage-luminance characteristics thereof. In addition, FIG. 42 shows the emission spectrum which was obtained at a current supply of 1 mA.

According to FIG. 42, it was found that excellent blue light emission of DPBAPBA having a peak at 458 nm was obtained from the light-emitting element D. The light-emitting element D) had CIE chromaticity coordinates (x=0.17, y=0.19) at a luminance of 970 cd/m$^2$ and exhibited favorable blue light emission. Further, the current efficiency, external quantum efficiency, voltage, current density, and power efficiency at the luminance of 970 cd/m$^2$ were 3.8 cd/A, 2.6%, 4.6 V, 25.6 mA/cm$^2$, and 2.6 lm/W, respectively.

According to FIG. 42, it was found that excellent blue light emission of DPBAPA having a peak at 464 nm was obtained from the light-emitting element E. The light-emitting element E had CIE chromaticity coordinates (x=0.15, y=0.20) at a luminance of 900 cd/m$^2$ and exhibited favorable blue light emission. Further, the current efficiency, external quantum efficiency, voltage, current density, and power efficiency at the luminance of 905 cd/m$^2$ were 6.9 cd/A, 4.8%, 4.2 V, 13.2 mA/cm$^2$, and 5.1 lm/W, respectively.

Figure 45:
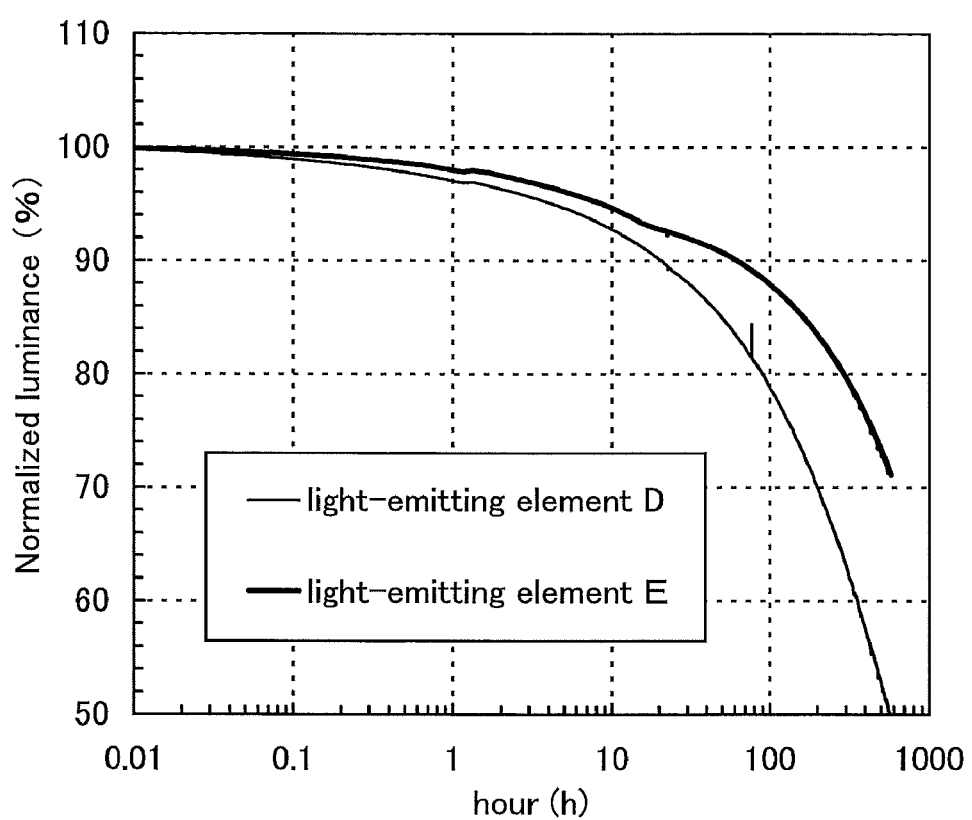
FIG. 45 is a graph showing a result of a reliability test of the light-emitting elements D and E.

Further, a reliability test of the manufactured light-emitting elements D and E was performed as follows. A current having the same value as that flows through the light-emitting elements D and E that emit light with a luminance of 1000 cd/m$^2$ in an initial state was continued to be flow. Then, every time a certain period passed, a luminance was measured. Results obtained by the reliability test of the light-emitting elements D and E are shown in FIG. 45. FIG. 45 shows the change with time of luminance. Note that in FIG. 45, the horizontal axis represents current flow time (hour) and the vertical axis represents the proportion of luminance with respect to the initial luminance at each time, that is, normalized luminance (%).

As described above, according to this example, the light-emitting elements D and E which emit blue light with high color purity and have high efficiency and high reliability can be obtained.

According to this example, it was confirmed that the light-emitting element of the present invention has sufficient characteristics to function as a light-emitting element. Further, from the results of the reliability test, it was found that a highly reliable light-emitting element can be obtained in which a short circuit due to defects of the film or the like is not caused even if the element is made to emit light continuously.

This application is based on Japanese Patent Application serial no. 2008-224805 filed with Japan Patent Office on Sep. 2, 2008, the entire contents of which are hereby incorporated by reference.

What is claimed is:

1. An anthracene derivative represented by a general formula (1),

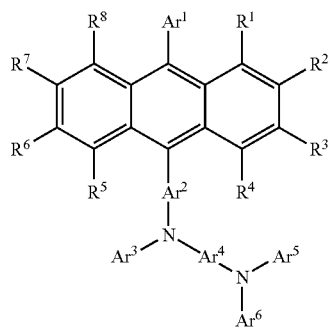

(1)

wherein:

$Ar^1$, $Ar^3$, $Ar^5$, and $Ar^6$ independently represent an aryl group having 6 to 13 carbon atoms, $Ar^2$ and $Ar^4$ independently represent an arylene group having 6 to 13 carbon atoms, and $R^1$ to $R^8$ independently represent hydrogen or an alkyl group having 1 to 4 carbon atoms, at least one of $Ar^1$ to $Ar^6$ independently has a substituent, two substituents selected from $Ar^1$ to $Ar^6$ are bonded to each other to form a ring when $Ar^1$ to $Ar^6$ independently have two or more substituents, or two substituents which a carbon atom of $Ar^1$ to $Ar^6$ has are bonded to each other to form a spiro ring.

2. An anthracene derivative represented by a general formula (2),

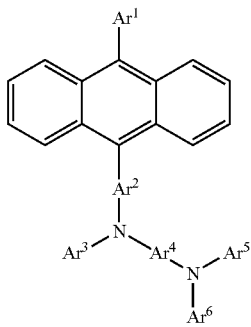

(2)

wherein:

$Ar^1$, $Ar^3$, $Ar^5$, and $Ar^6$ independently represent an aryl group having 6 to 13 carbon atoms, and $Ar^2$ and $Ar^4$ independently represent an arylene group having 6 to 13 carbon atoms, at least one of $Ar^1$ to $Ar^6$ independently has a substituent, two substituents selected from are bonded to each other to form a ring when $Ar^1$ to $Ar^6$ independently have two or more substituents, or two substituents which a carbon atom of $Ar^1$ to $Ar^6$ has are bonded to each other to form a spiro ring.

3. An anthracene derivative represented by a general formula (3),

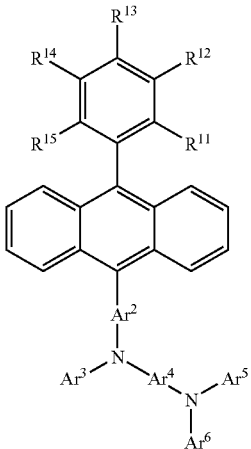

(3)

wherein:

$Ar^3$, $Ar^5$, and $Ar^6$ independently represent an aryl group having 6 to 13 carbon atoms, $Ar^2$ and $Ar^4$ independently represent an arylene group having 6 to 13 carbon atoms, and $R^{11}$ to $R^{15}$ independently represent hydrogen, an aryl group having 6 to 13 carbon atoms, an alkyl group having 1 to 4 carbon atoms, or a haloalkyl group having a carbon atom, at least one of $Ar^2$ to $Ar^6$ independently has a substituent, two substituents selected from $Ar^1$ to $Ar^6$ are bonded to each other to form a ring when $Ar^2$ to $Ar^6$ independently have two or more substituents, or two substituents which a carbon atom of $Ar^2$ to $Ar^6$ has are bonded to each other to form a spiro ring.

4. An anthracene derivative represented by a general formula (4),

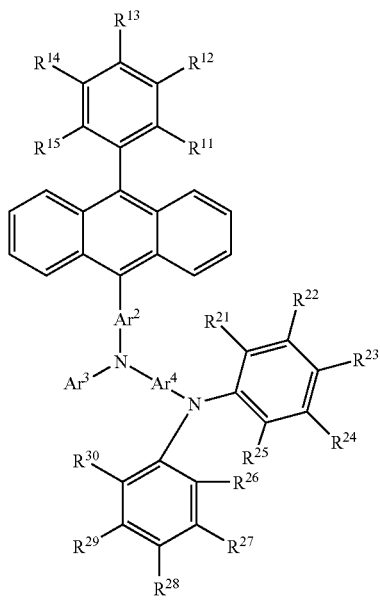

(4)

wherein:

$Ar^3$ represents an aryl group having 6 to 13 carbon atoms $Ar^2$ and $Ar^4$ independently represent an arylene group having 6 to 13 carbon atoms, and $R^{11}$ to $R^{15}$ and $R^{21}$ to $R^{30}$ independently represent hydrogen, an aryl group having 6 to 13 carbon atoms, an alkyl group having 1 to 4 carbon atoms, or a haloalkyl group having a carbon atom, at least one of Ar², Ar³, and Ar⁴ independently has a substituent, two substituents selected from Ar², Ar³, and Ar⁴ are bonded to each other to form a ring when Ar², Ar³, and Ar⁴ independently have two or more substituents, or two substituents which a carbon atom of Ar², Ar³, and Ar⁴ has are bonded to each other to form a spiro ring.

5. An anthracene derivative represented by a general formula (5),

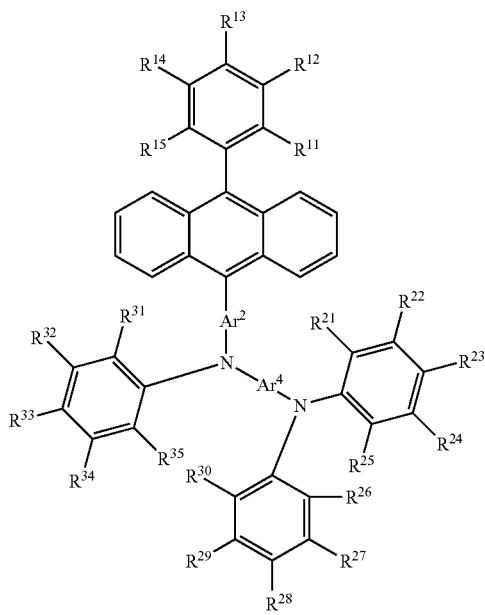

(5)

wherein:

Ar² and Ar⁴ independently represent an arylene group having 6 to 13 carbon atoms, and $R^{11}$ to $R^{15}$ and $R^{21}$ to $R^{35}$ independently represent hydrogen, an aryl group having 6 to 13 carbon atoms, an alkyl group having 1 to 4 carbon atoms, or a haloalkyl group having a carbon atom, at least one of Ar² and Ar⁴ independently has a substituent, two substituents selected from Ar¹ to Ar⁶ are bonded to each other to form a ring when Ar² and Ar⁴ independently have two or more substituents, or two substituents which a carbon atom of Ar² and Ar⁴ has are bonded to each other to form a spiro ring.

6. An anthracene derivative represented by a general formula (6),

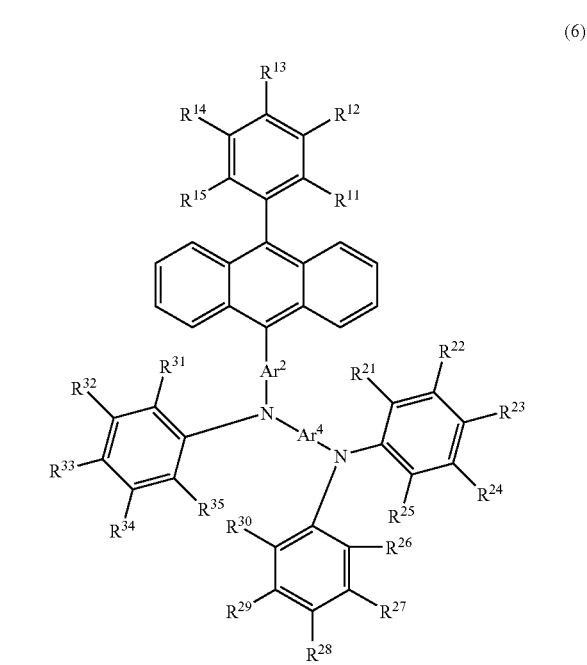

(6)

wherein Ar² and Ar⁴ independently represent a phenylene group or a biphenyl-diyl group, $R^{11}$ to $R^{15}$ and $R^{21}$ to $R^{35}$ independently represent hydrogen, an aryl group having 6 to 13 carbon atoms, an alkyl group having 1 to 4 carbon atoms, or a haloalkyl group having a carbon atom.

7. An anthracene derivative represented by a structural formula (101)

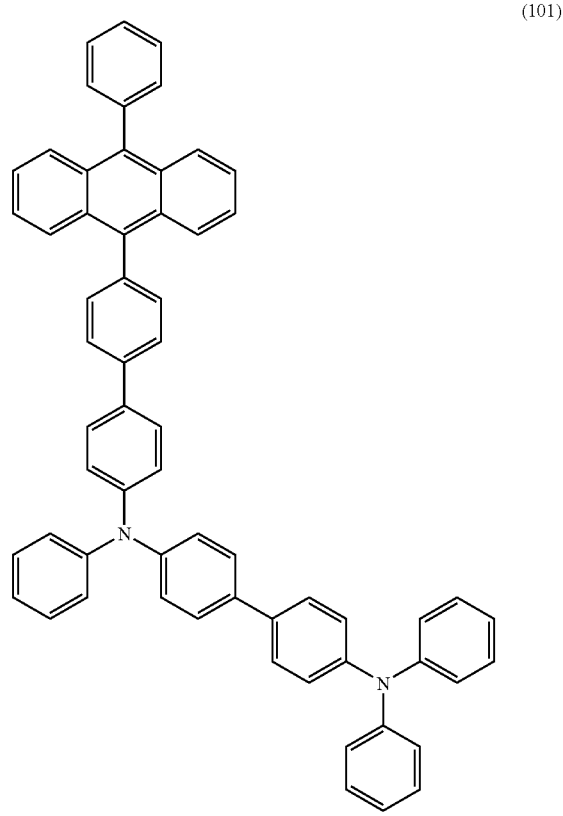

(101)

8. An anthracene derivative represented by a structural formula (201)

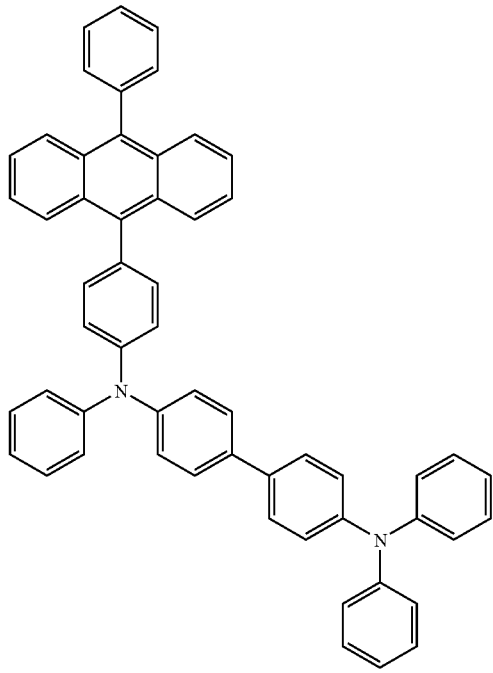

(201)

9. An anthracene derivative represented by a structural formula (301)

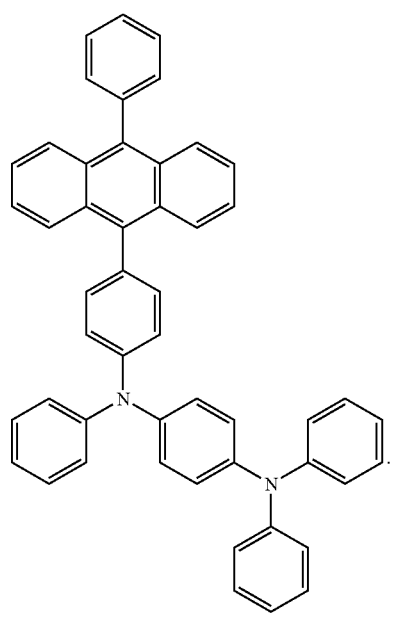

(301)

10. An anthracene derivative represented by a structural formula (401)

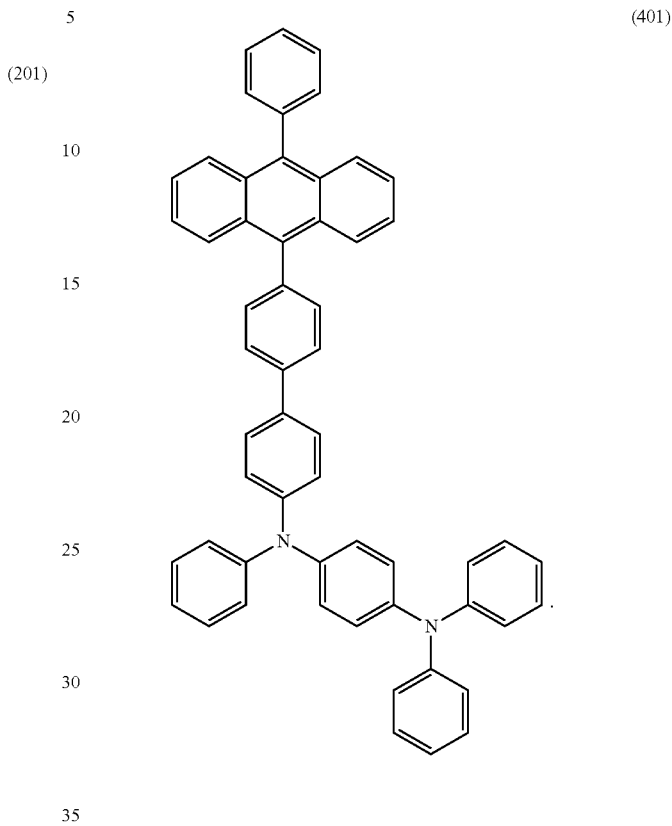

(401)

11. A material for a light-emitting element, comprising the anthracene derivative according to claim 1.

12. A light-emitting element comprising the anthracene derivative according to claim 1.

13. A light-emitting element wherein the anthracene derivative according to claim 1 is used for a light-emitting layer.

14. A light-emitting element, wherein the anthracene derivative according to claim 1 is used for an emission center material in a light-emitting layer.

15. A light-emitting device comprising the light-emitting element according to claim 12 and means for controlling the light-emitting element.

16. An electronic appliance comprising the light-emitting device according to claim 15 as a display portion.

* * * * *

UNITED STATES PATENT AND TRADEMARK OFFICE
CERTIFICATE OF CORRECTION

PATENT NO. : 8,110,122 B2
APPLICATION NO. : 12/550562
DATED : February 7, 2012
INVENTOR(S) : Sachiko Kawakami, Nobuharu Ohsawa and Satoshi Seo Page 1 of 5

It is certified that error appears in the above-identified patent and that said Letters Patent is hereby corrected as shown below:

In the Specification:

Column 3, line 39; Change "(3)" to --(4)--.
Column 3, lines 39 to 56;

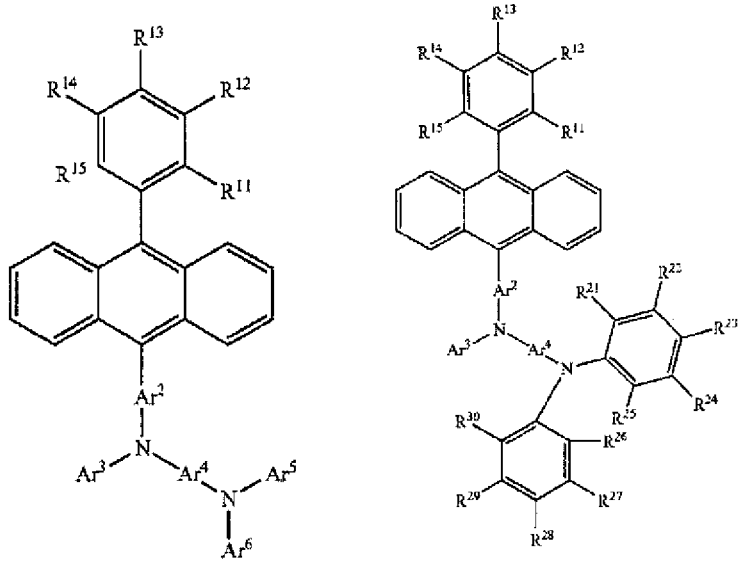

Change " " to -- --.
Column 8, line 49; Change "a H NMR" to --a $^1$H NMR--.

Signed and Sealed this
Eighteenth Day of March, 2014

Michelle K. Lee
*Deputy Director of the United States Patent and Trademark Office*

CERTIFICATE OF CORRECTION (continued)
U.S. Pat. No. 8,110,122 B2

In the Specification:

Columns 32 to 33, formula (226);

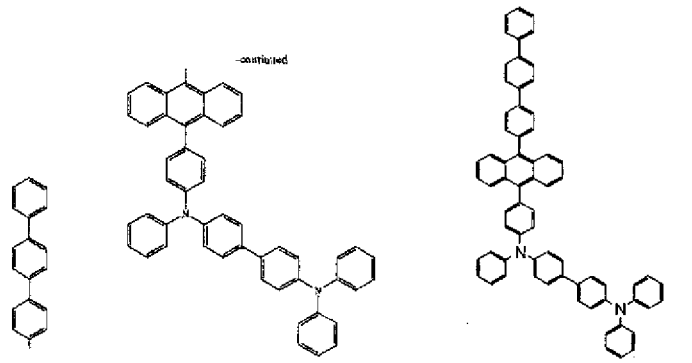

Change " " to -- --.

Columns 33 to 34, formula (228);

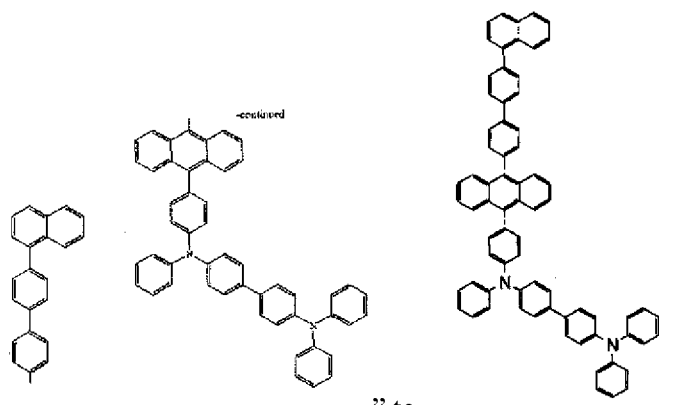

Change " " to -- --.

Columns 38 to 39, formula (239);

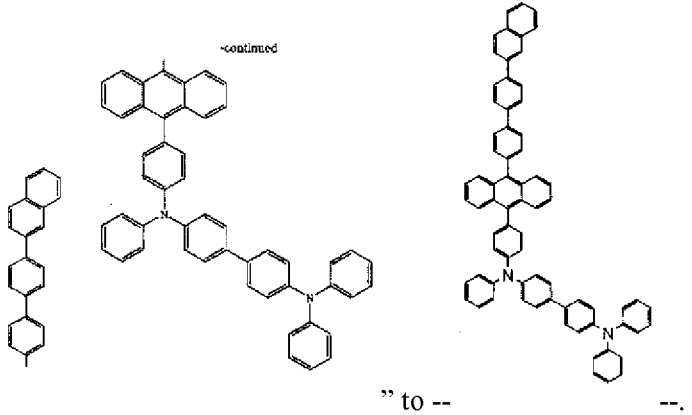

Change " " to -- --.

CERTIFICATE OF CORRECTION (continued)
U.S. Pat. No. 8,110,122 B2

In the Specification:

Columns 44 to 45, formula (309);

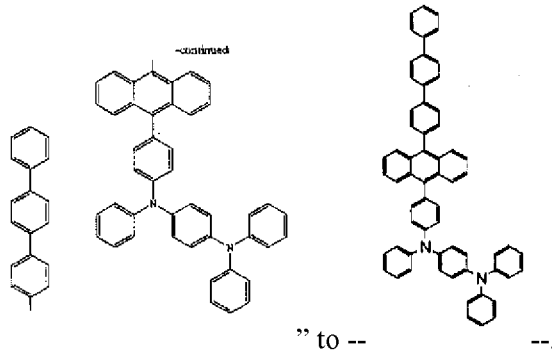

Change " " to -- --.

Column 47, formula (313);

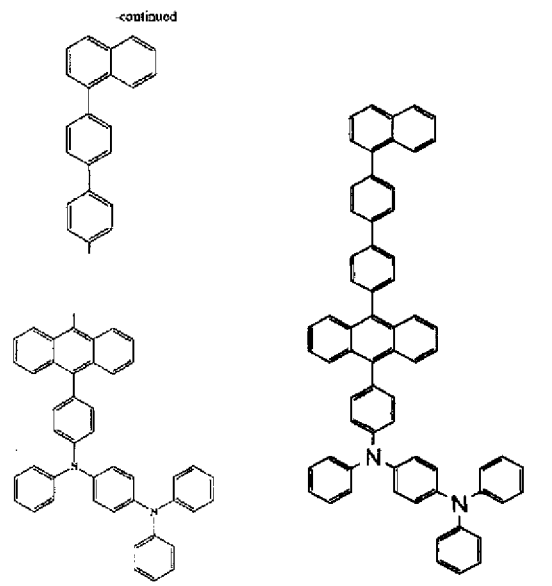

Change " " to -- --.

Columns 47 to 48, formula (314);

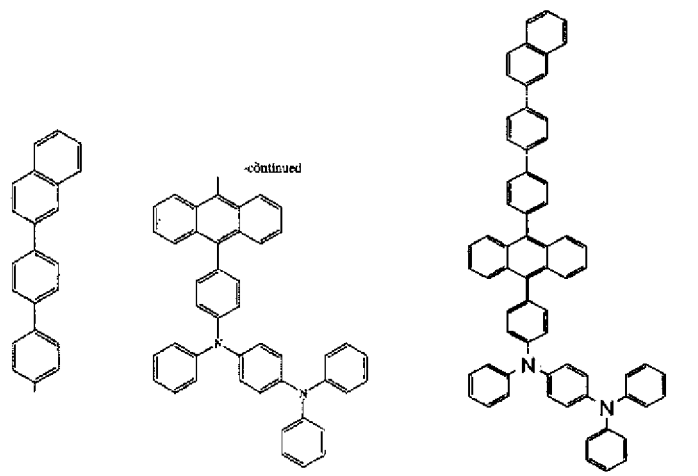

Change " " to -- --.

In the Specification:
Columns 75 to 76, formula (371);
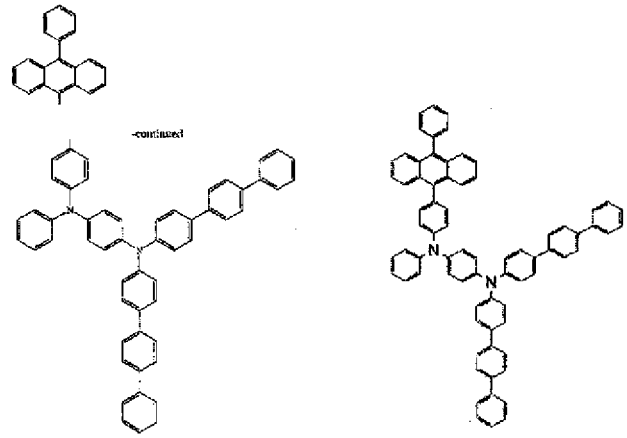
Change " " to -- --.
Columns 77 to 78, formula (376);
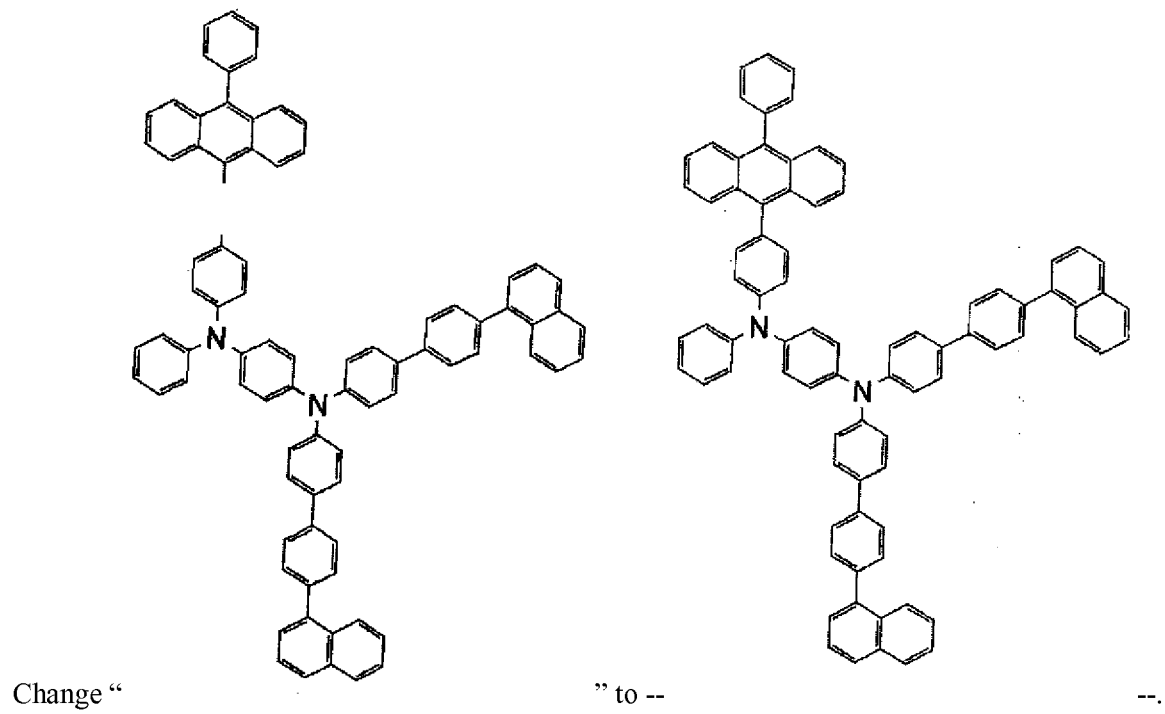
Change " " to -- --.

CERTIFICATE OF CORRECTION (continued)
U.S. Pat. No. 8,110,122 B2

In the Specification:

Column 78, formula (377);

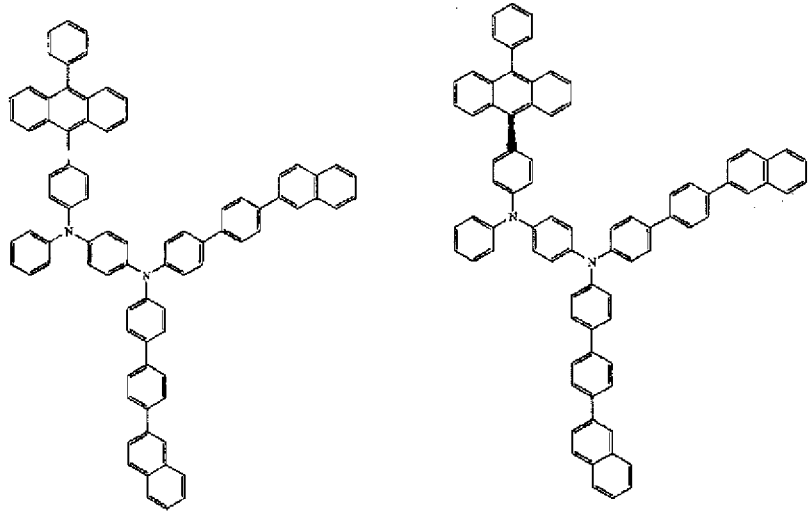

Change " " to -- --.
Column 98, line 3; Change "DC2);" to --DCM2);--.
Column 122, line 19; Change "(V-5550," to --(V-550,--.
Column 126, line 13; Change "(DM)" to --(DMF)--.
Column 129, line 44; Change "IDPBAPBA" to --DPBAPBA--.
Column 129, line 47; Change "860 cd/m$^2$" to --850 cd/m$^2$--.
Column 131, line 3; Change "D and B," to --D and E,--.